US011083787B2

(12) United States Patent
Chowdhury

(10) Patent No.: US 11,083,787 B2
(45) Date of Patent: Aug. 10, 2021

(54) BOVINE HERPESVIRUS TYPE 1 (BOHV-1) VECTOR AGAINST BOVINE RESPIRATORY DISEASE COMPLEX

(71) Applicant: Shafiqul I. Chowdhury, Baton Rouge, LA (US)

(72) Inventor: Shafiqul I. Chowdhury, Baton Rouge, LA (US)

(73) Assignee: Board of Supervisors of the Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/780,900

(22) PCT Filed: Dec. 2, 2016

(86) PCT No.: PCT/US2016/064775
§ 371 (c)(1),
(2) Date: Jun. 1, 2018

(87) PCT Pub. No.: WO2017/096267
PCT Pub. Date: Jun. 8, 2017

(65) Prior Publication Data
US 2018/0353596 A1  Dec. 13, 2018

Related U.S. Application Data

(60) Provisional application No. 62/262,450, filed on Dec. 3, 2015.

(51) Int. Cl.
*A61K 39/245* (2006.01)
*A61K 39/39* (2006.01)
(Continued)

(52) U.S. Cl.
CPC ............ *A61K 39/245* (2013.01); *A61K 39/12* (2013.01); *A61K 39/39* (2013.01); *C07K 14/005* (2013.01);
(Continued)

(58) Field of Classification Search
None
See application file for complete search history.

(56) References Cited

U.S. PATENT DOCUMENTS 5,616,477 A * 4/1997 Price .................... C07K 14/445
435/252.3
8,877,211 B2 * 11/2014 Chowdhury ............. C12N 7/00
424/229.1
(Continued)

FOREIGN PATENT DOCUMENTS

WO     2016/019244 A1     2/2016

OTHER PUBLICATIONS

Kim et al. Use of the human elongation factor 1a promoter as a versatile and efficient expression system. Gene, vol. 91, issue 2, pp. 217-223, Abstract Only (Year: 1990).*
(Continued)

*Primary Examiner* — Michelle S Horning
(74) *Attorney, Agent, or Firm* — Venable LLP; Keith G. Haddaway

(57) ABSTRACT

The application describes recombinant BoHV-1 triple mutant viruses that express protective antigens of other bovine respiratory viruses associated with Bovine respiratory disease complex (BRDC).

21 Claims, 45 Drawing Sheets

Specification includes a Sequence Listing.

(51) Int. Cl.
C07K 14/005 (2006.01)
A61K 39/12 (2006.01)
A61K 39/00 (2006.01)

(52) U.S. Cl.
CPC .............. A61K 2039/5254 (2013.01); A61K 2039/543 (2013.01); A61K 2039/552 (2013.01); A61K 2039/70 (2013.01); C12N 2710/16734 (2013.01); C12N 2710/16743 (2013.01); C12N 2710/16771 (2013.01); C12N 2760/18534 (2013.01); C12N 2770/24334 (2013.01)

(56) References Cited

U.S. PATENT DOCUMENTS

| | | | | |
|---|---|---|---|---|
| 2005/0287171 | A1* | 12/2005 | Meyers | C07K 14/005 424/204.1 |
| 2012/0034262 | A1 | 2/2012 | Osterrieder et al. | |
| 2013/0034585 | A1* | 2/2013 | Chowdhury | A61K 39/12 424/205.1 |
| 2014/0147466 | A1 | 5/2014 | Mahony | |

OTHER PUBLICATIONS

Taylor et al. Resistance to bovine respiratory syncytial virus (BRSV) induced in calves by a recombinant bovine herpesvirus-1 expressing the attachment glycoprotein of BRSV. Journal of General Virology vol. 79, Issue 7, 1759-1767. (Year: 1998).*
Al-Mubarak et al., "Glycoprotein E (gE) specified by bovine herpesvirus type 5 (BHV-5) enables trans-neuronal virus spread and neurovirulence without being a structural component of enveloped virions", Virology, 365, (2007) 398-409.
Al-Mubarak et al., "A Glycine-Rich Bovine Herpesvirus 5 (BHHV-5) gE-Specific Epitope within the Ectodomain Is Important for BHV-5 Neurovirulence", Journal of Virology, vol. 78, No. 9, May 2004, pp. 4806-4816.
Antonis, Adriaan F.G. et al., "Vaccine-Induced Immunopathology during Bovine Respiratory Syncytial Virus Infection: Exploring the Parameters of Pathogenesis", Journal of Virology, vol. 77, No. 22, Nov. 2003, pp. 12067-12073.
Antonis, Adriaan F.G. et al., "Vaccination with recombinant modified vaccinia virus Ankara expressing bovine respiratory syncytial virus (bRSV) proteins protects calves against RSV challenge", Vaccine 25 (2007), pp. 4818-4827.
Baker, John C., et al., "Bovine Respiratory Syncytial Virus", Veterinary Clinics of North America: Food Animal Practice, vol. 13, No. 3, Nov. 1997, pp. 425-454.
Baxi, Mohit K. et al., "Recombinant Bovine Adenovirus Type 3 Expressing Bovine Viral Diarrhea Virus Glycoprotein E2 Induces an Immune Response in Cotton Rats", Virology 278, (2000) pp. 234-243.
Berghaus, Londa J. et al., "Effects of dual vaccination for bovine respiratory syncytial virus and Haemophilus somnus on immune responses", Vaccine 24 (2006) 6018-6027.
Brackenbury, L.S. et al., "Aspects of the innate and adaptive immune responses to acute infections with BVDV", Veterinary Microbiology, 96, (2003), pp. 337-344.
Brock, Kenny V., "The persistence of bovine viral diarrhea virus", Biologicals 31, (2003), pp. 133-135.
Brum, Mario CS et al., "Bovine herpesvirus type 1 (BoHV-1) anterograde neuronal transport from trigeminal ganglia to nose and eye requires glycoprotein E", Journal of NeuroVirology, 15, pp. 196-201, 2009.
Butchi, N B et al., "Envelope protein Us9 is required for the anterograde transport of bovine herpesvirus type 1 from trigeminal ganglia to nose and eye upon reactivation", Journal of NeuroVirology, 13, pp. 384-388, 2007.

Chase, Chrisopher C.L., "The immune response to bovine viral diarrhea virus: a constantly changing picture", Vet Clin Food Anim, 20, (2004), pp. 95-114.
Chouljenko, Vladimir N., "Comparison of genomic and predicted amino acid sequences of respiratory and enteric bovine coronaviruses isolated from the same animal with fatal shipping pneumonia", Journal of General Virology, (2001), 82, pp. 2927-2933.
Chowdhury, S.I., "Fine Mapping of Bovine Herpesvirus 1 (BHV-1) glycoprotein C Neutralizing epitopes by type-specific monoclonal antibodies and synthetic peptides", Veterinary Microbiology, 58, (1997), pp. 309-314.
Chowdhury, S.I. e al., "The bovine herpesvirus type 1 envelope protein Us9 acidic domain is crucial for enterograde axonal transport", Veterinary Microbiology, 152, (2011), pp. 270-279.
Chowdhury, S I et al., "A bovine herpesvirus type 1 mutant virus with truncated glycoprotein E cytoplasmic tail has defective anterograde neuronal transport in rabbit dorsal root ganglia primary neuronal cultures in a microfluidic chamber system", Journal of NeuroVirology, 16, pp. 457-465, 2010.
Deplanche, Martine et al., "In vivo evidence for quasispecies distributions in the bovine respiratory syncytial virus genome", Journal of General Virology, (2007), 88, pp. 1260-1265.
Donofrio, Gaetano et al., "Establishment of a Bovine Herpesvirus 4 based vector expressing a secreted form of the Bovine Viral Diarrhoea Virus structural glycoprotein E2 for immunization purposes" BMC Biotechnology, 2007, 7, 68.
Durham, Peter L.K. et al, "Serological studies of infectious bovine rhinotracheitis, parainfluenza 3, bovine viral diarrhea, and bovine respiratory syncytial viruses in calves following entry to a bull test station", Can Vet J, vol. 32, Jul. 1991, pp. 427-429.
Elliott, Matthew et al., "Characterization of Recombinant Respiratory Syncytial Viruses with the Region Responsible for Type 2 T-Cell Responses and Pulmonary Eosinophilia Deleted from the Attachment (G) Protein", Journal of Virology, vol. 78, No. 16, Aug. 2004, pp. 8446-8454.
Ellis, John et al., "Longevity of protective immunity to experimental bovine herpesvirus-1 infection following inoculation with a combination modified-live virus vaccine in beef calves", JAVMA, vol. 227, No. 1, Jul. 1, 2005, pp. 123-128.
Ellis, J.A., "Update on viral pathogenesis in BRD", Animal Health Research Reviews 10(2), pp. 149-153 (2009).
Fulton, Robert W., "Bovine respiratory disease research (1983-2009)", Animal Health Research Reviews, 10(2), pp. 131-139 (2009).
Fulton, R.W. et al., "Humoral Immune Response and Assessment of Vaccine Virus Shedding in Calves Receiving Modified Live Virus Vaccines Containing Bovine Herpesvirus-1 and Bovine Viral Diarrhoea Virus 1a", J.Vet. Med. B 50, pp. 31-37 (2003).
Furze, J. et al., "Antigenic heterogeneity of the attachment protein of bovine respiratory syncytiai virus", Journal of General Virology (1994), 75, pp. 363-370.
Gershwin, Laurel J., "Bovine respiratory syncytial virus infection: immunopathogenic mechanisms", Animal Health Research Reviews 8(2); pp. 207-213 (2007).
Gershwin, Laurel J., "Immunology of bovine respiratory syncytial virus infection of cattle", Comparative Immunology, Microbiology and Infectious Diseases, 35, (2012), pp. 253-257.
Goens, S. Denise, "The evolution of bovine viral diarrhea: a review", Can Vet J, 2002, 43:pp. 946-954.
Hägglund, S. et al., "A six-year study on respiratory viral infections in a bull testing facility", The Veterinary Journal, 173, (2007), pp. 585-593.
Jericho, K.W.F. et al., "Pneumonia in Calves Produced with Aerosols of Bovine Herpesvirus 1 and Pasteurella haemolytica", Can. J. comp. Med., vol. 42—Jul. 1978, pp. 269-277.
Jones, Clinton et al., "Bovine Herpesvirus Type 1 (BHV-1) is an Important Cofactor in the Bovine Respiratory Disease Complex", Vet Clin Food Anim, 26, (2010), pp. 303-321.
Jones, Clinton J. et al., "A Review of the Biology of Bovine Herpesvirus Type 1 (BHV-I), Its Role as a Cofactor in the Bovine Respiratory Disease Complex and Development of Improved Vaccines", Animal Health Research Reviews, 3(2), pp. 187-205 (2008).
Jordan, Robert et al., "Inhibition of Host ER Glucosidase Activity Prevents Golgi Processing of Virion-Associated Bovine Viral Diarrhea Virus E2 Glycoproteins and Reduces Infectivity of Secreted Virions", Virology 295, 10-19, (2002), pp. 10-19.

(56) References Cited

OTHER PUBLICATIONS

Kaashoek, M.J. et al., "Virulence, immunogenicity and reactivation of bovine herpesvirus 1 mutants with a deletion in The gC, gG, g1, gE, or in both the g1 and gE gene", Vaccine. vol. 16, No. 8, pp. 802-809. 1998.

Kaashoek, M.J. et al., "Virulence and irnmunogenicity in calves of thymidine kinase- and glycoprotein E-negative bovine herpesvirus 1 mutants", Veterinary Microbiology, 48, (1996), pp. 143-153.

Kalina, Warren V. et al., "Formalin-inactivated bovine RSV vaccine influences antibody levels in bronchoalveolar lavage fluid and disease outcome in experimentally infected calves", Vaccine 23, (2005), pp. 4625-4630.

Karger, Axel et al., "Recombinant bovine respiratory syncytial virus with deletions of the G or SH genes: G and F proteins bind heparin", Journal of General Virology, (2001), 82, pp. 631-640.

Keles, I. et al., "In-vitro Studies on Mechanisms of Immunosuppression Associated with Bovine Respiratory Syncytial Virus", J. Comp. Path., 1998, vol. 118, pp. 337 345.

Kelling, Clayton L., "Evolution of bovine viral diarrhea virus vaccines", Vet Clin Food Anim, 20, (2004), pp. 115-129.

Kimman, T.G., "Diagnosis of bovine respiratory syncytial virus infections improved by virus detection in lung lavage samples", Am J Vet Res, vol. 47, No. 1, Jan. 1986, pp. 143-147.

Klink, Holly A. et al., "Influence of bovine respiratory syncytial virus F glycoprotein N-linked glycans on in vitro expression and on antibody responses in BALB/c mice", Vaccine, 24, (2006), pp. 3388-3395.

König, Patricia et al., "Glycoprotein M of bovine herpesvirus 1 (BHV-1) is nonessential for replication in cell culture and is involved in inhibition of bovine respiratory syncytial virus F protein induced syncytium formation in recombinant BHV-1 infected cells", Veterinary Microbiology, 86, (2002), pp. 37-49.

Koppers-Lalic, Danijela et al., "Varicelloviruses avoid T cell recognition by UL49.5-mediated inactivation of the transporter associated with antigen processing", pp. 5144-5149, PNAS, Apr. 5, 2005, vol. 102, No. 14.

Koppers-Lalic, Danijela et al., "Varicellovirus UL49.5 Proteins Differentially Affect the Function of the Transporter Associated with Antigen Processing, TAP", May 2008, vol. 4, Issue 5, e1000080.

Kühnle, Gisela et al., "The Class II Membrane Glycoprotein G of Bovine Respiratory Syncytial Virus, Expressed from a Synthetic Open Reading Frame, Is Incorporated into Virions of Recombinant Bovine Herpesvirus 1", Journa of Virology, Vo. 72, No. 5, May 1998, pp. 3804-3811.

Langedijk, Johannes P.M. et al., "Antigenic Structure of the Central Conserved Region of Protein G of Bovine Respiratory Syncytial Virus", Journal of Virology, vol. 71, No. 5, May 1997, pp. 4055-4061.

Laresen, L.E., "Bovine respiratory syncytial virus (BRSV): a review", Acta veterinaria scandinavica, vol. 41, No. 1, Date: 2000, pp. 1-24.

Larsen, L.E. et al., "Bovine Respiratory Syncytial Virus (BRSV) Pneumonia in Beef Calf Herds Despite Vaccination", Ata vet. scand. 2001, 42, pp. 113-121.

Lathrop, Sarah L. et al., "Antibody titers against bovine coronavirus and shedding of the virus via the respiratory tract feedlot cattle", AJVR, vol. 61, No. 9, Sep. 2000, pp. 1057-1061.

Leite, F. et al., "BHV-1 infection and inflammatory cytokines amplify the interaction of Mannheimia haemolytica leukotoxin with bovine peripheral blood mononuclear cells in vitro", Veterinary Immunology and Immunopathology, 99, (2004), pp. 193-202.

Lay, Christian T. et al.,"A Triple Gene Mutant of BoHV-1 Administered Intranasally in Lambs Replicates Efficiently in the Nasal Epithelium and Induces Neutralizing Antibody", International Journal of Vaccines and Immunization, vol. 2.1, pp. 1-4 (2016).

Lerch, Robert A. et al., "Nucleotide Sequence Analysis and Expression from Recombinant Vectors Demonstrate That the Attachment Protein G of Bovine Respiratory Syncytial Virus Is Distinct from that of Human Respiratory Syncytial Virus", Journal of Virology, vol. 64, No. 11, Nov. 1990, pp. 5559-5569.

Liang, R. et al., "DNA prime-protein boost strategies protect cattle from bovine viral diarrhea virus type 2 challenge", Journal of General Virology, (2008), 89, pp. 453-466.

Liang, R. et al., "Immunization with plasmid DNA encoding a truncated, secreted form of the bovine viral diarrhea virus E2 protein elicits strong humoral and cellular immune responses", Vaccine 23, (2005), pp. 5252-5262.

Lin, Guang-Jan et al., "Yeast-expressed classical swine fever virus glycoprotein E2 induces a protective immune response", Veterinary Microbiology, 139, (2009), pp. 369-374.

Liu, Z.F. et al., "A Bovine Herpesvirus Type 1 Mutant Virus Specifying a Carboxyl-Terminal Truncation of Glycoprotein E Is Defective in Anterograde Neuronal Transport in Rabbits and Calves", Journal of Virology, Aug. 2008, vol. 32, No. 15, pp. 7432-7442.

Lorenz, Ingrid et al., "Calf health from birth to weaning. III. housing and management of calf pneumonia", Irish Veterinary Journal, 2011, 64:14.

Mallipeddi, S.K. et al., "Analysis of polypeptides synthesized in bovine respiratory syncytial virus-infected cells", Arch Virol, (1990), 115, pp. 23-36.

Manoj, Sharmila et al., "Modulation of immune responses to bovine herpesvirus-1 in cattle by immunization with a DNA vaccine encoding glycoprotein D as a fusion protein with bovine CD154", Immunology, 2004, 112, pp. 328-338.

Martin, S.W. et al., "The Association of Titers to Bovine Coronavirus with Treatmentfor Bovine Respiratory Disease and Weight Gain in Feedlot Calves", Can J Vet Res, 1998, 62, pp. 257-261.

Martinod, S. et al., "Risk assessment related to veterinary biologicals: side-effects in target animals", Rev. sci. tech. Off. int. Epiz., 1995,14 (4), pp. 979-989.

McBride , Jere W. et al., "Primary and anamnestic responses of bovine bronchoalveolar and peripheral blood lymphocyte subsets to aerosolized Pasteurella haemolytica A1", Veterinary Immunology and Immunopathology, 67, (1999), pp. 161-170.

Meeusen, Els N.T. et al., "Current Status of Veterinary Vaccines", Clinical Microbiology Reviews, Jul. 2007, pp. 489-510.

Murray, Catherine L. et al., "Bovine Viral Diarrhea Virus Core Is an Intrinsically Disordered Protein That Binds RNA", Journal of Virology, vol. 82, No. 3, Feb. 2008, pp. 1294-1304.

Niataraj, Chandrasekaran et al., "Bovine Herpesvirus 1 Downregulates the Expression of Bovine MHC Class I Molecules", Viral Immunology, vol. 10, No. 1, 1997, pp. 21-34.

O'Toole, Donal et al., "Pathology in Practice", JAVMA, vol. 241, No. 2, Jul. 15, 2012, pp. 189-191.

O'Toole et al., "Letters to the Editor", JAVMA, vol. 237, No. 3, Aug. 1, 2010, pp. 257-260.

Plummer, Paul J. et al., "Effect of intranasal vaccination against bovine enteric coronavirus on the occurrence of respiratory tract disease in a commercial backgrounding feedlot", JAVMA, vol. 225, No. 5, Sep. 1, 2004, pp. 126-731.

Porgieter, LN et al., "Experimental production of bovine respiratory tract disease with bovine viral diarrhea virus", American Journal of Veterinary Research, vol. 45, 1984, pp. 1582-1585.

Ridpath, Julia F., "Bovine Viral Diarrhea Virus: Global Status", Vet Clin Food Anim, 26, (2010), pp. 105-121.

Ridpath, Julia, F. et al. "Immunology of BVDV vaccines", Biologicals, 41, (2013), pp. 14-19.

Rivera-Rivas, Jose J. et al., "Bovine herpesvirus type 1 infection of bovine bronchial epithelial cells increases neutrophil adhesion and activation", Veterinary Immunology and Immunopathology, 131, (2009), pp. 167-176.

Roth, James A. et al., "Suppresion of Neutrophil and Lymphocyte Function Induced by a Vaccinal Strain of Bovine Viral Diarrhea Virus With and Without the Administration of ACTH", American Journal of Veterinary Research, vol. 44, No. 12, pp. 2366-2372 (1984).

Saif, Linda J. et al., "Bovine Respiratory Coronavirus", Vet Clin Food Anim, 26, (2010), pp. 349-364.

Sandvik, Torstein et al., "Progress of control and prevention programs for bovine viral diarrhea virus in Europe", Vet Clin Food Anim, 20, (2004), pp. 151-169.

(56) References Cited

OTHER PUBLICATIONS

Schlender, Jorg et al. "Respiratory Syncytial Virus (RSV) Fusion Protein Subunit F2, Not Attachment Protein G, Determines the Specificity of RSV Infection", Journal of Virology, Apr. 2003, vol. 77, No. 8, pp. 4609-4616.
Schmidt, Ulrike, et al., "Mucosal Immunization with Live Recombinant Bovine Respiratory Syncytial Virus (BRSV) and Recombinant BRSV Lacking the Envelope Glycoprotein G Protects against Challenge with Wild-Type BRSV", Journal of Virology, Dec. 2002, vol. 76, No. 23, pp. 12355-12359.
Schmitt, Jutta et al., "Expression of bovine viral diarrhoea virus glycoprotein E2 by bovine herpesvirus-1 from a synthetic ORF and incorporation of E2 into recombinant virions", Journal of General Virology, (1999), 80, pp. 2839-2848.
Schrijver, Remco et al., "Comparison of DNA application methods to reduce BRSV shedding in cattle", Vaccine. vol. 16, No. 2/3, pp. 130-134, 1998.
Schrijver, Remco S. et al. "Immunization of cattle with a BHVI vector vaccine or a DNA vaccine both coding for the G protein of BRSV", Vaccine, vol. 15, No. 17/18, pp. 1908-1916, 1997.
Storz, Johannes et al., "Coronavirus and Pasteurella Infections in Bovine Shipping Fever Pneumonia and Evans' Criteria for Causation", Journal of Clinical Microbiology, Sep. 2000, Vo. 38, No. 9, pp. 3291-3298.
Taylor, Geraldine et al., "DNA vaccination against respiratory syncytial virus in young calves", Vaccine, 23, (2005), pp. 1242-1250.
Taylor, G. et al., "Resistance to bovine respiratory syncytial virus (BRSV) induced in calves by a recombinant bovine herpesvirus-1 expressing the attachment glycoprotein of BRSV", Journal of General Virology, (1998), 79, pp. 1759-1767.
Taylor, G. et al., "Protective epitopes on the fusion protein of respiratory syncytial virus recognized by murine and bovine monoclonal antibodies", Journal of General Virology, (1992), 73, pp. 2217-2223.
Taylor, G. et al., "Recombinant vaccinia viruses expressing the F, G or N, but not the M2, protein of bovine respiratory syncytial virus (BRSV) induce resistance to Brsv challenge in the calf and protect against the Development of pneumonic lesions", Journal of General Virology, (1997), 78, pp. 3195-3206.
Taylor, Jared, D. et al., "The epidemiology of bovine respiratory disease: What is the evidence for preventive measures?", Can Vet J, 2010, 51, pp. 1351-1359.
Tikoo, Suresh, K. et al., "Bovine Herpesvirus 1 (BHV-1): Biology, Pathogenesis, and Control", Advances in Virus Research, vol. 45 (1995).
Valarcher, J.-F. et al., "Bovine respiratory syncytial virus lacking the virokinin or with a mutation in furin cleavage site RA(R/K)R109 induces less pulmonary inflammation without impeding the induction of protective immunity in calves", Journal of General Virology, (2006), 87, pp. 1659-1667.
Van Drunen Littel-Van Den Hurk, S. et al., "Identification of a mutant bovine herpesvirus-1 (BHV-1) in post-arrival outbreaks of IBR in feedlot calves and protection with conventional vaccination", The Canadian Journal of Veterinary Research, 2001, 65, pp. 81-88.
Wei, Huiyong et al., "Bovine herpesvirus type 1 (BHV-1) mutant lacking UL49.5 luminal domain residues 30-32 and cytoplasmic tail residues 80-96 induces more rapid onset of virus neutralizing antibody and cellular immune responses in calves than the wild-type strain Cooper", Veterinary Immunology and Immunopathology, 147, (2012), pp. 223-229.
Wei, Huiyong et al., "Bovine Herpesvirus Type 1 (BHV-1) UL49.5 Luminal Domain Residues 30 to 32 Are Critical for MHC-I Down-Regulation in Virus-Infected Cells", BHV-1 UL49.5 Residues Important for TAP-Inhibition, Oct. 2011, vol. 6, Issue 10, e25742.
West, W.H.L. et al., "Biological activity, binding site and affinity of monoclonal antibodies to the fusion protein of respiratory syncytial virus", Journal of General Virology, (1994), 75, pp. 2813-2819.
Xue, Wenzhi et al., "Immunogenicity of a modified-live virus vaccine against bovine viral diarrhea virus types 1 and 2, infectious bovine rhinotracheitis virus, bovine parainfluenza-3 virus, and bovine respiratory syncytial virus when administered intranasally in young calves", Vaccine, 28, (2010), pp. 3784-3792.
Yoo, Dongwan et al., "A Single Amino Acid Change within Antigenic Domain II of the Spike Protein of Bovine Coronavirus Confers Resistance to Virus Neutralization", Clinical and Diagnostic Laboratory Immunology, vol. 8, No. 2 Mar. 2001, pp. 297-302.
Zemke, Johanna et al., "Novel BVDV-2 mutants as new candidates for modified-live vaccines", Veterinary Microbiology, 142, (2010), pp. 69-80.
Zimmer, Gert et al., "Proteolytic Activation of Respiratory Syncytial Virus Fusion Protein", The Journal of Biological Chemistry, vol. 276, No. 34, Issue of Aug. 24, pp. 31642-31650, 2001.
Chowdhury, Shafiqul I. et al., "A triple gene mutant of BoHV-1 administered intranasally issignificantly more efficacious than a BoHV-1 glycoprotein E-deletedvirus against a virulent BoHV-1 challenge", Vaccine, 32, (2014), pp. 4909-4915.
Baggiolini, Marco et al., "Chemokines and leukocyte traffic", Nature , vol. 392, Apr. 9, 1998, pp. 565-568.
Bryant, Neil A. et al., "Glycoprotein G Isoforms From Some Alphaherpesviruses Function As Broad-Spectrum Chemokine Binding Proteins", The EMBO Journal, vol. 22, No. 4 pp. 733-846, 2003.
Rosas, Christina T. et al., "Evaluation of the vaccine potential of an equine herpesvirus type 1 vector expressing bovine viral diarrhea virus structural proteins", Journal of General Virology, (2007), 88, pp. 748-757.
Extended European Search Report dated Dec. 8, 2020 in European Application No. EP20193609.3.
El-Kholy et al., "Baculovirus expression and diagnostic utility of the glycoprotein E of bovine herpesvirus-1.1 Egyptian strain "Abu-Hammad"", Journal of Virological Methods, Jul. 1, 2013, vol. 191, No. 1, pp. 33-40.
Letellier et al., "Characterization of monoclonal antiodies directed against the bovine herpesvirus-1 glycoprotein E and use for the differentiation between vaccinated and infected animals", Veterinary Microbiology, Dec. 1, 2001, vol. 83, No. 4, pp. 301-315.
Rijsewijk et al., "Epitopes on glycoprotein E and on the glycoprotein E/glycoprotein I complex of bovine herpesvirus 1 are expressed by all of 222 isolates and 11 vaccine strains", Archives of Virology, May 1, 2000, vol. 145, No. 5, pp. 921-936.
Wellenberg et al., "Antibodies against bovine herpesvirys (BHV) 5 may be differentiated from antibodies againsst BHV1 in a BHV1 glycoprotein E blocking ELISA", Verterinary Microbiology, Jan. 1, 2001, vol. 78, No. 1, pp. 79-84.

\* cited by examiner

BVDV genomic RNA

N^pro  C  E^rns  E1  E2  p7  NS2  NS3  4A  4B  NS5A  NS5B

E2 protein (374aa)

BRSV genomic RNA

NS1  NS2  N  P  M  SH  G  F  M2  L

F protein (574aa)

NH2—F2—FCS2 FCS1—F1—TM—COOH
109 pep27 136    523-551

G protein (257aa)

NH2—Intra—TM—Mucin-like—Mucin-like—COOH
       38 66
       Cysteine "noose" 157  189

FIG. 2

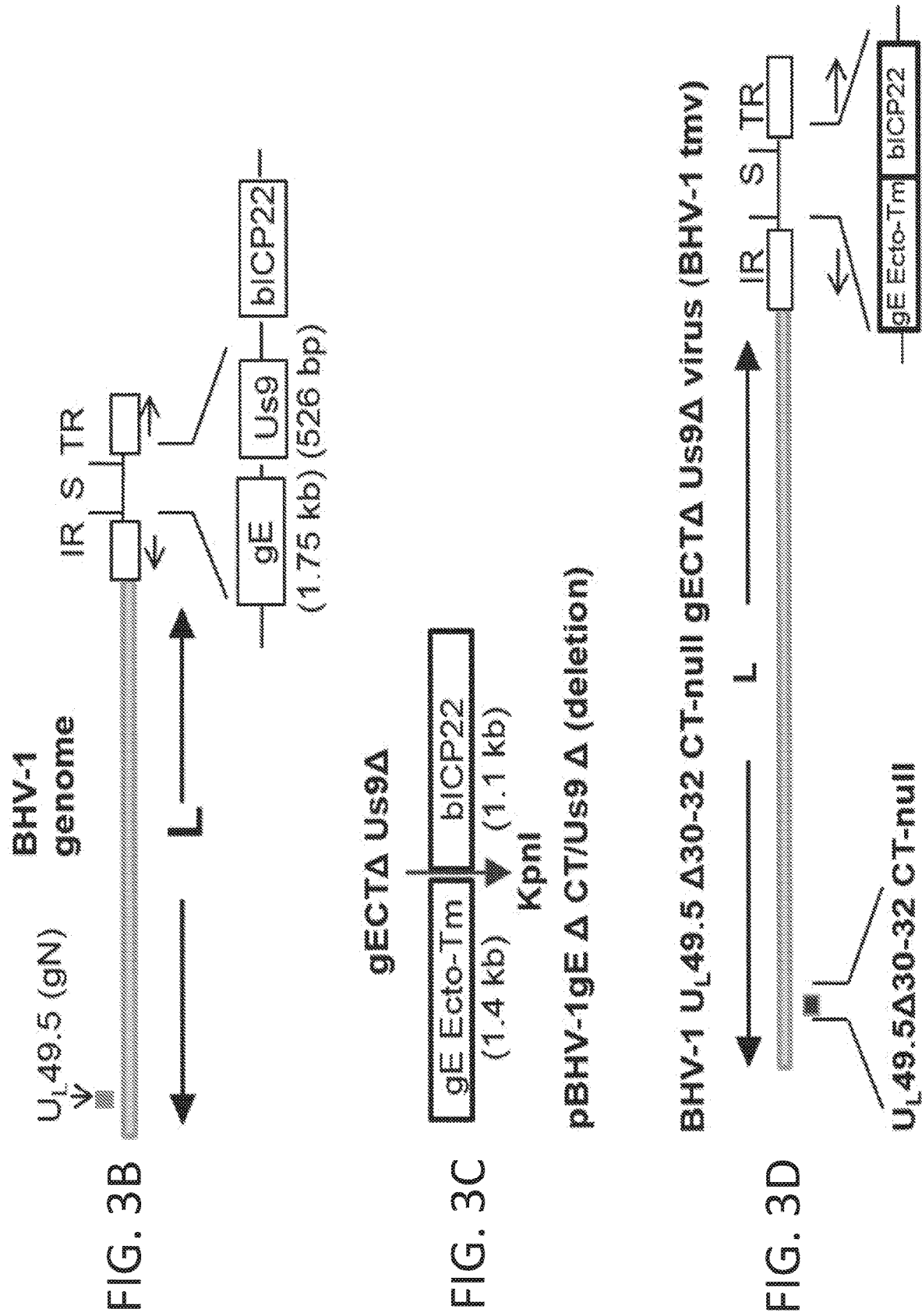

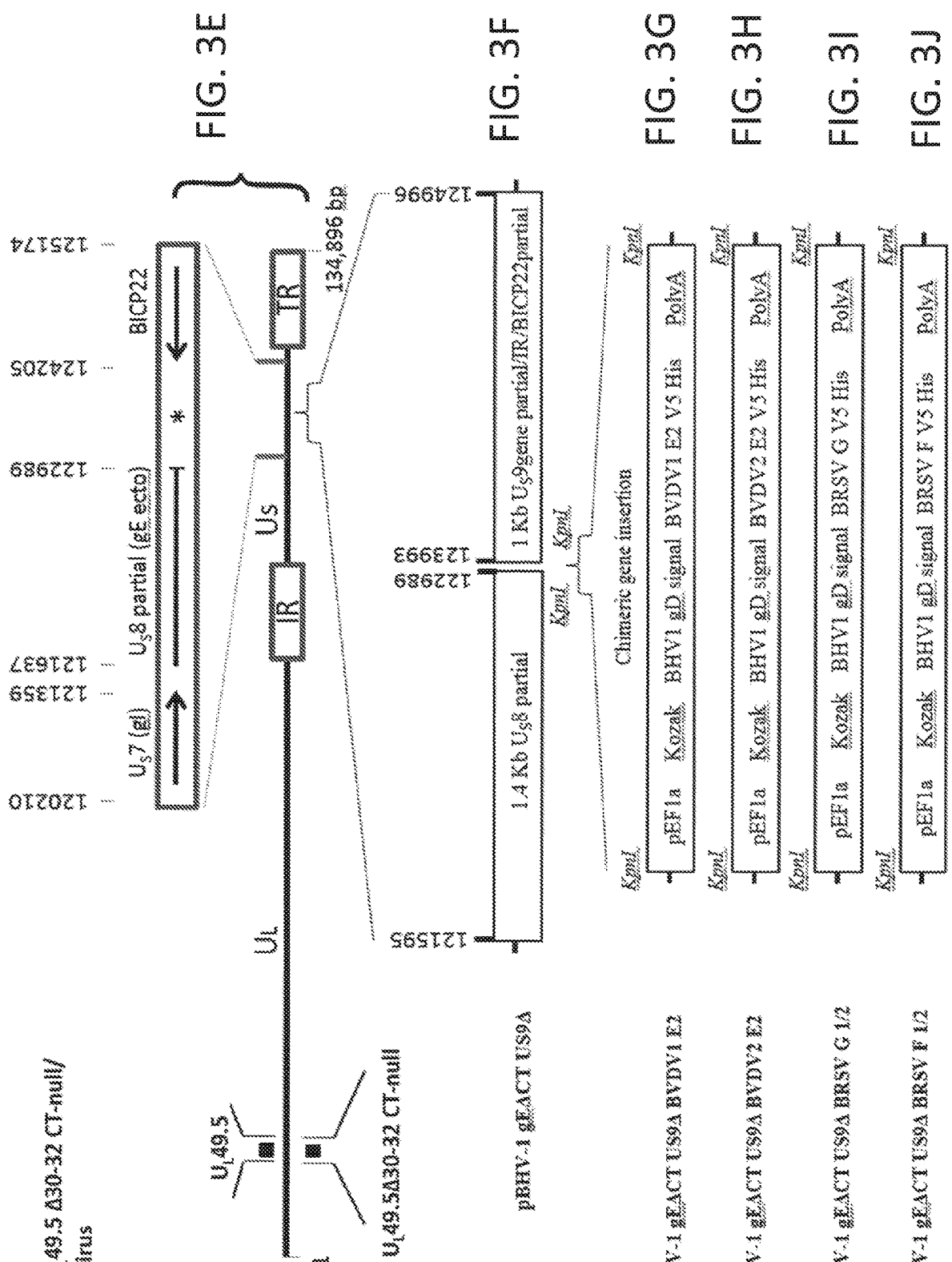

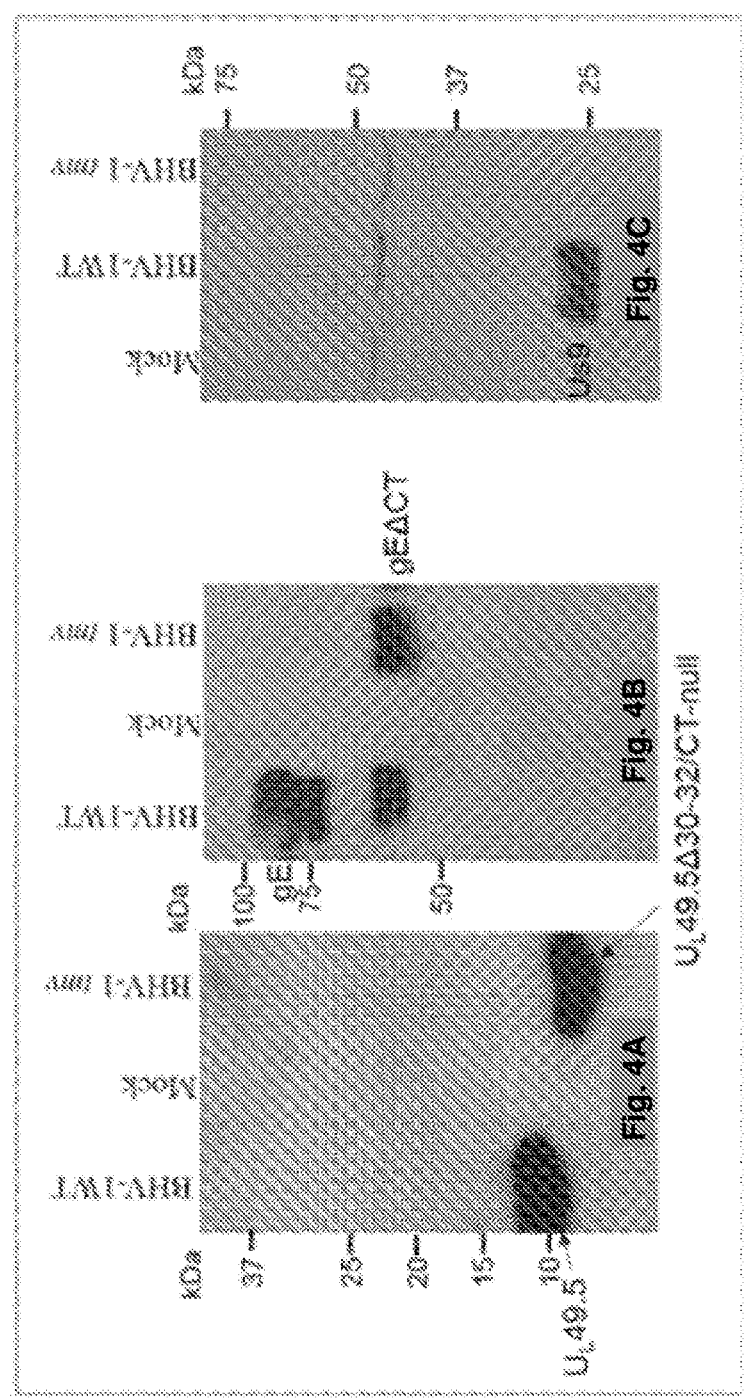

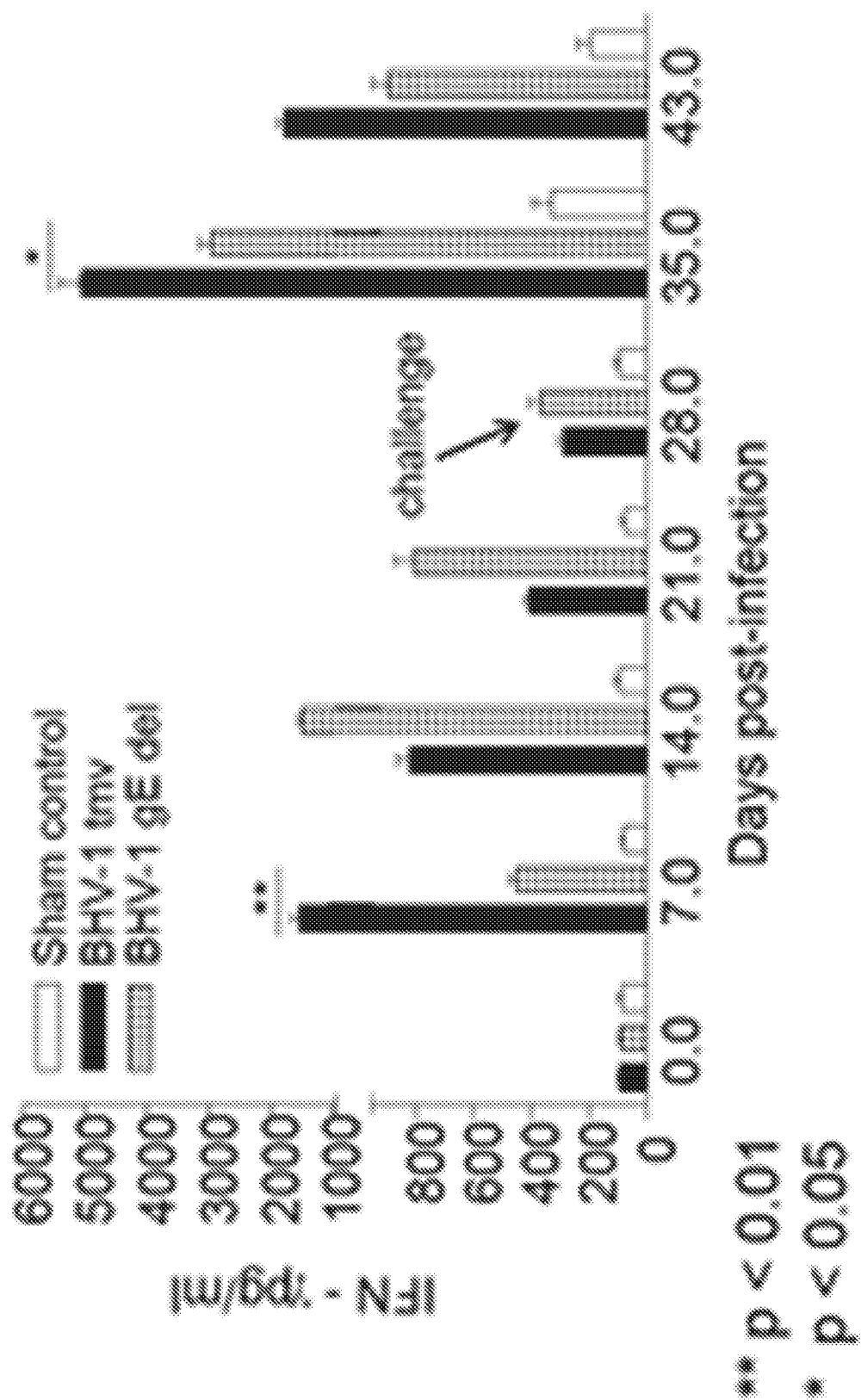

FIG. 7

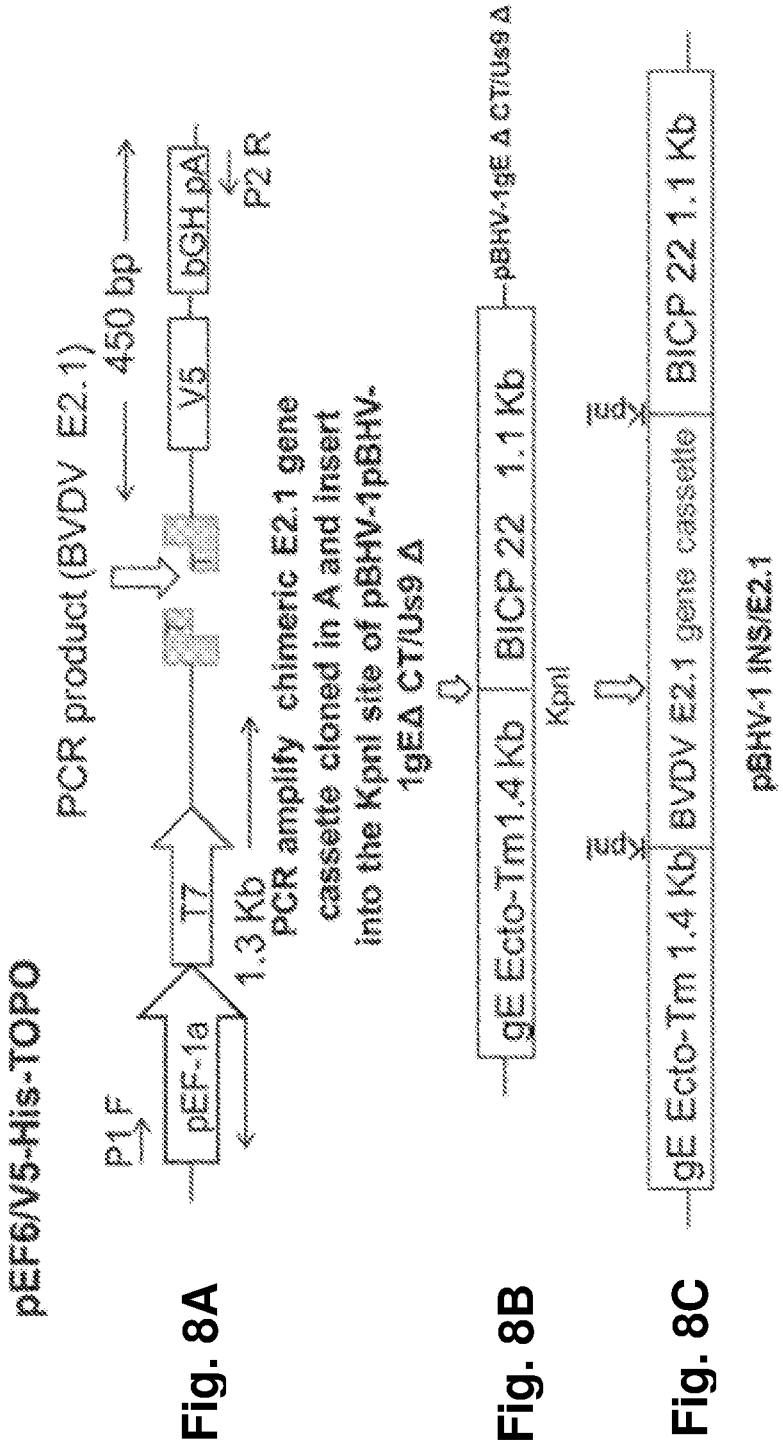

FIG. 9A Anti-V5 MAb

Lanes: Mock, BHV-1 tmv, BHV-1 tmv/E2.1

Markers: 75, 53 kD, 50, ER (43 kD), 37

FIG. 9B Goat anti-BVDV serum

Lanes: Mock, BVDV-1, BHV-1 tmv, BHV-1 tmv/E2.1

← Mature processed form 58-59 kD
← ER processed form 48 kD

```
                          hEF1-α promoter
5'- KpnI
    GGTACCCTCGTGAGGCTCCGGTGCCCGTCAGTGGGCAGAGCGGCACATCGCCCACAGTCCCGAGAAG
    TTGGGGGAGGGGTCGGCAATTGAACCGGTGCCTAGAAGGTGCCGGGGTAAACTGGGAAAGTG
    ATGTCGTGTACTGGCTCCGCCCGCCCTTTTCGCAACGGGTTTGCCGCCAGAACACAGTAAGTCCGTGTGTGGGCAGTAGTCGC
    CGTGAACGTTCTTTTTCGCAACGGGTTTGCCGCCAGAACACAGTAAGTCCGTGTGTGGCTGCAGTAGTCGC
    GGGCCTGGCCTCTTGACCCGAGCTTCGGGTTGAAGTCGGTGGAGAGTTCGAGAGTCGCCTTGCGCTTAAGGAGC
    TGATTCTTGATCCCGAGCTTCGGGTTGAAGTCGGTGGAGAGTTCGAGAGTCGCCTTGCGCTTAAGGAGC
    CCCTTCGCCCTGCTTGAGTGAGCTTCGGGTTGATAAGTCTCTAGCATTTAAAATTTTGATGACCTGCTG
    CACCTTCGCGCCTGTCTCGCCTGTTCTTGGGCAAGATAGTCTTGTAAATGCGGCCAAGATCTGCACACTGGTATTTCGT
    CGACGCTTTTTTCTCGGCAAGATAGTCTTGTAAATGCGGCCAAGATCTGCACACTGGTATTTCGT
    TTTTGGGCCCGGCGGCGACGGGCCCTGGTCGCCCAGCGCACATGTTCGGCAGGGGCCTG
    CGAGCGCGGCCACCGAGAATCGGACGGGGTAGTCCAAGGCTCGGTCCGCCGCTTGGTGCCTGGCC
    TCGCGCCGCGTGTATCGCCCCGCAGGCACCTGATTAGTTCTCGAGCTTTTGGAGTACGTCGTCTTT
    GGAAAGATGGCGCGTTCCCGGCGCTTTATGCCATGAATGGAAGCTCAAAATGGAGGACGCGCGAGAG
    CGGCGGGTGAGTCACCCACCACCAAAGAAAAGGCCTTTCGTCGATTAGTTCCCACACTGAGTGGTGAGACTGAGTTAGG
    CCACGGAGTACCGGCGGTTTTGATGTAATTCTCCTTGCCCTTTTGCCCTTTGAGTTTGAGTCTTGGTTCATTC
    AGGTTGGCCGCAGGGCGTTTTGATGTAATTCTCCTTGCCCTTTTGCCCTTTGAGTTTGAGTCTTGGTTCATTC
    CCAGCTTGGCACTTGATGTAATTCTCCTTGCCCTTTTGCCCTTTGAGTTTGAGTCTTGGTTCATTC
    TCAAGCCTCAGACAGTGGATATCTCAGGTTCAAAGTTTTTTTCCATTCAGGTGTCGTGAGACTAGTTGGT
    ACTAATACGACTCACTATAGGGAGACCCAAGCTGGCTAGTAAGTACGACTCGATCACTAGTCC
    AGTGTGGagatGATATCTCTAGAatgcatCATCATCACCATCACCATTGAgtgtaagcctatccctaaccctctcctcggtctcgat
         ClaI         NsiI    6xHis              Stop    V5 epitope
    tctacacgtaccggtCATCATCACCATCACCATTGAGTTTAAACCGCTGATCAGCCTCGACTGTGC
    CTTCTAGTTGCCAGCCATCGTTGTTTGCCCCCGTGCCTTCCTTGACCCTGGAAGGTGCCA
    BGH Poly A
    CTCCCCACTGTCCTTTCCTAATAAAATGAGGAAATTGCATCGCATTGTCTGAGTAGTGTCATTCTAT
    TCTGGGGGGGTGGGGGTGCAGGACAGCAAGGGGGAGGATTGGGAAGACAATAGCAGGCATGCTGGG
    GATGCGGTGGGCTCTATGGCTTGGTACC-3'
                             KpnI
```

FIG. 10 pEF1α - Kozak sequence-BHV1 gD signal -BVDV-E2/1 or 2 -V5 His PolyA

FIG. 11A

P chimeric BVDV E2-1 or -2 pBoHV-1 gEΔCTUS9Δ / BVDV E2-1 or 2 Insertion Vector pBoHV-1 gEΔCTUS9Δ gECT + Us9 + US9/bICP22 intergenic Deletion gE Ecto-Tm (1.38 Kb) | BICP22 flanking (1.23 Kb)

pEF1α - Kozak sequence-BHV1 gD signal -BVDV-E2/1 or 2 -V5 His PolyA

5' – KpnI

GGTACCCTCGTGAGGCTCCGGTGCCCGTCAGTGTGGCAGGCCACATCGCCCACAGTCCCCGAGAAG
TTGGGGAGGGGTCGGCAATTGAACCGGTGCCTAGAGAAGGTTGCGCGGGTAAACTGGAAAGTG
ATGTCGTGTACTGGCTCCGCCTTTTCCGAGGGTGGGAGAACAGGTAGAACCGTATAAGTGCAGTAGTCGC
CGTGAAGTTCTTTTCGCAAGCGGTTTGCGCAGAACACAGGTAAGTGCGTGTGGTTCCGTG
GGCCTGGCCTCTTTACGGTTATGCGCAGCTTGCGGTGTGCCTTGAATTACTTCCACCTGCTGCAGTACG
TGATTCTTGATCCGAGCTTCGGGTTGGAAGTGGGGAGAGTTCGAGGCCTTGCCTTAAGGAGC
CCCTTCGTGCTTGAGTTGAGGCCTGGGCCGCGCTGGGCCGTGCGCGTGCAATCTGGTGG
CACCTTCGCGGGCTCGGCGTATCCCGGCGGGTAGTCTCTAGCGCACATGTTCGCGAGGCCCTG
CGACGCTTTTTTTCTGGTCAAGATAGTCTGTAAATGCGGCCAAGATCTGCACACTGGTATTTCGGT
TTTTGGGCCCCGCGGGGGCGGAACGGATTGAAATGGAGAGCGGGGTGCCGAGCGGGGCCTG
CGAGCGCGGGCCACCGAGACGCGCTTCCCGGGCCCCTCAAGCTCTCAAGCCTTCGGCCAGTTGCTGAGC
TCGGCGGTGAGTACGAGCCTCGGCAGGAGCTCAAAATGGAGGACGCGGCCTCGCTTCATGTGACT
GGAAGATGCGGGTCACCACCGAGACGCCCTTTCCGTCCCTCAGCCGTCGCTTGAGATGTCTGTCTTT
CGGGCCGGGTGAGTCACCCACACAAGGAAAAGGCCCTGATTAGTTCGCCACACAGTGGGGAGACTGACT
CCAGGCCCACTGATGTAATTCTCGGAATTTGCCCATTTCTCCAAGGTACCCAAGATCTTGGTTCATTC
TCAAGCCTTGGCACTTGATGTAATTCTTGGAATTTGCCCATTTCTCCAAGGAGACCCAAGATCTTGGTTCATTC
ACTAATATACGCTCAGAACAGTGGTCAACTACTATAGGGAGACCCAAGCTGGCTAGTAAGCTTGGT
AGTGTGGatcgatCGCCGCCACCATGCAGGGACCACCCTGGGCCGTGTCGGCTCTGGCTGT ClaI    Kozak    BHV-1 gD signal sequence

Continued from FIG. 15A

GGCTGTGTCAGTTCTGCACCTGGATTGCAAGCCTGAGTTCTCATACGCCATCCTAAAGACGAGAGAATT
GGCCAGTGGGGCCGAAGGACTGACCACAACTTGGAAGGAGTATTCCAGCCATGAAACTGAAACTGGAAG
ATACCATGGTCATCGCTTGGTGCGAGGACGGGAAGCTGATGTACCTGCCAGCGGTGTCAAGAAACTGAAGAAAC
TCGATATCTGGCCATTCTGACATACTGGCATGTGGTGCCACCAGTGTGTCTTCAAGAACTGTTTGAC
GGACGGAAGCAGGACGATGTGGTCGAAATGAACGACAATTTCGAGTTTGGCCAGCTTTCAGATGGTGTG
CCAAGCCTATCGTGAGGGAAAATTCAACACCACACTGCTGAATGCCAGCTTTCAGATGGTGTG
CCCCATTGGCTGGACCGGACAGTGTCTCAAGCCCTTTCCTCACAGACAGGGCTGCATCCCAGAAAACCTGG
GTCCGCACTTACCGGAGGTCTAAGCTGCATAACTGCATTCTGGAGGAAATTGGACCTGCCTGCCAGGGACCAGCTGCTGTA
CAAGGAGGCTCCATCGAATCTTGAACGCTAAACTGGAAGCGAAACGGCTATCGCTGTGATTCGAATCATTAGCTCC
CACTATCCAATTGGAAAGTGTAACGGATCAAGAGGAAAACAAGATGGAAAATGGAAACGGAAGCAACAACTGT
GCAATAGGAGGAGTGGCTATCGCTGCCCTGGGCCAATGGGGCCCTGGTACCTTCAACTACACCCTGAAGATCATTAGCTGC
GCAGGTCATTGCTATGACACACTGCTAAACTGGGCCCCTGCAGACCTTAGACCTTAGAGATCATTAGCTCC
GAGGACCAGTGGAAAAGACCCGCCTTGTACCTTCAACTACACCCTGAAAACCTGAGAAGAACAAGTATTTCG
AACCCCGAGATTCCTACTTTGAAAGACCATATGGGGATTACTTGCCGAGACATCCTGGTGGCTCTGCCTCTGCTGGGGACCTTGA
AGTGACAGAACACCACATAGGGATTACTTTGCCGAGACATCCTGGTGCCGCGCTGCTGGACCTTGA
GGAGGCTAGTGTGGCTGGTGGTGACCTATATGTCCCTGTCCCGAGCAGAAGGCCCTGGGCatgc
                                                                Nsil
atggtaaggccctatcctaaccctcctcgattctacgcgtacgcgtCATCATCACCATCA
V5 epitope                                            6xHis
CCATTGAGTTTAAACCCGCTGATCAGCCTCGACTGTGCCTTCTAGTTGCCAGCCATCGTGTTGTTGC
Stop                                                 BGH Poly.A
CCCCTCCCCGTGCCTTCCTTGACCCTGGAAGGTGCCACTCCCACTGCCTCCTTGCCTAATAAATGAGG
AAATTGCATCGCATTTGTCTGAGTAGTTGTCATTCTATTCTGGGGGGTGGGGTGGGGCAGGACAGCAA
GGGGGAGGATTGGGGAAGACAATAGCAGGCATGCTGGGGATGCGGTGGGCTCTATGCCTTGGTACC-3'
                                                             KpnI

FIG. 15B

```
5'-ClaI      Kozak
ATCGAT    GCCGCCACC
→                        gD signal sequence
       M   Q   G   P   T   L   A   V   L   G   A   L   L   A   V   A   V   S     18
      ATG CAG GGA CCC ACC CTG GCC GTG CTG GGC GCT CTG CTG GCT GTG GCT GTC AGT    54
      ←   →            BVDVE2-1
       L   H   L   D   C   K   P   E   F   S   Y   A   I   A   K   D   E   R     36
      CTG CAC CTG GAT TGC AAG CCT GAG TTC TCA TAC GCC ATC GCT AAA GAC GAG AGA   108

I   G   Q   L   G   A   E   G   L   T   T   T   W   K   E   Y   S   P     54
      ATT GGC CAG CTG GGG GCC GAA GGA CTG ACC ACA ACT TGG AAG GAG TAT TCT CCA   162

G   M   K   L   E   D   T   M   V   I   A   W   C   E   D   G   K   L     72
      GGC ATG AAA CTG GAA GAT ACC ATG GTC ATC GCT TGG TGC GAG GAC GGG AAG CTG   216

M   Y   L   Q   R   C   T   R   E   T   R   Y   L   A   I   L   H   T     90
      ATG TAC CTG CAG CGG TGC ACA AGA GAA ACT CGA TAT CTG GCC ATT CTG CAT ACT   270

R   A   L   P   T   S   V   V   F   K   K   L   F   D   G   R   K   Q    108
      CGA GCT CTG CCC ACC AGT GTG GTC TTC AAG AAA CTG TTT GAC GGA CGG AAG CAG   324

E   D   V   V   E   M   N   D   N   F   E   F   G   L   C   P   C   D    126
      GAG GAT GTG GTC GAA ATG AAC GAC AAT TTC GAG TTT GGC CTG TGC CCC TGT GAT   378

A   K   P   I   V   R   G   K   F   N   T   T   L   L   N   G   P   A    144
      GCC AAG CCT ATC GTG AGG GGA AAA TTC AAC ACC ACA CTG CTG AAT GGC CCA GCT   432

F   Q   M   V   C   P   I   G   W   T   G   T   V   S   C   T   S   F    162
      TTT CAG ATG GTG TGC CCC ATT GGC TGG ACC GGG ACA GTC TCA TGT ACC AGC TTC   486

N   M   D   T   L   A   T   T   V   V   R   T   Y   R   R   S   K   P    180
      AAC ATG GAC ACT CTG GCC ACT ACC GTG GTC CGC ACT TAC CGG AGG TCT AAG CCC   540

F   P   H   R   Q   G   C   I   T   Q   K   N   L   G   E   D   L   H    198
      TTT CCT CAC AGA CAG GGC TGC ATC ACC CAG AAA AAC CTG GGG GAG GAT CTG CAT   594

N   C   I   L   G   G   N   W   T   C   V   P   G   D   Q   L   L   Y    216
      AAC TGC ATT CTG GGA GGA AAT TGG ACC TGC GTG CCA GGG GAC CAG CTG CTG TAC   648

K   G   G   S   I   E   S   C   K   W   C   G   Y   Q   F   K   E   S    234
      AAG GGA GGC TCC ATC GAA TCT TGC AAG TGG TGT GGC TAC CAG TTC AAA GAG AGC   702
                                                                              Continued
                                                                              in FIG. 15D
                        FIG. 15C
```

Continued from FIG. 15C

```
 E   G   L   P   H   Y   P   I   G   K   C   K   L   E   N   E   T   G   252
GAA GGG CTG CCT CAC TAT CCA ATT GGA AAG TGT AAA CTG GAG AAC GAA ACC GGC  756

Y   R   L   V   D   S   T   S   C   N   R   E   G   V   A   I   V   P   270
TAT CGG CTG GTG GAT TCT ACA AGT TGC AAT AGG GAG GGA GTG GCT ATC GTC CCT  810

Q   G   T   L   K   C   K   I   G   K   T   T   V   Q   V   I   A   M   288
CAG GGG ACA CTG AAG TGT AAA ATC GGA AAG ACA ACT GTG CAG GTC ATT GCT ATG  864

D   T   K   L   G   P   M   P   C   R   P   Y   E   I   I   S   S   E   306
GAC ACT AAA CTG GGG CCA ATG CCC TGC AGA CCT TAC GAG ATC ATT AGC TCC GAG  918

G   P   V   E   K   T   A   C   T   F   N   Y   T   K   T   L   K   N   324
GGA CCA GTG GAA AAG ACC GCC TGT ACC TTC AAC TAC ACT AAA ACC CTG AAG AAC  972

K   Y   F   E   P   R   D   S   Y   F   Q   Q   Y   M   L   K   G   E   342
AAG TAT TTC GAA CCC CGA GAT TCC TAC TTT CAG CAG TAT ATG CTG AAG GGC GAG  1026

Y   Q   Y   W   F   D   L   E   V   T   D   H   H   R   D   Y   F   A   360
TAC CAG TAT TGG TTC GAC CTG GAA GTG ACA GAC CAC CAT AGG GAT TAC TTT GCC  1080

E   S   I   L   V   V   V   V   A   L   L   G   G   R   Y   V   L   W   378
GAG AGC ATC CTG GTG GTC GTG GTC GCT CTG CTG GGA GGA CGC TAC GTG CTG TGG  1134

L   L   V   T   Y   M   V   L   S   E   Q   K   A   L   G              393
CTG CTG GTG ACC TAT ATG GTC CTG TCC GAG CAG AAG GCC CTG GGC              1179
```

ATGCAT-3'
NsiI

FIG. 15D

*BVDV E2-2*

5′ - Kpnl hEF1-α promoter

GGTACCCTCGTGAGGCTCCGGTGCCCGTCAGTGGGCAGAGCGCACATCGCCCACAGTCCCCGAGAAGTTG
GGGGGAGGGGTCGGCAATTGAACCGGTGCCTAGAGAAGGTGGCGCGGGGTAAACTGGGAAAGTGATGTCG
TGTACTGGCTCCGCCTTTTTCCCGAGGGTGGGGGAGAACCGTATATAAGTGCAGTAGTCGCCGTGAACGT
TCTTTTTCGCAACGGGTTTGCCGCCAGAACACAGGTAAGTGCCGTGTGTGGTTCCCGCGGGCCTGGCCTC
TTTACGGGTTATGGCCCTTGCGTGCCTTGAATTACTTCCACCTGGCTGCAGTACGTGATTCTTGATCCCG
AGCTTCGGGTTGGAAGTGGGTGGGAGAGTTCGAGGCCTTGCGCTTAAGGAGCCCCTTCGCCTCGTGCTTG
AGTTGAGGCCTGGCCTGGGCGCTGGGGCCGCCGCGTGCGAATCTGGTGGCACCTTCGCGCCTGTCTCGCT
GCTTTCGATAAGTCTCTAGCCATTTAAAATTTTTGATGACCTGCTGCGACGCTTTTTTTCTGGCAAGATA
GTCTTGTAAATGCGGGCCAAGATCTGCACACTGGTATTTCGGTTTTTGGGGCCGCGGGCGGCGACGGGGC
CCGTGCGTCCCAGCGCACATGTTCGGCGAGGCGGGGCCTGCGAGCGCGGCCACCGAGAATCGGACGGGGG
TAGTCTCAAGCTGGCCGGCCTGCTCTGGTGCCTGGCCTCGCGCCGCCGTGTATCGCCCCGCCCTGGGCGG
CAAGGCTGGCCCGGTCGGCACCAGTTGCGTGAGCGGAAAGATGGCCGCTTCCCGGCCCTGCTGCAGGGAG
CTCAAAATGGAGGACGCGGCGCTCGGGAGAGCGGGCGGGTGAGTCACCCACACAAAGGAAAAGGGCCTTT
CCGTCCTCAGCCGTCGCTTCATGTGACTCCACGGAGTACCGGGCGCCGTCCAGGCACCTCGATTAGTTCT
CGAGCTTTTGGAGTACGTCGTCTTTAGGTTGGGGGGAGGGGTTTTATGCGATGGAGTTTCCCCACACTGA
GTGGGTGGAGACTGAAGTTAGGCCAGCTTGGCACTTGATGTAATTCTCCTTGGAATTTGCCCTTTTTGAG
TTTGGATCTTGGTTCATTCTCAAGCCTCAGACAGTGGTTCAAAGTTTTTTTCTTCCATTTCAGGTGTCGT
GAGGAATTAGCTTGGTACTAATACGACTCACTATAGGGAGACCCAAGCTGGCTAGGTAAGTGTACGAGCT
CGATCACTAGTCCAGTGTGGatcgat*CGCCGCCACC*ATGCAGGGACCAACACTGGCCGTGCTGGGGGCTC ClaI Kozak BHV-1 gD signal sequence Continued in FIG. 16B

FIG. 16A

Continued from FIG. 16A

TGCTGGCTGTGGCTGTCTCCCCTGTTCCCCGAGTCGCAAGGAAGGATTTCAGTAGTACGCCATCAGCAAGGACCG
GAAATTGGACCACTGGGACCCAGAGTCCCTGACCAGAACCTGGCACCTGCCCACCAAGAAATCGTGGAC
TCTATGGTGCAGGTCTGGTGCGATGGCGCGCTCTGTCTACCAGTGCCGAGTTCATGCAGATCAGCTCCGAACAAA
ACCTGGGTGGCTGTGTCCACGAGCGCGCTCTGTCTACCAGTGCCGAGTTCATGCAGATCAGCTCCGAACAAA
GGGCCCCTGAAGTGATCGACATGCGACGACGATTTCGAATTTGGCCCTGCCCTGTGATAGTAAGCCTGTG
ATGCGCGGAAAATTCAAGCTTCACTGCTGCTAACCAGGACGATACCACAGTGGTGTGCCACAGGGGTGGA
CCGGAACAATCGAGTGTATTCTGGCTAACCAGGACGATACCACAGTGGTGTGCCGGACTTACCGGA
GACTACCCCTTTCAGCGCCAGAAAGTGGTGCACCTATGAGAAAATCATTGGCGAGGACATCCACGAGTGC
ATCCTGGGCGGGAATTGGACCCTGTATCCAGCCGACCATTCTAAGCTGCCTCATTATCCAATCGGCAAATGTATGCT
GCAAGTGGTGTGCCTACCACTTCTTTGATAGTGGACGATCAGCTGCAGGTCATTGCCACAGACTGCCTGCGGGAC
GTCAAACGAAAGCGGGTACAGATATGTGGAAAAAGCTACGTGCAGGGACCTGCAAGTACTGACCTGGGAC
ACTGGGACCCCTGAAGTGCTCCCAGATGAAGCATCGCCTTCTGAGGCCCGAGACCGGTACTTCCAGCAGTATATGCTGAAG
CAATGCCTTGCCAAGACACTGCCAACAAGTACTATGGACCAAGACCGGTACTTCCAGCAGTATATGCTGAAG
CTACTCCAAGACACTGGTTTGACCTGTGATCCGGATAACCGGTGGACCAACGGATTACTTCTCAGAGTTATCG
GGGAATGCCGTGGTCGCTCGTCTGCTGGGAAAGTACCGTGCTGGTCGTCACCTATATGATCCTGAG
TGAACAGATGGCCATGGGCatgtgaagcctatccctaaccctctcctcggtctcgattctacgcgt
NsiI V5 epitope accggtCATCATCATCATCATCATTGAGTTTAAACCCGCTGATCAGCCTCGACTGTGCCTTCTAGTGCC
6xHis Stop BGH PolyA
AGCCATCATCTGTGTGTTGCCCCCCGTGCCTTCCCGTGCCTTGACCCTGGAAGTGCCACTCCCACTGTCCTTC
AGCCATCATCTGTGTGTTGCCCCCCGTGCCTTCCCGTGCCTTGACCCTGGAAGTGCCACTCCCACTGTCCTTC
CTAATAAAATGAGGAAATTGCATCGCATTGTCTGAGTAGGTGTCATTCTATTCTGGGGGGTGGGG
CAGGACAGCAGCAAGGGGGAGGATTGGGAAGACAAATAGCAGGCATGCTGGGGATGCGGTGGGCTCTATGGCTT
GGTACC–3'
KpnI

FIG. 16B

```
5'-ClaI    Kozak
ATCGAT  GCCGCCACC
                                   gD signal sequence
         M   Q   G   P   T   L   A   V   L   G   A   L   L   A   V   A   V   S    18
        ATG CAG GGA CCA ACA CTG GCC GTG CTG GGG GCT CTG CTG GCT GTG GCT GTC TCC   54
                         BVDVE2-2
         L   F   P   E   C   K   E   G   F   Q   Y   A   I   S   K   D   R   K    36
        CTG TTC CCC GAG TGC AAG GAA GGA TTT CAG TAC GCC ATC AGC AAG GAC CGG AAA  108

I   G   P   L   G   P   E   S   L   T   T   T   W   H   L   P   T   K    54
        ATT GGA CCA CTG GGA CCA GAG TCC CTG ACC ACA ACT TGG CAC CTG CCC ACC AAG  162

K   I   V   D   S   M   V   Q   V   W   C   D   G   K   N   L   K   I    72
        AAA ATC GTG GAC TCT ATG GTG CAG GTC TGG TGC GAT GGC AAG AAC CTG AAA ATT  216

L   E   T   C   T   K   E   E   R   Y   L   V   A   V   H   E   R   A    90
        CTG GAG ACA TGT ACT AAG GAG GAG AGA TAC CTG GTG GCT GTC CAC GAG CGC GCT  270

L   S   T   S   A   E   F   M   Q   I   S   S   G   T   K   G   P   E   108
        CTG TCT ACC AGT GCC GAG TTC ATG CAG ATC AGC TCC GGA ACA AAG GGC CCT GAA  324

V   I   D   M   H   D   D   F   E   F   G   L   C   P   C   D   S   K   126
        GTG ATC GAC ATG CAC GAC GAT TTC GAA TTT GGC CTG TGC CCC TGT GAT AGT AAG  378

P   V   M   R   G   K   F   N   A   S   L   L   N   G   P   A   F   Q   144
        CCT GTG ATG CGC GGA AAA TTC AAC GCT TCA CTG CTG AAT GGC CCT GCC TTT CAG  432

M   V   C   P   Q   G   W   T   G   T   I   E   C   I   L   A   N   Q   162
        ATG GTG TGC CCA CAG GGG TGG ACC GGA ACA ATC GAG TGT ATT CTG GCT AAC CAG  486

D   T   L   D   T   T   V   V   R   T   Y   R   R   T   T   P   F   Q   180
        GAC ACA CTG GAT ACC ACA GTG GTC CGG ACT TAC CGG AGG ACT ACC CCT TTT CAG  540

R   R   K   W   C   T   Y   E   K   I   I   G   E   D   I   H   E   C   198
        CGC AGA AAG TGG TGC ACC TAT GAG AAA ATC ATT GGC GAG GAC ATC CAC GAG TGC  594

I   L   G   G   N   W   T   C   I   T   G   D   H   S   K   L   K   D   216
        ATC CTG GGC GGG AAT TGG ACC TGT ATC ACA GGC GAC CAT TCT AAG CTG AAA GAT  648

G   P   I   K   K   C   K   W   C   G   Y   D   F   E   D   S   E   G   234
        GGG CCA ATT AAG AAA TGC AAG TGG TGT GGC TAC GAC TTC TTT GAT AGT GAG GGA  702
```

Continued from FIG. 16C

| | | | | | | | | | | | | | | | | | | |
|---|---|---|---|---|---|---|---|---|---|---|---|---|---|---|---|---|---|---|
| L | P | H | Y | P | I | G | K | C | M | L | S | N | E | S | G | Y | R | 252 |
| CTG | CCT | CAT | TAT | CCA | ATC | GGC | AAA | TGT | ATG | CTG | TCA | AAC | GAA | AGC | GGG | TAC | AGA | 756 |
| Y | V | D | D | T | S | C | D | R | G | G | V | A | I | V | P | T | G | 270 |
| TAT | GTG | GAC | GAT | ACT | AGC | TGC | GAT | CGA | GGA | GGA | GTG | GCT | ATC | GTC | CCA | ACT | GGG | 810 |
| T | L | K | C | R | I | G | K | A | T | V | Q | V | I | A | T | N | T | 288 |
| ACC | CTG | AAG | TGT | AGG | ATC | GGA | AAA | GCT | ACC | GTG | CAG | GTC | ATT | GCC | ACA | AAT | ACT | 864 |
| D | L | G | P | M | P | C | S | P | D | E | V | I | A | S | E | G | P | 306 |
| GAC | CTG | GGA | CCA | ATG | CCT | TGC | TCC | CCA | GAT | GAA | GTG | ATC | GCT | TCT | GAG | GGA | CCT | 918 |
| V | E | K | T | A | C | T | F | N | Y | S | K | T | L | P | N | K | Y | 324 |
| GTC | GAA | AAG | ACT | GCC | TGT | ACC | TTC | AAC | TAC | TCC | AAG | ACA | CTG | CCA | AAC | AAG | TAC | 972 |
| Y | E | P | R | D | R | Y | F | Q | Q | Y | M | L | K | G | E | W | Q | 342 |
| TAT | GAG | CCC | CGA | GAC | CGG | TAC | TTC | CAG | CAG | TAT | ATG | CTG | AAG | GGG | GAA | TGG | CAG | 1026 |
| Y | W | F | D | L | D | T | V | D | H | H | K | D | Y | F | S | E | F | 360 |
| TAC | TGG | TTT | GAC | CTG | GAT | ACC | GTG | GAC | CAC | CAT | AAG | GAT | TAC | TTC | TCA | GAG | TTT | 1080 |
| I | V | I | A | V | V | A | L | L | G | G | K | Y | V | L | W | L | L | 378 |
| ATC | GTG | ATT | GCC | GTG | GTC | GCT | CTG | CTG | GGG | GGA | AAG | TAC | GTG | CTG | TGG | CTG | CTG | 1134 |
| V | T | Y | M | I | L | S | E | Q | M | A | M | G | | | | | | 390 |
| GTC | ACC | TAT | ATG | ATC | CTG | AGT | GAA | CAG | ATG | GCC | ATG | GGC | | | | | | 1179 |

ATGCAT-3'
NsiI

FIG. 16D

BRSV-F version-1

5' – KpnI  hEF1-α promoter

GGTACCCTCGTGAGGCTCCGGTGCCCGTCAGTGAGCGAGGCCAGAGCCCACAGTCCCGAGAAG
TTGGGGGGAGGGTGGCAATTGAACCGGTGCCTAGAGAGCCGTGGGTAAACTGGGAAGTG
ATGTCCGTGTACTGGCTCCGGTTCCCGGAGAACACAGGGTAATAAGTGCAGTAGTCGC
CGTGAAGTTCTTTTCGCAACGGGTTGCCGCAGAACACAGGTAAGTGCCGTGTGTTCCCGC
GGGCTGGCCTCTTACGGGTTATGGCCCTTGCGTGCCAGGCCCTTGCGCTTGCCAGTACG
TGATTCTTGATCCGAGTTCGGGTTGAGGCCTTGAGGTGGCTGGAAGTTCGAGGCCTTAAGGAGC
CCCTTCGCCTCGTGCTTCGCCTGTCTTCGATAAGTCTTAGCCATTTAAAATTTGATGACCTGCTG
CACCTTCGGGCTTTTCTCCAAGATAGTCTTGTAATGCGGGCCAAGACTTCACACTGGTATTTCGGT
CGACGCTTTTTCGGGGGCCGCCGCCCCGCGTATCCCCGGGAATCTGTTCGGGAGGGGCCTG
TTTGGGCGGGCCAGGCCAGAGAATCGCCCCCGCCCCCTGCTCAAGGCTAGTCTCAAGGCTGTGCCC
GCAGCGGGGGGACCCCAGAGAAATCGCCCCCGCCCCCTGCTCAAGGAGCTCAAATGCCACAGTGCCGTGAGC
TCGCGCCGGCGTTGCCCCGCGCCGCCCCCTGCTCCCAGGAGCTCAAATGGAGGACCGCGGGTCGGGACGAG
GGAAAGATGGCCGGGTCAACACCTGCCTGCCAGGAGCTCAAATGGAGGACCGCGGCTTCGGGACGAG
CGGCCGGTGAATGGCCGCCGCGCCGCCCAGCCAAGAAAAAGGCACCTCGATTAGTTCGAGCTTTGATCATGGACT
CCACGGAGTACCGGGGAGGGTTTTATGCCAGGTAAATGCAGATCGAGTTTCCCACACTGAGTGGGTGAGACTGAAGTTAGG
AGTTGGGGGAGGGTTTTATGCCAGGTAATGCCAGATCGAGTTTCCCACACTGAGTGGGTGAGACTGAAGTTAGG
CCAGCTTGGCACTTGATGTAGACAGTGTTGGAATCCTTCAAAGTTTTTTCCATTTGCAGGTGTCGTGGGAATTAGTTGGTCATTC
TCAAGCCTGACTTCAGACAGTGTTGGAATCTTCAAAGTTTTTTCCATTTGCAGGTGTCGTGAGAATTAGTTGGT
ACTAATACGACTCACTATAGGGAGACCCAAGCTGGCTAGCTAAGTCTACGAGCTCGATCACTACTCC
AGTGTGGATCGATGCCGCCACCATGCAGGGACCAACTGGCTGCTGTGTGGGGCTGCTGGTTGGCTGCTGTCC
  ClaI   Kozak   BHV-1 gD signal sequence

```
GCCGTCTCTGCCTATGGCTACAACCGCTACAACCGCTACAACATCATCTTCCACCT
ACGTGACCCACATCACCCTGTGCCGCTGTCCGCTCTGAGAGCCACCAGTCCACGCTGT
GTCCAGGGCTACCTGTCCGCTCTGAGAGCCACCGGCTACACCCGTGTACAAGCTGAGC
AAGATCCAGAAGAACGTGTGCAAGAACGCCGACTCCAAGGTGAATCAAGCTGAGAGC
GGTACAACAAGCCGTGGTGGTGAGCTGCAGAGCCTGATGCAGAACGAGCCTGTTCCTTCAGCGTGC
TAAGGCCTCCATCCCTGACTGATCCACCAAGGAACAGCACCAAGAAGTTCTACGGCTGATG
GGCAAGAGAAGGCAAGGCGCCTTCCTGGGCTTGAGGGCGAGGTGAACAAGATCAAGAACGCCCTGTGAGCAC
TGGCTGTGTCCAAGGTGCTGCAGCCCTGAGCAACAAGCCGCTCCAAGGTGTGACCTGAAG
CAACAAGGCCGTGCTGACCCCTGAGCAACTGCTGAGTCAACAACCACGACTGCCGGATCTCCAACATCGCCA
AACTACAATGACAAGGAGCTGCCAGCAGAGAACAACCGGCTGCTGGAGATCGCCTGTCCCGTGAACGC
CCGTGATCGAGTTCCAGCAGACCTGCAAGGTGCAGTCAATCGGTGCAACCGGTGTCCTGTCCCTGATCAACGAC
CGGCATCACCACCTCTGAGCCAGGAGTGCAAGCTGAACCTCAAGCTGCCAAGCAGTCCT
ATGCCCATCATCGATCATGAGCTGTGAAGAAAGCTCCAACGTGCAGATCGTGAGCAGTCCT
ACAGCATCATGAGCCCTTGCTGGAAGCTGGTGCACACCAGGTGCCAGCTGCCCATCTACGGCGT
GATGCGACACCCTGCCTGACCCGCGACAACGCCGACTCGTGCACCATCGCCA
AACATCTGCCTGGCCGAGACGTGCAAGGTCCAGTGCAATCTTCAACACCAAGTACAGCAGCTGACCT
CTCCAGCGAGACCGTGAACCCTGAACTGTTCTGCGACCAATGACTGCTACGAGACAACAGCCTGACCT
GCCCACGACAGTGACCCTGAAACATCAGCTTCAACACCAACATCTTCAACACCGCGATCCGCAGATCATGACC
AGCAAGAACCGACATCAGCTTCAACACAGAAGGCCATCATCAAGACCTTCCAAGCGCTCGTCCTGCTACGGCAAGA
CCAAGTGCACGACAAGGGCTGAGATCAAAGAGGCCATCATCAAGACCTTCCAACGGCTGCGACTACGT
GAGCAACAAGGCGTTGGACACCCGTGAGCCGGTGACGCTGAACAAGCTGGAGGGC
AAGCCCTGTACATCAAGGCCGAGAGCGAGCCCATCAATCAACTACACGACCCGTGCCTTCCATCCGGAGACG
AGTTCGACAAGATCCCTCCAATCCGTGAACGCCGCGGTAGCAGCCAACCAGAGAGACCGTGCTGACCACCAATCA
CGAGACGCTGCACTGTCGTGGTGATCCTGATCCGTGAACCACCATCA
CACACCTATTATGCTGGCAAGACCGTGAGCCGACCAGCTGAGAATCAACATCTGTCATTTCTAAGatgcat
                                                            NsiI
```

FIG. 17B

Continued from FIG. 17B ggtaagcctatccctaacccctctcctcgattctacgcgtaccgtcCATCATCACCATCACC
                    V5 epitope                    6xHIS ATTGAGTTTAAACCCGCTCGAGTCAGCCCTCGACTGTGCCTTCTAGTTGCCAGCCATCTGTTGTTTGCCC
stop                                                              BGH Poly A
CTCCCCCGTGCCTTCCTTGACCCTGGAAGGTGCCACTCCCACTGTCCTTTCCTAATAAAATGAGGAA
ATTGCATCGCATTGTCTGAGTAGTGTCATTCTATTCTGGGGGGTGGGGTGGGGCAGGACAGCAAGG
GGGAGGATTGGGAAGACAATAGCAGGCATGCTGGGGATGCGGTGGGCTCTATGGCTTGGTACC-3'
                                                                    KpnI

FIG. 17C

```
5'-ClaI      Kozak
ATCGAT  GCCGCCACC
→                                    gD signal sequence
   M   Q   G   P   T   L   A   V   L   G   A   L   L   A   V   A   V   S   18
  ATG CAG GGA CCA ACT CTG GCT GTG CTG GGG GCT CTG CTG GCT GTC GCC GTC TCT  54
        ←   →   BRSV F version-1
   L   P   M   A   T   T   A   M   T   M   I   I   S   I   I   F   I   S   36
  CTG CCT ATG GCT ACA ACC GCT ATG ACT ATG ATT ATC AGC ATC ATC TTC ATC TCC 108
   T   Y   V   T   H   I   T   L   C   Q   N   I   T   E   E   F   Y   Q   54
  ACC TAC GTG ACC CAC ATC ACC CTG TGC CAG AAC ATC ACC GAG GAG TTC TAC CAG 162
   S   T   C   S   A   V   S   R   G   Y   L   S   A   L   R   T   G   W   72
  TCC ACC TGC AGC GCT GTG TCC AGG GGC TAC CTG TCC GCT CTG AGA ACC GGC TGG 216
   Y   T   S   V   V   T   I   E   L   S   K   I   Q   K   N   V   C   K   90
  TAC ACC TCC GTG GTG ACC ATC GAG CTG AGC AAG ATC CAG AAG AAC GTG TGC AAG 270
   S   T   D   S   K   V   K   L   I   K   Q   E   L   E   R   Y   N   N  108
  AGC ACC GAC TCC AAG GTG AAG CTG ATC AAG CAG GAG CTG GAG CGG TAC AAC AAC 324
                                                                      →
   A   V   V   E   L   Q   S   L   M   Q   N   E   P   A   S   F   S   A  126
  GCC GTG GTG GAG CTG CAG AGC CTG ATG CAG AAC GAG CCT GCT TCC TTC AGC GCT 378
        FCS 1 ←
   A   K   A   S   I   P   E   L   I   H   Y   T   R   N   S   T   K   K  144
  GCT AAG GCC TCC ATC CCT GAG CTG ATC CAC TAC ACC AGG AAC AGC ACC AAG AAG 432
                              → FCS 2 ←
   F   Y   G   L   M   G   K   K       —       F   L   G   F   L   L  162
  TTC TAC GGC CTG ATG GGC AAG AAG GCC AAG GCC GCC TTC CTG GGC TTC CTG CTG 486
   G   I   G   S   A   I   A   S   G   V   A   V   S   K   V   L   H   L  180
  GGA ATC GGC AGC GCT ATC GCT TCC GGA GTG GCT GTG TCC AAG GTG CTG CAC CTG 540
   E   G   E   V   N   K   I   K   N   A   L   L   S   T   N   K   A   V  198
  GAG GGC GAG GTG AAC AAG ATC AAG AAC GCC CTG CTG AGC ACC AAC AAG GCC GTG 594
   V   S   L   S   N   G   V   S   V   L   T   S   K   V   L   D   L   K  216
  GTG TCC CTG AGC AAC GGC GTG AGC GTG CTG ACC TCC AAG GTG CTG GAC CTG AAG 648
                                                                Continued
                                                                in FIG. 17E
```

FIG. 17D

Continued from FIG. 17D

```
 N   Y   I   D   K   E   L   L   P   K   V   N   N   H   D   C   R   I  234
AAC TAC ATC GAC AAG GAG CTG CTG CCT AAG GTC AAC AAC CAC GAC TGC CGG ATC 702

S   N   I   A   T   V   I   E   F   Q   Q   K   N   N   R   L   L   E  252
TCC AAC ATC GCC ACC GTG ATC GAG TTC CAG CAG AAG AAC AAC CGG CTG CTG GAG 756

I   A   R   E   F   S   V   N   A   G   I   T   T   P   L   S   T   Y  270
ATC GCC AGG GAG TTC TCC GTG AAC GCC GGC ATC ACC ACC CCT CTG AGC ACC TAC 810

M   L   T   N   S   E   L   L   S   L   I   N   D   M   P   I   T   N  288
ATG CTG ACC AAC AGC GAG CTG CTG TCC CTG ATC AAC GAC ATG CCC ATC ACC AAC 864

D   Q   K   K   L   M   S   S   N   V   Q   I   V   R   Q   Q   S   Y  306
GAC CAG AAG AAG CTG ATG AGC TCC AAC GTG CAG ATC GTG AGG CAG CAG TCC TAC 918

S   I   M   S   V   V   K   E   E   V   I   A   Y   V   V   Q   L   P  324
AGC ATC ATG AGC GTG GTG AAG GAG GAG GTG ATC GCC TAC GTG GTG CAG CTG CCC 972

I   Y   G   V   I   D   T   P   C   W   K   L   H   T   S   P   L   C  342
ATC TAC GGC GTG ATC GAC ACC CCT TGC TGG AAG CTG CAC ACC TCC CCC CTG TGC 1026

T   T   D   N   K   E   G   S   N   I   C   L   T   R   T   D   R   G  360
ACC ACC GAC AAC AAG GAG GGC AGC AAC ATC TGC CTG ACC CGC ACC GAC AGA GGC 1080

W   Y   C   D   N   A   G   S   V   S   F   F   P   Q   A   E   T   C  378
TGG TAC TGC GAC AAC GCC GGC TCC GTG AGC TTC TTC CCT CAG GCC GAG ACC TGC 1134

K   V   Q   S   N   R   V   F   C   D   T   M   N   S   L   T   L   P  396
AAG GTG CAG TCC AAC CGC GTG TTC TGC GAC ACC ATG AAC AGC CTG ACC CTG CCC 1188

T   D   V   N   L   C   N   T   D   I   F   N   T   K   Y   D   C   K  414
ACC GAC GTG AAC CTG TGC AAC ACC GAC ATC TTC AAC ACC AAG TAC GAC TGC AAG 1241

I   M   T   S   K   T   D   I   S   S   S   V   I   T   S   I   G   A  432
ATC ATG ACC AGC AAG ACC GAC ATC AGC TCC AGC GTG ATC ACC AGC ATC GGC GCC 1296
```

Continued from FIG. 17E

```
      I   V   S   C   Y   G   K   T   K   C   T   A   S   N   K   N   R   G   450
     ATC GTG TCC TGC TAC GGC AAG ACC AAG TGC ACC GCC TCC AAC AAG AAC AGA GGC 1350

I   I   K   T   F   S   N   G   C   D   Y   V   S   N   K   G   V   D   468
     ATC ATC AAG ACC TTC TCC AAC GGC TGC GAC TAC GTG AGC AAC AAG GGC GTG GAC 1404

T   V   S   V   G   N   T   L   Y   Y   V   N   K   L   E   G   K   A   486
     ACC GTG AGC GTG GGC AAC ACC CTG TAC TAC GTG AAC AAG CTG GAG GGC AAG GCC 1458

L   Y   I   K   G   E   P   I   I   N   Y   Y   D   P   L   V   F   P   504
     CTG TAC ATC AAG GGC GAG CCC ATC ATC AAC TAC TAC GAC CCC CTG GTG TTC CCT 1512

S   D   E   F   D   A   S   I   A   Q   V   N   A   K   I   N   Q   S   522
     AGC GAC GAG TTC GAC GCC TCC ATC GCC CAG GTG AAC GCC AAG ATC AAC CAG TCC 1566

L   A   F   I   R   R   S   D   E   L   L   H   S   V   D   V   G   K   540
     CTG GCC TTC ATC CGG AGG AGC GAC GAG CTG CTG CAC TCC GTG GAC GTG GGC AAG 1620

S   T   T   N   V   V   I   T   T   I   I   I   V   I   V   V   V   I   558
     AGC ACC ACC AAC GTG GTG ATC ACC ACC ATC ATC ATC GTG ATC GTG GTG GTG ATC 1674

L   M   L   I   A   V   G   L   L   F   Y   C   K   T   R   S   T   P   576
     CTG ATG CTG ATC GCC GTG GGC CTG CTG TTC TAC TGC AAG ACC CGC AGC ACA CCT 1728

I   M   L   G   K   D   Q   L   S   G   I   N   N   L   S   F   S   K   594
     ATT ATG CTG GGC AAG GAC CAG CTG AGC GGA ATC AAC AAT CTG TCA TTT TCT AAG 1782
     NsiI →                    V5 Epitope
      M   H   G   K   P   I   P   N   P   L   L   G   L   D   S   T   R   T   612
     ATG CAT GGT AAG CCT ATC CCT AAC CCT CTC CTC GGT CTC GAT TCT ACG CGT ACC 1836
          →    6xHis    ←
      G   H   H   H   H   H   H   stop                                     619
     GGT CAT CAT CAC CAT CAC CAT TGA-3'                                     1857
```

FIG. 17F

BRSV F Version 2

5'-ClaI      Kozak

ATCGAT GCCGCCACC

→                gD signal sequence

```
           M   Q   G   P   T   L   A   V   L   G   A   L   L   A   V   A   V   S   18
          ATG CAG GGA CCA ACT CTG GCT GTG CTG GGG GCT CTG CTG GCT GTC GCC GTC TCT  54
              ←  →   BRSV F version-2
           L   P   M   A   T   T   A   M   T   M   I   I   S   I   I   F   I   S   36
          CTG CCT ATG GCT ACA ACC GCT ATG ACT ATG ATT ATC AGC ATC ATC TTC ATC TCC 108

T   Y   V   T   H   I   T   L   C   Q   N   I   T   E   E   F   Y   Q   54
          ACC TAC GTG ACC CAC ATC ACC CTG TGC CAG AAC ATC ACC GAG GAG TTC TAC CAG 162

S   T   C   S   A   V   S   R   G   Y   L   S   A   L   R   T   G   W   72
          TCC ACC TGC AGC GCT GTG TCC AGG GGC TAC CTG TCC GCT CTG AGA ACC GGC TGG 216

Y   T   S   V   V   T   I   E   L   S   K   I   Q   K   N   V   C   K   90
          TAC ACC TCC GTG GTG ACC ATC GAG CTG AGC AAG ATC CAG AAG AAC GTG TGC AAG 270

S   T   D   S   K   V   K   L   I   K   Q   E   L   E   R   Y   N   N   108
          AGC ACC GAC TCC AAG GTG AAG CTG ATC AAG CAG GAG CTG GAG CGG TAC AAC AAC 324
                                                                                →
           A   V   V   E   L   Q   S   L   M   Q   N   E   P   A   S   F   S   R   126
          GCC GTG GTG GAG CTG CAG AGC CTG ATG CAG AAC GAG CCT GCT TCC TTC AGC CGT 378
           FCS 1 ←
           A   A   A   S   I   P   E   L   I   H   Y   T   R   N   S   T   K   K   144
          GCT GCC GCC TCC ATC CCT GAG CTG ATC CAC TAC ACC AGG AAC AGC ACC AAG AAG 432
                                        →   FCS 2 ←
           F   Y   G   L   M   G   K   K   A   A   A   A   F   L   G   F   L   L   162
          TTC TAC GGC CTG ATG GGC AAG AAG GCC GCC GCC GCC TTC CTG GGC TTC CTG CTG 486

G   I   G   S   A   I   A   S   G   V   A   V   S   K   V   L   H   L   180
          GGA ATC GGC AGC GCT ATC GCT TCC GGA GTG GCT GTG TCC AAG GTG CTG CAC CTG 540

E   G   E   V   N   K   I   K   N   A   L   L   S   T   N   K   A   V   198
          GAG GGC GAG GTG AAC AAG ATC AAG AAC GCC CTG CTG AGC ACC AAC AAG GCC GTG 594

V   S   L   S   N   G   V   S   V   L   T   S   K   V   L   D   L   K   216
          GTG TCC CTG AGC AAC GGC GTG AGC GTG CTG ACC TCC AAG GTG CTG GAC CTG AAG 648
```

Continued from FIG. 18A

| | | | | | | | | | | | | | | | | | |
|---|---|---|---|---|---|---|---|---|---|---|---|---|---|---|---|---|---|
| N | Y | I | D | K | E | L | L | P | K | V | N | N | H | D | C | R | I 234 |
| AAC | TAC | ATC | GAC | AAG | GAG | CTG | CTG | CCT | AAG | GTC | AAC | AAC | CAC | GAC | TGC | CGG | ATC 702 |

| S | N | I | A | T | V | I | E | F | Q | Q | K | N | N | R | L | L | E 252 |
|---|---|---|---|---|---|---|---|---|---|---|---|---|---|---|---|---|---|
| TCC | AAC | ATC | GCC | ACC | GTG | ATC | GAG | TTC | CAG | CAG | AAG | AAC | AAC | CGG | CTG | CTG | GAG 756 |

| I | A | R | E | F | S | V | N | A | G | I | T | T | P | L | S | T | Y 270 |
|---|---|---|---|---|---|---|---|---|---|---|---|---|---|---|---|---|---|
| ATC | GCC | AGG | GAG | TTC | TCC | GTG | AAC | GCC | GGC | ATC | ACC | ACC | CCT | CTG | AGC | ACC | TAC 810 |

| M | L | T | N | S | E | L | L | S | L | I | N | D | M | P | I | T | N 288 |
|---|---|---|---|---|---|---|---|---|---|---|---|---|---|---|---|---|---|
| ATG | CTG | ACC | AAC | AGC | GAG | CTG | CTG | TCC | CTG | ATC | AAC | GAC | ATG | CCC | ATC | ACC | AAC 864 |

| D | Q | K | K | L | M | S | S | N | V | Q | I | V | R | Q | Q | S | Y 306 |
|---|---|---|---|---|---|---|---|---|---|---|---|---|---|---|---|---|---|
| GAC | CAG | AAG | AAG | CTG | ATG | AGC | TCC | AAC | GTG | CAG | ATC | GTG | AGG | CAG | CAG | TCC | TAC 918 |

| S | I | M | S | V | V | K | E | E | V | I | A | Y | V | V | Q | L | P 324 |
|---|---|---|---|---|---|---|---|---|---|---|---|---|---|---|---|---|---|
| AGC | ATC | ATG | AGC | GTG | GTG | AAG | GAG | GAG | GTG | ATC | GCC | TAC | GTG | GTG | CAG | CTG | CCC 972 |

| I | Y | G | V | I | D | T | P | C | W | K | L | H | T | S | P | L | C 342 |
|---|---|---|---|---|---|---|---|---|---|---|---|---|---|---|---|---|---|
| ATC | TAC | GGC | GTG | ATC | GAC | ACC | CCT | TGC | TGG | AAG | CTG | CAC | ACC | TCC | CCC | CTG | TGC 1026 |

| T | T | D | N | K | E | G | S | N | I | C | L | T | R | T | D | R | G 360 |
|---|---|---|---|---|---|---|---|---|---|---|---|---|---|---|---|---|---|
| ACC | ACC | GAC | AAC | AAG | GAG | GGC | AGC | AAC | ATC | TGC | CTG | ACC | CGC | ACC | GAC | AGA | GGC 1080 |

| W | Y | C | D | N | A | G | S | V | S | F | F | P | Q | A | E | T | C 378 |
|---|---|---|---|---|---|---|---|---|---|---|---|---|---|---|---|---|---|
| TGG | TAC | TGC | GAC | AAC | GCC | GGC | TCC | GTG | AGC | TTC | TTC | CCT | CAG | GCC | GAG | ACC | TGC 1134 |

| K | V | Q | S | N | R | V | F | C | D | T | M | N | S | L | T | L | P 396 |
|---|---|---|---|---|---|---|---|---|---|---|---|---|---|---|---|---|---|
| AAG | GTG | CAG | TCC | AAC | CGC | GTG | TTC | TGC | GAC | ACC | ATG | AAC | AGC | CTG | ACC | CTG | CCC 1188 |

| T | D | V | N | L | C | N | T | D | I | F | N | T | K | Y | D | C | K 414 |
|---|---|---|---|---|---|---|---|---|---|---|---|---|---|---|---|---|---|
| ACC | GAC | GTG | AAC | CTG | TGC | AAC | ACC | GAC | ATC | TTC | AAC | ACC | AAG | TAC | GAC | TGC | AAG 1241 |

Continued from FIG. 18B

```
       I   M   T   S   K   T   D   I   S   S   S   V   I   T   S   I   G   A   432
      ATC ATG ACC AGC AAG ACC GAC ATC AGC TCC AGC GTG ATC ACC AGC ATC GGC GCC 1296

I   V   S   C   Y   G   K   T   K   C   T   A   S   N   K   N   R   G   450
      ATC GTG TCC TGC TAC GGC AAG ACC AAG TGC ACC GCC TCC AAC AAG AAC AGA GGC 1350

I   I   K   T   F   S   N   G   C   D   Y   V   S   N   K   G   V   D   468
      ATC ATC AAG ACC TTC TCC AAC GGC TGC GAC TAC GTG AGC AAC AAG GGC GTG GAC 1404

T   V   S   V   G   N   T   L   Y   Y   V   N   K   L   E   G   K   A   486
      ACC GTG AGC GTG GGC AAC ACC CTG TAC TAC GTG AAC AAG CTG GAG GGC AAG GCC 1458

L   Y   I   K   G   E   P   I   I   N   Y   Y   D   P   L   V   F   P   504
      CTG TAC ATC AAG GGC GAG CCC ATC ATC AAC TAC TAC GAC CCC CTG GTG TTC CCT 1512

S   D   E   F   D   A   S   I   A   Q   V   N   A   K   I   N   Q   S   522
      AGC GAC GAG TTC GAC GCC TCC ATC GCC CAG GTG AAC GCC AAG ATC AAC CAG TCC 1566

L   A   F   I   R   R   S   D   E   L   L   H   S   V   D   V   G   K   540
      CTG GCC TTC ATC CGG AGG AGC GAC GAG CTG CTG CAC TCC GTG GAC GTG GGC AAG 1620

S   T   T   N   V   V   I   T   T   I   I   I   V   I   V   V   V   I   558
      AGC ACC ACC AAC GTG GTG ATC ACC ACC ATC ATC ATC GTG ATC GTG GTG GTG ATC 1674

L   M   L   I   A   V   G   L   L   F   Y   C   K   T   R   S   T   P   576
      CTG ATG CTG ATC GCC GTG GGC CTG CTG TTC TAC TGC AAG ACC CGC AGC ACA CCT 1728

I   M   L   G   K   D   Q   L   S   G   I   N   N   L   S   F   S   K   594
      ATT ATG CTG GGC AAG GAC CAG CTG AGC GGA ATC AAC AAT CTG TCA TTT TCT AAG 1782
      ATGCAT-3'
       NsiI
```

FIG. 18C

5' – KpnI hEF1-α promoter

GGTACCCCTCGTGTCTGAGGCTCCGGTGCCGTGCCAATTGAACGGTTCAGTGGCCAGAGCGCCACATCGCCCACAGTCCCCGAGAAG
TTGGGGGAGGGGTGGGCAATTGAACGGTTCAGTGGCCAGAGAAGTGGCGGGGTAAACTGGGAAGTG
ATGTCGTGTACTGGCTCCGCCTTTTTCCCGAGGGTGGGGAGAACCGTATATAAGTGCAGTAGTCGC
CGTTGAACGTTCTTTTCGCAACGGGTTTGCCGCAGTAAGTGCCGTGGTGGTTCCCGC
GGGCCTGGCCTCTTTACGGGTTATGGCCCTTGTGCGTTGAATTACTTCCACCTGGCTGCAGTACG
TGATTCTTGATCCCGAGCTTCGGGTTGAAGTTGGGTGGGAGAGTTCGAGGCCTTGCGCTTAAGGAGC
CCCTTGCCGTGTTGAGTTGAGCTGCTTCGATAAGTCTCTAGCCATTTAAAATTTTTGATGACCTGCTG
CACCTTCGCGGCTTCACCAGAAATCGCGGGCCAAGATCTGCACACTGGTATTTCGGT
TTTTGGGGCCGCGGCCAGAATGCGACGGGGCCCGGGCCCCAGCCGCACATGTTCGGCGAGGCGGGCCTG
CGAGCGGCGGCCCAGAATGCGCCCCGGGCCCCCGGCCTAGTCTCAAGGCTCCGGTCGGCACCAGTTGCGTGAGC
TCGCGGCCGGCCGTGTATCGCGCTTCCCGGCCCTGCAGGGAGCTCAAAATGGAGGACGGGGCTCGGGAGAG
GGAAAGATGGCCGTTCGAGTCGAGAAAAAGGGCCCTTCCGTCCCACCTGAGTGGGTGAGACTGAAGTTAGG
CGGGGTGGAGTCGAGTTCCTGCTCAGGAGCTCAAAATGGAGGACGGGGTCGGGAGAG
CCACGGAGTACCGGGGCCGTCCACTGGGGTTTTATGCGATGGAGTTTCCCACACTGAGTGGGTGAGACTGAAGTTAGG
AGTTGGGCGAGGGTTTTATGCGATGGAGTTTCCCACACTGAGTGGGTGAGACTGAAGTTAGG
CCAAGCTTGGCACTGATGTAATTCTCCTTGGAATTGCCCTTTTGCCTTTTGAGTTTGATCTTGGTCATTC
TCAAGCCTCAGACGTTCAAAGTTTTTCCATTTCAGGTCTAGGTAAGTGTAGAGCTCGATCACTAGTCC
ACTAATACGACTCACTATAGGGAGACCCAAGCTGGCTAGTTAAGTGACCAACTTCGATCACTAGTCC
AGTGTGGatcgat*gccgccACCATGCAGGACCAACTCTGGCTGTGCTGGGGCTCTCGTGCTGTC*

ClaI  Kozak  BHV-1 gD sign

Continued from FIG. 19A

GCTGTGTCACTGCCTATGTCTAACCATACTCACCATCTGAAGTTCAAGACCCTGAAGCGGGCCTGGA
AGGCCTCCAAGTACTTCATCGTGGGCCTGAGCGTGCCTGTACAAGTTCAACCTGAAGAGCCTGGTGCA
GACCGGCTCTGACCACCCTGGCCATGATCACCCTGGATCACGGCCATCATCTACATC
AGCGTGGGCAAGCGCCAAGCCCACCTGCCAAGCTACAAGTCCACACCTGGATCCAGAGCCTCCAGA
ACCACACCAGCCCTTCTTCACCGAGCACAATACAAGTCCACACCTCCATCCAGAGCACCAC
CCTGTCCCAGCTGCCTAACACCCGACACCGAGACCACCTACAGCCACTCCATCCAGAGACC
CAGAACCGAAGATCAAGAGCCAGTCCACCCCCTGCCTGCCAGAAAGCCCCTATCAACCCAGCG
GCTCCCCCCTGAGAACCCAACACAAGAACCACCCTGGACCTGTCCCAGCTGGTCCAGCTC
CACCTCCGAGGAAACCTGGCTAGCCTCCCCTGTCCCTGAGCCAGATCGAGAGGCTCCTAGCAGG
GCTCCCACCATCACCTGAAGAAGAGACCCCAAGCCTAAGCCCCAAGAAGCCACCAAGACCACCA
TCCACCACAGACCTCCCCTGAGGCTAAGCTGCAGCCACACAACAACCGCGCCCCCAGCAGG
AATCCCTGAGCCACACCAACCAGAGACCACTACCCAGATC atgcat ggtaagcctatc
                                          NsiI
cctaaccctctcctcggtctcgattctacgcgtaccggt CATCATCATCATCACCATTGA GTTTAAA
V5 epitope                                    6xHIS              stop
CCCGCTGATCAGCCTCGACTGTGCCTTGCCTTCTAGTTGCCAGCCATCTGTTGTTTGCCCTCCCCCGTGCC
                        BGH PloyA
TTCCTTGACCCTGGAAGGTGCCACTCCCACTGTCCTTTCCTAATAAAATGAGGAAATTGCATCGCAT
TGTCTGAGTAGGTGTCATTCTATTCTGGGGGGTGGGGTGGGGCAGGACAGCAAGGGGGAGGATTGGG
AAGACAATAGCAGGCATGCTGGGGATGCGGTGGGCTCTATGGCTT GGTACC -3'
                                               KpnI

FIG. 19B hEF1-α promoter

5'– KpnI
GGTACCCTCGTGAGGCTCCGGTGCCCGTCAGTGGGCAGAGCGCACAATCGCCCACAGTCCCCGAGAAG
TTGGGGGGAGGGGTCGGCAATTGAACCGGTGCCTAGAGAAGGTGGCGCGGGGTAAACTGGGAAAGTG
ATGTCGTGTACTGGCTCCGCCTTTTTCCCGAGGTGGGGGAGAACACAGGTATATAAGTGCAGTAGTCGC
CGTGAACGTTCTTTTTCGCAACGGTTTGCGCGCAGAACACACAGGTAAGTGCCGTGTGTGGTTCCCGC
GGGCCTGGCTCTTTACGGGTTATGGCCCTTGCCTGAATTACTCACCTGGATGGGGGCTTGCAGTACG
TGATTCTTGATCCCGAGTTTCGGGTTGGAAGTGGGTGGAGAGTTCGAGGCTTCGAGGCTTAAGGAGC
CCCTTCGCTCGTGTTTGAGTGCTTCGCTGTCTCGATAAGTCTCTAGCCATTTAAAATTTTGATGACCTGCTG
CACCTTCGCGCCTGTCTCCGGTCTTGTAAATGCGGGCCAAGATCGTCGGACACTGGTATTTCGGT
CGAGGCTTTTTCTGGCAAGATAGTCTTGTAAATGCGGGCCAAGATCGTCGGACACTGGTATTTCGGT
TTTTGGGCGGGGCGGGCCCAGGCACGGGCCCCCTGGGGCTGCAGGTCTCAAGCTCCAGTTGCCTGGCC
CGAGCGGCGGCCACGAGAATCGCCCGAGACGGGTAGTCTCAAGCTCTGGCCCCCAGTTGCGTGAGC
TCGCGCGCCGTGTATCGCCGTTCCCGGCCTTCGGGCTGCCCAAGGCTGCCCCCCAGTTGCGTGAGC
GGAAAGATGGCCGGGGTTCCCGGCCACCACAAAGAAAATGGGAGCTCAAAATGGAGGACGCGGCGGAGAG
CGGGCGGTGAGTCACCCAGCCTCGATTAGTTCCGCCTCCTCCGCCTTTGAGTACGTCGTCTTT
CCACGGGAGTACGCAGGGGTTTATGCGAGTTTCCCACACTGAGTGGTGGAGACTGAAGTTAGG
AGGTTGGGGAGGGTTTTATGTAATTCCTCCTTGAATTGCCCCTTTTGACTTTGGATCTCGTTCATTC
CCAGCTTGCACTTGATGTAATTCCTCCTTGAATTGCCCCTTTTGACTTTGGATCTCGTTCATTC
TCAAGCCTCAGAGTGGTCAAAGTTCTTCCCATTCATTTCCAGGTGTGCAGGTAAGTTAGCTTGGT
ACTAATACGACTCACTATAGGGAGACCCAAGGACCAACTCGGCTAGTAAGTGTACGAGCTCGATCACTAGTCC
AGTGTGGAtcgatGCCGCCACCATGCAGGACCAACTCGGCTAGTAAGTGTACGAGCTCGATCACTAGTCC ClaI   Kozak   BHV-1 gD signal sequence Continued in FIG. 20B

FIG. 20A

Continued from FIG. 20A

GCTGTGTCACTGCCTATGTCTCTTAACCATACTCACCATCTGAAGTTCAAGACCCTGAAGGGGCCTGGA
AGGCCTCCAAGTACTTCATGTGGGCCTGAGCCTGTGCCTGTACAAGTTCAACCTGAAGAGCCTGGTGCA
GACCGCTCTGACCACCGTCCTGAGATCACCCTGGATCACCGCCATCATCGCCATCATCTACATC
AGCGGTGGCAACGCCAAGCGCCAAGCCCACCTCCAAGCCATCCAGACACAAGTACACAGCCCTGAGA
ACCACACAGCCCCTTCTTCACCGAGACCGACACACCAAGTCCAGACCTCCATCCATCCAGAGCACCAC
CCTGTCCCAGCTGCCTAACACACCGACACCAGTCCAGAGACCGCCACTACAGCCCTACGAGAAACCCAGACC
CAGAACCGCTGACAAGATCAAGAACACCCCAGAACACACAGCCCTGCCACCAAACAGCCCCTATCAACCCAGCG
GCTCCAACCCCAACCCCTGAGAACACAACAAGCCAGACCCCCAAGACCCCTACGTGCCTCAGAT
CGGACCTGAGAGGGCTCCTAGCAGGGCTCCACCAGAACACCTGAAGAGAGACCCAAGCTAAGACC
ACCAAGAAGCCCACCAAGAGACCATCCACCAAGAGGCTAAGCTGCAGCAAGAACCAGAGCACTAC
ACAACCGCGCCGCCCCCCCCAACAGGAATCTGAGCAGCCCGAACACACAAACCAGAGCACTAC
CCAGATCAtgcatggtaagcctatccctaaccctctcctcggtctcgattctacgcgtaccggtCAT
                  NsiI                                            V5 epitope
CATCACCATCACCATTGAGTTTAAACCCGCTGATCAGCCTCGACTGTGCCTTCTAGTTGCCAGCCAT
6xHIS           stop                                              BGH PolyA
CTGTTGTTTGCCCCTCCCCCGTGCCTTGACCCTGGAAGGTGCCACTCCCACTGTCCTTTCCTA
ATAAAATGAGGAAATTGCATCGCATTGGTCTGAGTAGGTGTCATTCTATTCTGGGGGGTGGGG
CAGGACAGCAAGGGGGAGGATTGGGAAGACAATAGCAGGCATGCTGGGGATGCGGTGGGCTCTATGG
CTTGGTACC-3'
   KpnI

FIG. 20B

5′ – PacI

Kozak BHV-1 gD signal sequence ttaattaaCGCCACCatgcaggggacctactctggctgtgctggggctctgctggctgtcgccgtc
agtctgGAAAACATCACTCAGTGGAATCTGCAGGATAACGGCACCGAGGGGATCCAGCGCGCCATG
TTCCAGCGAGGCGTGAACCGGTCACTGCACGGGATCTGGCCAGAAAAGATTTGCACCGGAGTCCCA
AGCCACCTGGCTACCGACATCGAGCTGAAGACAATTCATGGAATGATGGATGCTAGCGAAAAAACC
AACTACACATGCTGTCGGCTGCAGAGGCACGAGTGGAATAAGCATGGCTGGTGTAACTGGTATAAT BVDV1E[rns]

ATCGAACCCTGGATCCTGGTCATGAACAGAACACAGGCCAATCTGACTGAGGGACAGCCACCTCGA
GAATGCGCTGTCACTTGTCGCTACGACAGAGCTAGCGATCTGAACGTGGTCACACAGGCTCGAGAC
TCCCCAACTCCTCTGACCGGCTGCAAGAAAGGGAAGAACTTCTCCTTTGCTGGGATCCTGATGCGC
GGACCCTGTAATTTTGAGATTGCCGCTTCTGATGTGCTGTTCAAAGAGCACGAAAGAATCAGTATG
TTTCAGGACACCACACTGTACCTGGTGGATGGCCTGACCAACTCCCTGGAGGGAGCTAGGCAGGGA
ACAGCTAAGCTGACTACCTGGCTGGGGAAACAGCTGGGAATTCTGGGCAAGAAACTGGAAAACAAG
TCTAAAACCTGGTTCGGAGCCTATGCTATGTGGCTGCAGAATCTGCTGCTGCTGGGCACAGTGGTC
TGCTCTTTTAGTGCCCCTACTAGGCCACCCAATACAGCTACTCGCCCATGGCAGCACGTGGACGCC
ATCAAGGAGGCTCTGAGTCTGCTGAACCATAGCTCCGACACTGATGCCGTGATGAATGACACCGAG

GM-CSF

GTGGTCTCCGAAAAATTTGATTCTCAGGAGCCCACCTGTCTGCAGACACGGCTGAAGCTGTACAAA
AACGGGCTGCAGGGATCACTGACCAGCCTGATGGGAAGCCTGACTATGATGGCCACCCACTATGAG
AAGCATTGCCCTCCAACACCTGAAACTAGTTGTGGACCCAGTTCATCAGCTTCAAGAATTTCAAA
GAAGACCTGAAAGAGTTCCTGTTTATCATTCCATTTGACTGTTGGGAGCCAGCCCAGAAAGGTAAG
CCTATCCCTAACCCTCTCCTCGGTCTCGATTCTACGTAAgcggccgc–3′

V5 epitope Stop NotI

FIG. 21A

5' - PacI  Kozak              BHV-1 gD signal sequence
ttaattaaCgCCACCatgcaaggaccactctggctgtctggggctgtgctggctgtgctctc
tgGAAAACATTACTCAGTGGAATCTGATGCACCCAGGATCCGAAGGATCCAGCAGCCATGTTTCTGCG
AGCCGTGAACCGGTCTCTGCTGAGAA

FIG. 22

BHV-1 gG deletion vector

5'— EcoRV

Continued from FIG. 23A

CCTTCTAGTTGCCAGCCATCTGTGTTGTTTGCCCCTCCCCGTGCCTTCCTTGACCTGGAAGGTGC
CACTCCCACTGTCCTTTCCTAATAAAATGAGGAAATTGCATGCATTGTCTGAGTAGGTGTCATT
CTATTCTGGGGGGTGGGGTGGGGCAGGACAGCAAGGGGGAGGATTGGGAAGACAATAGCAGGCAT
GCTGGGGATGCGGTGGGCTCTATGGTCGCCGGCACCCCAGCCCGCGCCCCGCTGTCCCGCG
TTTACAAATAAACAGTTATTCTTACCAACGTTGGTGCGCCTGTCGCGTGTCTATTGCGAGTTAAAC
        US3PolyA CGAGTGCCCACCCAGGCAGGGCAGGGGTTGGGCCGCAGCCCGCTGGGTATATATCCC
CGACGGGCGACTAGAGATACACTCGCCCGTGCTGCGAGCGGCGAACATGCAAGGCC
GACATTGGCCGCTGCTGGGCCGGCTGCCGCCCGTTGCGGTGAGCTTGCCTACACCGCCGCCGGG
TGACGGTATACGTCGACCGGCCGGGATACCGTACCGCCGGATACAACTACACGTGAACGCTGGCAC
ACTACCGGCCCATACCGTCGCCCTTGCGACACGCGGCGTGCCGTGAGGGTGCGCTACGC
GACCGGCTACCGTGCCGACATGCTGGCCGCTGATCGCAGACGGCCAGCAGCACCGCACGCTGT
GGGAAGCGGTACGGCCGCCGGTACACGGAGTACACGCCGAGTTCCTGCGGGCTTCGCCAAGATGCGAGAGC
GGGTCTGGGACTTCGGGCCGCTGTATACAGAGTACACAGTCATGGTACGGAAGCACTTTGGTA
CTGCCGCTACCGCACACCCCGTTTGGACACAGCTTCCTGCGGCTTCGCCTACCCCACGGACG
ACGAGCTGGGACTGATTATGCGGGCGCCGACTTCGGTCGAGGCCAGTACCGACGCCGCTG
TACATCGACGGTTCTGCGCCCTGACGTATCTCACGCAGTACTACCCGGGCCGGATTACGAGC
CTCGAAACTGGGGCGTACCTTTGCTGTTCCGGCGTGCTTCCCGGCGCCCGGGATTACGAGC
AAAGAAGGTTCTGAGCCACGGGCCGTTCCGCGGAGGACACAAGGCCATA
GTTCGACTACTGGTTCATGCGCCACGGGCCGTTCCGCGGAGGACACAAGGCCATA
GTTCGACTACTGGTTCATGCGCCACGGGCCGTTGTTCCGGCCCGTATTTTGACTAAGCTT-3'
                                                        HindIII

BOVINE HERPESVIRUS TYPE 1 (BOHV-1) VECTOR AGAINST BOVINE RESPIRATORY DISEASE COMPLEX

This application claims benefit of the priority filing date of U.S. Provisional Patent Application Ser. No. 62/262,450, filed Dec. 3, 2015, the contents of which are specifically incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 6, 2020, is named 144240_514996_SL.txt and is 170,521 bytes in size.

This invention was made with government support under 2015-67015-23277 awarded by the U.S. Department of Agriculture National Institute of Food and Agriculture. The government has certain rights in the invention.

BACKGROUND

Bovine respiratory disease complex (BRDC) is a multifactorial disease in cattle that involves initial viral respiratory infection followed by secondary bacterial infection and severe bronchopneumonia. BRDC costs the US cattle industry more than $1 billion annually. Bovine herpesvirus type 1 (BoHV-1), bovine respiratory syncytial virus (BRSV), and bovine viral diarrheal virus (BVDV) are important viral agents involved in BRDC. Because of the immunosuppressive properties of BoHV-1, BVDV, and BRSV, and the higher mutation rates of BVDV and BRSV, currently available modified live vaccines are not safe and are not adequately efficacious against the BRDC associated viral infections.

An improved BoHV-1 recombinant vaccine strain has been developed by the inventors that can beneficially replace the currently available BoHV-1 gE-deleted vaccine. Compared to wild type BoHV-1, the newly developed vaccine BoHV-1 triple mutant strain lacks the immunosuppressive functions encoded within UL49.5 (i.e., the vaccine does not have UL49.5 amino acids 30-32 and 80-96). In addition, the BoHV-1 vaccine lacks the gE cytoplasmic tail (i.e., the gE CT residues 451-575 are missing), which is associated with virulence function. Furthermore, the BoHV-1 tmv vaccine has a deletion of the entire envelope protein Us9 (important for virulence and anterograde neuronal transport). This new recombinant vaccine virus has been named BoHV-1 triple mutant virus (BoHV-1tmv).

Because of the gE cytoplasmic tail and Us9 deletions, BoHV-1tmv is not expected to shed in the nasal secretions following latency reactivation. A vaccine efficacy study results reported recently (Chowdhury et al., Vaccine 32 (39):4909-4915 (2014)) documented that the calves vaccinated with the BoHV-1 tmv generated significantly better protective immune responses against virulent BoHV-1 challenge when compared with a BoHV-1 gE-deleted virus-infected calves. The inventors have also developed a gE-CT based serological marker assay that would distinguish a vaccinated animal form a wild type virus-infected animal (data not shown).

SUMMARY

The BoHV-1 recombinant vaccine strain is described herein that can be used as a vector for expressing carefully engineered protective antigens of other viruses, including respiratory RNA viruses. Examples of respiratory viruses from with such protective antigens can be obtained include BVDV and BRSV, for which current vaccine strategies are not safe or have not been adequately efficacious. More specifically, the BoHV-1 tmv vector virus can express chimeric BVDV types 1 and 2 E2 (E2-1 or E2-2). BVDV Erns, or BRSV F and G proteins. Hence, such recombinant BoHV-1 viruses can serve as live attenuated vaccines against BoHV-1 and BVDV, and BoHV-1 and BRSV, which are the important viral agents associated with bovine respiratory disease complex.

A BoHV-1 recombinant vector can be employed that includes at least one heterologous antigen inserted therein, where the BoHV-1 vector has a deletion of a cytoplasmic tail of envelope glycoprotein gE (gE-CT), a deletion of an entire envelope protein, a deletion of envelope protein ULA49.5 residues 30-32, a deletion of UL49.5 cytoplasmic tail residues 80-96, or a combination thereof. One example of such a BoHV-1 recombinant vector is a BoHV-1 tmv vector.

The BoHV-1 tmv vector virus lacks the ability to down regulate cellular immune response and cannot shed viruses in the nasal secretions following reactivation from latency. Therefore, recombinant BoHV-1 tmv viruses expressing BVDV types 1 and/or 2 E2, and BRSV F and G proteins separately can induce better protective immune responses against BoHV-1 and BVDV types 1 and/or 2 and BoHV-1 and BRSV. Both BVDV and BRSV immunogenic proteins (e.g., E2-1 and/or 2 and BRSV F+G) can be incorporated in a single BoHV-1 tmv vector (BoHV-1 tmv BVDV E2-1/2, Erns, BRSV F+G) which can serve as BoHV-1 tmv vectored trivalent vaccine against BoHV-1, BVDV and BRSV. Importantly, the BoHV-1 multivalent vector can induce better immune responses against the three most important viral agents associated with BRD compared with currently available multivalent modified live or inactivated vaccines against BoHV-1, BVDV and BRSV.

DESCRIPTION OF THE FIGURES

FIG. 1 shows a schematic diagram of the BVDV genome illustrating the location of various BVDV encoded proteins, including the E2 coding region, which is enlarged and shows the location of the Transmembrane™ region.

FIG. 2 schematically illustrates the structure of a BRSV genome showing various BRSV encoded proteins. The BRSV F and G protein regions are enlarged. Furin cleavage sites (FCS 1 and FCS2) and the pep 27 of BRSV F are also shown. In addition, a cysteine noose region within the BRSV G protein (residues 157-188) is shown.

FIG. 3A-3I illustrate schematic diagrams of BoHV-1 vector development. FIG. 3A shows a schematic diagram of BoHV-1 $U_L49.5$ Δ30-32 CT-null/gE-CTΔ/Us9Δ virus genome (BoHV-1 tmv) showing (1) a schematic of the BoHV-1 genome with the locations of $U_L49.5$ (gN), gE, Us9 and bICP22 open reading frames; (2) a schematic of the BoHV-1 $U_L49.5$ Δ30-32 CT-null genome; and (3) a schematic of pBoHV-1 gE-CTΔ/Us9Δ plasmid showing the location and sizes of deleted sequences (gE CT, Us9 and Us9-bICP22 intergenic region), the flanking upstream gE (ectodomain and transmembrane) and downstream bICP22 sequences. Arrows indicate open reading frames of corresponding genes. FIG. 3B shows a schematic diagram of a wild type BoHV-1 genome showing the locations of UL 49.5 (gN), gE, Us9 and bICP 22 open reading frames (ORFs). FIG. 3C shows a schematic diagram of a BoHV-1 gE ΔCT/Us9Δ deletion (pBoHV-1 gE ΔCT/Us9Δ) vector. FIG.

3D shows a schematic diagram illustrating the BoHV-1 tmv ($U_L$49.5 Δ30-32 CT-null/gEΔCT/Us9Δ virus) genome. FIG. 3E shows a schematic diagram illustrating BHV-1 tmv virus vector organization showing UL49.5, gE CT/Us9 deletion sites. Arrows indicate open reading frames of corresponding genes. The asterisks (*) identifies a deletion of 3.44 kb nucleotides spanning the gE CT, Us9. The gE CT/Us9 deletion locus is flanked by gE ecto domain on the left and Us9-bICP22 intergenic region and carboxy terminal bICP22 gene sequence on the right. FIG. 3F shows a schematic diagram illustrating a pBHV-1 gEΔCT US9Δ deletion vector showing the gECT/$U_S$9 deletion site (nucleotides 122989-123993) and the location of an $U_S$8 (gE) partial gene (nucleotides 121637 . . . 122989; gE Ecto) as well as the downstream 1 Kb Us9/bICP22 intergenic and partial carboxy terminal bICP22 (nucleotides 123993-124996). Nucleotide numbers refer to gene locations. FIG. 3G shows a schematic diagram of a BVDV1 E2 expression cassette. FIG. 3H shows a schematic diagram of a BVDV2 E2 expression cassette. FIG. 3I shows a schematic diagram of a BRSV G expression cassette. FIG. 3J shows a schematic diagram of a BRSV F expression cassette. As illustrated, FIGS. 3G-3J illustrate the insertion site of respective sequences. Nucleotide numbers are based on GenBank accession #JX898220).

FIG. 4A-4C illustrate characterization of the BoHV-1 tmv mutant virus. FIG. 4A illustrates an immunoblot of Mock-infected, BoHV-1 wild type-infected, and BoHV-1 tmv-infected cell lysates probed with an anti-BoHV-1 UL49.5 specific antibody. FIG. 4B illustrates an immunoblot of Mock-infected, BoHV-1 wild type-infected, and BoHV-1 tmv-infected cell lysates probed with an anti-BoHV-1 gE-specific antibody. FIG. 4C illustrates an immunoblot of Mock-infected, BoHV-1 wild type-infected, and BoHV-1 tmv-infected cell lysates probed with a BoHV-1 Us9-specific antibody. Note that UL49.5 Δ30-32 CT-null (FIG. 4A) and gE ΔCT-specific bands (FIG. 4B) of BoHV-1 tmv mutant virus are smaller than their respective corresponding bands of wild type BoHV-1. In addition, the Us9 band is lacking in the BoHV-1 tmv-infected cell lysates.

FIG. 5 graphically illustrates growth of BHV-tmv virions. Growth of BHV-tmv viruses compared with BoHV-1 gE-deleted (i.e., complete deletion of gE) and wild type BoHV-1 viruses was performed in Madin-Darby bovine kidney (MDBK) cells obtained from the American Type Culture Collection (Manassas, Va.). Confluent MDBK cells were infected with the respective viruses at a multiplicity of infection of five plaque forming units (PFU) per cell. After 1 h of adsorption at 4° C., residual input viruses were removed. The cultures were washed three times with phosphate-buffered saline, and 5 ml of medium was added to each flask before further incubation (37° C.). At the indicated time intervals, replicate cultures were frozen. Virus yields were determined by plaque assay. Each data point represents the average of duplicate samples obtained from separate infections.

FIG. 6A-6D graphically illustrate the pathogenicity and vaccine efficacy of the BoHV-1 tmv. FIG. 6A graphically illustrates the clinical scores of calves that were subjected to primary intranasal infection/immunization with BoHV-1 tmv viruses or BoHV-1 gE-deleted viruses, followed by virulent wild type BoHV-1 viral challenge. As a control, sham-infected calves were also tested with mock primary infection/immunization, followed by actual challenge with virulent wild type BoHV-1. FIG. 6B graphically illustrates nasal virus shedding following primary intranasal infection/immunization with BoHV-1 tmv viruses or BoHV-1 gE-deleted viruses followed by challenge with virulent wild type BoHV-1 virus. As a control, sham-infected calves were also tested during primary infection and after challenge with virulent wild type BoHV-1 viruses. FIG. 6C graphically illustrates virus neutralizing antibody titers in calves following primary intranasal infection/immunization with BoHV-1 tmv or BoHV-1 gE-deleted viruses followed by challenge with virulent wild type BoHV-1. As a control, sham-infected calves were also tested by mock-primary infection/immunization followed by challenge with virulent wild type BoHV-1 virus. FIG. 6D illustrates serum interferon γ levels in calves sham infected/immunized (control), or infected/immunized with BoHV-1 tmv or BoHV-1 gE-deleted viruses followed by virulent wild type BoHV-1 challenge. High binding EIA plate (Costar, Corning, N.Y.) wells coated with anti-bovine IFNγ-specific rabbit polyclonal antibodies (10 μg/ml; Endogen, Rockford, Ill.) were used to capture IFN-γ in serially diluted calf sera (100 μl) from different treatment groups. As a control, 100 μl of the serial diluted recombinant bovine IFNγ (Thermo, Pierce, Ill.) were added instead of sample sera. After incubation (for 1 hour), the test wells were washed and incubated (1 hr) with biotinylated rabbit anti-bovine IFNγ polyclonal Ab (Endogen, Rockford, Ill.). After washing, the test wells were incubated (for 1 hour) further with avidin-HRP (eBioscience, San Diego, Calif.) and developed with substrate 2,2'-azino-bis(3-ethylbenzothiazoline-6-sulphonic acid) (ABTS, Sigma). The test results were measured at $OD_{405}$ by using an ELISA reader.

FIG. 7 shows an immunoblot illustrating a BoHV-1 gE CT-specific mouse monoclonal antibody. Note that the antibody recognized the 92 kD gE-specific band in the wild type BoHV-1-infected cell lysate but not the gE CT-deleted BoHV-1 tmv-infected cell lysate.

FIG. 8 shows a schematic diagram illustrating construction of a BVDV E2.1 chimeric gene and a BoHV-1 E2.1 insertion plasmid (pBoHV-1 INS/E2.1). Panel A shows the locations of PCR primers P1 Forward (P1 F) and P2 Reverse (P2R) for PCR amplification of an E2.1 chimeric expression cassette within a pEF6/v5-His-TOPO vector. Panel B shows the location of KpnI site in pBoHV-1 gECTΔ/Us9Δ for insertion of chimeric E2.1 gene. Panel C shows the pBoHV-1 INS/E2.1 plasmid containing BVDV E2.1 expression cassette flanked by gE CT upstream gE Ecto and transmembrane (Tm) nucleic acid segments, and the Us9 downstream bICP 22 nucleic acid segments.

FIG. 9A-9B shows immunoblots of proteins expressed by a BoHV-1 tmv vector encoding the BVDV type 1 chimeric E2 (E2.1) protein. FIG. 9A shows an immunoblot of lysates of mock-infected control cells and cells infected with BoHV-1 tmv or the modified BoHV-1 tmv that encodes a chimeric E2 (E2.1) protein, after probing with an anti-V5 monoclonal antibody. FIG. 9B shows an immunoblot of lysates of mock-infected control cells, BVDV-infected cells, and cells infected with BoHV-1 tmv or the modified BoHV-1 tmv that encodes a chimeric E2 (E2.1) protein, after probing with a polyclonal anti-BVDV antibody. As shown FIG. 9B, there is a 43 kD protein visible in BVDV-infected lysates, which is a precursor endoplasmic reticulum-processed form of E2.1. Also, shown in FIG. 9B, there is a 53-54 kD protein band in the BVDV lysates, which is the Golgi processed EndoH resistant mature E2.1. The molecular masses of both the ER and Golgi processed forms of the BoHV-1 tmv expressed chimeric E2.1 shown in FIG. 9B are 5 kD larger (48 kD and 58/59 kD, respectively), due to the additional V5 and His tag residues (see also FIG. 9A).

FIG. 10 illustrates a nucleotide sequence (SEQ ID NO: 1) of a portion of an expression cassette that can be part of a vector (e.g., BoHV-1 tmv vector) and that can be used for insertion of a BVDV E2 protein antigen, BRSV F protein antigen, BRSV G protein antigen, or a combination thereof. This sequence is referred to as a pPreBVDV-E2/BRSV-F or G sequence. The SEQ ID NO: 1 sequence is composed in the 5'-3' direction of the following: (i) human elongation factor 1α promoter sequence flanked by KpnI/ClaI restriction sites (underlined) (ii) 12 bp spacer and NsiI restriction site (iii) V5-epitope coding sequence (lower case, italic) (iv) 6×His coding sequence (bolded) (v) a stop codon (TGA) (vi) bovine growth hormone polyadenylation signal sequence (BGH poly A)(underlined, italic) and (vii) KpnI site.

FIG. 11A-11B show schematic diagrams illustrating the strategy of the construction of chimeric BVDV E2 1 or 2 expression cassette, and BoHV-1 gEΔCTUs9Δ/BVDV E2-1 or 2 insertion vector. FIG. 11A shows a schematic diagram of a chimeric BVDV E2-1 or 2 gene expression cassette. FIG. 11B shows a schematic diagram illustrating a BoHV-1 gE CT and Us9 deletion and chimeric BVDV E2-1 or 2 nucleic acid insertion sites.

FIG. 12A shows an immunoblot of MDBK cell lysates that were either mock-transfected or transfected with BoHV-1tmv recombinant vectors expressing either BVDV type 1 (BoHV-1 tmv E2-1 clone 8 and clone 2) or type 2 E2 proteins (BoHV-1 tmv E2-2) as detected by a BVDV type 1 E2-specific monoclonal antibody (VMRD #157). FIG. 12B shows an immunoblot of MDBK cell lysates that were either mock-transfected or transfected with BoHV-1tmv recombinant vectors expressing either BVDV type 1 (BoHV-1 tmv E2-1 clone 8 and clone 2) or type 2 E2 proteins (BoHV-1 tmv E2-2) as detected by a BVDV type 2 E2-specific monoclonal antibody (VMRD # BA-2). As control, the reactivity of the monoclonal antibody Ab 157 and the monoclonal antibody mAb BA-2 is illustrated for mock and BVDV-1 type 1 (strain sanger) and BVDV type 2 (strain 125) infected MDBK cell lysates.

FIG. 14 graphically illustrates the plaque morphology of BoHV-1 tmv/E2-1 and BoHV-1tmv/E2. Plaque sizes produced by parental BoHV-1tmv, BoHV-1 tmv/E2-1 and BoHV-1tmv/E2 viruses were measured at 48 hours post-infection. Average plaque diameters of 50 randomly selected plaques are shown as mean±standard deviation.

FIG. 15A-15D illustrate a nucleotide sequence of a chimeric BVDVE2-1 expression cassette (SEQ ID NO:9) and the encoded amino acid sequence. FIG. 15A shows a nucleotide sequence for a human elongation factor 1α promoter flanked by KpnI/ClaI restriction sites (KpnI sequence underlined), followed by a Kozak sequence, and part of a coding region for a BHV-1 gD signal sequence (GenBank accession # AFV53430.1, amino acid 1-19). The sequence continues in FIG. 15B. FIG. 15B continues from FIG. 15A and shows the 3' end of the coding region for a BHV-1 gD signal sequence (GenBank accession # AFV53430.1, aa 1-19) followed by a *Bos taurus* codon optimized, nucleotide sequence for BVDV E2-1 (GenBank accession # NP_776263.1). Hence, the sequence shown in FIG. 15A-15B is a nucleotide sequence for a BVDVE2-1 chimeric coding region contained within ClaI and NsiI sites. The sequence includes the following in the 5'-3' direction: Kozak sequence, coding sequence for a BHV-1 gD signal sequence (GenBank accession # AFV53430.1, amino acid 1-19), *Bos taurus* codon optimized nucleotide sequence for BVDV E2-1 coding region (GenBank accession # NP_776263.1). The 1.235 bp ClaI/NsiI fragment was cloned into the corresponding ClaI/NsiI sites of the pPreBVDV-E2 chimeric vector (FIG. 10; SEQ ID NO: 1) resulting in BVDVE2-1 chimeric gene expression cassette. BVDV E2-1 sequence is indicated by uppercase letters without underlining. FIG. 15C shows the amino acid sequence (SEQ ID NO:55) and nucleotide sequence (SEQ ID NO:56) of a fusion protein that has a BHV1 gD signal sequence (amino acid 1-19)(GenBank accession # AFV53430.1) fused to a portion of the BVDVE2-1 sequence (GenBank accession # NP_776263.1). The gD-BVDVE2-1 fusion protein nucleotide and amino acid sequences continue in FIG. 15D. Hence, FIG. 15D shows nucleotide and amino acid sequences for the C-terminal 235-373 amino acids of the gD signal sequence-BVDVE2-1 fusion protein.

FIG. 16A-16D illustrate a nucleotide sequence of a chimeric BVDVE2-2 expression cassette (SEQ ID NO: 14). FIG. 16A shows a nucleotide sequence for a human elongation factor 1α promoter flanked by KpnI/ClaI restriction sites (KpnI sequence underlined), followed by a Kozak sequence, and part of a coding region for a BHV-1 gD signal sequence (GenBank accession # AFV53430.1, amino acid 1-19). FIG. 16B continues from FIG. 16A and shows the 3' end of the coding region for a BHV-1 gD signal sequence (GenBank accession # AFV53430.1, amino acid 1-19) followed by a *Bos taurus* codon-optimized, nucleotide sequence for BVDV E2-2 (GenBank accession # AAC72814.1). The 1.195 bp ClaI/NsiI fragment was cloned into the corresponding ClaI/NsiI sites of the pPreBVDV-E2 chimeric vector (SEQ ID NO: 1) resulting in BVDVE2-2 chimeric gene expression cassette. FIG. 16C shows the amino acid sequence (SEQ ID NO:57) and nucleotide sequence (SEQ ID NO:58) of a fusion protein that has a BHV1 gD signal sequence (aa 1-19) (GenBank accession # AFV53430.1) fused to a portion of the BVDVE2-2 sequence (GenBank accession # AAC72814.1). The gD-BVDVE2-2 fusion protein nucleotide and amino acid sequences continue in FIG. 15D. Hence, FIG. 15D shows nucleotide and amino acid sequences for the C-terminal 235-390 amino acids of the gD signal sequence-BVDVE2-1 fusion protein.

FIG. 17A-17F show a nucleotide sequence for a BRSV F-version 1 expression cassette (SEQ ID NO: 19) as well as amino acid and nucleotide sequences for a BRSV-F1-V5/6×His fusion protein sequences (SEQ ID NOs: 20 and 21, respectively). FIG. 17A-17C show a nucleotide sequence for a BRSV F version 1 expression cassette (SEQ ID NO:19) that includes a BRSV F version 1 sequence (GenBank accession # GI: 3451386/CAA 76980.1) contained within ClaI and NsiI sites that were cloned in to the corresponding ClaI/NsiI sites of the pPreBVDV-E2/BRSV-F or G chimeric vector (SEQ ID NO:1) resulting in the BRSV F-version 1 expression cassette. The BRSV F version-1 sequence is indicated by uppercase. The BRSV-F protein has separate Furin cleavage sites (FCS 1 and FCS 2). BRSV-F version 1 protein is generated by mutating two arginine residues of FCS 1 (RAKR) to alanine (AAKA) and all three arginine residues of FCS2 (RKRR) to alanine (AKAA). The BRSV-F version 1 nucleotide sequence is codon optimized for *Bos taurus*, and has an upstream Kozak sequence as well as a BHV-1 gD signal sequence. FIG. 17A shows a nucleotide sequence for a human elongation factor 1α promoter flanked by KpnI/ClaI restriction sites (KpnI sequence underlined), followed by a Kozak sequence, and part of a coding region for a BHV-1 gD signal sequence (GenBank accession #

AFV53430.1, amino acid 1-19). FIG. 17B continues from FIG. 17A and shows the 3' end of the coding region for a BHV-1 gD signal sequence (GenBank accession # AFV53430.1, aa 1-19) followed by a *Bos taurus* codon-optimized, nucleotide sequence for BRSV F version 1 sequence (GenBank accession # GI: 3451386/CAA 76980.1). FIG. 17C continues from FIG. 17B and shows the V5 epitope, histidine tail, and polyA sequences. FIG. 17D-17F show amino acid and nucleotide sequences for a BRSV-F1-V5/6×His fusion protein sequences (SEQ ID NOs: 20 and 21, respectively). FIG. 17D shows the first 216 amino acids of the fusion protein, and the corresponding nucleotide sequence therefor. FIG. 17E is a continuation of the fusion protein sequence, showing amino acids 217-432 of the fusion protein, and the corresponding nucleotide sequence therefor. FIG. 17F is a continuation of the fusion protein sequence, showing amino acids 433-619 of the fusion protein, and the corresponding nucleotide sequence therefor. The SEQ ID NO:21 nucleotide sequence is codon optimized for *Bos taurus*. The SEQ ID NOs: 20 and 21 sequences include the following: BHV1 gD signal sequence (amino acid 1-20)(GenBank accession #AFV53430.1) fused to the BRSV-F version 1 sequence (GenBank accession # GI: 3451386/CAA 76980.1), followed by a V5 epitope and a string of six histidines (6×His). The BRSV-F protein has two separate Furin cleavage sites (FCS 1 and FCS 2). In the BRSV-F version 1 chimeric protein, two arginine residues of FCS 1 (RAKR; SEQ ID NO:51) are exchanged with alanine (AAKA: SEQ ID NO:52) and three arginine residues of FCS 2 (RKRR; SEQ ID NO:53) are exchanged with alanine (AKAA; SEQ ID NO:54). The gD signal, BRSV-F1, V5 epitope and 6×His sequence are identified.

FIG. 18A-18C show a fusion protein BRSV-F version 2 protein sequence (SEQ ID NO:24) aligned with the corresponding nucleotide sequence (SEQ ID NO:25). FIG. 18A shows amino acids 1-216 of the fusion protein. FIG. 18B is a continuation of the fusion protein sequence, showing amino acids 217-414 of the fusion protein, and the corresponding nucleotide sequence therefor. FIG. 18C is a continuation of the fusion protein sequence, showing amino acids 415-594 of the fusion protein, and the corresponding nucleotide sequence therefor. The fusion protein nucleotide sequence (SEQ ID NO:25) is codon optimized for *Bos taurus* expression. The fusion protein includes a BHV1 gD signal sequence (amino acid 1-20)(GenBank accession # AFV53430.1) fused to the BRSV-F version 2 sequence (GenBank accession # GI: 3451386/CAA 76980.1). BRSV-F protein has two separate Furin cleavage sites (FCS 1 and FCS 2). The BRSV-F version 2 protein shown has a FCS 1 (usually RAKR; SEQ ID NO:51) sequence that has been modified to include alanine residues (AAAA; SEQ ID NO:52) and a FCS 2 (usually RKRR; SEQ ID NO:53) sequence modified to include alanine (AAAA: SEQ ID NO:54). The codon optimized chimeric BRSV-F version 2 sequence shown has an upstream Kozak sequence and BHV-1 gD signal sequence at the N-terminus.

FIG. 19A-19B illustrate a nucleotide sequence of a chimeric BRSV G version 1 expression cassette (SEQ ID NO:33). FIG. 19A shows a nucleotide sequence for a human elongation factor 1α promoter flanked by KpnI/ClaI restriction sites (KpnI sequence underlined), followed by a Kozak sequence, and part of a coding region for a BHV-1 gD signal sequence (GenBank accession # AFV53430.1, aa 1-19). FIG. 19B continues from FIG. 19A and shows the 3' end of the coding region for a BHV-1 gD signal sequence (underlined, GenBank accession # AFV53430.1, aa 1-19) followed by a *Bos taurus* codon-optimized, nucleotide sequence for BRSV G version 1 (not underlined; GenBank accession # GI: 17939989/AAL49398.1). The ClaI/NsiI fragment was cloned into the corresponding ClaI/NsiI sites of an expression system (e.g., a vector having SEQ ID NO: 1) resulting in a BRSV G version 1 chimeric gene expression cassette.

FIG. 20A-20B illustrate a nucleotide sequence of a chimeric BRSV G version 2 expression cassette (SEQ ID NO:38). FIG. 38A shows a nucleotide sequence for a human elongation factor 1α promoter flanked by KpnI/ClaI restriction sites (KpnI sequence underlined), followed by a Kozak sequence, and part of a coding region for a BHV-1 gD signal sequence (GenBank accession # AFV53430.1, aa 1-19). FIG. 20B continues from FIG. 20A and shows the 3' end of the coding region for a BHV-1 gD signal sequence (underlined) followed by a *Bos taurus* codon-optimized, nucleotide sequence for BRSV G version 2 (not underlined: GenBank accession # AFV53430.1). The ClaI/NsiI fragment was cloned into the corresponding ClaI/NsiI sites of an expression system (e.g., a vector having SEQ ID NO: 1) resulting in a BRSV G version 1 chimeric gene expression cassette.

FIG. 21A-21B illustrate examples of BVDV ERNS expression cassettes. FIG. 21A illustrates a nucleotide sequence (SEQ ID NO:40) an expression module encoding a BVDV1 ERNS fusion protein. Expression cassettes for BVDV1 ERNS can include, for example, the following components in a 5'-3' direction: i) Restriction site for PacI (lower case, bold, underlined) ii) Kozak sequence (upper case, italicized) iii) 57 bps BHV1gD signal (lower case, underlined; GenBank accession #AFV53430.1) iv) 681 bps BVDV1E.sup.rns coding sequence (upper case, bold; GenBank accession #NP_776261.1) v) 429 bps *Bos taurus* GM-CSF coding sequence (uppercase, underlined; GenBank accession # NP_776452.1) vi) 42 bps V5 epitope coding sequence (upper case, italicized) vii) a stop codon (TAA) (uppercase, bold, italicized) viii) Restriction site for NotI (lower case, bold, underlined). FIG. 21B illustrates a nucleotide sequence (SEQ ID NO:41 SEQ ID NO:59) of an expression cassette for BVDV2 ERNS that includes the following in a 5'-3' direction: i) Restriction site for PacI (lower case, bold, underlined) ii) Kozak sequence (upper case, italicized) iii) 57 bps BHV1gD signal (lower case, underlined; GenBank accession #AFV53430.1) iv) 681 bps BVDV2E.sup.rns coding sequence (upper case, bold; GenBank accession #NP_777483.1) v) 429 bps *Bos taurus* GM-CSF coding sequence (uppercase, underlined: GenBank accession # NP_776452.1) vi) 42 bps V5 epitope coding sequence (upper case, italicized) vii) a stop codon (TAA) (uppercase, bold) viii) Restriction site for NotI (lower case, bold, underlined).

Figure 22:
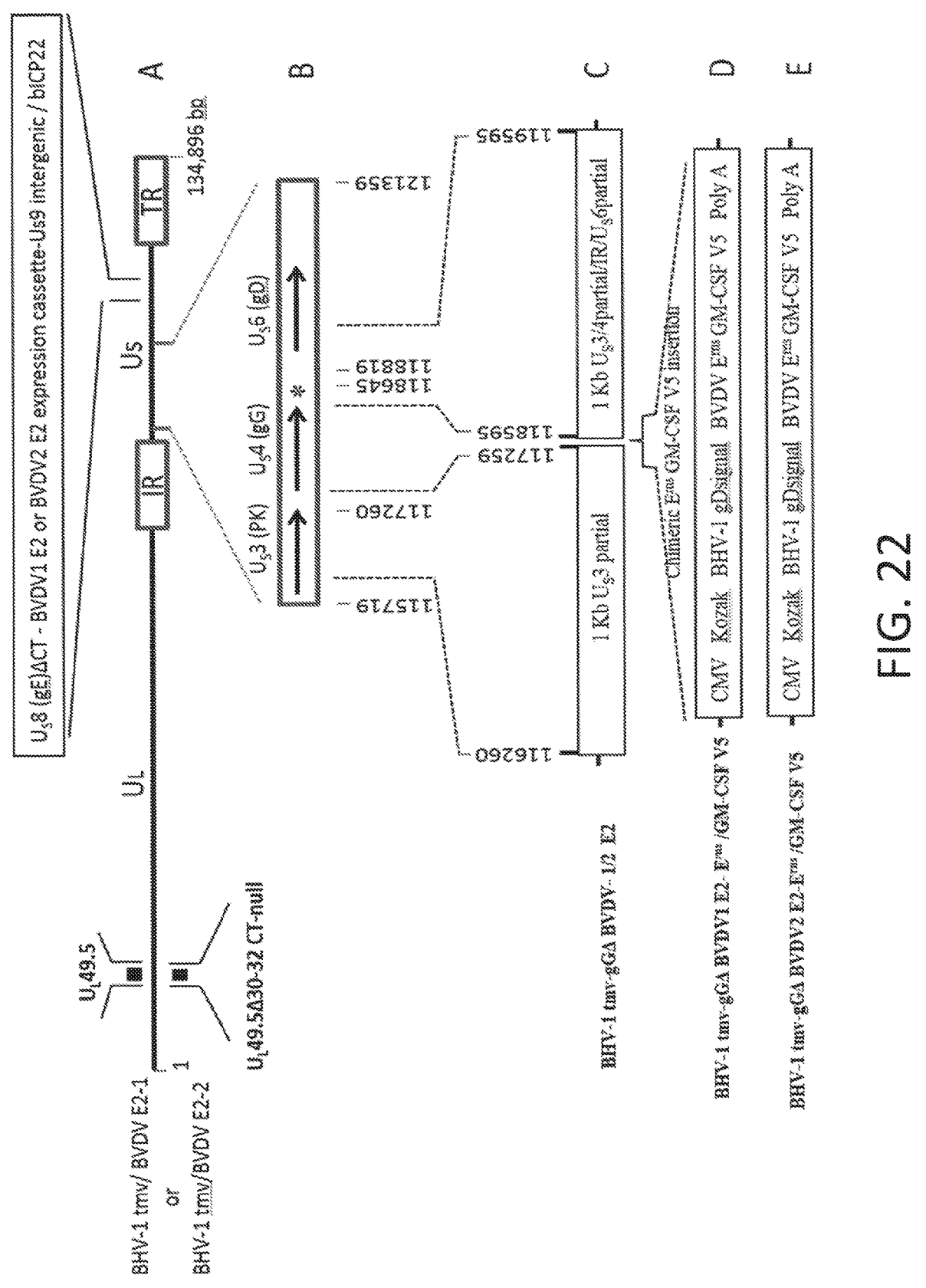

FIG. 22 shows schematic diagram of vectors and antigenic inserts for such vectors. Panel A is a schematic diagram of BHV-1 tmv (BHV-1 $U_L$49.5 Δ30-32 CT-null/ gECTΔ/Us9Δ) viral vector that can express BVDV1 E2 or BVDV2 E2 (BHV-1 tmv BVDV1 E2 or BVDV2 E2). Panel B schematically illustrates a construct of $U_S$4/gG gene (nucleotides 117260 . . . 118645) and surrounding genes that can be located in BHV-1 tmv BVDV E2 or BVDV2 E2. Nucleotide numbers refer to gene locations. Arrows indicate open reading frames of corresponding genes. The asterisks symbol (*) identifies a polyadenylation signal of $U_S$3 and $U_S$4. Panel C shows a schematic diagram of BHV-1 tmv containing an additional gG gene deletion, showing the gG deletion site (nucleotides 117260-118594) (BHV-1 tmv-gGΔ BVDV1/2). Panel D is a schematic diagram of BHV-1 tmv-gGΔ BVDV1 E2/E$^{rns}$/GM-CSF. Panel E is a schematic diagram of BVDV2 E2/E$^{rns}$/GM-CSF. Panels D and E illustrate the gG and the respective $E^{rns}$/GM-CSF insertion sites. Nucleotide numbers are based on GenBank accession #JX898220.

FIG. 23A-B illustrate a nucleotide sequence (SEQ ID NO:49) of BHV-1 gG deletion vector. The vector has the following in the 5'-3' direction: (i) An EcoRV restriction site, a 1 kb US3 sequence (upper case underlined, GenBank accession # JX898220.1, protein ID-AFV53428.1, nucleotides 116260-117125) followed by 588 bps CMV immediate early promoter sequence (lower case underlined), PacI and NotI sites with a eight base pair spacer (GTGTGTGTGT (SEQ ID NO:50) in between, followed by a 1 kb US6 downstream sequence (underlined italic, GenBank accession #JX898220.1, protein ID-AFV53430.1, nucleotides 118595-119595), 225 bps BGH poly A (uppercase) and a HindIII restriction site at the 3' end.

FIG. 24A-24C illustrate expression of BRSV F and G proteins from recombinant BHV-1 tmv. FIG. 24A illustrates expression of BRSV F protein from recombinant BHV-1 tmv as determined by a rabbit anti-BRSV F specific antibody (GenScript) staining of an immunoblot of infected Botur cell lysates. Lysate from BRSV Nebraska 236-652 strain infected Botur cells served as positive control. FIG. 24B illustrates expression of BRSV G protein from recombinant BHV-1 tmv as determined by anti-V5 specific monoclonal antibody (Invitrogen, #R960-25) staining of immunoblots of infected MDBK cell lysate. FIG. 24C illustrates expression of BRSV G protein from recombinant BHV-1 tmv as determined by rabbit anti-BRSV G specific antibody (GenScript) staining of an immunoblot of infected Botur cell lysates.

DETAILED DESCRIPTION

Figure 3A:
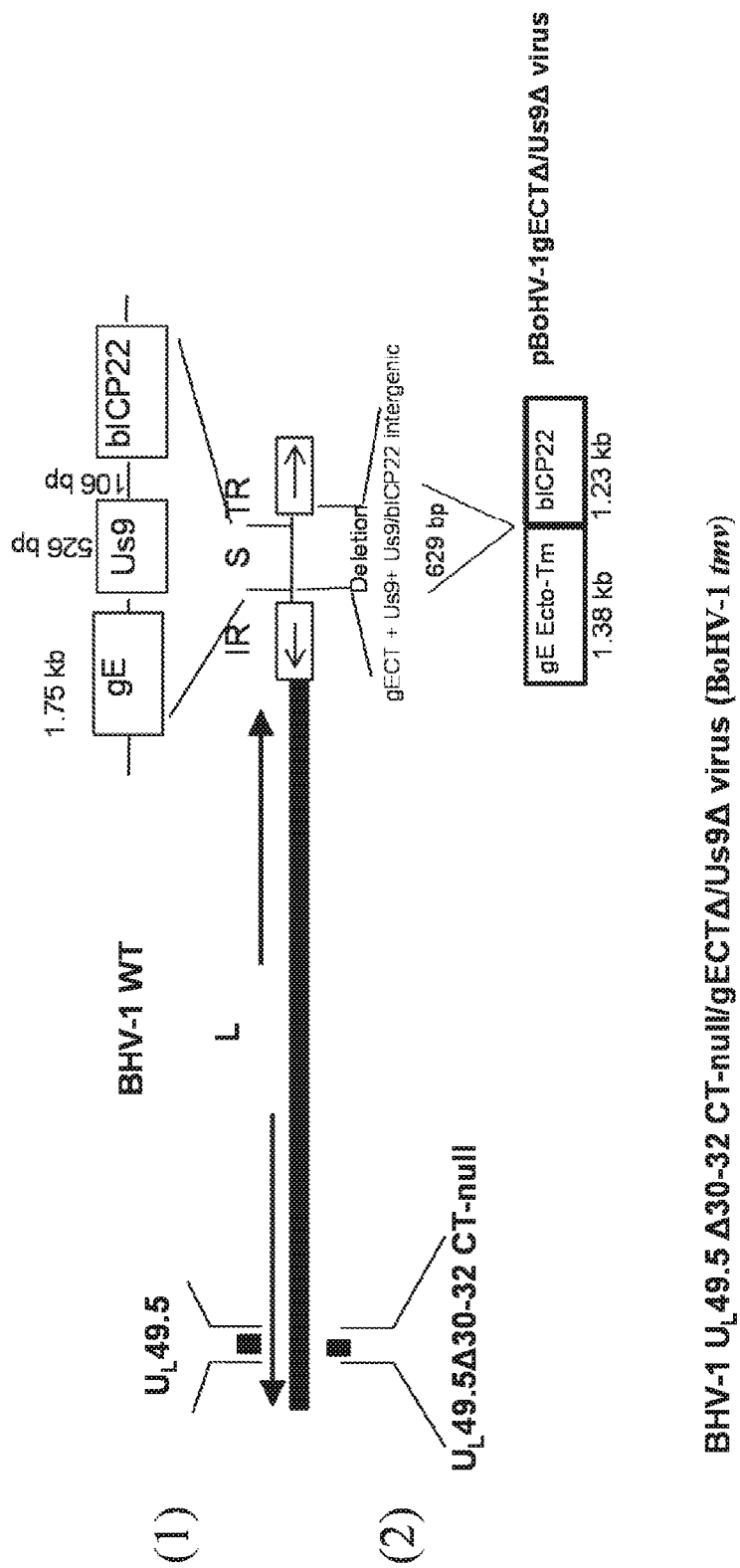

For many years, bovine respiratory disease complex (BRDC), a multifactorial disease in cattle, has been the most costly disease of the beef cattle industry in North America, costing the US cattle industry more than a billion dollars per year (31, 32). BRDC is also a significant problem for dairy cattle and cow-calf operations. Economic losses due to BRDC arise from a combination of mortality, metaphylactic, and therapeutic use of antibiotics, and reduced growth performance of affected cattle. BRDC typically involves an initial viral respiratory infection followed by a secondary bacterial infection, where the bacterial infection can involve *Mannheimia haemolytica* (*M. haemolytica*). It is generally accepted that initial respiratory viral infection(s) creates a favorable condition for colonization of the lungs by bacteria, commonly by *M. haemolytica*, resulting in severe pneumonia and death of infected cattle, especially in the feed lots (85).

Five viruses, bovine herpesvirus type 1 (BoHV-1), bovine respiratory syncytial virus (BRSV), bovine viral diarrheal virus (BVDV), respiratory bovine coronavirus (RBCoV), and parainfluenza 3 virus (PI-3) are involved in BRDC (19, 22, 23, 40, 48, 69, 73, 85). Based on the severity, pathogenicity and prevalence of the diseases caused by these viruses in cattle, BoHV-1, BRSV and BVDV are more significant. All the BRDC associated viruses, except BoHV-1, are RNA viruses and BoHV-1, BVDV, and BRSV are often immunosuppressive (8, 12, 38, 43, 44, 62, 64, 69, 72).

Traditional modified live virus (MLV) vaccines against these viruses are efficacious as judged by virus shedding and clinical scores following experimental vaccination and challenge (24, 31, 32, 93). However, recent reports indicate that multivalent vaccines against BoHV-1, BVDV and BRSV can be associated with outbreaks of respiratory disease and abortions under field conditions (21, 65, 66, 89).

The problems associated with modified live virus vaccines in the field are due to the following:

i) Like wild-type (wt) BoHV-1 virions, modified live virus vaccine strains are immunosuppressive, they establish latency in the trigeminal ganglia following intranasal infection, and following reactivation from latency they are shed in the nasal secretions (31, 32, 60). Consequently, the modified live virus vaccine strains may circulate in the cattle population and therefore may have the potential to revert to wild type (39, 60).

ii) Both BVDV and BRSV have RNA genomes that have high mutation rates and that can cause problems both in vaccine production and vaccine use. Therefore, deliberate and regular use of modified live virus vaccines in cattle population could be a major contributing factor in the emergence of mutant variants in the field (17). Such problems with modified live BRSV and BVDV vaccine viruses are further complicating the epidemiology of the diseases in the field and raising questions on the long-term benefits of modified live virus vaccines (12, 28, 39, 48).

iii) Notably, BVDV is highly immunosuppressive and this property is maintained in BVDV modified live virus vaccine strains (12, 70, 72). Therefore, the combined immunosuppressive effects of BoHV-1 and BVDV in the multivalent vaccine formulations described herein can synergistically interfere further with the protective immune response against the vaccine viruses.

iv) BRSV has a role in immunopathogenesis especially after reinfection and/or challenge infection (3, 27).

A substantial improvement in vaccine technology is described herein.

Previous work by the inventor shows that calves latently infected with envelope proteins gE cytoplasmic tail truncated (gE CT-null) or Us9-deleted BoHV-1 mutant viruses do not shed virus in the nose following reactivation and that both gE CT and Us9 are required for anterograde neuronal transport of the virus (11, 15, 16, 55). In addition, the inventor has determined that relative to calves infected with wild type BoHV-1, calves infected with a recombinant BoHV-1 virus lacking immunosuppressive domain of envelope protein $U_L49.5$ (BoHV-1 UL49.5Δ30-32 CT-null) have higher BoHV-1-specific serum neutralizing titers and earlier cellular immune responses (90). Hence the inventor has incorporated the gE CT and Us9 sequence deletions into the BoHV-1UL49.5Δ30-32 CT-null virus and thereby constructed a BoHV-1UL49.5Δ30-32 CT-null/gEΔCT/Us9Δ virus (BoHV-1 triple mutant virus).

Results obtained by the inventor show that the BoHV-1 triple mutant virus (BoHV-1 tmv) is significantly more efficacious than a gE-deleted BoHV-1. The triple gene mutated BoHV-1 tmv is not only a superior vaccine against BoHV-1, but it can be used as a vector for expressing carefully engineered protective antigens of other respiratory RNA viruses such as BVDV and BRSV. Information on the BoHV-1 triple mutant virus (BoHV-1 tmv, also called BoHV-1 tmv) is also provided in PCT Application PCT/US2015/043112 (published Feb. 4, 2016 as WO 2016/019244, and incorporated herein by reference in its entirety).

As described herein, a BoHV-1 tmv vector can be used to express the BVDV type 1 or type 2 envelope protein, E2, and/or the BRSV envelope proteins G or F. The BoHV-1 tmv vectored subunit vaccines are efficacious in calves against the respective subunit vaccine-specific virulent virus challenges (BVDV types 1 or 2, or BRSV). Methods and immunological compositions described herein can vaccinate beef and dairy cattle against BoHV-1, BVDV and BRSV, the three most significant bovine respiratory viruses that predispose to fatal secondary bacterial pneumonia.

Bovine Respiratory Disease Complex

Bovine respiratory disease complex (BRDC) is a multifactorial disease condition clinically characterized by acute bronchopneumonia. The causes of BRDC are multiple and complex, but in most cases stress and/or viral infection followed by bacterial infection can be involved (31, 32, 85). Five viruses, bovine herpesvirus type (BoHV-1), bovine respiratory syncytial virus (BRSV), bovine viral diarrheal virus (BVDV), respiratory bovine corona virus (RBCoV) and parainfluenza 3 virus (PI-3) can be associated with BRDC (5, 22, 23, 26, 40, 48, 69, 73, 85). These viruses generally produce mild respiratory signs by themselves but may produce severe respiratory signs when combined with stress or other viral and bacterial agents.

Four bacterial agents, *M. hemolytica, Pasteurella maltocida, Histophilus somni* and *Mycoplasma bovis*, have been implicated in BRDC (7, 23, 85). *M. hemolytica* has traditionally been the most common bacterial isolate. However, there is an apparent increase in prevalence of other agents such as *M. bovis* (85). All of these bacterial pathogens are normal flora in the upper respiratory tracts. However, due to stress and/or viral respiratory infection(s), these bacteria may colonize the lungs and cause severe bronchopneumonia.

BRD-like symptoms have been induced experimentally upon exposure of animals to *M. haemolytica* following infection by BoHV-1 (30). Similar results were obtained with endobronchial instillation of BVDV followed by *M. hemolytica* by five days later (68). BRD outbreaks have also been linked serologically to BRSV and BVDV (19, 29). Occasionally, viral agents may produce clinical syndromes consistent with BRDC in the absence of bacterial co-infection, but their involvement is generally considered as antecedent to, or concurrent with, bacterial infection. Recent reports also linked RBCoV to BRDC, although it has received considerably less attention than other viral agents (49, 59, 67, 80).

In summary, initial respiratory viral infection plays a crucial role in triggering severe bacterial pneumonia.

Bovine Herpesvirus Type 1 (BoHV-1)

BoHV-1 is an important viral pathogen of cattle that can cause severe respiratory tract infections known as infectious bovine rhinotracheitis (IBR), abortion in pregnant cows, and is an important component of the BRDC (31, 32). The ability of BoHV-1 to immunosuppress the infected cattle (43, 64), establish a lifelong latent infection in the trigeminal ganglia (TG) of infected animals, reactivate from latency upon stress, and be transported anterogradely from neuron cell bodies in the TG to axon termini in the nasal epithelium followed by replication and nasal virus shedding allows the virus to circulate in susceptible cattle populations (31, 32).

A variety of mechanisms have been proposed to explain the role of BoHV-1 in viral-bacterial synergism in BRDC. One mechanism may involve BoHV-1 induction of inflammatory cytokines, which activate lymphocyte function-associated antigen-1 (LFA-1) on bovine leukocytes, thereby increasing susceptibility to *M. haemolytic* leukotoxin (LKT) (50). Such susceptibility contributes to the recruitment and activation of neutrophils which in turn amplifies the detrimental effects of LKT resulting in erosive lesions in the upper respiratory tract (71). Another mechanism can involve BoHV-1 induction of immunosuppression by causing abortive infection and subsequent apoptosis of CD4+ T lymphocytes (87). A further mechanism can involve BoHV-1 down-regulation of MHC class I molecule cell surface expression (43), which consequently suppresses the development of cytotoxic T lymphocytes. Therefore, during both the primary infection and latency reactivation, the immunosuppressive effects of virus replication combined with erosive lesions in the respiratory epithelium promote the establishment of bacterial pathogens, for example *M. haemolytica*, in the lower respiratory tract (31, 32, 85).

A variety of different vaccine approaches have been utilized over the years with variable success to prevent and control BoHV-1 dissemination in cattle. These approaches include: traditional modified live virus (MLV), traditional inactivated vaccines, entire gE gene-deleted MLV that allows differentiation between vaccinated and infected animals (DIVA, marker vaccine), inactivated marker vaccine, and protein/DNA based subunit vaccines (31, 32, 62).

Traditional MLV vaccines can in some cases be efficacious in reducing virus shedding and clinical disease in the vaccinated animals. However, there are important problems associated with traditional modified live virus vaccines. Traditional modified live virus vaccines cannot be distinguished from the wild type virus based on serological markers in a vaccinated animal when compared with an infected animal. Like wild type viruses, traditional modified live virus vaccines are shed following latency reactivation of the virus. Multivalent modified live virus BRD vaccines have been linked to recent outbreaks of respiratory infection in vaccinated feedlot cattle (89) and abortions in pregnant heifers (65, 66).

Currently, a gE-deleted marker vaccine is favored over traditional modified MLV because the virus is significantly attenuated, the virus does not shed following latency reactivation and it has a serological marker (10, 31, 32, 62). However, gE-deleted viruses induce significantly less serum neutralizing antibody relative to traditional modified live virus gC-deleted and TK-deleted viruses (31, 32, 34, 55) while the gC-deleted virus retains some degree of virulence and both gC-deleted and TK-deleted viruses are shed following latency reactivation (34, 35). Most importantly, traditional modified live virus, live gC-deleted viruses, gE-deleted viruses, and TK-deleted viruses have intact immunosuppressive properties (31, 32, 62).

Problems associated with inactivated and protein-based subunit viral vaccines include that they require at least two vaccinations and, more importantly, they do not induce a cellular immune response (31, 32, 62). Experimentally, DNA based envelope glycoprotein gD subunit vaccine induced protective serum neutralizing antibodies and cellular immune response (58), however it required two immunizations, which may not be cost effective for the cattle industry.

BoHV-1 envelope glycoprotein $U_L49.5$ interferes with transporter associated with antigen processing (TAP) functions required for peptide transport through the ER and subsequent loading into MHC-I. As a consequence, MHC-I surface expression is down regulated (43, 44). We have identified that the $U_L49.5$ luminal domain residues 30-32 together with $U_L49.5$ CT residues 80-96 promote efficient TAP inhibition and MHC-I down regulation functions (91). Following intranasal infection in calves, a $U_L49.5$ subdomain deletion mutant (BoHV-1$U_L$ 49.5Δ30-32 CT-null virus) lacking these sequences induced better serum neutralizing and cellular immune responses (90).

BoHV-1 envelope proteins gE and Us9 are not essential for retrograde transport from sensory nerve endings of the trigeminal ganglia neurons in the nasal epithelium to neuronal cell bodies in the trigeminal ganglia. However, they are needed for viral anterograde transport from trigeminal ganglia neurons to their processes in the nose. As a result, the deletion mutants are not shed from the nose following latency reactivation (10, 11, 16, 55). BoHV-1 gE-deleted viruses are highly attenuated in calves infected intranasally (34).

The inventor and coworkers have also determined that like a currently available gE-deleted virus, the BoHV-1 tmv virus with the gE cytoplasmic tail (CT) deletion is also highly attenuated and is not shed following latency reactivation (55). In microfluidic chambers of primary rabbit dorsal root ganglionic neuron cultures, the inventor and coworkers have confirmed that both Us9-deleted and gE CT-null (gE Am453) viruses have anterograde spread defects, but their retrograde transport is not affected (16, 55).

To construct a novel BoHV-1 tmv vaccine vector that lacks the immunosuppressive property and at the same time is not shed following latency reactivation, the inventor and coworkers have combined the individual deletions/mutations described above with respect to $U_L49.5$, gE CT and Us9 in a single virus, BoHV-1$U_L$ 49.5 Δ30-32 CT-null/gEΔCT/Us9Δ (BoHV-1 tmv). This novel triple mutant virus can be a more efficacious vaccine than the gE-deleted virus (current marker vaccine). By deleting the gE CT and entire Us9, the virus can be attenuated, and at the same time its safety can be maximized with respect to latency reactivation.

A recent comparative vaccine efficacy study comparing the BoHV-1 tmv with a gE-deleted virus demonstrates the benefits of the BoHV-1 tmv and the results are presented in the Examples section. These results demonstrate that the calves vaccinated with the BoHV-1 tmv generated significantly better protective immune response against virulent BoHV-1 challenge compared with the gE-deleted virus-infected calves.

Bovine Viral Diarrhea Virus (BVDV)

BVDV, a Pestivirus, is a significant pathogen of cattle that causes acute respiratory and enteric infections as well as reproductive disease of varying severity depending on the BVDV strain (69). Acute BVDV infections caused by type 1 strains result in mild disease characterized by fever, respiratory signs, diarrhea and leukopenia whereas infections caused by type 2 strains are more severe, usually characterized by high fever, hemorrhage, diarrhea, leukopenia and death. Regardless of type 1 or type 2, all BVDV infections in cattle, including MLV vaccine strains, are accompanied by immunosuppression due, at least in part, to the death of B and T cells within lymph nodes and gut associated lymphoid tissues as well as reduction in numbers of circulating white blood cells (12, 70, 72). In addition, BVDV regulates MHC-II expression and T helper 2 (Th2) responses (8). Consequently, the immunosuppression leaves the infected animal vulnerable to secondary and opportunistic infections, even after recovery, resulting in BRDC/shipping fever (8, 85).

BVDV has a positive stranded 12.3 Kb RNA genome which encodes a single polyprotein of approximately 4000 amino acids that is co- and post-translationally cleaved by the host and viral proteases to produce mature structural and nonstructural proteins of the virus (63). The order of proteins in the polyprotein is Npro (a nonstructural auto-protease), the capsid protein (C), the envelope glycoproteins (Erns, E1, and E2), and the nonstructural proteins (p7, NS/NS3, NS4A, NS4B, NS5A, and NS5B) (see FIG. 1).

Both MLV and killed vaccines have been used extensively in the US over the years, however the incidence of BRD and epidemiological situation in the vaccinated herds has not improved noticeably (31, 32, 56). The killed vaccines do not provide adequate protection against subsequent infection in the vaccinated population (31, 32). BVDV MLV vaccines are usually administered as multivalent (BoHV-1, BRSV, BVDV and PI3) vaccines and can sometimes be efficacious under experimental conditions (93), however they may serve as a source of in utero infection and immunosuppression (12, 70, 72). While inactivated vaccines are not desirably efficacious, the immunosuppressive effects of modified live BVDV alone could facilitate secondary bacterial infections (8, 23, 62). In addition, there is a concern that MLV BVDV vaccine virus may confound the BVD problem in the field further because of higher mutation rates associated with RNA viruses (9). Because of these problems associated with BVDV vaccines, Europeans have adopted a "test and cull" policy that does not permit BVDV MLV vaccination in cattle (74).

Protective Antigens of BVDV

The E2 protein, also known as gP 53, plays a major role in virus attachment and entry of BVDV. In addition, BVDV E2 is important for the induction of neutralizing antibodies and protection against BVDV challenge in cattle. The E2 protein of the NADL strain consists of about 370-410 amino acids and has a predicted molecular weight of about 40-55 kD.

A sequence of a BVDV strain NADL polyprotein, which includes the E2 protein, is available in the NCBI database (GI:7960753) and is shown below as SEQ ID NO:2.

```
  1   MELITNELLY KTYKQKPVGV EEPVYDQAGD PLFGERGAVH
 41   PQSTLKLPHK RGERDVPTNL ASLPKRGDCR SGNSRGPVSG
 81   IYLKPGPLFY QDYKGPVYHR APLELFEEGS MCETTKRIGR
121   VTGSDGKLYH IYVCIDGCII IKSATRSYQR VFRWVHNRLD
161   CPLWVTSCSD TKEEGATKKK TQKPDRLERG KMKIVPKESE
201   KDSKTKPPDA TIVVEGVKYQ VRKKGKTKSK NTQDGLYHNK
241   NKPQESRKKL EKALLAWAII AIVLFQVTMG ENITQWNLQD
281   NGTEGIQRAM FQRGVNRSLH GIWPEKICTG VPSHLATDIE
321   LKTIHGMMDA SEKTNYTCCR LQRHEWNKHG WCNWYNIEPW
361   ILVMNRTQAN LTEGQPPREC AVTCRYDRAS DLNVVTQARD
401   SPTPLTGCKK GKNTSFAGIL MRGPCNFEIA ASDVLFKEHE
441   RISMFQDTTL YLVDGLTNSL EGARQGTAKL TTWLGKQLGI
481   LGKKLENKSK TWFGAYAASP YCDVDRKIGY IWYTKNCTPA
521   CLPKNTKIVG PGKFDTNAED GKILHEMGGH LSEVLLLSLV
561   VLSDFAPETA SVMYLILHFS IPQSHVDVMD CDKTQLNLTV
601   ELTTADVIPG SVWNLGKWVC IRPNWWPYET TVVLAFEEVS
641   QVVKLVLRAL RDLTRIWNAA TTTAFLICLV KIVRGQMVQG
681   ILWLLLITGV QGHLDCKPEF SYAIAKDERI GQLGAEGLTT
721   TWKEYSPGMK LEDTMVIAWC EDGKLMYLQR CTRETRYLAI
761   LHTRALPTSV VFKKLFDGRK QEDVVEMNDN FEFGLCPCDA
801   KPIVRGKFNT TLLNGPAFQM VCPIGWTGTV SCTSFNMDTL
841   ATTVVRTYRR SKPFPHRQGC ITQKNLGEDL HNCILGGNWT
881   CVPGDQLLYK GGSIESCKWC GYQFKESEGL PHYPIGKCKL
921   ENETGYRLVD STSCNREGVA IVPQGTLKCK IGKTTVQVIA
```

```
 961  MDTKLGPMPC RPYEIISSEG PVEKTACTFN YTKTLKNKYF
1001  EPRDSYFQQY MLKGEYQYWF DLEVTDHHRD YFAESILVVV
1041  VALLGGRYVL WLLVTYMVLS EQKALGIQYG SGEVVMMGNL
1081  LTHNNIEVVT YFLLLYLLLR EESVKKWVLL LYHILVVHPI
1121  KSVIVILLMI GDVVKADSGG QEYLGKIDLC FTTVVLIVIG
1161  LIIARRDPTI VPLVTIMAAL RVTELTHQPG VDIAVAVMTI
1201  TLLMVSYVTD YFRYKKWLQC ILSLVSGVFL IRSLIYLGRI
1241  EMPEVTIPNW RPLTLILLYL ISTTIVTRWK VDVAGLLLQC
1281  VPILLLVTTL WADFLTLILI LPTYELVKLY YLKTVRTDIE
1321  RSWLGGIDYT RVDSIYDVDE SGEGVYLFPS RQAKQGNFSI
1361  LLPLIKATLI SCVSSKWQLI YMSYLTLDFM YYMHRKVIEE
1401  ISGGTNIISR LVAALIELNW SMEEEESKGL KKFYLLSGRL
1441  RNLIIKHKVR NETVASWYGE EEVYGMPKIM TIIKASTLSK
1481  SRHCIICTVC EGREWKGGTC PKCGRHGKPI TCGMSLADFE
1521  ERHYKRIFIR EGNFEGMCSR CQGKHRRFEM DREPKSARYC
1561  AECNRLHPAE EGDFWAESSM LGLKITYFAL MDGKVYDITE
1601  WAGCQRVGIS PDTHRVPCHI SFGSRMPFRQ EYNGFVQYTA
1641  RGQLFLRNLP VLATKVKMLM VGNLGEEIGN LEHLGWILRG
1681  PAVCKKITEH EKCHINILDK LTAFFGIMPR GTTPRAPVRF
1721  PTSLLKVRRG LETGWAYTHQ GGISSVDHVT AGKDLLVCDS
1761  MGRTRVVCQS NNRLTDETEY GVKTDSGCPD GARCYVLNPE
1801  AVNISGSKGA VVHLQKTGGE FTCVTASGTP AFFDLKNLKG
1841  WSGLPIFEAS SGRVVGRVKV GKNEESKPTK IMSGTQTVSK
1881  NTADLTEMVK KITSMNRGDF KQITLATGAG KTTELPKAVI
1921  EEIGRHKRVL VLIPLRAAAE SVYQYMRLKH PSISFNLRIG
1961  DMKEGDMATG ITYASYGYFC QMPQPKLRAA MVEYSYIFLD
2001  EYHCATPEQL AIIGKIHRFS ESIRVVAMTA TPAGSVTTTG
2041  QKHPIEEFIA PEVMKGEDLG SQFLDIAGLK IPVDEMKGNM
2081  LVFVPTRNMA VEVAKKLKAK GYNSGYYYSG EDPANLRVVT
2121  SQSPYVIVAT NAIESGVTLP DLDTVIDTGL KCEKRVRVSS
2161  KIPFIVTGLK RMAVTVGEQA QRRGRVGRVK PGRYYRSQET
2201  ATGSKDFHYD LLQAQRYGIE DGINVTKSFR EMNYDWSLYE
2241  EDSLLITQLE ILNNLLISED LPAAVKNIMA RTDHPEPIQL
2281  AYNSYEVQVP VLFPKIRNGE VTDTYENYSF LNARKLGEDV
2321  PVYIYATEDE DLAVDLLGLD WPDPGNQQVV ETGKALKQVT
2361  GLSSAENALL VALFGYVGYQ ALSKRHVPMI TDIYTIEDQR
2401  LEDTTHLQYA PNAIKTDGTE TELKELASGD VEKIMGAISD
2441  YAAGGLEFVK SQAEKIKTAP LFKENAEAAK GYVQKFIDSL
2481  IENKEEIIRY GLWGTHTALY KSIAARLGHE TAFATLVLKW
2521  LAFGGESVSD HVKQAAVDLV VYYVMNKPSF PGDSETQQEG
2561  RRFVASLFIS ALATYTYKTW NYHNLSKVVE PALAYLPYAT
2601  SALKMFTPTR LESVVILSTT IYKTYLSIRK GKSDGLLGTG
2641  ISAAMEILSQ NPVSVGISVM LGVGAIAAHN AIESSEQKRT
2681  LLMKVFVKNF LDQAATDELV KENPEKIIMA LFEAVQTIGN
2721  PLRLIYHLYG VYYKGWEAKE LSERTAGRNL FTLIMFEAFE
2761  LLGMDSQGKI RNLSGNYILD LIYGLHKQIN RGLKKMVLGW
2801  APAPFSCDWT PSDERIRLPT DNYLRVETRC PCGYEMKAFK
2841  NVGGKLTKVE ESGPFLCRNR PGRGPVNYRV TKYYDDNLRE
2881  IKPVAKLEGQ VEHYYKGVTA KIDYSKGKML LATDKWEVEH
2921  GVITRLAKRY TGVGFNGAYL GDEPNHRALV ERDCATITKN
2961  TVQFLKMKKG CAFTYDLTIS NLTRLIELVH RNNLEEKEIP
3001  TATVTTWLAY TFVNEDVGTI KPVLGERVIP DPVVDINLQP
3041  EVQVDTSEVG ITIIGRETLM TTGVTPVLEK VEPDASDNQN
3081  SVKIGLDEGN YPGPGIQTHT LTEEIHNRDA RPFIMILGSR
3121  NSISNRAKTA RNINLYTGND PREIRDLMAA GRMLVVALRD
3161  VDPELSEMVD FKGTFLDREA LEALSLGQPK PKQVTKEAVR
3201  NLIEQKKDVE IPNWFASDDP VFLEVALKND KYYLVGDVGE
3241  VKDQAKALGA TDQTRIIKEV GSRTYAMKLS SWFLQASNKQ
3281  MSLTPLFEEL LLRCPPATKS NKGHMASAYQ LAQGNWEPLG
3321  CGVHLGTIPA RRVKIHPYEA YLKLKDFIEE EEKKPRVKDT
3361  VIREHNKWIL KKIRFQGNLN TKKMLNPGKL SEQLDREGRK
3401  RNIYNHQIGT IMSSAGIRLE KLPIVRAQTD TKTFHEAIRD
3441  KIDKSENRQN PELHNKLLEI FHTIAQPTLK HTYGEVTWEQ
3481  LEAGINRKGA AGFLEKKNIG EVLDSEKHLV EQLVRDLKAG
3521  RKIKYYETAI PKNEKRDVSD DWQAGDLVVE KRPRVIQYPE
3561  AKTRLAITKV MYNWVKQQPV VIPGYEGKTP LFNIFDKVRK
3601  EWDSFNEPVA VSFDTKAWDT QVTSKDLQLI GEIQKYYYKK
3641  EWHKFIDTIT DHMTEVPVIT ADGEVYIRNG QRGSGQPDTS
3681  AGNSMLNVLT MMYAFCESTG VPYKSFNRVA RIHVCGDDGF
3721  LITEKGLGLK FANKGMQILH EAGKPQKITE GEKMKVAYRF
3761  EDIEFCSHTP VPVRWSDNTS SHMAGRDTAV ILSKMATRLD
3801  SSGERGTTAY EKAVAFSFLL MYSWNPLVRR ICLLVLSQQP
3841  ETDPSKHATY YYKGDPIGAY KDVIGRNLSE LKRTGFEKLA
3881  NLNLSLSTLG IWTKHTSKRI IQDCVAIGKE EGNWLVNADR
3921  LISSKTGHLY IPDKGFTLQG KHYEQLQLRT ETNPVMGVGT
3961  ERYKLGPIVN LLLRRLKILL MTAVGVSS
```

Any antigenic segment or fragment of the NADL polyprotein can be used as an antigen for expression by the expression cassettes and vectors described herein.

The E2 protein of the NADL strain can include about amino acids 660-1066 of the SEQ ID NO:2 polyprotein (see UniProt database sp|P19711|660-1066); the E2 protein with amino acids 660-1066 is shown below as SEQ ID NO:3.

```
  1    ATTTAFLVCL VKIVRGQMVQ GILWLLLITG VQGHLDCKPE
 41    FSYAIAKDER IGQLGAEGLT TTWKEYSPGM KLEDTMVIAW
 81    CEDGKLMYLQ RCTRETRYLA ILHTRALPTS VVFKKLFDGR
121    KQEDVVEMND NFEFGLCPCD AKPIVRGKFN TTLLNGPAFQ
161    MVCPIGWTGT VSCTSFNMDT LATTVVRTYR RSKPFPHRQG
201    CITQKNLGED LHNCILGGNW TCVPGDQLLY KGGSIESCKW
241    CGYQFKESEG LPHYPIGKCK LENETGYRLV DSTSCNREGV
281    AIVPQGTLKC KIGKTTVQVI AMDTKLGPMP CRPYEIISSE
321    GPVEKTACTF NYTKTLKNKY FEPRDSYFQQ YMLKGEYQYW
361    FDLEVTDHHR DYFAESILVV VVALLGGRYV LWLLVTYMVL
401    SEQKALG
```

The C-terminus of E2 includes about 30 hydrophobic amino acids (FIG. 1), which can serve as a transmembrane anchor for the full length E2, which remains cell associated in virus-infected cells (53).

In another example, BVDV E2 protein with an amino acid sequence provided by GenBank accession# GI 3859502 (1.18 kb) (shown below as SEQ ID NO:4) can be incorporated into the vectors and compositions described herein.

```
  1    FPECKEGFQY AISKDRKIGP LGPFSLTTTW HLPTKKIVDS
 41    MVQVWCDGKN LKILETCTKE ERYLVAVHER ALSTSAEFMQ
 81    ISSGTKGPEV IDMHDDFEFG LCPCDSKPVM RGKFNASLLN
121    GPAFQMVCPQ GWTGTIECIL ANQDTLDTTV VRTYRRTTPF
161    QRRKWCTYEK IIGEDIHECI LGGNWTCITG DHSKLKDGPI
201    KKCKWCGYDF FDSEGLPHYP IGKCMLSNES GYRIVDDTSC
241    DRGGVAIVPT GTLKCRIGKA TVQVIATNTD LGPMPCSPDE
281    VIASEGPVEK TACTFNYSKT LPNKYYEPRD RYFQQYMLKG
321    EWQYWFDLDT VDHHKDYFSE FIVIAVVALL GGKYVLWLLV
361    TYMILSEQMA MG
```

An example of a BVDV E2-1 protein with an amino acid sequence provided below as SEQ ID NO:5 can be encoded within the expression cassettes, vectors and compositions described herein.

```
  1    HLDCKPEFSY AIAKDERIGQ LGAEGLTTTW KEYSPGMKLE
 41    DTMVIAWCED GKLMYLQRCT RETRYLAILH TRALPTSVVF
 81    KKLFDGRKQE DVVEMNDNFE FGLCPCDAKP IVRGKFNTTL
121    LNGPAFQMVC PIGWTGTVSC TSFNMDTLAT TVVRTYRRSK
161    PFPHRQGCIT QKNLGEDLHN CILGGNWTCV PGDQLLYKGG
201    SIESCKWCGY QFKESEGLPH YPIGKCKLEN ETGYRLVDST
241    SCNREGVAIV PQGTLKCKIG KTTVQVIAMD TKLGPMPCRP
281    YEIISSEGPV EKTACTFNYT KTLKNKYFEP RDSYFQQYML
321    KGEYQYWFDL EVTDHHRDYF AESILVVVVA LLGGRYVLWL
361    LVTYMVLSEQ KALG
```

A Bos taurus codon optimized nucleic acid segment encoding the BVDV E2-1 protein with SEQ ID NO:5, for example, can have the following nucleotide sequence, shown below as SEQ ID NO:6.

```
   1   CACCTGGATT GCAAGCCTGA GTTCTCATAC GCCATCGCTA
  41   AAGACGAGAG AATTGGCCAG CTGGGGGCCG AAGGACTGAC
  81   CACAACTTGG AAGGAGTATT CTCCAGGCAT GAAACTGGAA
 121   GATACCATGG TCATCGCTTG GTGCGAGGAC GGGAAGCTGA
 161   TGTACCTGCA GCGGTGCACA AGAGAAACTC GATATCTGGC
 201   CATTCTGCAT ACTCGAGCTC TGCCCACCAG TGTGGTCTTC
 241   AAGAAACTGT TTGACGGACG GAAGCAGGAG GATGTGGTCG
 281   AAATGAACGA CAATTTCGAG TTTGGCCTGT GCCCCTGTGA
 321   TGCCAAGCCT ATCGTGAGGG GAAAATTCAA CACCACACTG
 361   CTGAATGGCC CAGCTTTTCA GATGGTGTGC CCCATTGGCT
 401   GGACCGGGAC AGTCTCATGT ACCAGCTTCA ACATGGACAC
 441   TCTGGCCACT ACCGTGGTCC GCACTTACCG GAGGGTCAAG
 481   CCCTTTCCTC ACAGACAGGG CTGCATCACC CAGAAAAACC
 521   TGGGGGAGGA TCTGCATAAC TGCATTCTGG GAGGAAATTG
 561   GACCTGCGTG CCAGGGGACC AGCTGCTGTA CAAGGGAGGC
 601   TCCATCGAAT CTTGCAAGTG GTGTGGCTAC CAGTTCAAAG
 641   AGAGCGAAGG GCTGCCTCAC TATCCAATTG GAAGTGTAA
 721   ACTGGAGAAC GAAACCGGCT ATCGGCTGGT GGATTCTACA
 761   AGTTGCAATA GGGAGGGAGT GGCTATCGTC CCTCAGGGGA
 801   CACTGAAGTG TAAAATCGGA AAGACAACTG TGCAGGTCAT
 841   TGCTATGGAC ACTAAACTGG GGCCAATGCC CTGCAGACCT
 881   TACGAGATCA TTAGCTCCGA GGGACCAGTG GAAAAGACCG
 921   CCTGTACCTT CAACTACACT AAAACCCTGA AGAACAAGTA
 961   TTTCGAACCC CGAGATTCCT ACTTTCAGCA GTATATGCTG
1001   AAGGGCGAGT ACCAGTATTG GTTCGACCTG GAAGTGACAG
1041   ACCACCATAG GGATTACTTT GCCGAGAGCA TCCTGGTGGT
1081   CGTGGTCGCT CTGCTGGGAG GACGCTACGT GCTGTGGCTG
1121   CTGGTGACCT ATATGGTCCT GTCCGAGCAG AAGGCCCTGG
1161   GC
```

An example of an amino acid sequence of a BVDV E2-1 protein with an N-terminal gD signal sequence is provided below as SEQ ID NO:7. This fusion protein can be encoded within the expression cassettes, vectors and compositions described herein.

```
  1    MQGPTLAVLG ALLAVAVSLH LDCKPEFSYA IAKDERIGQL
 41    GAEGLTTTWK EYSPGMKLED TMVIAWCEDG KLMYLQRCTR
 81    ETRYLAILHT RALPTSVVFK KLFDGRKQED VVEMNDNFEF
121    GLCPCDAKPI VRGKFNTTLL NGPAFQMVCP IGWTGTVSCT
```

```
161   SFNMDTLATT VVRTYRRSKP FPHRQGCITQ KNLGEDLHNC

201   ILGGNWTCVP GDQLLYKGGS IESCKWCGYQ FKESEGLPHY

241   PIGKCKLENE TGYRLVDSTS CNREGVAIVP QGTLKCKIGK

281   TTVQVIAMDT KLGPMPCRPY EIISSEGPVE KTACTFNYTK

321   TLKNKYFEPR DSYFQQYMLK GEYQYWFDLE VTDHHRDYFA

361   ESILVVVVAL LGGRYVLWLL VTYMVLSEQK ALG
```

A *Bos taurus* codon optimized nucleic acid segment encoding the gD-BVDV E2-1 fusion protein with SEQ ID NO:7, for example, can have the following nucleotide sequence, shown below as SEQ ID NO:8.

```
   1   ATCGATGCCG CCACCATGCA GGGACCAACA CTGGCCGTGC

41   TGGGGGCTCT GCTGGCTGTG GCTGTCTCCC TGTTCCCCGA

81   GTGCAAGGAA GGATTTCAGT ACGCCATCGA CAAGGACCGG

121   AAAATTGGAC CACTGGGACC AGAGTCCCTG ACCACAACTT

161   GGCACCTGCC CACCAAGAAA ATCGTGGACT CTATGGTGCA

201   GGTCTGGTGC GATGGCAAGA ACCTGAAAAT TCTGGAGACA

241   TGTACTAAGG AGGAGAGATA CCTGGTGGCT GTCCACGAGC

281   GCGCTCTGTC TACCAGTGCC GAGTTCATGC AGATCAGCTC

321   CGGAACAAAG GGCCCTGAAG TGATCGACAT GCACGACGAT

361   TTCGAATTTG GCCTGTGCCC CTGTGATAGT AAGCCTGTGA

401   TGCGCGGAAA ATTCAACGCT TCACTGCTGA ATGGCCCTGC

441   CTTTCAGATG GTGTGCCCAC AGGGGTGGAC CGGAACAATC

481   GAGTGTATTC TGGCTAACCA GGACACACTG GATACCACAG

521   TGGTCCGGAC TTACCGGAGG ACTACCCCTT TCAGCGCAG

561   AAAGTGGTGC ACCTATGAGA AAATCATTGG CGAGGACATC

601   CACGAGTGCA TCCTGGGCGG GAATTGGACC TGTATCACAG

641   GCGACCATTC TAAGCTGAAA GATGGGCCAA TTAAGAAATG

681   CAAGTGGTGT GGCTACGACT TCTTTGATAG TGAGGGACTG

721   CCTCATTATC CAATCGGCAA ATGTATGCTG TCAAACGAAA

761   GCGGGTACAG ATATGTGGAC GATACTAGCT GCGATCGAGG

801   AGGAGTGGCT ATCGTCCCAA CTGGGACCCT GAAGTGTAGG

841   ATCGGAAAAG CTACCGTGCA GGTCATTGCC ACAAATACTG

881   ACCTGGGACC AATGCCTTGC TCCCCAGATG AAGTGATCGC

921   TTCTGAGGGA CCTGTCGAAA AGACTGCCTG TACCTTCAAC

961   TACTCCAAGA CACTGCCAAA CAAGTACTAT GAGCCCCGAG

1001   ACCGGTACTT CCAGCAGTAT ATGCTGAAGG GGGAATGGCA

1041   GTACTGGTTT GACCTGGATA CCGTGGACCA CCATAAGGAT

1081   TACTTCTCAG AGTTTATCGT GATTGCCGTG GTCGCTCTGC

1121   TGGGGGGAAA GTACGTGCTG TGGCTGCTGG TCACCTATAT

1161   GATCCTGAGT GAACAGATGG CCATGGGCAT GCAT
```

An expression cassette with a ClaI-NsiI nucleic acid segment that includes the SEQ ID NO:7 BVDV E2-1 nucleotide sequence has been made. This BVDV E2-1 expression cassette includes the following in the 5'-3' direction: a Kozak sequence, nucleic acid segment for BHV-1 gD signal sequence (GenBank accession # AFV53430.1, aa 1-19), a *Bos taurus* codon-optimized nucleotide sequence for BVDV E2-1 (GenBank accession # NP_776263.1), and is provided below as SEQ ID NO:9 (and shown in FIG. 15A-15B).

```
   1   GGTACCCTCG TGAGGCTCCG GTGCCCGTCA GTGGGCAGAG

41   CGCACATCGC CCACAGTCCC CGAGAAGTTG GGGGGAGGGG

81   TCGGCAATTG AACCGGTGCC TAGAGAAGGT GGCGCGGGGT

121   AAACTGGGAA AGTGATGTCG TGTACTGGCT CCGCTTTTTT

161   CCCGAGGGTG GGGGAGAACC GTATATAAGT GCAGTAGTCG

201   CCGTGAACGT TCTTTTTCGC AACGGGTTTG CCGCCAGAAC

241   ACAGGTAAGT GCCGTGTGTG GTTCCCGCGG GCCTGGCCTC

281   TTTACGGGTT ATGGCCCTTG CGTGCCTTGA ATTACTTCCA

321   CCTGGCTGCA GTACGTGATT CTTGATCCCG AGCTTCGGGT

361   TGGAAGTGGG TGGGAGAGTT CGAGGCCTTG CGCTTAAGGA

401   GCCCCTTCGC CTCGTGCTTG AGTTGAGGCC TGGCCTGGGC

441   GCTGGGGCCG CCGCGTGCGA ATCTGGTGGC ACCTTCGCGC

431   CTGTCTCGCT GCTTTCGATA AGTCTCTAGC CATTTAAAAT

521   TTTTGATGAC CTGCTGCGAC GCTTTTTTTC TGGCAAGATA

561   GTCTTGTAAA TGCGGGCCAA GATCTGCACA CTGGTATTTC

601   GGTTTTTGGG GCCGCGGGCG GCGACGGGGC CCGTGCGTCC

641   CAGCGCACAT GTTCGGCGAG GCGGGGCCTG CGAGCGCGGC

681   CACCGAGAAT CGGACGGGGG TAGTCTCAAG CTGGCCGGCC

721   TGCTCTGGTG CCTGGCCTCG CGCCGCCGTG TATCGCCCCG

761   CCCTGGGCGG GAAGGCTGGC CCGGTCGGCA CCAGTTGCGT

801   GAGCGGAAAG ATGGCCGCTT CCCGGCCCTG CTGCAGGGAG

841   CTCAAAATGG AGGACGCGGC GCTCGGGAGA GCGGGCGGGT

881   GAGTCACCCA CACAAAGGAA AAGGGCCTTT CCGTCCTCAG

921   CCGTCGGTTC ATGTGACTCC ACGGAGTACC GGGCGCCGTC

961   CAGGCACCTC GATTAGTTCT CGAGCTTTTG GAGTACGTCG

1001   TCTTTAGGTT GGGGGGAGGG GTTTTATGCG ATGGAGTTTC

1041   CCCACACTGA GTGGGTGGAG ACTGAAGTTA GGCCAGCTTG

1081   GCACTTGATG TAATTCTCCT TGGAATTTGC CCTTTTTGAG

1121   TTTGGATCTT GGTTCATTCT CAAGCCTCAG ACAGTGGTTC

1161   AAAGTTTTTT TCTTCCATTT CAGGTGTCGT GAGGAATTAG

1201   CTTGGTACTA ATACGACTCA CTATAGGGAG ACCCAAGCTG

1241   GCTAGGTAAG TGTACGAGCT CGATCACTAG TCCAGTGTGG

1281   ATCGATCGCC GCCACCATGC AGGGACCCAC CCTGGCCGTG

1321   CTGGGCGCTC TGCTGGCTGT GGCTGTCAGT CTGCACCTGG

1361   ATTGCAAGCC TGAGTTCTCA TACGCCATCG CTAAAGACGA

1401   GAGAATTGGC CAGCTGGGGG CCGAAGGACT GACCACAACT
```

-continued

```
1441 TGGAAGGAGT ATTCTCCAGG CATGAAACTG GAAGATACCA
1481 TGGTCATCGC TTGGTGCGAG GACGGGAAGC TGATGTACCT
1521 GCAGCGGTGC ACAAGAGAAA CTCGATATCT GGCCATTCTG
1561 CATACTCGAG CTCTGCCCAC CAGTGTGGTC TTCAAGAAAC
1601 TGTTTGACGG ACGGAAGCAG GAGGATGTGG TCGAAATGAA
1641 CGACAATTTC GAGTTTGGCC TGTGCCCCTG TGATGCCAAG
1681 CCTATCGTGA GGGGAAAATT CAACACCACA CTGCTGAATG
1721 GCCCAGCTTT TCAGATGGTG TGCCCCATTG GCTGGACCGG
1761 GACAGTCTCA TGTACCAGCT TCAACATGGA CACTCTGGCC
1801 ACTACCGTGG TCCGCACTTA CCGGAGGTCT AACCCCTTTC
1841 CTCACAGACA GGGCTGCATC ACCCAGAAAA ACCTGGGGGA
1881 GGATCTGCAT AACTGCATTC TGGGAGGAAA TTGGACCTGC
1921 GTGCCAGGGG ACCAGCTGCT GTACAAGGGA GGCTCCATCG
1961 AATCTTGCAA GTGGTGTGGC TACCAGTTCA AGAGAGCGA
2001 AGGGCTGCCT CACTATCCAA TTGGAAAGTG TAAACTGGAG
2041 AACGAAACCG GCTATCGGCT GGTGGATTCT ACAAGTTGCA
2081 ATAGGGAGGG AGTGGCTATC GTCCCTCAGG GGACACTGAA
2121 GTGTAAAATC GGAAAGACAA CTGTGCAGGT CATTGCTATG
2161 GACACTAAAC TGGGGCCAAT GCCCTGCAGA CCTTACGAGA
2201 TCATTAGCTC CGAGGGACCA GTGGAAAAGA CCGCCTGTAC
2241 CTTCAACTAC ACTAAAACCC TGAAGAACAA GTATTTCGAA
2281 CCCCGAGATT CCTACTTTCA GCAGTATATG CTGAAGGGCG
2321 AGTACCAGTA TTGGTTCGAC CTGGAAGTGA CAGACCACCA
2361 TAGGGATTAC TTTGCCGAGA GCATCCTGGT GGTCGTGGTC
2401 GCTCTGCTGG GAGGACGCTA CGTGCTGTGG CTGCTGGTGA
2441 CCTATATGGT CCTGTCCGAG CAGAAGGCCC TGGGCATGCA
2481 TGGTAAGCCT ATCCCTAACC CTCTCCTCGG TCTCGATTCT
2521 ACGCGTACCG GTCATCATCA CCATCACCAT TGAGTTTAAA
2561 CCCGCTGATC AGCCTCGACT GTGCCTTCTA GTTGCCAGCC
2601 ATCTGTTGTT TGCCCCTCCC CCGTGCCTTC CTTGACCCTG
2641 GAAGGTGCCA CTCCCACTGT CCTTTCCTAA TAAAATGAGG
2681 AAATTGCATC GCATTGTCTG AGTAGGTGTC ATTCTATTCT
2721 GGGGGGTGGG GTGGGCAGG ACAGCAAGGG GGAGGATTGG
2761 GAAGACAATA GCAGGCATGC TGGGGATGCG GTGGGCTCTA
2801 TGGCTTGGTA CC.
```

The 1.235 bp ClaI/NsiI fragment encoding the gD signal sequence-BVDV E2-1 fusion protein was cloned into the corresponding ClaI/NsiI sites of the pPreBVDV-E2 chimeric vector (which includes SEQ ID NO: 1) resulting in a BVDVE2-1 chimeric gene expression cassette (SEQ ID NO:9).

An example of a BVDV E2-2 protein with an amino acid sequence provided below as SEQ ID NO: 10 can be encoded within the expression cassettes, vectors and compositions described herein.

```
  1 FPECKEGFQY AISKDRKIGP LGPESLTTTW HLPTKKIVDS
 41 MVQVWCDGKN LKILETCTKE ERYLVAVHER ALSTSAEFMQ
 81 ISSGTKGPEV IDMHDDFEFG LCPCDSKPVM RGKFNASLLN
121 GPAFQMVCPQ GWTGTIECIL ANQDTLDTTV VRTYRRTTPF
161 QRRKWCTYEK IIGEDIHECI LGGNWTCITG DHSKLKDGPI
201 KKCKWCGYDF FDSEGLPHYP IGKCMLSNES GYRYVDDTSC
241 DRGGVAIVPT GTLKCRIGKA TVQVIATNTD LGPMPCSPDE
281 VIASEGPVEK TACTFNYSKT LPNKYYEPRD RYFQQYMLKG
321 EWQYWFDLDT VDHHKDYFSE FIVIAVVALL GGKYVLWLLV
361 TYMILSEQMA MG
```

A *Bos taurus* codon optimized nucleic acid segment encoding the BVDV E2-2 protein with SEQ ID NO: 10, for example, can have the following nucleotide sequence, shown below as SEQ ID NO:11.

```
  1 TTCCCCGAGT GCAAGGAAGG ATTTCAGTAC GCCATCAGCA
 41 AGGACCGGAA AATTGGACCA CTGGGACCAG AGTCCCTGAC
 81 CACAACTTGG CACCTGCCCA CCAAGAAAAT CGTGGACTCT
121 ATGGTGCAGG TCTGGTGCGA TGGCAAGAAC CTGAAAATTC
161 TGGAGACATG TACTAAGGAG GAGAGATACC TGGTGGCTGT
201 CCACGAGCGC GCTCTGTCTA CCAGTGCCGA GTTCATGCAG
241 ATCAGCTCCG GAACAAGGG CCCTGAAGTG ATCGACATGC
281 ACGACGATTT CGAATTTGGC CTGTGCCCCT GTGATAGTAA
321 GCCTGTGATG CGCGGAAAAT TCAACGCTTC ACTGCTGAAT
361 GGCCCTGCCT TTCAGATGGT GTGCCCACAG GGGTGGACCG
401 GAACAATCGA GTGTATTCTG GCTAACCAGG ACACACTGGA
441 TACCACAGTG GTCCGGACTT ACCGGAGGAC TACCCCTTTT
481 CAGCGCAGAA AGTGGTGCAC CTATGAGAAA ATCATTGGCG
521 AGGACATCCA CGAGTGCATC CTGGGCGGGA ATTGGACCTG
561 TATCACAGGC GACCATTCTA AGCTGAAAGA TGGGCCAATT
601 AAGAAATGCA AGTGGTGTGG CTACGACTTC TTTGATAGTG
641 AGGGACTGCC TCATTATCCA ATCGGCAAAT GTATGCTGTC
681 AAACGAAAGC GGGTACAGAT ATGTGGACGA TACTAGCTGC
721 GATCGAGGAG GAGTGGCTAT CGTCCCAACT GGGACCCTGA
761 AGTGTAGGAT CGGAATAGCT ACCGTGCAGG TCATTGCCAC
801 AAATACTGAC CTGGGACCAA TGCCTTGCTC CCAGATGAA
841 GTGATCGCTT CTGAGGGACC TGTCGAAAAG ACTGCCTGTA
881 CCTTCAACTA CTCCAAGACA CTGCCAAACA AGTACTATGA
921 GCCCCGAGAC CGGTACTTCC AGCAGTATAT GCTGAAGGGG
```

```
 961   GAATGGCAGT ACTGGTTTGA CCTGGATACC GTGGACCACC
1001   ATAAGGATTA CTTCTCAGAG TTTATCGTGA TTGCCGTGGT
1041   CGCTCTGCTG GGGGGAAAGT ACGTGCTGTG GCTGCTGGTC
1081   ACCTATATGA TCCTGAGTGA ACAGATGGCC ATGGGC
```

An example an amino acid sequence of a BVDV E2-2 protein with an N-terminal gD signal sequence is provided below as SEQ ID NO: 12. This fusion protein can be encoded within the expression cassettes, vectors and compositions described herein.

```
  1   MQGPTLAVLG ALLAVAVSLF PECKEGFQYA ISKDRKIGPL
 41   GPESLTTTWH LPTKKTVDSM VQVWCDGKNL KILETCTKEE
 81   RYLVAVHERA LSTSAEFMQI SSGTKGPEVI DMHDDFEFGL
121   CPCDSKPVMR GKFNASLLNG PAFQMVCPQG WTGTIECILA
121   NQDTLDTTVV RTYRRTTPFQ RRKWCTYEKI IGEDIHECIL
121   GGNWTCITGD HSKLKDGPIK KCKWCGYDFF DSEGLPHYPI
121   GKCMLSNESG YRYVDDISCD RGGVAIVPTG TLKCRIGKAT
121   VQVIATNTDL GPMPCSPDEV IASEGPVEKT ACTFNYSKTL
121   PNKYYEPRDR YFQQYMLKGE WQYWFDLDTV DHHKDYFSEF
121   IVIAVVALLG GKYVLWLLVT YMILSEOMAM GMH
```

A *Bos taurus* codon optimized nucleic acid segment encoding the gD-BVDV E2-2 fusion protein with SEQ ID NO: 12, for example, can have the following nucleotide sequence, shown below as SEQ ID NO: 13.

```
  1   ATGCAGGGAC CAACACTGGC CGTGCTGGGG GCTCTGCTGG
 41   CTGTGGCTGT CTCCCTGTTC CCCGAGTGCA AGGAAGGATT
 81   TCAGTACGCC ATCAGCAAGG ACCGGAAAAT TGGACCACTG
121   GGACCAGAGT CCCTGACCAC AACTTGGCAC CTGCCCACCA
161   AGAAAATCGT GGACTCTATG GTGCAGGTCT GGTGCGATGG
201   CAAGAACCTG AAAATTCTGG AGACATGTAC TAAGGAGGAG
241   AGATACCTGG TGGCTGTCCA CGAGCGCGCT CTGTCTACCA
281   GTGCCGAGTT CATGCAGATC AGCTCCGGAA CAAAGGGCCC
321   TGAAGTGATC GACATGCACG ACGATTTCGA ATTTGGCCTG
361   TGCCCCTGTG ATAGTAAGCC TGTGATGCGC GGAAAATTCA
401   ACGCTTCACT GCTGAATGGC CCTGCCTTTC AGATGGTGTG
441   CCCACAGGGG TGGACCGGAA CAATCGAGTG TATTCTGGCT
481   AACCAGGACA CACTGGATAC CACAGTGGTC CGGACTTACC
521   GGAGGACTAC CCCTTTTCAG CGCAGAAAGT GGTGCACCTA
561   TGAGAAAATC ATTGGCGAGG ACATCCACGA GTGCATCCTG
601   GGCGGGAATT GGACCTGTAT CACAGGCGAC CATTCTAAGC
641   TGAAAGATGG GCCAATTAAG AAATGCAAGT GGTGTGGCTA
681   CGACTTCTTT GATAGTGAGG GACTGCCTCA TTATCCAATC
721   GGCAAATGTA TGCTGTCAAA CGAAAGCGGG TACAGATATG
761   TGGACGATAC TAGCTGCGAT CGAGGAGGAG TGGCTATCGT
801   CCCAACTGGG ACCCTGAAGT GTAGGATCGG AAAAGCTACC
841   GTGCAGGTCA TTGCCACAAA TACTGACCTG GGACCAATGC
881   CTTGCTCCCC AGATGAAGTG ATCGCTTCTG AGGGACCTGT
921   CGAAAAGACT GCCTGTACCT TCAACTACTC CAAGACACTG
961   CCAAACAAGT ACTATGAGCC CCGAGACCGG TACTTCCAGC
1001  AGTATATGCT GAAGGGGGAA TGGCAGTACT GGTTTGACCT
1041  GGATACCGTG GACCACCATA AGGATTACTT CTCAGAGTTT
1081  ATCGTGATTG CCGTGGTCGC TCTGCTGGGG GGAAAGTACG
1201  TGCTGTGGCT GCTGGACACC TATATGATCC TGAGTGAACA
1261  GATGGCCATG GGCATGCAT
```

An expression cassette with a ClaI-NsiI nucleic acid segment that includes the SEQ ID NO: 13 nucleotide sequence of the BVDV E2-2 fusion protein has been made. This BVDV E2-2 expression cassette includes the following in the 5'-3' direction: a Kozak sequence, nucleic acid segment for BHV-1 gD signal sequence (GenBank accession # AFV53430.1, aa 1-19), a *Bos taurus* codon-optimized nucleotide sequence for BVDV E2-2 (GenBank accession # AAC72814.1), and is provided below as SEQ ID NO: 14 (and shown in FIG. 16A-16B).

```
  1   GGTACCCTCG TGAGGCTCCG GTGCCCGTCA GTGGGCAGAG
 41   CGCACATCGC CCACACTCCC CGAGAAGTTG GGGGGAGGGG
 81   TCGGCAATTG AACCGGTGCC TAGAGAAGGT GGCGCGGGGT
121   AAACTGGGAA AGTGATGTCG TGTACTGGCT CCGCCTTTTT
161   CCCGAGGGTG GGGGAGAACC GTATATAAGT GCAGTAGTCG
201   CCGTGAACGT TCTTTTTCGC AACGGGTTTG CCGCCAGAAC
241   ACAGGTAAGT GCCGTGTGTG GTTCCCGCGG GCCTGGCCTC
281   TTTACGGGTT ATGGCCCTTG CGTGCCTTGA ATTACTTCCA
321   CCTGGCTGCA GTACGTGATT CTTGATCCCG AGCTTCGGGT
361   TGGAAGTGGG TGGGAGAGTT CGAGGCCTTG CGCTTAAGGA
401   GCCCCTTCGC CTCGTGCTTG AGTTGAGGCC TGGCCTGGGC
441   GCTGGGGCCG CCGCGTGCGA ATCTGGTGGC ACCTTCGCGC
481   CTGTCTCGCT GCTTTCGATA AGTCTCTAGC CATTTAAAAT
521   TTTTGATGAC CTGCTGCGAC GCTTTTTTTC TGGCAAGATA
561   GTCTTGTAAA TGCGGGCCAA GATCTGCACA CTGGTATTTC
601   GGTTTTTGGG GCCGCGGGCG GCGACGGGGC CCGTGCGTCC
641   CAGCGCACAT GTTCGGCGAG GCGGGGCCTG CGAGCGCGGC
681   CACCGAGAAT CGGACGGGGG TAGTCTCAAG CTGGCCGGCC
721   TGCTCTGGTG CCTGGCCTCG CGCCGCCGTG TATCGCCCCG
761   CCCTGGGCGG CAAGGCTGGC CCGGTCGGCA CCAGTTGCGT
801   CACCCGAAAG ATGGCCGCTT CCCGGCCCTG CTGCAGGGAG
841   CTCAAAATGG AGGACGCGGC GCTCGGGAGA GCGGGCGGGT
```

-continued

```
881   GAGTCACCCA CACAAAGGAA AAGGGCCTTT CCGTCCTCAG
921   CCGTCGCTTC ATGTGACTCC ACGGAGTACC GGGCGCCGTC
961   CAGGCACCTC GATTAGTTCT CGAGCTTTTG GAGTACGTCG
1001  TCTTTAGGTT GGGGGGAGGG GTTTTATGCG ATGGAGTTTC
1041  CCCACACTGA GTGGGTGGAG ACTGAAGTTA GGCCAGCTTG
1081  GCACTTGATG TAATTCTCCT TGGAATTTGC CCTTTTTGAG
1121  TTTGGATCTT GGTTCATTCT CAAGCCTCAG ACAGTGGTTC
1161  AAAGTTTTTT TCTTCCATTT CAGGTGTCGT GAGGAATTAG
1201  CTTGGTACTA ATACGACTCA CTATAGGGAG ACCCAAGCTG
1241  GCTAGGTAAG TGTACGAGCT CGATCACTAG TCCAGTGTGG
1281  ATCGATCGCC GCCACCATGC AGGGACCAAC ACTGGCCGTG
1321  CTGGGGGCTC TGCTGGCTGT GGCTGTCTCC CTGTTCCCCG
1361  AGTGCAAGGA AGGATTTCAG TACGCCATCA GCAAGGACCG
1401  GAAAATTGGA CCACTGGGAC CAGAGTCCCT GACCACAACT
1441  TGGCACCTGC CCACCAAGAA AATCGTGGAC TCTATGGTGC
1481  AGGTCTGGTG CGATGGCAAG AACCTGAAAA TTCTGGAGAC
1521  ATGTACTAAG GAGGAGAGAT ACCTGGTGGC TGTCCACGAG
1561  CGCGCTCTGT CTACCAGTGC CGAGTTCATG CAGATCAGCT
1601  CCGGAACAAA GGGCCCTGAA GTGATCGACA TGCACGACGA
1641  TTTCGAATTT GGCCTGTGCC CCTGTGATAG TAAGCCTGTG
1681  ATGCGCGGAA AATTCAACGC TTCACTGCTG AATGGCCCTG
1721  CCTTTCAGAT GGTGTGCCCA CAGGGGTGGA CCGGAACAAT
1761  CGAGTGTATT CTGGCTAACC AGGACACACT GGATACCACA
1801  GTGGTCCGGA CTTACCGGAG GACTACCCCT TTTCAGCGCA
1841  GAAAGTGGTG CACCTATGAG AAAATCATTG GCGAGGACAT
1881  CCACGAGTGC ATCCTGGGCG GGAATTGGAC CTGTATCACA
1921  GGCGACCATT CTAAGCTGAA AGATGGGCCA ATTAAGAAAT
1961  GCAAGTGGTG TGGCTACGAC TTCTTTGATA GTGAGGGACT
2001  GCCTCATTAT CCAATCGGCA AATGTATGCT GTCAAACGAA
2041  AGCGGGTACA GATATGTGGA CGATACTAGC TGCGATCGAG
2081  GAGGAGTGGC TATCGTCCCA ACTGGGACCC TGAAGTGTAG
2121  GATCGGAAAA GCTACCGTGC AGGTCATTGC CACAAATACT
2161  GACCTGGGAC CAATGCCTTG CTCCCCAGAT GAAGTGATCG
2201  CTTCTGAGGG ACCTGTCGAA AAGACTGCCT GTACCTTCAA
2241  CTACTCCAAG ACACTGCCAA AGAAGTACTA TGAGCCCCGA
2281  GACCGGTACT TCCAGCAGTA TATGCTGAAG GGGGAATGGC
2321  AGTACTGGTT TGACCTGGAT ACCGTGGACC ACCATAAGGA
2361  TTACTTCTCA GAGTTTATCG TGATTGCCGT GGTCGCTCTG
2401  CTGGGGGGAA AGTACGTGCT GTGGCTGCTG GTCACCTATA
2441  TGATCCTGAG TGAACAGATG GCCATGGGCA TGCATGGTAA
```

-continued

```
2481  GCCTATCCCT AACCCTCTCC TCGGTCTCGA TTCTACGCGT
2521  ACCGGTCATC ATCACCATCA CCATTGAGTT TAAACCCGCT
2561  GATCAGCCTC GACTGTGCCT TCTAGTTGCC AGCCATCTGT
2601  TGTTTGCCCC TCCCCCGTGC CTTCCTTGAC CCTGGAAGGT
2641  GCCACTCCCA CTGTCCTTTC CTAATAAAAT GAGGAAATTG
2681  CATCGCATTG TCTGAGTAGG TGTCATTCTA TTCTGGGGGG
2721  TGGGGTGGGG CAGGACAGCA AGGGGGAGGA TTGGGAAGAC
2761  AATAGCAGGC ATGCTGGGGA TGCGGTGGGC TCTATGGCTT
2801  GGTACC
```

Some studies have reported that immunization with E2 glycoproteins cloned in live recombinant virus vectors induced BVDV-specific neutralizing antibody (6, 18, 77). Subunit E2 protein based vaccines, expressed in yeast, have been tested against classical swine fever, a related pestivirus of swine (54). Even though a protective serum neutralizing response may in some cases have been observed for a subunit E2 protein vaccine, more than one injection was required for such a response in animals, and such treatment did not provide a cellular immune response (54). In addition, the cost of protein expression and purification may not be economically feasible for cattle (62).

Vaccination of mice with an experimental DNA plasmid encoding the E2 glycoprotein of BVDV type 1 (E2.1) produced some humoral and cellular immune responses (53). In cattle, animals vaccinated with DNA plasmid encoding E2.1 were partially protected against BVDV type 2 challenge, whereas animals vaccinated with plasmids encoding both E2.1 and E2.2 (BVDV type 2 E2) were well protected from challenge with BVDV type 2 when they were subsequently boosted with E2.2 encoding DNA or E2 protein (52). Therefore, such DNA based subunit E2 vaccines require at least two injections, which may not be cost effective for the cattle industry.

The inventor and coworkers have successfully incorporated a chimeric gene cassette encoding BVDV type 1 E2 ORF (BVDV E2.1) into the novel BoHV-1 tmv vector. Such a vector can achieve good immunological reactions in animals after just one administration.

Erns Antigens

Another BVDV antigen that can be encoded within and expressed by the expression systems described herein is an envelope Erns (about 227 amino acids) glycoprotein. Erns and E1 are synthesized early as a heterodimer (Erns-E1 precursor), but at later stages of polypeptide processing, Erns forms a disulfide bonded homodimer (Rumenapf et al., 1993; Konig et al., 1995), whereas E2 forms a disulfide-linked homodimer and also a heterodimer with E1 (Weiland et al., 1990: Rumenapf et al., 1991). Erns and E2 are located at the surface of infected cells (Weiland et al., 1999), and may induce virus-neutralizing antibodies. Erns is secreted from infected cells but it is also a structural component of the virus particle (Rumenapf et al., 1993; Weiland et al., 1992). Some studies indicate that Erns may be a ribonuclease.

Erns has a mass of 44-48 kDa (Ahn et al. 1996), and its C-terminus functions as (1) a membrane anchor: (2) a retention/secretion signal; (3) a binding site for cell surface glycosaminoglycans (GAGs); and (4) a signal peptidase cleavage site. In one example, a BVDV1 Erns can have the following amino acid sequence (SEQ ID NO:39).

```
  1  ENITQWNLQD NGTEGIQRAM FQRGVNRSLH GIWPEKICTG

41  VPSHLATDIE LKTIHGMMDA SEKTNYTCCR LQRHEWNKHG

81  WCNWYNIEPW ILVMNRTQAN LTEGQPPREC AVTCRYDRAS

121  DLNVVTQARD SPTPLTGCKK GKNFSFAGIL MRGPCNFEIA

161  ASDVLFKEHE RISMFQDTTL YLVDGLTNSL EGARQGTAKL

201  TTWLGKQLGI LGKKLENKSK TWFGAYA
```

A fusion protein of the BVDV1 envelope Erns protein with a gD signal sequence and a GMCSF (GenBank accession # NP_776452.1) fusion partner can have a nucleotide sequence, for example, as shown below as SEQ ID NO:40 (see also FIG. 21A).

```
   1  TTAATTAACG CCACCATGCA GGGACCTACT CTGGCTGTGC
  41  TGGGGGCTCT GCTGGCTGTC GCCGTCAGTC TGGAAAACAT
  81  CACTCAGTGG AATCTGCAGG ATAACGGCAC CGAGGGGATC
 121  CAGCGCGCCA TGTTCCAGCG AGGCGTGAAC CGGTCACTGC
 161  ACGGGATCTG GCCAGAAAAG ATTTGCACCG GAGTCCCAAG
 201  CCACCTGGCT ACCGACATCG AGCTGAAGAC AATTCATGGA
 241  ATGATGGATG CTAGCGAAAA AACCAACTAC ACATGCTGTC
 281  GGCTGCAGAG GCACGAGTGG AATAAGCATG GCTGGTGTAA
 321  CTGGTATAAT ATCGAACCCT GGATCCTGGT CATGAACAGA
 361  ACACAGGCCA ATCTGACTGA GGGACAGCCA CCTCGAGAAT
 401  GCGCTGTCAC TTGTCGCTAC GACAGAGCTA GCGATCTGAA
 441  CGTGGTCACA CAGGCTCGAG ACTCCCCAAC TCCTCTGACC
 481  GGCTGCAAGA AAGGGAAGAA CTTCTCCTTT GCTGGGATCC
 521  TGATGCGCGG ACCCTGTAAT TTTGAGATTG CCGCTTCTGA
 561  TGTGCTGTTC AAAGAGCACG AAAGAATCAG TATGTTTCAG
 601  GACACCACAC TGTACCTGGT GGATGGCCTG ACCAACTCCC
 641  TGGAGGGAGC TAGGCAGGGA ACAGCTAAGC TGACTACCTG
 681  GCTGGGGAAA CAGCTGGGAA TTCTGGGCAA GAAACTGGAA
 721  AACAAGTCTA AAACCTGGTT CGGAGCCTAT GCTATGTGGC
 761  TGCAGAATCT GCTGCTGCTG GGCACAGTGG TCTGCTCTTT
 801  TAGTGCCCCT ACTAGGCCAC CCAATACAGC TACTCGCCCA
 841  TGGCAGCACG TGGACGCCAT CAAGGAGGCT CTGAGTCTGC
 881  TGAACCATAG CTCCGACACT GATGCCGTGA TGAATGACAC
 921  CGAGGTGGTC TCCGAAAAAT TTGATTCTCA GGAGCCCACC
 961  TGTCTGCAGA CACGGCTGAA GCTGTACAAA AACGGGCTGC
1001  AGGGATCACT GACCAGCCTG ATGGGAAGCC TGACTATGAT
1041  GGCCACCCAC TATGAGAAGC ATTGCCCTCC AACACCTGAA
1081  ACTAGTTGTG GGACCCAGTT CATCAGCTTC AAGAATTTCA
1121  AAGAAGACCT GAAAGAGTTC CTGTTTATCA TTCCATTTGA
1181  CTGTTGGGAG CCAGCCCAGA AAGGTAAGCC TATCCCTAAC
1201  CCTCTCCTCG GTCTCGATTC TACGTAAGCG GCCGC
```

Another example of a BVDV2 Erns that has the following amino acid sequence (SEQ ID NO:42).

```
  1  ENITQWNLMD NGTEGIQQAM FLRGVNRSLH GIWPEKICTG

41  VPTHLATDYE LKEIVGMMDA SEKTNYTCCR LQRHEWNKHG

81  WCNWFHIEPW IWLMNKTQNN LTEGQPLREC AVTCRYDKET

121  ELNIVTQARD RPTTLTGCKK GKNFSFAGVI LDGPCNFKVS

161  VEDVLFKEHD CGNMLQETAI QLLDGATNTI EGARVGTAKL

201  TTWLGKQLGI LGKELENKSK AWFGAHA
```

An example of a fusion protein of the BVDV2 envelope Erns protein with a gD signal sequence and a GMCSF (GenBank accession # NP_776452.1) fusion partner can have a nucleotide sequence, for example, as shown below as SEQ ID NO:59 (see also FIG. 21B).

A gG-deletion BoHV-1 virus was generated to attenuate the virus with respect to immune evasion and to provide a vector for insertion of an Erns-GMSF chimeric gene cassette at the gG locus. BHV-1 gG is secreted after proteolytic processing. In addition, gG is present on the virus envelope and is associated with infected cell membranes (Bryant et al., 2003). Like other alpha herpesvirus gG homologues, the BHV-1 gG has chemokine binding activity and it blocks the interaction of chemokines with cellular receptors and glycolaminoglycans (GAGs). The chemokine binding activity of gG also occurs on cell membranes because membrane-anchored forms of gG bind to various chemokines (Bryant et al., 2003). Chemokines are small proteins (8-10 kd) that function as cytokines, and thus regulate trafficking and effector functions of leukocytes Baggiolini (1998). As such, chemokines are important regulators of inflammation, immune surveillance, and they have potent anti-viral functions. Functionally, chemokines can be divided into two groups: pro-inflammatory chemokines that are inducible and housekeeping chemokines that are constitutively expressed. Activation of chemokine functions are dependent on selective recognition and activation of chemokine receptors belonging to the seven-membrane domain. G protein-coupled receptor super family. Chemokines can also bind to glycosamino-glycans (GAGS). Chemokine binding to GAGS on cells, in particular endothelial cells, results in chemotactive chemokine gradients that allow the correct presentation of chemokines to leukocytes and therefore enable target cells to cross the endothelial barrier and migrate to tissues. BoHV-1, BoHV-5, and equine herpesvirus 1 encode a glycoprotein (gG) that is secreted from infected cells, and can bind to a broad range of chemokines (Bryant et al. (2003). Interactions between gG and chemokines block chemokine activity by preventing their interactions with specific receptors and GAGS. By preventing chemokine-GAG interactions, gG disrupts chemokine gradients, which controls the local environment surrounding an infected cell. A BoHV-1 gG deletion mutant was reported to have reduced virulence [78] suggesting gG is a viral immune evasion gene. Deletion of the BoHV-1 gene encoding gG leads to viral attenuation in calves because the mutant virus is more immunogenic (Kaashock et al., 1998). The chemokine binding activity encoded by BoHV-1 gG is responsible for the attenuated phenotype following infection of calves (Bryant et al. 2003). Removal of the gG locus reduces many of negative effects that could otherwise occur.

FIG. 21B illustrates an example of a nucleotide sequence of a fusion protein of the BVDV2 envelope Erns protein with a gD signal sequence and a GMCSF (GenBank accession # NP_776452.1) fusion partner can have (SEQ ID NO:41) that can be inserted in the gG-deleted BoHV vector. An example of a nucleotide sequence of a BoHV-1 gG deletion vector is shown below as SEQ ID NO:49 (see also FIG. 23).

```
   1 GATATCAGGC AACGGGCCT GCTCCCGCGC AGGAGCACGT
  41 GGTGCTCAAG ATCGGGGCCT CGGCCTCTAC GCTGGCCGAG
  81 GCTATGCTAC TGCGAACCTT GGACCACGCC AACGTGGTCA
 121 AGCTGAAGGC CGTGCTCTTC CACGGGGAGC TGGTGTGCGT
 161 GGTGCTGGCG CGCTACCGCG AGGACCTGCA CACGCACCTC
 201 TGGAGAATCA ACCGCCCGCT GGCGCTCCCC GCGGCGCTGG
 241 CGGTGACGCG GGCCGTGCTG CGGGGCCTCG CGTACCTGCA
 281 CTCCCGCCGG ATCGCTCACC GGGACGTCAA AACGGAAAAC
 321 GTCTTCCTCA ACGGCCCAGG CGACGTGTGC CTGGGCGACT
 361 TTGGCGCGGC ACACGGGCCG GTCACCGAGC CCGCTACTA
 401 CGGCCTGGCC GGCACCCTGG AGACGAACTC GCCAGAGCTG
 441 CTGGCGCGCG CGCGCTACGA CTGCCGCACG GACGTGTGGA
 481 GCGCGGGCGT CGTCGCGTAC GAGATGCTGG CATACCCGCG
 521 CGCGCTGTTC GACAGCCCCG CGGGCCCGCA GGGCGAGGAC
 561 GCCGAGGCAT CGGGCCCGCC GACGATCTTG GGCGACCGCG
 601 ACTGCGCCCG GCAGCTGCTC CGCGTGATTC GCCGGCTGGC
 641 CGTGCACGCC GAAGAGTTTC CACCCAGCCC CACTGACCGG
 681 CTGACCCGCA ACTTCAAGCG CCACGCGAGC ACGCGCCGAG
 721 AGCCGCACAG CCCGTACCGC TGCCTGGCGG TGCTCCGGCT
 761 GCCCTGCGAC GCCGACCGCC TCCTACACCA GATGCTGACC
 801 TTTGACTTTC GCGCGCGCCC CACCGCCGCG GAGCTGCTGG
 841 AGCACCCCGT CTTCGGTGCG GCCTCGGGGT AGCCCCGGGG
 881 GTTTCCCGCA AAACTGAGGC ATATAAGGCG CGGGCACCGG
 921 CAAGTTTGGC ATCCACACTT CGCGCTGTGG ACACGAGAGC
 961 GAACGCGAGC GAACGCGAGC GGAAGCGCGA GCACACGACT
1001 GCGATCGTTG ACATTGATTA TTGACTAGTT ATTAATAGTA
1041 ATCAATTACG GGGTCATTAG TTCATAGCCC ATATATGGAG
1081 TTCCGCGTTA CATAACTTAC GGTAAATGGC CCGCCTGGCT
1121 GACCGCCCAA CGACCCCGC CCATTGACGT CAATAATGAC
1161 GTATGTTCCC ATAGTAACGC CAATAGGGAC TTTCCATTGA
1201 CGTCAATGGG TGGAGTATTT ACGGTAAACT GCCCACTTGG
1241 CAGTACATCA AGTGTATCAT ATGCCAAGTA CGCCCCCTAT
1281 TGACGTCAAT GACGGTAAAT GGCCCGCCTG GCATTATGCC
1321 CAGTACATGA CCTTATGGGA CTTTCCTACT TGGCAGTACA
1361 TCTACGTATT AGTCATCGCT ATTACCATGG TGATGCGGTT
1401 TTGGCAGTAC ATCAATGGGC GTGGATAGCG GTTTGACTCA
1441 CGGGGATTTC CAAGTCTCCA CCCCATTGAC GTCAATGGGA
1481 GTTTGTTTTG GCACCAAAAT GAACGGGACT TTCCAAAATG
1521 TCGTAACAAC TCCGCCCCAT TGACGCAAAT GGGCGGTAGG
1561 CGTGTACGGT GGGAGGTCTA TATAAGCAGA GCTCTTAATT
1601 AAGTGTGTGT GTGCGGCCGC CTGTGCCTTC TAGTTGCCAG
1641 CCATCTGTTG TTTGCCCCTC CCCCGTGCCT TCCTTGACCC
1681 TGGAAGGTGC CACTCCCACT GTCCTTTCCT AATAAAATGA
1721 GGAAATTGCA TCGCATTGTC TGAGTAGGTG TCATTCTATT
1761 CTGGGGGGTG GGGTGGGGCA GGACAGCAAG GGGGAGGATT
1801 GGGAAGACAA TAGCAGGCAT GCTGGGGATG CGGTGGGCTC
1841 TATGGTCGCC GGCACCCCAC GCCGCCCCGA CCCCGCTGTC
1881 CCGCGTTTAC AATAAACAGT TATTCTTACC AACGTTGGTG
1921 CGCCTGTCGC GTGTCTATTG CGAGTTAAAC CGAGTGCCCC
1961 ACCCAGGCAG GGCGGGGGTT GGGCCGGGCC GCAGCCCCGG
2001 CTGGGTATAT ATCCCCGACG GGCGACTAGA GATACACTCG
2041 CCCCGCGCGG CTGCTGCGAG CGGGCGAACA TGCAAGGGCC
2081 GACATTGGCC GTGCTGGGCG CGCTGCTCGC CGTTGCGGTG
2121 AGCTTGCCTA CACCCGCGCC GCGGGTGACG GTATACGTCG
2161 ACCCGCCGGC GTACCCGATG CCGCGATACA ACTACACTGA
2201 ACGCTGGCAC ACTACCGGGC CCATACCGTC GCCCTTCGCA
2241 GACGGCCGCG AGCAGCCCGT CGAGGTGCGC TACGCGACGA
2281 GCGCGGCGGC GTGCGACATG CTGGCGCTGA TCGCAGACCC
2321 GCAGGTGGGG CGCACGCTGT GGGAAGCGGT ACGCCGGCAC
2361 GCGCGCGCGT ACAACGCCAC GGTCATATGG TACAAGATCG
2401 AGAGCGGGTG CGCCCGGCCG CTGTACTACA TGGAGTACAC
2441 CGAGTGCGAG CCCAGGAAGC ACTTTGGGTA CTGCCGCTAC
2481 CGCACACCCC CGTTTTGGGA CAGCTTCCTG GCGGGCTTCG
2521 CCTACCCCAC GGACGACGAG CTGGGACTGA TTATGGCGGC
2561 GCCCGCGCGG CTCGTCGAGG GCCAGTACCG ACGCGCGCTG
2601 TACATCGACG GCACGGTCGC CTATACAGAT TTCATGGTTT
2641 CGCTGCCGGC CGGGGACTGC TGGTTCTCGA AACTCGGCGC
2681 GGCTCGCGGG TACACCTTTG GCGCGTGCTT CCCGGCCCGG
2721 GATTACGAGC AAAAGAAGGT TCTGCGCCTG ACGTATCTCA
2761 CGCAGTACTA CCCGCAGGAG GCACACAAGG CCATAGTCGA
2801 CTACTGGTTC ATGCGCCACG GGGCGTCGT TCCGCCGTAT
2841 TTTGAGAAGC TT
```

Expression of granulocyte-macrophage colony-stimulating factor (GM-CSF) can stimulate the immune response against antigens such as those described herein. Accordingly, GM-CSF can be expressed separately or as a fusion partner with one or more of the antigens described herein. The expression module with the nucleotide sequence shown as SEQ ID NO:40 is just one example of a use for GM-CSF.

An example of a *Bos taurus* GM-CSF amino acid sequence that can be encoded in any of the expression cassettes or vectors described herein, or that can serve as a fusion partner with any of the antigens described herein, is shown below as SEQ ID NO: 41.

```
  1    MNLQNLLLLG TVVCSFSAPT RPPNTATRPW QHVDAIKEAL
 41    SLLNHSSDTD AVMNDTEVVS EKFDSQEPTC LQTRLKLYKN
 81    GLQGSLTSLM GSLTMMATHY EKHCPPTPET SCGTQFISFK
121    NFKEDLKEFL FIIPFDCWEP AQK
```

Bovine Respiratory Syncytia Virus (BRSV)

BRSV, a pneumovirus, is a major etiological agent of respiratory tract disease in calves, and has been frequently seen in conjunction with *H. somnus* in BRDC (7). BRSV seasonal outbreaks in young calves are common due to stress of weaning, crowding and temperature changes. Persistent BRSV infections in cattle have been suspected and may serve as a source of virus transmission to susceptible animals (7, 47).

BRSV has a negative stranded RNA genome of approximately 15.2 Kb, which encodes two non-structural proteins (NS1 and NS2) and eight virion-associated structural proteins: nucleocapsid, phosphoprotein (P), matrix protein (M), small hydrophobic protein (SH), glycoprotein (G), fusion protein (F), matrix protein 2 (M2) and large or RNA dependent RNA polymerase protein (L) (47) (FIG. 2).

Of the eight structural proteins, G, F and SH are surface/envelope glycoproteins (47). Neither G nor SH is required for BRSV infectivity in cell culture (37). Even though G and SH are not essential for virus replication in vitro, recombinant BRSV lacking G and SH are highly attenuated in vivo indicating that the G and SH proteins are important for BRSV pathogenesis (47). The F protein is indispensable for virus replication (37). Transfection of cells with BRSV F gene results in formation of multinucleated syncytia (37, 42) and co-expression of F with G enhances fusion activity in the transfected cells (75). Taken together, such data indicate that the BRSV G protein is needed for enhanced fusogenic and infective property of the virus.

Most anti BRSV neutralizing antibodies have been mapped to the fusion glycoprotein F (83, 92). The BRSV F protein is a type I membrane protein. The BRSV F mRNA (e.g., 1899 nucleotides long excluding the poly A tail) can contain a single ORF that is predicted to encode a protein of 574 amino acids with a molecular weight of 63.8 kD. BRSV F protein is synthesized as an inactive precursor F0 (70 kD), which is not fusogenic. The F0 of BRSV contains two Furin cleavage sequence (FCS) motifs FCS 1 (133RKKR136) and FCS 2 (106RARR109) (88, 96) (FIG. 2). Cleavage at both sites by Furin leads to the release of pep27 and generation of the fusogenic form F1/F2 complex (88, 96). Following cleavage, F1 and F2 are linked by a disulfide bridge and an N-glycosylated peptide of 27 amino acids (pep 27) is released (88, 96).

In BRSV infected cells in vitro, pep27 can be subjected to post-translational modifications and can be converted into virokinin, a member of the tachykinin family. The tachykinin family of peptides can have pro-inflammatory and immunomodulatory properties (88). Some data indicate that BRSV virokinin may cause bronchoconstriction, for example, because it induces smooth muscle contraction (96). A recombinant BRSV lacking the pep27 induced less pulmonary inflammation in calves without affecting the induction of protective immunity in calves (88). A DNA vaccine encoding the F gene of BRSV induced significant protection against BRSV infection in young calves (81).

BRSV F Protein Antigens

An example of a BRSV F protein sequence lacking its signal sequence (approximately 1.76 Kb) and encoded by a 1700 nucleotide nucleic acid segment is available as GenBank accession GI 210828, and provided below as SEQ ID NO: 15.

```
  1    MAATAMRMII SIIFISTYMT HITLCQNITE EFYQSTCSAV
 41    SRGYLSALRT GWYTSVVTIE LSKIQKNVCK STDSKVKLIK
 81    QELERYNNAV IELQSLMQNE PASFSRAKRG IPELIHYTRN
121    STKRFYGLMG KKRKRRFLGF LLGIGSAIAS GVAVSKVLHL
161    EGEVNKIKNA LLSTNKAVVS LSNGVSVLTS KVLDLKNYID
201    KELLPKVNNH DCRISNIETV IEFQQKNNRL LEIAREFSVN
241    AGITTPLSTY MLTNSELLSL INDMPITNDQ KKLMSSNVQI
281    VRQQSYSIMS VVKEEVIAYV VQLPIYGVID TPCWKLHTSP
321    LCTTDNKEGS NICLTRTDRG WYCDNAGSVS FFPQAETCKV
361    QSNRVFCDTM NSLTLPTDVN LCNTDIFNTK YDCKIMTSKT
401    DISSSVITSI GAIVSCYGKT KCTASNKNRG IIKTFSNGCD
441    YVSNKGVDTV SVGNTLYYVN KLEGKALYIK GEPIINYYDP
481    LVFPSDEFDA SIAQVNAKIN QSLAFIRRSD ELLHSVDVGK
521    STTNVVITTI IIVIVVVILM LIAVGLLFYC KTRSTPIMLG
561    KDQLSGINNL SFSK
```

BRSV-F proteins typically have two separate Furin cleavage sites (FCS 1 and FCS 2). In some cases, BRSV F protein can be designed such that both the FCS 1 (106RAKR109) and FCS 2 (133RKRR136) highlighted above can be mutated to 106AAKA109 and 133AKAA136, respectively. The rational for the changes to the F protein sequence is twofold. First, without Furin cleavage the fusogenic form of the F1/F2 complex will not be generated and second, a functional pep27 virokinin associated with pulmonary inflammation will not be released (96). A modification of the SEQ ID NO: 15 BRSV F protein sequence with these changes is shown below as SEQ ID NO:16.

```
  1    MAATAMRMII SIIFISTYMT HITLCQNITE EFYQSTCSAV
 41    SRGYLSALRT GWYTSVVTIE LSKIQKNVCK STDSKVKLIK
 81    QELERYNNAV IELQSLMQNE PASFSAAKAG IPELIHYTRN
121    STKRFYGLMG KKAKAAFLGF LLGIGSAIAS GVAVSKVLHL
161    EGEVNKIKNA LLSTNKAVVS LSNGVSVLTS KVLDLKNYID
201    KELLPKVNNH DCRISNIETV IEFQQKNNRL LEIAREFSVN
241    AGITTPLSTY MLTNSELLSL INDMPITNDQ KKLMSSNVQI
281    VRQQSYSIMS VVKEEVIAYV VQLPIYGVID TPCWKLHTSP
```

```
321    LCTTDNKEGS NICLTRTDRG WYCDNAGSVS FFPQAFTCKV
361    QSNRVFCDTM NSLTLPTDVN LCNTDIFNTK YDCKIMTSKT
401    DISSSVITSI GAIVSCYGKT KCTASNKNRG IIKTFSNGCD
441    YVSNKGVDTV SVGNTLYYVN KLEGKALYIK GEPIINYYDP
481    LVFPSDEFDA SIAQVNAKIN QSLAFIRRSD ELLHSVDVGK
521    STTNVVITTI IIVIVVVILM LIAVGLLFYC KTRSTPIMLG
561    KDQLSGINNL SFSK
```

In another example, a BRSV-F version 1 protein is shown below as SEQ ID NO: 17.

```
  1    MATTAMTMII SIIFISTYVT HITLCQNITE EFYQSTCSAV
 41    SRGYLSALRT GWYTSVVTIE LSKIQKNVCK STDSKVKLIK
 81    QELERYNNAV VELQSLMQNE PASFSAAKAS IPELIHYTRN
121    STKKFYGLMG KKAKAAFLGF LLGIGSAIAS GVAVSKVLHL
161    EGEVNKIKNA LLSTNKAVVS LSNGVSVLTS KVLDLKNYID
201    KELLPKVNNH DCRISNIATV IEFQQKNNRL LEIAREFSVN
241    AGITTPLSTY MLTNSELLSL INDMPITNDQ KKLMSSNVQI
281    VRQQSYSIMS VVKEEVIAYV VQLPIYGVID TPCWKLHTSP
321    LCTTDNKEGS NICLTRTDRG WYCDNAGSVS FFPQAETCKV
361    QSNRVFCDTM NSLTLPTDVN LCNTDIFNTK YDCKIMTSKT
401    DISSSVITSI GAIVSCYGKT KCTASNKNRG IIKTFSNGCD
441    YVSNKGVDTV SVGNTLYYVN KLEGKALYIK GEPIINYYDP
481    LVFPSDEFDA SIAQVNAKIN QSLAFIRRSD ELLHSVDVGK
521    STTNVVITTI IIVIVVVILM LIAVGLLFYC KTRSTPIMLG
561    KDQLSGINNL SFSK
```

A codon optimized chimeric BRSV F version 1 nucleic acid segment encoding the SEQ ID NO: 17 protein can, for example, have the nucleotide sequence shown below as SEQ ID NO: 18.

```
   1   ATGGCTACAA CCGCTATGAC TATGATTATC ACCATCATCT
  41   TCATCTCCAC CTACGTGACC CACATCACCC TGTGCCAGAA
  81   CATCACCGAG GAGTTCTACC AGTCCACCTG CAGCGCTGTG
 121   TCCAGGGCCT ACCTGTCCGC TCTGAGAACC GGCTGGTACA
 161   CCTCCGTGGT GACCATCGAG CTGAGCAAGA TCCAGAAGAA
 201   CGTGTGCAAG AGCACCGACT CCAAGGTGAA GCTGATCAAG
 241   CAGGAGCTGG AGCGGTACAA CAACGCCGTG GTGGAGCTGC
 281   AGAGCCTGAT GCAGAACGAG CCTGCTTCCT TCAGCGCTGC
 321   TAAGGCCTCC ATCCCTGAGC TGATCCACTA CACCAGGAAC
 361   AGCACCAAGA AGTTCTACGG CCTGATGGGC AAGAAGGCCA
 401   AGGCCGCCTT CCTGGGCTTC CTGCTGGGAA TCGGCAGCGC
 441   TATCGCTTCC GGAGTGGCTG TGTCCAAGGT GCTGCACCTG
 481   GAGGGCGAGG TGAACAAGAT CAAGAACGCC CTGCTGAGCA
 521   CCAACAAGGC CGTGGTGTCC CTGAGCAACG GCGTGAGCGT
 561   GCTGACCTCC AAGGTGCTGG ACCTGAAGAA CTACATCGAC
 601   AAGGAGCTGC TGCCTAAGGT GAAGAACCAC GACTGCCGGA
 641   TCTCCAACAT CGCCACCGTG ATCGAGTTCC AGCAGAAGAA
 681   CAACCGGCTG CTGGAGATCG CCAGGGAGTT CTCCGTGAAC
 721   GCCGGCATCA CCACCCCTCT GAGCACCTAC ATCCTGACCA
 761   ACAGCGAGCT GCTGTCCCTG ATCAACGACA TGCCCATCAC
 801   CAACGACCAG AAGAAGCTGA TGAGCTCCAA CGTGCAGATC
 841   GTGAGGCAGC AGTCCTACAG CATCATGAGC GTGGTGAAGG
 881   AGGAGGTCAT CGCCTACGTG GTGCAGCTGC CATCTACGC
 921   CGTGATCGAC ACCCCTTGCT GGAAGCTGCA CACCTCCCCC
 961   CTGTGCACCA CCGACAACAA GGAGGGCAGC AACATCTGCC
1001   TGACCCGCAC CGACAGAGGC TGGTACTGCG ACAACGCCGG
1041   CTCCGTGAGC TTCTTCCCTC AGGCCGAGAC CTGCAAGGTG
1081   CAGTCCAACC GCGTGTTCTG CGACACCATG AACAGCCTGA
1121   CCCTGCCCAC CGACGTGAAC CTGTGCAACA CCGACATCTT
1141   CAACACCAAG TACGACTGCA AGATCATGAC CAGCAAGACC
1181   GACATCAGCT CCAGCGTGAT CACCAGCATC GGCGCCATCG
1201   TGTCCTGCTA CGGCAAGACC AAGTGCACCG CCTCCAACAA
1241   GAACAGAGGC ATCATCAAGA CCTTCTCCAA CGGCTGCGAC
1281   TACGTGAGCA ACAAGGGCGT GGACACCGTG AGCGTGGGCA
1321   ACACCCTGTA CTACGTGAAC AAGCTGGAGG GCAAGGCCCT
1361   GTACATCAAG GGCGAGCCCA TCATCAACTA CTACGACCCC
1401   CTGGTGTTCC CTAGCGACGA GTTCGACGCC TCCATCGCCC
1441   AGGTGAACGC CAAGATCAAC CAGTCCCTGG CCTTCATCCG
1481   GAGGAGCGAC GAGCTGCTGC ACTCCGTGGA CGTGGGCAAG
1521   AGCACCACCA ACGTGGTGAT CACCACCATC ATCATCGTGA
1561   TCGTGGTGGT GATCCTGATG CTGATCGCCG TGGGCCTGCT
1601   CTTCTACTGC AAGACCCGCA GCACACCTAT TATGCTGGGC
1641   AAGGACCAGC TGAGCGGAAT CAACAATCTG TCATTTTCTA
1681   AG
```

FIG. 17A-17C show an example of a nucleotide sequence for a BRSV F version 1 expression cassette. FIG. 17D-17F show examples of amino acid and nucleotide protein sequences (SEQ ID NOs: 20 and 21, respectively) of a fusion protein that includes the foregoing SEQ ID NO: 17 and SEQ ID NO: 18 BRSV F version 1 amino acid and nucleotide sequences. The BRSV F version 1 fusion protein (FIG. 17) includes a gD signal sequence at the N-terminus, and at the C-terminus a V5 epitope and a series of six histidines. In some cases, the BRSV F version 1 protein can be encoded in an expression cassette without the gD signal sequence and without the C-terminal V5 epitope and histidine tail.

In another example, a BRSV-F version 2 protein sequence is shown below as SEQ ID NO:22.

```
  1  MATTAMTMII SIIFISTYVT HITLCQNITE EFYQSTCSAV

41  SRGYLSALRT GWYTSVVTIE LSKIQKNVCK STDSKVKLIK

81  QELERYNNAV VELQSLMQNE PASFSAAAAS IPELIHYTRN

121  STKKFYGLMG KKAAAAFLGF LLGIGSAIAS GVAVSKVLHL

161  EGEVNKIKNA LLSTNKAVVS LSNGVSVLTS KVLDLKNYID

201  KELLPKVNNH DCRISNIATV IEFQQKNNRL LEIAREFSVN

241  AGITTPLSTY MLTNSELLSL INDMPITNDQ KKLMSSNVQI

281  VRQQSYSIMS VVKEEVIAYV VQLPIYGVID TPCWKLHTSP

321  LCTTDNKEGS NICLTRTDRG WYCDNAGSVS FFPQAETCKV

361  QSNRVFCDTM NSLTLPTDVN LCNTDIFNTK YDCKIMTSKT

401  DISSSVITST GAIVSCYGKT KCTASNKNRG IIKTFSNGCD

441  YVSNKGVDTV SVGNTLYYVN KLEGKALYIK GEPIINYYDP

481  LVFPSDEFDA SIAQVNAKIN QSLAFIRRSD ELLHSVDVGK

521  STTNVVITTI IIVIVVVILM LIAVGLLFYC KTRSTPIMLG

561  KDQLSGINNL SFSK
```

A codon optimized chimeric BRSV F version 2 nucleic acid segment encoding the SEQ ID NO:22 protein can, for example, have the nucleotide sequence shown below as SEQ ID NO:23.

```
   1  ATGGCTACAA CCGCTATGAC TATGATTATC AGCATCATCT
  41  TCATCTCCAC CTACGTGACC CACATCACCC TGTGCCAGAA
  81  CATCACCGAG GAGTTCTACC AGTCCACCTG CAGCGCTGTG
 121  TCCAGGGGCT ACCTGTCCGC TCTGAGAACC GGCTGGTACA
 161  CCTCCGTGGT GACCATCGAG CTGAGCAAGA TCCAGAAGAA
 201  CGTGTGCAAG AGCACCGACT CCAAGGTGAA GCTGATCAAG
 241  CAGGAGCTGG AGCGGTACAA CAACGCCGTG GTGGAGCTGC
 281  AGAGCCTGAT GCAGAACGAG CCTGCTTCCT TCAGCGCTGC
 321  TGCCGCCTCC ATCCCTGAGC TGATCCACTA CACCAGGAAC
 361  AGCACCAAGA AGTTCTACGG CCTGATGGGC AAGAAGGCCG
 401  CCGCCGCCTT CCTGGGCTTC CTGCTGGGAA TCGGCAGCGC
 441  TATCGCTTCC GGAGTGGCTG TGTCCAAGGT GCTGCACCTG
 481  GAGGGCGAGG TGAACAAGAT CAAGAACGCC CTGCTGAGCA
 521  CCAACAAGGC CGTGGTGTCC CTGAGCAACG GCGTGAGCGT
 561  GCTGACCTCC AAGGTGCTGG ACCTGAAGAA CTACATCGAC
 601  AAGGAGCTGC TGCCTAAGGT CAACAACCAC GACTGCCGGA
 641  TCTCCAACAT CGCCACCGTG ATCGAGTTCC AGCAGAAGAA
 681  CAACCGGCTG CTGGAGATCG CCAGGGAGTT CTCCGTGAAC
 721  GCCGGCATCA CCACCCCTCT GAGCACCTAC ATGCTGACCA
 761  ACAGCGAGCT GCTGTCCCTG ATCAACGACA TGCCCATCAC
 801  CAACGACCAG AAGAAGCTGA TGAGCTCCAA CGTGCAGATC
 841  GTGAGGCAGC AGTCCTACAG CATCATGAGC GTGGTGAAGG
 881  AGGAGGTGAT CGCCTACGTG GTGCAGCTGC CCATCTACGG
 921  CGTGATCGAC ACCCCTTGCT GGAAGCTGCA CACCTCCCCC
 961  CTGTGCACCA CCGACAACAA GGAGGGCAGC AACATCTGCC
1001  TGACCCGCAC CGACAGAGGC TGGTACTGCG ACAACGCCGG
1041  CTCCGTGAGC TTCTTCCCTC AGGCCGAGAC CTGCAAGGTG
1081  CAGTCCAACC GCGTGTTCTG CGACACCATG AACAGCCTGA
1121  CCCTGCCCAC CGACGTGAAC CTGTGCAACA CCGACATCTT
1161  CAACACCAAG TACGACTGCA AGATCATGAC CAGCAAGACC
1201  GACATCAGCT CCAGCGTGAT CACCAGCATC GGCGCCATCG
1241  TGTCCTGCTA CGGCAAGACC AAGTGCACCG CCTCCAACAA
1281  GAACAGAGGC ATCATCAAGA CCTTCTCCAA CGGCTGCGAC
1321  TACGTGAGCA ACAAGGGCGT GGACACCGTG AGCGTGGGCA
1361  ACACCCTGTA CTACGTGAAC AAGCTGGAGG GCAAGGCCCT
1401  GTACATCAAG GGCGAGCCCA TCATCAACTA CTACGACCCC
1441  CTGGTGTTCC CTAGCGACGA GTTCGACGCC TCCATCGCCC
1481  AGGTGAACGC CAAGATCAAC CAGTCCCTGG CCTTCATCCG
1521  GAGGAGCGAC GAGCTGCTGC ACTCCGTGGA CGTGGGCAAG
1561  AGCACCACCA ACGTGGTGAT CACCACCATC ATCGTCGTGA
1601  TCGTGGTGGT GATCCTGATG CTGATCGCCG TGGGCCTGCT
1641  GTTCTACTGC AAGACCCGCA GCACACCTAT TATGCTGGGC
1681  AAGGACCAGC TGAGCGGAAT CAACAATCTG TCATTTTCTA
1721  AG
```

FIG. 18A-18C show examples of amino acid and nucleotide protein sequences (SEQ ID NOs: 24 and 25, respectively) of a fusion protein that includes the foregoing SEQ ID NO:22 and 23 BRSV F version 2 amino acid and nucleotide sequences. The BRSV F version 2 fusion protein (FIG. 18A-18C) includes a gD signal sequence at the N-terminus. In some cases, a BRSV F version 2 fusion protein can have a V5 epitope and/or a series of histidines at the C-terminus. Such BRSV F version 2 fusion protein sequences can be encoded in an expression in a manner that is similar to the BRSV F version 1-containing expression cassette shown in FIG. 17A-17C.

BRSV F nucleic acid segments can also be obtained by amplification from various BRSV genomic sources or from plasmids that encode BRSV sequences. For example, plasmid pEF6/V5-His-TOPO (FIG. 8A) can be a source of BRSV F nucleic acid segments. The BRSV F nucleic acids obtained can be verified by sequencing and then inserted in an expression cassette, for example, in a manner that is similar to the BRSV F version 1-containing expression cassette shown in FIG. 17A-17C.

BRSV G Protein Antigens

BRSV G protein is type II integral membrane protein. The BRSV G protein mRNA (e.g., 838 nucleotides long excluding the poly A tail) contains a single ORF which encodes a polypeptide of 257 amino acids (47). The amino terminal 37 aa are predicted to be within the cytoplasm which is followed by a membrane spanning domain (aa 38-66) and a large ectodomain (aa 67-257) (FIG. 2). The ectodomain has a central conserved folded region also known as a cysteine "noose" (aa 158-189) which is flanked by two highly glycosylated, mucin like regions (46, 47)(FIG. 2). The BRSV G protein, especially the cysteine noose domain, contributes to immunopathogenesis of the virus by inducing unbalanced T cell responses (26). A peptide spanning amino acids 149 to 200 of G protein has recently been shown to prime naïve inbred mice for polarized type 2 T-cell responses and pulmonary eosinophilia (20).

In spite of the problems associated with the G protein in the epizootiology and disease pathogenesis, antibodies and CD8+ T cells directed against the G protein-specific B cell and T cell epitopes are important for virus clearance and protection against the disease (19, 82-84).

An example, of a BRSV G protein amino acid sequence is available from GenBank (accession # GI 1912278; and encoded by a 729 nucleotide nucleic acid) segment. An example of such a BRSV G protein amino acid sequence is shown below as SEQ ID NO:26.

```
  1  MSNHTHHLKF KTLKRAWKAS KYFIVGLSCL YKFNLKSLVQ
 41  TALTTLAMIT LTSLVITAII YISVGNAKAK PTSKPTIQQT
 81  QQPQNHTSPF FTEHNYKSTH TSIQSTTLSQ LPNTDTTRET
121  TYSHSINETQ NRKIKSQSTL PATRKPPINP SGSNPPENHQ
161  DHNNSQTLPY VPCSTCEGNL ACLSLCQIGP ERAPSRAPTI
201  TLKKTPKPKT TKKPTKTTIH HRTSPEAKLQ PKNNTAAPQQ
241  GILSSPEHHT NQSTTQI
```

The BRSV G protein employed in the expression can be modified by deletion of a cysteine noose domain (173 CSTCEGNLACLSLC 186 (SEQ ID NO:27 highlighted above). An example of a modified BRSV G protein with such a deletion has the sequence shown below as SEQ ID NO:28.

```
  1  MSNHTHHLKF KTLKRAWKAS KYFIVGLSCL YKFNLKSLVQ
 41  TALTTLAMIT LTSLVITAII YISVGNAKAK PTSKPTIQQT
 81  QQPQNHTSPF FTEHNYKSTH TSIQSTTLSQ LPNTDTTRET
121  TYSHSINETQ NRKIKSQSTL PATRKPPINP SGSNPPENHQ
161  DHNNSQTLPY VPQIGPERAP SRAPTITLKK TPKPKTTKKP
201  TKTTIHHRTS PEAKLQPKNN TAAPQQGILS SPEHHTNQST
241  TQI
```

This deletion can be made by deleting the 42 nucleotides that encode the CSTCEGNLACLSLC (SEQ ID NO:27) peptide. The rational for this deletion is that removal of the central core of the cysteine noose will eliminate the protein region associated with immunopathogenesis (20).

An example, of a BRSV G version 1 protein amino acid sequence is available from GenBank (accession # GI: 17939989/AAL49398.1) and shown below as SEQ ID NO:29.

```
  1  MSNHTHHLKF KTLKRAWKAS KYFIVGLSCL YKFNLKSLVQ
 41  TALTTLAMIT LTSLVITAII YISVGNAKAK PTSKPTIQQT
 81  QQPQNHTSPF FTEHNYKSTH TSIQSTTLSQ LPNTDTTRET
121  TYSHSINETQ NRKIKSQSTL PATRKPPINP SGSNPPENHQ
161  DHNNSQTLPY VPSSTSEGNL ASLSLSQIGP ERAPSRAPTI
201  TLKKTPKPKT TKKPTKTTIH HRTSPEAKLQ PKNNTAAPQQ
241  GILSSPEHHT NQSTTQI
```

A *Bos taurus* codon optimized nucleic acid segment encoding the BRSV G version 1 protein with SEQ ID NO:29, for example, can have the following nucleotide sequence, shown below as SEQ ID NO:30.

```
  1  ATGTCTAACC ATACTCACCA TCTGAAGTTC AAGACCCTGA
 41  AGCGGGCCTG GAAGGCCTCC AAGTACTTCA TCGTGGGCCT
 81  GAGCTGCCTG TACAAGTTCA ACCTGAAGAG CCTGGTGCAG
121  ACCGCTCTGA CCACCCTGGC CATGATCACC CTGACCTCCC
161  TGGTGATCAC CGCCATCATC TACATCAGCG TGGGCAACGC
201  CAAGGCCAAG CCCACCTCCA AGCCTACCAT CCAGCAGACC
241  CAGCAGCCTC AGAACCACAC CAGCCCCTTC TTCACCGAGC
281  ACAACTACAA GTCCACCCAC ACCTCCATCC AGAGCACCAC
321  CCTGTCCCAG CTGCCTAACA CCGACACCAC CCGCGAGACC
361  ACCTACGCC ACTCCATCAA CGAGACCCAG AACCGCAAGA
401  TCAAGAGCCA GTCCACCCTG CCTGCCACCA GAAAGCCCCC
441  TATCAACCCC AGCGGCTCCA ACCCCCCTGA GAACCACCAG
481  GACCACAACA ACAGCCAGAC CCTGCCCTAC GTGCCTAGCT
521  CCACCTCCGA GGGAAACCTG GCTAGCCTGT CCCTGAGCCA
561  GATCGGACCT GAGAGGGCTC CTAGCAGGGC TCCCACCATC
601  ACCCTGAAGA AGACCCCCAA GCCTAAGACC ACCAAGAAGC
641  CCACCAAGAC CACCATCCAC CACAGGACCT CCCCTGAGGC
681  TAAGCTGCAG CCCAAGAACA ACACCGCCGC CCCCCAGCAG
721  GGAATCCTGA GCAGCCCCGA ACACCACACA AACCAGAGCA
761  CTACCCAGAT C
```

An example of a fusion protein sequence that includes a gD signal sequence with the BRSV G version 1 protein amino acid sequence having SEQ ID NO:29, is shown below with SEQ ID NO:31.

```
  1  MQGPTLAVLG ALLAVAVSLP MSNHTHHLKF KTLKRAWKAS
 41  KYFIVGLSCL YKFNLKSLVQ TALTTLAMIT LTSLVITAII
 81  YISVGNAKAK PTSKPTIQQT OQPQNHTSPF FTEHNYKSTH
121  TSIQSTTLSQ LPNTDTTRET TYSHSINETQ NRKIKSQSTL
161  PATRKPPINP SGSNPPENHQ DHNNSQTLPY VPSSTSEGNL
201  ASLSLSQIGP ERAPSRAPTI TLKKTPKPKT TKKPTKTTIH
241  HRTSPEAKLQ PKNNTAAPQQ GILSSPEHHT NQSTTQI
```

A *Bos taurus* codon optimized nucleic acid segment encoding the SEQ ID NO:31 fusion protein that includes the gD signal sequence and the BRSV G version 1 protein can, for example, have the following nucleotide sequence, shown below as SEQ ID NO:32.

```
  1 ATGCAGGGAC CAACTCTGGC TGTGCTGGGG GCTCTGCTGG
 41 CTGTCGCTGT GTCACTGCCT ATGTCTAACC ATACTCACCA
 81 TCTGAAGTTC AAGACCCTGA AGCGGGCCTG GAAGGCCTCC
121 AAGTACTTCA TCGTGGGCCT GAGCTGCCTG TACAAGTTCA
161 ACCTGAAGAG CCTGGTGCAG ACCGCTCTGA CCACCCTGGC
201 CATGATCACC CTGACCTCCC TGGTGATCAC CGCCATCATC
241 TACATCAGCG TGGGCAACGC CAAGGCCAAG CCCACCTCCA
281 AGCCTACCAT CCAGCAGACC CAGCAGCCTC AGAACCACAC
321 CAGCCCCTTC TTCACCGAGC ACAACTACAA GTCCACCCAC
361 ACCTCCATCC AGAGCACCAC CCTGTCCCAG CTGCCTAACA
401 CCGACACCAC CCGCGAGACC ACCTACAGCC ACTCCATCAA
441 CGAGACCCAG AACCGCAAGA TCAAGAGCCA GTCCACCCTG
481 CCTGCCACCA GAAAGCCCCC TATCAACCCC AGCGGCTCCA
521 ACCCCCCTGA GAACCACCAG GACCACAACA ACAGCCAGAC
561 CCTGCCCTAC GTGCCTAGCT CCACCTCCGA GGGAAACCTG
601 GCTAGCCTGT CCCTGAGCCA GATCGGACCT GAGAGGGCTC
641 CTAGCAGGGC TCCCACCATC ACCCTGAAGA AGACCCCCAA
681 GCCTAAGACC ACCAAGAAGC CCACCAAGAC CACCATCCAC
721 CACAGGACCT CCCCTGAGGC TAAGCTGCAG CCCAAGAACA
761 ACACCGCCGC CCCCCAGCAG GGAATCCTGA GCAGCCCCGA
801 ACACCACACA AACCAGAGCA CTACCCAGATC
```

An expression cassette that encodes the fusion protein with the gD signal sequence and the BRSV G version 1 (GenBank accession # GI: 17939989/AAL49398.1) is shown below as SEQ ID NO:33 (and in FIG. 19A-19B).

```
  1 GGTACCCTCG TGAGGCTCCG GTGCCCGTCA GTGGGCAGAG
 41 CGCACATCGC CCACAGTCCC CGAGAAGTTG GGGGGAGGGG
 81 TCGGCAATTG AACCGGTGCC TAGAGAAGGT GGCGCGGGGT
121 AAACTGGGAA AGTGATGTCG TGTACTGGCT CCGCCTTTTT
161 CCCGAGGGTG GGGGAGAACC GTATATAAGT GCAGTAGTCG
201 CCGTGAACGT TCTTTTTCGC AACGGGTTTG CCGCCAGAAC
241 ACAGGTAAGT GCCGTGTGTG GTTCCGCGG GCCTGGCCTC
281 TTTACGGGTT ATGGCCCTTG CGTGCCTTGA ATTACTTCCA
321 CCTGGCTGCA GTACGTGATT CTTGATCCCG AGCTTCGGGT
361 TGGAAGTGGG TGGGAGAGTT CGAGGCCTTG CGCTTAAGGA
401 GCCCCTTCGC CTCGTGCTTG AGTTGAGGCC TGGCCTGGGC
441 GCTGGGGCCG CCGCGTGCGA ATCTGGTGGC ACCTTCGCGC
481 CTGTCTCGCT GCTTTCGATA AGTCTCTAGC CATTTAAAAT
521 TTTTGATGAC CTGCTGCGAC GCTTTTTTTC TGGCAAGATA
561 GTCTTGTAAA TGCGGGCCAA GATCTGCACA CTGGTATTTC
601 GGTTTTTGGG GCCGCGGGCG GCGACGGGGC CCGTGCGTCC
641 CAGCGCACAT GTTCGGCGAG GCGGGGCCTG CGAGCGCGGC
681 CACCGAGAAT CGGACGGGGG TAGTCTCAAG CTGGCCGGCC
721 TGCTCTGGTG CCTGGCCTCG CGCCGCCGTG TATCGCCCCG
761 CCCTGGGCGG CAAGGCTGGC CCGGTCGGCA CCAGTTGCGT
801 GAGCGGAAAG ATGGCCGCTT CCCGGCCCTG CTGCAGGGAG
841 CTCAAAATGG AGGACGCGGC GCTCGGGAGA GCGGGCGGGT
881 GAGTCACCCA CACAAAGGAA AAGGGCCTTT CCGTCCTCAG
921 CCGTCGCTTC ATGTGACTCC ACGGAGTACC GGGCGCCGTC
961 CAGGCACCTC GATTAGTTCT CGAGCTTTTG GAGTACGTCG
1001 TCTTTAGGTT GGGGGGAGGG GTTTTATGCG ATGGAGTTTC
1041 CCCACACTGA GTGGGTGGAG ACTGAAGTTA GGCCAGCTTG
1081 GCACTTGATG TAATTCTCCT TGGAATTTGC CCTTTTTGAG
1121 TTTGGATCTT GGTTCATTCT CAAGCCTCAG ACAGTGGTTC
1161 AAAGTTTTTT TCTTCCATTT CAGGTGTCGT GAGGAATTAG
1201 CTTGGTACTA ATACGACTCA CTATAGGGAG ACCCAAGCTG
1241 GCTAGGTAAG TGTACGAGCT CGATCACTAG TCCAGTGTGG
1281 ATCGATGCCG CCACCATGCA GGGACCAACT CTGGCTGTGC
1121 TGGGGCTCT GCTGGCTGTC GCTGTGTCAC TGCCTATGTC
1161 TAACCATACT CACCATCTGA AGTTCAAGAC CCTGAAGCGG
1201 GCCTGGAAGG CCTCCAAGTA CTTCATCGTG GGCCTGAGCT
1241 GCCTGTACAA GTTCAACCTG AAGAGCCTGG TGCAGACCGC
1281 TCTGACCACC CTGGCCATGA TCACCCTGAC CTCCCTGGTG
1321 ATCACCGCCA TCATCTACAT CAGCGTGGGC AACGCCAAGG
1361 CCAAGCCCAC CTCCAAGCCT ACCATCCAGC AGACCCAGCA
1401 GCCTCAGAAC CACACCAGCC CCTTCTTCAC CGAGCACAAC
1441 TACAAGTCCA CCCACACCTC CATCCAGAGC ACCACCCTGT
1481 CCCAGCTGCC TAACACCGAC ACCACCCGCG AGACCACCTA
1521 CAGCCACTCC ATCAACGAGA CCCAGAACCG CAAGATCAAG
1561 AGCCAGTCCA CCCTGCCTGC CACCAGAAAG CCCCCTATCA
1601 ACCCCAGCGG CTCCAACCCC CCTGAGAACC ACCAGGACCA
1641 CAACAACAGC CAGACCCTGC CCTACGTGCC TAGCTCCACC
1681 TCCGAGGGAA ACCTGGCTAG CCTGTCCCTG AGCCAGATCG
1721 GACCTGAGAG GGCTCCTAGC AGGGCTCCCA CCATCACCCT
1761 GAAGAAGACC CCCAAGCCTA AGACCACCAA GAAGCCCACC
1801 AAGACCACCA TCCACCACAG GACCTCCCCT GAGGCTAAGC
1841 TGCAGCCCAA GAACAACACC GCCGCCCCCC AGCAGGGAAT
1881 CCTGAGCAGC CCCGAACACC ACACAAACCA GAGCACTACC
1921 CAGATCATGC ATGGTAAGCC TATCCCTAAC CCTCTCCTCG
1961 GTCTCGATTC TACGCGTACC GGTCATCATC ACCATCACCA
2001 TTGAGTTTAA ACCCGCTGAT CAGCCTCGAC TGTGCCTTCT
2041 AGTTGCCAGC CATCTGTTGT TTGCCCCTCC CCCGTGCCTT
```

-continued

```
2081 CCTTGACCCT GGAAGGTGCC ACTCCCACTG TCCTTTCCTA
2121 ATAAAATGAG GAAATTGCAT CGCATTGTCT GAGTAGGTGT
2161 CATTCTATTC TGGGGGGTGG GGTGGGGCAG GACAGCAAGG
2201 GGGAGGATTG GGAAGACAAT AGCAGGCATG CTGGGGATGC
2241 GGTGGGCTCT ATGGCTTGGT ACC
```

An example of a BRSV G version 2 protein amino acid sequence is available from GenBank (accession # GI: 17939989/AAL49398.1) and shown below as SEQ ID NO:34.

```
  1 MSNHTHHLKF KTLKRAWKAS KYFIVGLSCL YKFNLKSLVQ
 41 TALTTLAMIT LTSLVITAII YISVGNAKAK PTSKPTIQQT
 81 QQPQNHTSPF FTEHNYKSTH TSIQSTTLSQ LPNTDTTRET
121 TYSHSINETQ NRKIKSQSTL PATRKPPINP SGSNPPENHQ
161 DHNNSQTLPY VPQIGPERAP SRAPTITLKK TPKPKTTKKP
201 TKTTIHHRTS PEAKLQPKNN TAAPQQGILS SPEHHTNQST
241 TQI
```

A *Bos taurus* codon optimized nucleic acid segment encoding the BRSV G version 2 protein with SEQ ID NO:34, for example, can have the following nucleotide sequence, shown below as SEQ ID NO:35.

```
  1 ATGTCTAACC ATACTCACCA TCTGAAGTTC AAGACCCTGA
 41 AGCGGGCCTG GAAGGCCTCC AAGTACTTCA TCGTGGGCCT
 81 GAGCTGCCTG TACAAGTTCA ACCTGAAGAG CCTGGTGCAG
121 ACCGCTCTGA CCACCCTGGC CATGATCACC CTGACCTCCC
161 TGGTGATCAC CGCCATCATC TACATCAGCG TGGGCAACGC
201 CAAGGCCAAG CCCACCTCCA AGCCTACCAT CCAGCACACC
241 CAGCAGCCTC AGAACCACAC CAGCCCCTTC TTCACCGAGC
281 ACAACTACAA GTCCACCCAC ACCTCCATCC AGAGCACCAC
321 CCTGTCCCAG CTGCCTAACA CCGACACCAC CCGCGAGACC
361 ACCTACAGCC ACTCCATCAA CGAGACCCAG AACCGCAAGA
401 TCAAGAGCCA GTCCACCCTG CCTGCCACCA GAAAGCCCCC
441 TATCAACCCC AGCGGCTCCA ACCCCCCTGA GAACCACCAG
481 GACCACAACA ACAGCCAGAC CCTGCCCTAC GTGCCTCAGA
521 TCGGACCTGA GAGGGCTCCT AGCAGGGCTC CCACCATCAC
561 CCTGAAGAAG ACCCCCAAGC CTAAGACCAC CAAGAAGCCC
601 ACCAAGACCA CCATCCACCA CAGGACCTCC CCTGAGGCTA
641 AGCTGCAGCC CAAGAACAAC ACCGCCGCCC CCAGCAGGG
681 AATCCTGAGC AGCCCCGAAC ACCACACAAA CCAGAGCACT
721 ACCCAGATC
```

An example of a fusion protein sequence that includes a gD signal sequence with the BRSV G version 2 sequence having SEQ ID NO:34, is shown below with SEQ ID NO:36.

```
  1 MQGPTLAVLG ALLAVAVSLP MSNHTHHLKF KTLKRAWKAS
 41 KYFIVGLSCL YKFNLKSLVQ TALTTLAMIT LTSLVITAII
 81 YISVGNAKAK PTSKPTIQQT QQPQNHTSPF FTEHNYKSTH
121 TSIQSTTLSQ LPNTDTTRET TYSHSINETQ NREIKSQSTL
161 PATRKPPINP SGSNPPENHQ DHNNSQTLPY VPQIGPERAP
201 SRAPTITLKK TPKPKTTKKP TKTTIHHRTS PEAKLQPKNN
241 TAAPQQGILS SPEHHTNQST TQI
```

A *Bos taurus* codon optimized nucleic acid segment encoding the SEQ ID NO:36 fusion protein that includes the gD signal sequence and the BRSV G version 2 protein can, for example, have the following nucleotide sequence, shown below as SEQ ID NO:37.

```
  1 ATGCAGGGAC CAACTCTGGC TGTGCTGGGG GCTCTGCTGG
 41 CTGTCGCTGT GTCACTGCCT ATGTCTAACC ATACTCACCA
 81 TCTGAAGTTC AAGACCCTGA AGCGGGCCTG GAAGGCCTCC
121 AAGTACTTCA TCGTGGGCCT GAGCTGCCTG TACAAGTTCA
161 ACCTGAAGAG CCTGGTGCAG ACCGCTCTGA CCACCCTGGC
201 CATGATCACC CTGACCTCCC TGGTGATCAC CGCCATCATC
241 TACATCAGCG TGGGCAACGC CAAGGCCAAG CCCACCTCCA
281 AGCCTACCAT CCAGCAGACC CAGCAGCCTC AGAACCACAC
321 CAGCCCCTTC TTCACCGAGC ACAACTACAA GTCCACCCAC
361 ACCTCCATCC AGAGCACCAC CCTGTCCCAG CTGCCTAACA
401 CCGACACCAC CCGCGAGACC ACCTACAGCC ACTCCATCAA
441 CGAGACCCAG AACCGCAAGA TCAAGAGCCA GTCCACCCTG
481 CCTGCCACCA GAAAGCCCCC TATCAACCCC AGCGGCTCCA
521 ACCCCCCTGA GAACCACCAG GACCACAACA ACAGCCAGAC
561 CCTGCCCTAC GTGCCTCAGA TCGGACCTGA GAGGGCTCCT
601 AGCAGGGCTC CCACCATCAC CCTGAAGAAG ACCCCCAAGC
641 CTAAGACCAC CAAGAAGCCC ACCAAGACCA CCATCCACCA
681 CAGGACCTCC CCTGAGGCTA AGCTGCAGCC CAAGAACAAC
721 ACCGCCGCCC CCAGCAGGG AATCCTGAGC AGCCCCGAAC
761 ACCACACAAA CCAGAGCACT ACCCAGATC
```

An expression cassette that encodes the fusion protein with the gD signal sequence and the BRSV G version 2 (GenBank accession # GenBank accession # GI: 17939989/ AAL49398.1) is shown below as SEQ ID NO:38 (and in FIG. 20).

```
  1 GGTACCCTCG TGAGGCTCCG GTGCCCGTCA GTGGGCAGAG
 41 CGCACATCGC CCACAGTCCC CGAGAAGTTG GGGGAGGGG
 81 TCGGCAATTG AACCGGTGCC TAGAGAAGGT GGCGCGGGGT
121 AAACTGGGAA AGTGATGTCG TGTACTGGCT CCGCCTTTTT
161 CCCGAGGGTG GGGGAGAACC GTATATAAGT GCAGTAGTCG
```

```
201 CCGTGAACGT TCTTTTTCGC AACGGGTTTG CCGCCAGAAC
241 ACAGGTAAGT GCCGTGTGTG GTTCCCGCGG GCCTGGCCTC
281 TTTACGGGTT ATGGCCCTTG CGTGCCTTGA ATTACTTCCA
321 CCTGGCTGCA GTACGTGATT CTTGATCCCG AGCTTCGGGT
361 TGGAAGTGGG TGGGAGAGTT CGAGGCCTTG CGCTTAAGGA
401 GCCCCTTCGC CTCGTGCTTG AGTTGAGGCC TGGCCTGGGC
441 GCTGGGGCCG CCGCGTGCGA ATCTGGTGGC ACCTTCGCGC
481 CTGTCTCGCT GCTTTCGATA AGTCTCTAGC CATTTAAAAT
521 TTTTGATGAC CTGCTGCGAC GCTTTTTTTC TGGCAAGATA
561 GTCTTGTAAA TGCGGGCCAA GATCTGCACA CTGGTATTTC
601 GGTTTTTGGG GCCGCGGGCG GCGACGGGGC CCGTGCGTCC
641 CAGCGCACAT GTTCGGCGAG GCGGGGCCTG CGAGCGCGGC
681 CACCGAGAAT CGGACGGGGG TAGTCTCAAG CTGGCCGGCC
721 TGCTCTGGTG CCTGGCCTCG CGCCGCCGTG TATCGCCCCG
761 CCCTGGGCGG CAAGGCTGGC CCGGTCGGCA CCAGTTGGGT
801 GAGCGGAAAG ATGGCCGCTT CCCGGCCCTG CTGCAGGGAG
841 CTCAAAATGG AGGACGCGGC GCTCGGGAGA GCGGGCGGGT
881 GAGTCACCCA CACAAAGGAA AAGGGCCTTT CCGTCCTCAG
921 CCGTCGCTTC ATGTGACTCC ACGGAGTACC GGGCGCCGTC
961 CAGGCACCTC GATTAGTTCT CGAGCTTTTG GAGTACGTCG
1001 TCTTTAGGTT GGGGGGAGGG GTTTTATGCG ATGGAGTTTC
1041 CCCACACTGA GTGGGTGGAG ACTGAAGTTA GGCCAGCTTG
1081 GCACTTGATG TAATTCTCCT TGGAATTTGC CCTTTTTGAG
1121 TTTGGATCTT GGTTCATTCT CAAGCCTCAG ACAGTGGTTC
1161 AAAGTTTTTT TCTTCCATTT CAGGTGTCGT GAGGAATTAG
1201 CTTGGTACTA ATACGACTCA CTATAGGGAG ACCCAAGCTG
1241 GCTAGGTAAG TGTACGAGCT CGATCACTAG TCCAGTGTGG
1281 ATCGATGCCG CCACCATGCA GGGACCAACT CTGGCTGTGC
1321 TGGGGCTCT GCTGGCTGTC GCTGTGTCAC TGCCTATGTC
1361 TAACCATACT CACCATCTGA AGTTCAAGAC CCTGAAGCGG
1401 GCCTGGAAGG CCTCCAAGTA CTTCATCGTG GGCCTGAGCT
1441 GCCTGTACAA GTTCAACCTG AAGAGCCTGG TGCAGACCGC
1481 TCTGACCACC CTGGCCATGA TCACCCTGAC CTCCCTGGTG
1521 ATCACCGCCA TCATCTACAT CAGCGTGGGC AACGCCAAGG
1561 CCAAGCCCAC CTCCAAGCCT ACCATCCAGC AGACCCAGCA
1601 GCCTCAGAAC ACACCAGCC CCTTCTTCAC CGAGCACAAC
1641 TACAAGTCCA CCCACACCTC CATCCAGAGC ACCACCCTGT
1681 CCCAGCTGCC TAACACCGAC ACCACCCGCG AGACCACCTA
1721 CAGCCACTCC ATCAACGAGA CCCAGAACCG CAAGATCAAG
1761 AGCCAGTCCA CCCTGCCTGC CACCAGAAAG CCCCCTATCA
1801 ACCCCAGCGG CTCCAACCCC CTGAGAACC ACCAGGACCA
```

```
1841 CAACAACAGC CAGACCCTGC CCTACGTGCC TCAGATCGGA
1881 CCTGAGAGGG CTCCTAGCAG GGCTCCCACC ATCACCCTGA
1921 AGAAGACCCC CAAGCCTAAG ACCACCAAGA AGCCCACCAA
1961 GACCACCATC CACCACAGGA CCTCCCCTGA GGCTAAGCTG
2001 CAGCCCAAGA ACAACACCGC CGCCCCCAG CAGGGAATCC
2041 TGAGCAGCCC CGAACACCAC ACAAACCAGA GCACTACCCA
2081 GATCATGCAT GGTAAGCCTA TCCCTAACCC TCTCCTCGGT
2121 CTCGATTCTA CGCGTACCGG TCATCATCAC CATCACCATT
2161 GAGTTTAAAC CCGCTGATCA GCCTCGACTG TGCCTTCTAG
2201 TTGCCAGCCA TCTGTTGTTT GCCCCTCCCC CGTGCCTTCC
2241 TTGACCCTGG AAGGTGCCAC TCCCACTGTC CTTTCCTAAT
2281 AAAATGAGGA AATTGCATCG CATTGTCTGA GTAGGTGTCA
2321 TTCTATTCTG GGGGGTGGGG TGGGGCAGGA CAGCAAGGGG
2361 GAGGATTGGG AAGACAATAG CAGGCATGCT GGGGATGCGG
2401 TGGGCTCTAT GGCTTGGTAC C
```

Other BRSV G nucleic acid sequences can be obtained from various genomic, cDNA, and plasmid sources by PCR using primer pairs specific for amino terminal BRSV G sequence and verified by sequencing before or after insertion into an expression cassette or vector.

Live attenuated vaccines are currently available for BRSV as multivalent BoHV-1, BVDV, BRSV and PI3 vaccines. However, reduced clinical disease and lung lesions (i.e., criteria for the vaccine efficacy) following experimental challenge with such vaccines, have not been achieved consistently for treatment of BRSV. Vaccine development against BRSV has been hampered by enhanced BRSV disease in vaccinated animals after subsequent infection (3, 20, 26, 36, 47, 76). In addition, the virus replicates poorly in cell cultures. DNA plasmid and vaccinia virus-based subunit vaccines carrying envelope proteins G and F proteins have been tested and are reported to be protective against BRSV challenge (4, 78, 79, 81).

Protection against respiratory viruses is better when animals are vaccinated intranasally (natural route). However, vaccinia virus is administered intradermally and the DNA plasmid vaccine is administered in the muscle. Such routes of administration are not optimal for immunization of cattle. In addition, the DNA vaccine may not be cost effective for use in cattle because two injections are needed.

Chimeric BRSV F and G gene expression cassettes that lack the sequences associated with immune mediated pathogenesis have been prepared that can exhibit efficacy and protective immune responses against virulent BRSV challenge.

In summary, current vaccines against the viruses associated with BRDC are not highly efficacious for several reasons:
  i) In the case of BoHV-1, MLV vaccine viruses, including the gE gene-deleted marker vaccine, have intact immunosuppressive properties, while the killed inactivated vaccines are not adequately protective because they do not generate cellular immunity (31, 32).
  ii) ii) For the modified live RNA vaccine strains, their immunosuppressive properties combined with a higher mutation rate complicates successful immunization/ protection and safety in the field (9, 13, 25, 38, 62, 69, 73, 94). Taken together, a different vaccine approach against BoHV-1 as well as against BRDC associated respiratory RNA viruses is essential.

Antigen Sequence Variants

The antigen that can be encoded into the recombinant BoHV-1 tmv viruses described herein include variants of the specific nucleic acids, polypeptides or peptides that are described herein. A variant nucleic acid or a polypeptide is substantially the same as an antigen (e.g., an E2, F, or F) nucleic acid or polypeptide sequence defined by any of the SEQ ID NOs described herein but has at least one nucleotide or amino acid difference relative an antigen (e.g., an E2, F, or F) nucleic acid or polypeptide sequence defined by SEQ ID NO herein. For example, the variant nucleic acid or a polypeptide can have at least 80%, 90%, 92%, 95%, 97% or 99% sequence identity to a SEQ ID NO provided herein. The range of percent sequence identity can include at least any percent between 80 and 100 relative an antigen (e.g., an E2, F, or F) nucleic acid or polypeptide sequence defined by SEQ ID NO herein. The percent identical nucleotides or amino acids can be contiguous or dispersed across the sequences. Such variant nucleic acids or polypeptides can, for example, have substitutions that are mostly conservative.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine: a group of amino acids having amide-containing side chains is asparagine and glutamine: a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the antigen (e.g., an E2, Erns, F, or G) polypeptide has one or more, for instance, at least 2, 3, 4, 5, 6, 7, 8, 9, 10, 12, 14, 15, or 20, nonconservative amino acid substitutions, relative to a polypeptide defined by one of the SEQ ID NOs described herein. In one embodiment, the antigen (e.g., an E2, Erns, F, or G) polypeptide has one or more, for instance, at least 2, 3, 4, 5, 6, 7, 8, 9, 10, 12, 14, 15, or 20, conservative amino acid substitutions, relative to a polypeptide defined by one of SEQ ID NOs described herein. In some cases, the antigen (e.g., an E2, Erns, F, or G) polypeptide has less than 100, 95, 90, 80, 75, 60, 50, 40, 35, 30, or 25, nonconservative amino acid substitutions, relative to a polypeptide defined by one of SEQ ID NOs described herein. In some cases, the antigen (e.g., an E2, Erns, F, or G) polypeptide has less than 100, 95, 90, 80, 75, 60, 50, 40, 35, 30, or 25, conservative amino acid substitutions, relative to a polypeptide defined by one of SEQ ID NOs described herein.

Construction of BoHV-1 Tmv Vector Encoding BVDV and/or BRSV Antigens

The selected antigens for insertion into BoHV-1 tmv vector can be encoded by nucleic acid segments that are synthesized by various procedures. As discussed above, these antigens can include a BVDV E2 protein, BVDV Erns protein, a BRSV F protein, a BRSV G protein, or any combination thereof. In some cases, the nucleic acids encoding such antigen can be codon-optimized, with a bias for expression in bovine cells.

The nucleic acids encoding such antigens can have a consensus Kozak sequence (e.g., GCCATGG) at the 5' end of the coding region. In some cases, the nucleic acids encoding such antigens can also encode signal sequence at the amino terminal end of the coding region of the protein. For example, such a signal sequence can be a BoHV-1 gD signal sequence. In some cases, the BRSV G protein may not have a signal sequence, because the absence of such a signal sequence can help the G protein to retain its type II membrane topography. The nucleic acids encoding each antigen can in some cases be cloned separately into a convenient plasmid or vector and then combined into the BoHV-1 tmv vector.

The nucleic acid segments encoding the selected protein antigens for insertion into BoHV-1 tmv vector can be inserted into an expression cassette that includes a promoter to facilitate expression of the protein antigens. Host cells can be transformed by the expression cassette or expression vector. Some procedures for making such expression cassettes, expression vectors, and genetically modified host cells are described below.

The nucleic acid segments encoding protein antigens can be operably linked to a promoter, which provides for expression of an mRNA encoding the protein antigens, polypeptides or peptides. The promoter can be a promoter functional in a host cell such as a viral promoter, a bacterial promoter or a mammalian promoter. The promoter can be a heterologous promoter. As used herein, "heterologous" when used in reference to a gene or nucleic acid refers to a gene or nucleic acid that has been manipulated in some way. For example, a heterologous promoter can be a promoter that contains sequences that are not naturally linked to an associated coding region. Thus, for example, a heterologous promoter may not in some cases be the same as the natural viral promoter that drives expression of BVDV E2 protein, BVDV Erns, a BRSV F protein, or a BRSV G protein.

Nucleic acid segments encoding protein antigens are operably linked to the promoter when so that the coding region(s) of the protein antigen(s) is located downstream from the promoter. The operable combination of the promoter with a protein antigen coding region is a key part of the expression cassette or expression vector.

Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired. In some embodiments, the promoter is an inducible promoter and/or a tissue-specific promoter.

Examples of promoters that can be used include, but are not limited to, a human elongation factor 1α promoter, a T7 promoter (e.g., optionally with the lac operator), the CaMV 35S promoter (Odell et al., *Nature*. 313:810-812 (1985)), the CaMV 19S promoter (Lawton et al., *Plant Molecular Biology*. 9:315-324 (1987)), nos promoter (Ebert et al., *Proc. Natl. Acad. Sci. USA*. 84:5745-5749 (1987)), Adh1 promoter (Walker et al., *Proc. Natl. Acad. Sci. USA*. 84:6624-6628 (1987)), sucrose synthase promoter (Yang et al., *Proc. Natl. Acad. Sci. USA*. 87:4144-4148 (1990)), α-tubulin promoter, ubiquitin promoter, actin promoter (Wang et al., *Mol. Cell. Biol.* 12:3399 (1992)), cab (Sullivan et al., *Mol. Gen. Genet*. 215:431 (1989)), PEPCase promoter (Hudspeth et al., *Plant Molecular Biology*. 12:579-589 (1989)), the CCR promoter (cinnamoyl CoA:NADP oxidoreductase, EC 1.2.1.44) isolated from *Lollium perenne*, (or a perennial ryegrass) and/or those associated with the R gene complex (Chandler et al., *The Plant Cell*. 1:1175-1183 (1989)).

Other constitutive or inducible promoters can be used with or without associated enhancer elements. Examples include a baculovirus derived promoter, the p10 promoter. Typically, a viral or mammalian promoter is employed, but in some cases, plant or yeast promoters can also be used.

Alternatively, novel tissue specific promoter sequences may be employed in the practice of the present invention. Coding regions from a particular cell type or tissue can be identified and the expression control elements of those coding regions can be identified using techniques available to those of skill in the art.

The nucleic acid encoding the protein antigens or peptide therefrom can be combined with the promoter by available methods to yield an expression cassette, for example, as described in Sambrook et al. (Molecular Cloning: A Laboratory Manual. Second Edition (Cold Spring Harbor, N.Y.: Cold Spring Harbor Press (1989); Molecular Cloning: A Laboratory Manual. Third Edition (Cold Spring Harbor, N.Y.: Cold Spring Harbor Press (2000)). For example, a plasmid containing a promoter such as the T7-lac promoter can be constructed or obtained from Snap Gene. These and other plasmids are constructed to have multiple cloning sites having specificity for different restriction enzymes downstream from the promoter. The nucleic acid encoding the BoHV-1 protein antigens or peptide therefrom can be subcloned downstream from the promoter using restriction enzymes and positioned to ensure that the DNA is inserted in proper orientation with respect to the promoter so that the DNA can be expressed as sense RNA.

Expression cassettes that include a promoter operably linked to a protein antigen, polypeptide or peptide coding region can include other elements such as a segment encoding 3' nontranslated regulatory sequences, and restriction sites for insertion, removal and manipulation of segments of the expression cassettes. The 3' nontranslated regulatory DNA sequences can act as a signal to terminate transcription and allow for the polyadenylation of the resultant mRNA. The 3' nontranslated regulatory DNA sequence preferably includes from about 300 to 1,000 nucleotide base pairs and contains prokaryotic or eukaryotic transcriptional and translational termination sequences. Various 3' elements that are available to those of skill in the art can be employed. These 3' nontranslated regulatory sequences can be obtained as described in An (*Methods in Enzymology.* 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of a BoHV-1 protein antigens polypeptide or peptide coding region by available methods.

Once the nucleic acid encoding the protein antigens or peptide therefrom is operably linked to a promoter (e.g., and other selected elements), the expression cassette so formed can be subcloned into a plasmid or other vector (e.g., an expression vector). Such expression vectors can have a prokaryotic or eukaryotic replication origin, for example, to facilitate episomal replication in bacterial, vertebrate and/or yeast cells.

Examples of vectors that provide for easy selection, amplification, and transformation of the expression cassette in prokaryotic and eukaryotic cells include pET-43.1a(+), pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, such as antibiotic or herbicide resistance, unique multiple cloning sites providing for multiple sites to insert DNA sequences, and/or sequences that enhance transformation of prokaryotic and eukaryotic cells.

In order to improve identification of transformed cells, a selectable or screenable marker gene can be employed in the expression cassette or expression vector. “Marker genes” are genes that impart a distinct phenotype to cells expressing the marker gene and thus allow such transformed cells to be distinguished from cells that do not have the marker. Such genes may encode either a selectable or screenable marker, depending on whether the marker confers a trait which one can ‘select’ for by chemical means, i.e., through the use of a selective agent (e.g., an antibiotic), or whether it is simply a trait that one can identify through observation or testing, i.e., by ‘screening’ (e.g., the R-locus trait). Of course, many examples of suitable marker genes are known to the art and can be employed in the practice of the invention.

Included within the terms selectable or screenable “marker” genes are genes which encode a “secretable marker” whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

Possible selectable markers for use in connection with the present invention include, but are not limited to, an ampicillin gene, which codes for the ampicillin antibiotic. Other examples include a neo gene (Potrykus et al., *Mol. Gen. Genet.* 199:183-188 (1985)) which codes for kanamycin resistance and can be selected for using kanamycin, G418, and the like; a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon: a mutated anthranilate synthase gene that confers resistance to 5-methyl tryptophan: a β-galactosidase gene, which encodes an enzyme for which there are chromogenic substrates: a luciferase (lux) gene (Ow et al.,

*Science.* 234:856-859, 1986), which allows for bioluminescence detection: or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995).

One example of an expression vehicle that can be modified to include one or more nucleic acid segment encoding one or more protein antigens (e.g., a BVDV E2 protein, BVDV Erns protein, a BRSV F protein, a BRSV G protein, or any combination thereof) is a pPreBVDV-E2/BRSV-F or G vehicle which includes a sequence shown in FIG. 10, also provided below as SEQ ID NO: 1.

```
   1 GGTACCCTCG TGAGGCTCCG GTGCCCGTCA GTGGGCAGAG
  41 CGCACATCGC CCACAGTCCC CGAGAAGTTG GGGGGAGGGG
  81 TCGGCAATTG AACCGGTGCC TAGAGAAGGT GGCGCGGGGT
 121 AAACTGGGAA AGTGATGTCG TGTACTGGCT CCGCCTTTTT
 161 CCCGAGGGTG GGGGAGAACC GTATATAAGT GCAGTAGTCG
 201 CCGTGAACGT TCTTTTTCGC AACGGGTTTG CCGCCAGAAC
 241 ACAGGTTAGT GCCGTGTGTG GTTCCCGCGG GCCTGGCCTC
 281 TTTACGGGTT ATGGCCCTTG CGTGCCTTGA ATTACTTCCA
 321 CCTGGCTGCA GTACGTGATT CTTGATCCCG AGCTTCGGGT
 361 TGGAAGTGGG TGGGAGAGTT CGAGGCCTTG CGCTTAAGGA
 401 GCCCCTTCGC CTCGTGCTTG AGTTGAGGCC TGGCCTGGGC
 441 GCTGGGGCCG CCGCGTGCGA ATCTGGTGGC ACCTTCGCGC
 481 CTGTCTCGCT GCTTTCGATA AGTCTCTAGC CATTTAAAAT
 521 TTTTGATGAC CTGCTGCGAC GCTTTTTTTC TGGCAAGATA
 561 GTCTTGTAAA TGCGGGCCAA GATCTGCACA CTGGTATTTC
 601 GGTTTTTGGG GCCGCGGGCG GCGACGGGGC CCGTGCGTCC
 641 CAGCGCACAT GTTCGGCGAG GCGGGGCCTG CGAGCGCGGC
 681 CACCGAGAAT CGGACGGGGG TAGTCTCAAG CTGGCCGGCC
 721 TGCTCTGGTG CCTGGCCTCG CGCCGCCGTG TATCGCCCCG
 761 CCCTGGGCGG CAAGGCTGGC CCGGTCGGCA CCAGTTGCGT
 801 GAGCGGAAAG ATGGCCGCTT CCCGGCCCTG CTGCAGGGAG
 841 CTCAAAATGG AGGACGCGGC GCTCGGGAGA GCGGGCGGGT
 881 GAGTCACCCA CACAAAGGAA AAGGGCCTTT CCGTCCTCAG
 921 CCGTCGCTTC ATGTGACTCC ACGGAGTACC GGGCGCCGTC
 961 CAGGCACCTC GATTAGTTCT CGAGCTTTTG GAGTACGTCG
1001 TCTTTAGGTT GGGGGGAGGG GTTTTATGCG ATGGAGTTTC
1041 CCCACACTGA GTGGGTGGAG ACTGAAGTTA GGCCAGCTTG
1081 GCACTTGATG TAATTCTCCT TGGAATTTGC CCTTTTTGAG
1121 TTTGGATCTT GGTTCATTCT CAAGCCTCAG ACAGTGGTTC
1161 AAAGTTTTTT TCTTCCATTT CAGGTGTCGT GAGGAATTAG
1201 CTTGGTACTA ATACGACTCA CTATAGGGAG ACCCAAGCTG
1241 GCTAGGTAAG TGTACGAGCT CGATCACTAG TCCAGTGTGG
1281 ATCGATGATA TCTCTAGAAT GCATGGTAAG CCTATCCCTA
1321 ACCCTCTCCT CGGTCTCGAT TCTACGCGTA CCGGTCATCA
1361 TCACCATCAC CATTGAGTTT AAACCCGCTG ATCAGCCTCG
1241 ACTGTGCCTT CTAGTTGCCA GCCATCTGTT GTTTGCCCCT
1281 CCCCCGTGCC TTCCTTGACC CTGGAAGGTG CCACTCCCAC
1321 TGTCCTTTCC TAATAAAATG AGGAAATTGC ATCGCATTGT
1361 CTGAGTAGGT GTCATTCTAT TCTGGGGGGT GGGGTGGGGC
1401 AGGACAGCAA GGGGGAGGAT TGGGAAGACA ATAGCAGGCA
1441 TGCTGGGGAT GCGGTGGGCT CTATGGCTTG GTACC
```

For example, a BVDV E2 protein, a BVDV Erns protein, a BRSV F protein, a BRSV G protein, or any combination thereof, can be inserted into a pPreBVDV-E2/BRSV-F or G vehicle at a KpnI site as illustrated in FIGS. 8 and 11.

The expression cassettes and/or expression vectors can be introduced into a recipient host cell to create a transformed cell by available methods. As illustrated in the Examples, many of the vectors can infect some mammalian cells types, for example, the Madin-Darby bovine kidney (MDBK) cell line obtained from the American Type Culture Collection (Manassas, Va.) can be used for growth, culturing, and analysis of expression cassettes, expression vectors, and viruses that may express the protein antigens. Such MDBK cells can be maintained in Dulbecco's modified Eagle's medium (DMEM) supplemented with 5-10% heat-inactivated fetal bovine serum (FBS) (HyClone Laboratories, Inc., South Logan, Utah).

The frequency of occurrence of cells taking up exogenous (foreign) DNA some transformation procedures can be low, and it is likely that not all recipient cells receiving DNA segments or sequences will result in a transformed cell. Some may show only initial and transient gene expression. However, cells from virtually any species can be stably transformed, and those cells can be utilized to generate antigenic polypeptides or peptides.

Transformation of the host cells with expression cassettes or expression vectors can be conducted by any one of a number of methods available to those of skill in the art. Examples are: transformation by direct DNA transfer into host cells by electroporation, direct DNA transfer into host cells by PEG precipitation, direct DNA transfer to plant cells by microprojectile bombardment, and calcium chloride/heat shock.

Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

For example, the Madin-Darby bovine kidney (MDBK) cell line obtained from the American Type Culture Collection (Manassas, Va.) can be used for growth, culturing, and analysis of expression cassettes, expression vectors, and viruses that may express the protein antigens. Such MDBK cells can be maintained in Dulbecco's modified Eagle's medium (DMEM) supplemented with 5-10% heat-inactivated fetal bovine serum (FBS) (HyClone Laboratories, Inc., South Logan, Utah).

Once the expression cassette or vector encoding one or more protein antigens has been constructed and introduced into a host cell, the host cells can be screened for the ability to express the encoded protein antigens by available methods. For example, when the protein antigens has a poly-histidine tag, and the His-tagged protein antigens can be detected or isolated by use of anti-His tag antibodies. In another example, protein antigens can be detected using antibodies that bind to the polypeptides or peptides (e.g., via western blot or ELISA). Nucleic acids encoding the protein antigens can be detected by Southern blot, or nucleic acid amplification using complementary probes and/or primers. Sequencing of the nucleic acids can be performed to confirm the expression cassette or vector sequences.

For example, protein antigens (e.g., a BVDV E2 protein, a BRSV F protein, a BRSV G protein, or any combination thereof) within an expression cassette that includes V5 epitope (e.g., an expression cassette that includes portions of SEQ ID NO:1) can be expressed transiently in 293T transfected cells and verified by immuno-fluorescence using V5 epitope specific antibody (Invitrogen, R960-25). For example, expression of a BVDV E2 protein, a BRSV F protein, a BRSV G protein, or any combination thereof can be detected by use of protein-specific antibodies such as BVDV type 2 E2-specific MAb (VMRD BA-2); or BRSV F specific MAb 8G12 (41). Other antibodies can also be used such as a BRSV F specific rabbit polyclonal ab45478 (abcam) or a BRSV antibody (Rabbit anti BRSV polyclonal antibody PAB 14559, Abnova corporation; MAb RSV 133/cat# ab94966, abcam).

Protection of animals against viral infection, or the symptoms thereof can be compared to infection and symptoms of a virulent viral infection, for example, an infection by a BHV-1 Cooper (Colorado-1) strain, which can be obtained from the American Type Culture Collection (Cat # CRL-1390; Manassas, Va.). Propagation of such a virulent BHV-1 strain can be performed as described by Chowdhury (Microbiol 52(1-2): 13-23 (1996)).

Vaccines

A vaccine includes at least one isolated recombinant BoHV-1 tmv virus that can express one or more heterologous antigens, peptides or polypeptides, and optionally one or more other isolated viruses including other isolated recombinant BoHV-1 tmv viruses, one or more antigens, immunogenic proteins or glycoproteins of one or more isolated viruses or one or more other pathogens, e.g., an immunogenic protein from one or more bacteria, non-BoHV viruses, yeast or fungi, or isolated nucleic acid encoding one or more viral proteins (e.g., DNA vaccines). For example, the BoHV-1 tmv viral construct may be a vaccine for pathogens that contribute to bovine respiratory disease complex (BRDC). In some cases, the vaccines can in GM-CSF either as protein within the vaccine composition, or expressed from an expression cassette or expression vector.

A complete vaccine may be concentrated (e.g., by ultrafiltration) and then at least partially purified (e.g., by zonal centrifugation or by chromatography). Viruses other than the BoHV-1 tmv virus, such as a multivalent vaccine, can also be included in the vaccine compositions. The vaccine can be inactivated before or after purification, for example, using formalin or beta-propiolactone, for instance.

A subunit vaccine can include purified peptides and/or polypeptides (e.g., glycoproteins) as antigens or as immunological stimulants. Such a vaccine may be prepared as follows: using viral suspensions fragmented by treatment with detergent, the antigenic (e.g., surface) polypeptides and/or peptides can be purified, by ultracentrifugation, for example. A detergent may be used such as a cationic detergent. For example, a detergent such as hexadecyl trimethyl ammonium bromide (Bachmeyer, 1975), an anionic detergent such as ammonium deoxycholate (Laver & Webster, 1976): or a nonionic detergent such as that commercialized under the name TRITON X100 can be employed. The subunit vaccine can, for example, be combined with a BoHV-1 tmv virus of the invention in a multivalent vaccine.

A split vaccine can include virions that have been subjected to treatment with agents that dissolve lipids. A split vaccine can be prepared as follows: an aqueous suspension of purified virus, inactivated or not, is treated, under stirring, by lipid solvents such as ethyl ether or chloroform, associated with detergents. The dissolution of the viral envelope lipids results in fragmentation of the viral particles. Then the residual infectious particles are inactivated if this has not already been done. The split vaccine may be combined with an attenuated virus of the invention in a multivalent vaccine.

Inactivated Vaccines

BoHV-1 tmv replicates like wild type BoHV-1 virions and expresses antigens that reduce the incidence of disease. However, there may be cases where it may be useful for a recombinant BoHV-1 tmv to be inactivated. Inactivated recombinant BoHV-1 tmv viruses and other viral vaccines constructs can be provided by inactivating replicated virus using available methods, such as, but not limited to, treatment of viral solutions at temperatures from 60° C. to 80° C., or at low pH (1.7-4.0), or by use of ethanol, methanol, guanidine hydrochloride, formalin or β-propiolactone. Inactivated viral constructs and/or vaccines that can be used can include whole-virus (WV) vaccines or subvirion (SV) (split) vaccines. Vaccines can contain intact, inactivated viruses, or purified viruses that have been disrupted with detergents that solubilize the lipid-containing viral envelope, followed by chemical inactivation of residual virus.

Live Attenuated Virus Vaccines

Live, attenuated recombinant BoHV-1 tmv virus vaccines, such as those including a recombinant BoHV-1 tmv virus can be used for preventing or treating various viral infections of cattle or other animals. Attenuation may be achieved in a single step by transfer of attenuated genes from an attenuated donor virus to a replicated isolate or reassorted virus according to available methods. The attenuated genes are derived from an attenuated parent virus.

Pharmaceutical Compositions

Pharmaceutical compositions include one or more BoHV-1 tmv viral vector isolates, e.g., one or more recombinant BoHV-1 tmv viral vector, a subunit thereof, isolated protein(s) thereof, and/or isolated nucleic acid encoding one or more proteins thereof, optionally further comprising sterile aqueous or non-aqueous solutions, suspensions, and emulsions. The compositions can include other viral vaccines, and polypeptides and/or peptides that are either antigenic or that can stimulate an immune response. The compositions can further comprise auxiliary agents or excipients, available in the art. The compositions can be presented in the form of individual doses (unit doses).

Conventional vaccines generally contain about 0.1 to 200 μg, e.g., 30 to 100 μg, of each recombinant BoHV-1 tmv virus type within the composition. The vaccine forming the main constituent of the vaccine composition of the invention may comprise a single recombinant BoHV-1 tmv virus, or a combination of recombinant BoHV-1 tmv viruses, for example, two or three recombinant BoHV-1 tmv viruses.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents available in the art, such as purified water. Besides the inert diluents, such compositions can also include adjuvants, wetting agents, emulsifying and suspending agents, or sweetening, flavoring, or perfuming agents.

When a composition is used for administration to an animal, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing at least two recombinant BoHV-1 tmv virus types, such as 2-20 types, or any range or value between 2-20. Vaccines can be provided for variations in a single strain of a recombinant BoHV-1 tmv virus, using techniques available in the art.

A pharmaceutical composition can further or additionally include additional ingredients, for example, for gene therapy, anti-inflammatory agents or immune enhancers, and for vaccines, GM-CSF, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions are provided before symptoms or clinical signs of a pathogen (e.g., viral) infection becomes manifest. The prophylactic administration of the composition serves to prevent or attenuate any subsequent infection. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compositions serves to attenuate infection.

Thus, a recombinant BoHV-1 tmv viral composition can be provided either before the onset of infection (so as to prevent or attenuate an anticipated infection) or after the initiation of an actual infection.

A composition or component thereof is said to be "pharmacologically acceptable" if its administration can be tolerated by a recipient mammal. Such a composition or component thereof is said to be administered in a "therapeutically effective amount" if the amount administered is physiologically significant. A composition is physiologically significant if its presence results in a detectable change in the physiology of a recipient patient, e.g., enhances at least one primary or secondary humoral or cellular immune response against at least one strain of an infectious virus.

Any "protection" provided by the compositions described herein need not be absolute, i.e., the viral infection need not be totally prevented or eradicated, if there is a statistically significant improvement compared with a control population or set of mammals. Protection may be limited to mitigating the severity or rapidity of onset of symptoms or clinical signs of the viral infection.

Pharmaceutical Administration

Compositions are described herein that can include any of the expression cassettes, expression vectors, or recombinant viruses described herein. In some cases the compositions can include a carrier, for example, a carrier formulated to facilitate administration of any of the compositions containing any such expression cassettes, expression vectors, or recombinant viruses described herein. Although the compositions can include any expression cassettes, expression vectors, or recombinant viruses described herein, in some cases the compositions include one or more recombinant BoHV-1 tmv virus, for example, one or more recombinant BoHV-1 tmv virus that can express an E2 protein, BVDV Erns protein, BRSV F protein, BRSV G protein, or a combination thereof.

A composition may confer resistance to one or more pathogens, e.g., one or more virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain.

Hence, methods are provided herein that involve administering at least one of the BoHV-1 recombinant vectors described herein to an animal. Such administration can reduces the incidence or severity of respiratory symptoms in the mammal. While various types of animals or mammals can be administered the compositions described herein, in some cases, the mammal is a wild or domesticated bovine animal. In some cases, the animal administered is an experimental animal. For example, the compositions can be administered to wild or domesticated cattle, buffalo, oxen, pigs, horses, poultry, goats, rats, mice, and/or any animal that may be susceptible to respiratory diseases. In some cases the compositions are administered to mammals that may be susceptible to bovine respiratory disease complex (BRDC).

In some cases, the compositions containing recombinant BoHV-1 tmv virus can be administered to young cattle (calves). In other cases, the compositions containing recombinant BoHV-1 tmv virus are administered to a female cow (at or prior to pregnancy or parturition), under conditions of time and amount sufficient to cause the production of an immune response which serves to protect both the female and the fetus or newborn (via passive incorporation of the antibodies across the placenta or in the mother's milk).

Methods for preventing or attenuating a disorder or disease, e.g., an infection by at least one strain of pathogen, are also described herein. As used herein, a vaccine is said to prevent or attenuate a disease if its administration results either in the total or partial attenuation (i.e., suppression) of a clinical sign or condition of the disease, or in the total or partial immunity of the individual to the disease.

For example, administration of the compositions described herein can reduce the incidence of shedding viruses (e.g., in nasal secretions) by the animals to which the composition was administered by at least 50%, or at least 60%, or at least 70%, or at least 80%, or at least 85%, or at least 90%, or at least 95%, or at least 97%, or at least 98%, or at least 99%. Such reduction in virus shedding can be in comparison to an animal of the same species that has not received a composition described herein and that can be infected by BoHV, BVDV, BRSV, or a combination thereof.

For example, administration of the compositions described herein can increase the titer of neutralizing antibodies against BoHV, BVDV, or BRSV in an animal administered a composition described herein by at least two-fold, at least five-fold, at least seven-fold, at least ten-fold, at least fifteen-fold, at least twenty-fold, or at least twenty five-fold. Such a fold increase in neutralizing antibodies against BoHV, BVDV, or BRSV can be in comparison to an animal of the same species that has not received a composition described herein. In some cases, the fold increase in neutralizing antibodies can in comparison to animals that are infected by BoHV, BVDV, BRSV, or a combination thereof, and that have not been administered a composition described herein.

A composition having at least one recombinant BoHV-1 tmv virus, can in some cases be is combined with one or more other isolated viral compositions (e.g., other types of viral vaccines), or can be combined with one or more isolated viral proteins, or can be combined with one or more isolated nucleic acid molecules encoding one or more viral proteins, or a combination thereof. Such compositions and combinations of compositions, may be administered by any means that achieve the intended purposes.

For example, administration of such a composition may be by various parenteral routes such as intranasal, subcutaneous, intravenous, intradermal, intramuscular, intraperitoneal, oral, nasal, or transdermal routes. Parenteral administration can be accomplished by bolus injection or by gradual perfusion over time.

A typical regimen for preventing, suppressing, or treating viral disease includes administration of an effective amount of an immunological composition (e.g., a vaccine composition) as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed recombinant virus composition for an animal such as a mammalian adult organism may be from about $10^2$-$10^{15}$, $10^3$-$10^{12}$, $10^3$-$10^{11}$, $10^4$-$10^{11}$, plaque forming units (PFU)/kg, or any range or value therein. The dose of inactivated viral proteins may range from about 0.1 to 1000, e.g., 10 to 100 µg, such as about 15 µg, of viral protein. However, the dosage should be a safe and effective amount as determined by conventional methods, using existing vaccines as a starting point.

The dosage of immunoreactive viral protein in each dose of replicated virus vaccine may be standardized to contain a suitable amount, e.g., 30 to 100 µg or any range or value therein, such as about 15 µg, or the amount recommended by government agencies or recognized professional organizations. The quantity of protein or recombinant virus can also be standardized.

Definitions

Within this application, a wild type or a naturally-occurring BoHV virus means a BoHV virus which has not been genetically engineered, and includes, but is not limited to, wild-type BoHV viruses and BoHV viruses selected from BoHV viruses that exist in nature and have spontaneous deletions.

As used herein, nonessential gene means a gene that is not essential for viral replication.

As used herein, an "infectious, biologically contained" virus means that the virus is incapable of producing progeny in normal cells or incapable of significant replication in vitro or in vivo, e.g., titers of less than about $10^2$ to $10^3$ PFU/mL, in the absence of helper virus or a viral protein stably supplied in trans.

A used herein, "replication-deficient" virus means that the virus can replicate to a limited extent in vitro or in vivo, e.g., titers of at least about $10^2$ to $10^3$ PFU/mL, in the absence of helper virus or a viral protein supplied in trans.

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture in cells and propagation, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or non-recombinant techniques.

As used herein, the term "recombinant nucleic acid" or "recombinant DNA sequence or segment" refers to a nucleic acid, e.g., to RNA or DNA, that has been derived or isolated from a source, that may be subsequently chemically altered in vitro so that its sequence is not naturally occurring or does not identically correspond to naturally occurring sequences. For example, a recombinant nucleic acid can have segments that are not positioned as they would be positioned in a native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, or modified, by genetic engineering methods.

As used herein, a "heterologous" nucleic acid segment is from a source other than a parent virus or genome. For example, a "heterologous" nucleic acid segment can be a segment that includes a promoter sequence, a nucleotide sequence encoding a peptide (e.g., an antigenic peptide) from another virus or organism, a nucleotide sequence encoding a polypeptide (e.g., an antigenic polypeptide) from another virus or organism, or a reporter gene or a gene from another virus or organism. Such a "heterologous" nucleic acid segment can encode a heterologous peptide or polypeptide.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a non-recombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm. Conserved and non-conserved sequence domains can be identified by alignment of sequences.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information. The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix. Alignment may also be performed manually by inspection.

For sequence comparison, typically one sequence acts as a reference sequence to which test sequences are compared. For example, any of the sequences defined by SEQ ID NO herein can be a reference sequence. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As used herein, "individual" (as in the subject of the treatment) means a mammal. Mammals include, for example, humans; non-human primates, e.g., apes and monkeys, and non-primates, e.g., dogs, cats, rats, mice, pigs, cattle, horses, sheep, and goats. Non-mammals include, for example, fish and birds. In some cases, the mammal is a bovine animal (e.g., a calf, cow, steer, or any type of cattle).

The term "disease" or "disorder" are used interchangeably, and are used to refer to diseases or conditions caused by viral or microbial infection.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, "inhibiting" means inhibition of further progression or worsening of the symptoms associated with the disorder or disease, and "preventing" refers to prevention of the symptoms associated with the disorder or disease.

As used herein, an "effective amount" or a "therapeutically effective amount" of an agent of the invention e.g., a recombinant BoHV-1 tmv encoding a gene product, refers to an amount of the agent that alleviates, in whole or in part, symptoms associated with the disorder or condition, or halts or slows further progression or worsening of those symptoms, or prevents or provides prophylaxis for the disorder or condition, e.g., an amount that is effective to prevent, inhibit or treat in the individual one or more respiratory (e.g., bovine respiratory disease complex (BRDC)) symptoms.

In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

A "vector" as used herein refers to a macromolecule or association of macromolecules that comprises or associates with a polynucleotide and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic interest) and/or a selectable or detectable marker.

Where transcription of the heterologous nucleic acid segment is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and may be preferred when it is desired that the therapeutic or prophylactic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the human elongation factor 1α (hEF-1α) promoter, SV40 late promoter from simian virus 40, the Baculovirus polyhedron enhancer/promoter element. Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide generally comprises at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The following non-limiting Examples illustrate some of the materials and methods employed in development of the invention.

Example 1: Construction of a BoHV-1gE CT/Us9 Deletion/Chimeric Gene Insertion Plasmid This Example illustrates construction of a pBoHV-1 gEΔCT/Us9Δ plasmid.

As depicted in FIG. 3A-3B, the Us9 gene is located immediately downstream of the gE cytoplasmic tail (gE CT residues 451-575) coding region. The pBoHV-1 gEΔCT/Us9Δ plasmid contains a deletion of the BHV gE cytoplasmic tail and Us9 coding sequences, leaving the 1.4 kB region upstream of the gE and CT coding regions. The 1.4 kB region upstream region contains the gE ecto and transmembrane (Tm) domains. A downstream region contains a partial 1.1 Kb Us9 region containing partial bICP22 sequences flanking a unique KpnI site incorporated at the deletion locus (FIG. 3C).

In the resulting pBoHV-1 gE ΔCT/Us9Δ plasmid, the KpnI site created in the gE CT and Us9 deletion locus allows for the insertion of a KpnI/KpnI fragment containing the BVDV E2, BRSV F and G ORF coding chimeric gene sequences (see FIG. 8).

Example 2: Construction and Characterization of a BoHV-1 UL49.5 Δ30-32 CT-Null/gECTΔ/Us9Δ Virus (BHV-1 Tmv Vector)

This Example describes construction and characterization of a BoHV-1 vector that lacks the gE cytoplasmic tail (gE CT residues 451-575), which is associated with virulence function, and that lacks the entire 435 base pair long Us9 open reading frame. This vector is called the BoHV-1 UL49.5 Δ30-32 CT-null/gECTΔ/Us9Δ virus, or the BoHV-1 tmv vector.

To construct the BoHV-1 tmv vector, the pBoHV-1 gE ΔCT/ΔUs9 plasmid was cotransfected with a full-length BoHV-1$U_L$49.5 Δ30-32 CT-null parental viral DNA generated earlier (91). One putative triple mutant virus (BoHV-1 tmv) harboring the intended deletion was plaque purified and the nucleotide sequence spanning the $U_L$49.5, gE and Us9 genes was identified by such procedures.

Immunoblotting and one-step growth curve analyses of the identified BoHV-1 tmv were performed. Growth of BHV-tmv viruses compared with BoHV-1 gE-deleted and wild type BoHV-1 viruses in MDBK cells is shown as a one-step growth curve. Confluent MDBK cells were infected with the respective viruses at a multiplicity of infection of five plaque forming units (PFU) per cell. After 1 h of adsorption at 4° C., residual input viruses were removed. The cultures were washed three times with phosphate-buffered saline, and 5 ml of medium was added to each flask before further incubation (37° C.). At the indicated time intervals, replicate cultures were frozen. Virus yields were determined by plaque assay. Each data point represents the average of duplicate samples obtained from separate infections.

Figure 5:
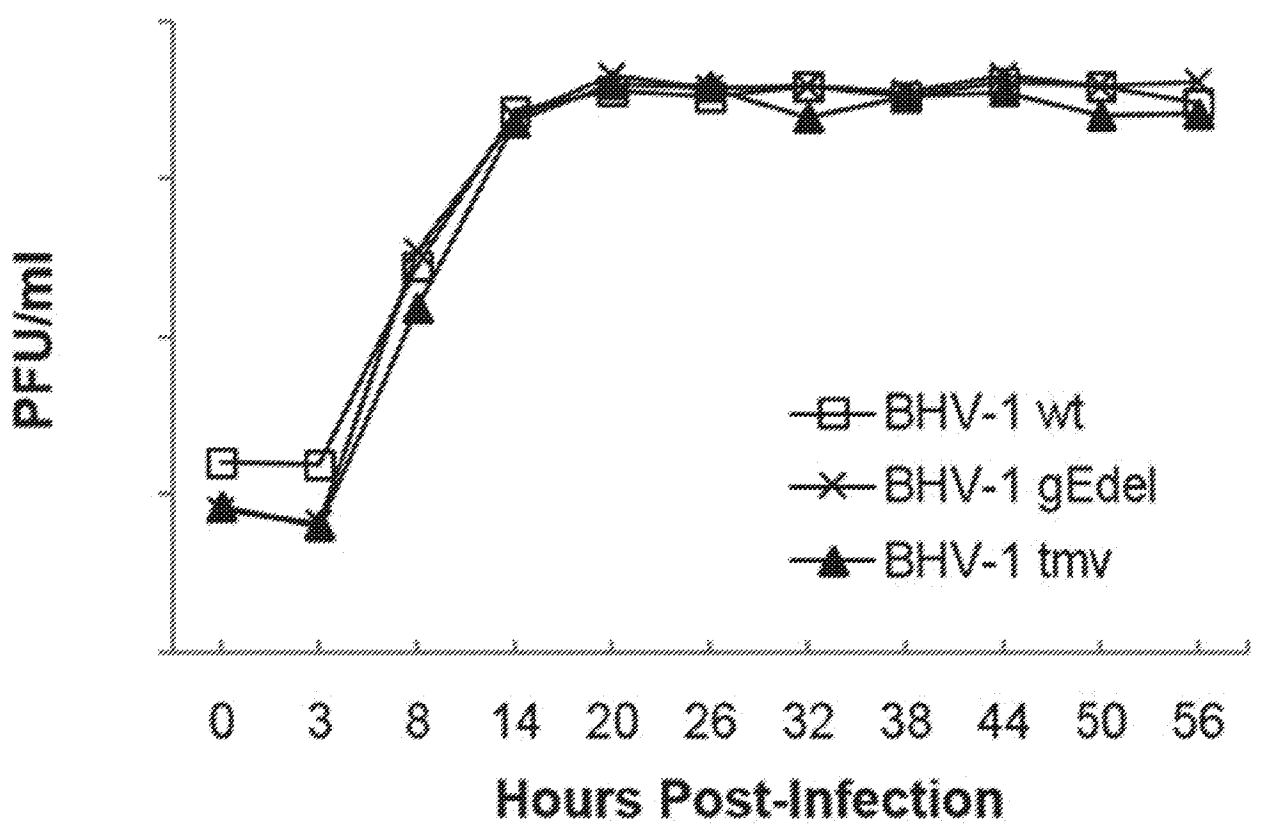

The nucleotide sequence data and immunoblotting data (FIG. 4) confirmed that the intended deletions were present while the growth curve results demonstrated that BoHV-1 tmv replicates like wild type BoHV-1 virions (FIG. 5).

Example 3: Pathogenicity and Vaccine Efficacy of BoHV-1 Tmv Relative to BoHV-1 gE-Deleted Virus Against Virulent Wild Type BoHV-1 Challenge To determine pathogenicity and vaccine efficacy of the BoHV-1 tmv was compared to a gE-deleted virus (where the entire gE gene is deleted, not just the gE cytoplasmic tail (CT)-truncated BoHV-1 virus prepared by the inventor), followed by challenge with virulent wild type BoHV-1 virus.

Fifteen BoHV-1 and BVDV negative, 4-month-old crossbred bull calves were selected and randomly assigned into six rooms: three calves each into three rooms and two calves each into another three rooms at the LSU Ag-center large animal isolation facility. Animal infection, handling, sample collection and euthanasia protocols were previously approved by the LSU Institutional Animal Care and Use Committee.

Five calves of a "triple mutant" group were inoculated with 1 ml/nostril of BoHV-1 tmv (in DMEM) containing $1\times10^7$ PFUs for a total of $2\times10^7$ PFUs/animal. Five calves in "gE-deleted" group were similarly inoculated with $1\times10^7$ PFUs/nostril of the gE-deleted virus, and five calves in the control group were similarly inoculated with cell culture media (Table 1).

Following primary infection, calves were observed for clinical signs of BoHV-1 infection daily for nine days. Nasal swabs were collected daily. Subsequently, calves were observed on alternate days and nasal swabs collected once a week until 28 days post-infection with the BoHV-1 tmv virus or the gE-deleted virus.

On day 28, calves in all three groups were challenged with 1 ml/nostril of virulent wild type BoHV-1 Cooper strain virus containing $2\times10^7$ PFUs/ml for a total of $4\times10^7$ PFUs/animal.

Following challenge, the animals were observed and nasal swabs collected similarly as above daily for 12 days. On day 15 post challenge, all the infected calves were euthanized and necropsied (Table 1).

TABLE 1

Summary of Viral Vaccination and Challenge Procedure

| BHV-1 tmv | BHV-1 gE -del | Control |
|---|---|---|
| 5 calves | 5 calves | 5 calves |
| Day 0 | Day 0 | Day 0 |
| $1 \times 10^7$ PFUs/ml/nostril | $1 \times 10^7$ PFUs/ml/nostril | Sham-infected with 1 ml media/nostril |

Day 1, 2, 3, 4, 5, 6, 7, 8, 9, 12, 15, 21, 28 post infection nasal swabs, temps and clinical scores
Day 0, 7, 14, 21, 28 serum
28 dpi (vaccination) intranasal challenge with BHV-1 Cooper strain-$4 \times 10^7$ PFUs ($2 \times 10^7$ PFUs/ml/nostril).
Day 0, 1, 2, 3, 4, 5, 6, 7, 8, 9, 10, 12, 14 post challenge nasal swabs, temps and clinical scores
Day 0, 7, 14 post challenge - whole blood and serum
Day 15 post challenge euthanize-necropsy Clinical records, including rectal temperatures, nasal discharge and nasal lesions, were recorded during each visit and clinical scores were assigned for each parameter. Rectal temperatures were scored 0-4 (less than 39.0° C., 39.5° C., 40.0° C., greater than 40.9° C.), nasal discharges were scored 0-4 (normal, serous, mild and severe mucopurulent), and nasal lesions were scored 0-3 (normal, hyperemia, pustules, ulcers).

The clinical score data following primary infection/vaccination showed that like the gE-deleted BoHV-1, BoHV-1 tmv is highly attenuated in calves because the infected calves did not show any detectable clinical signs and their clinical scores were not significantly different from sham-infected controls.

Figure 6A:
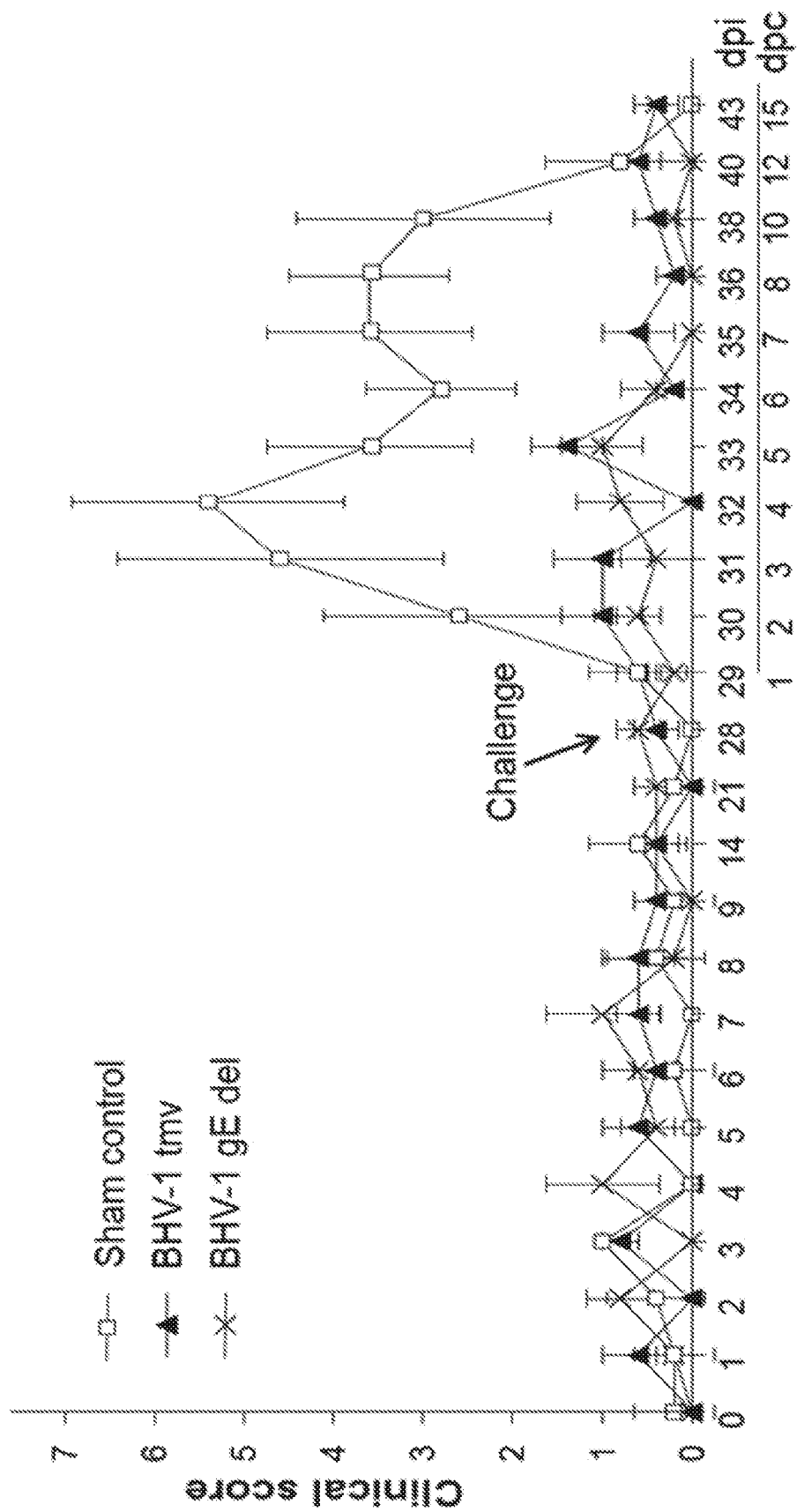

Following virulent wild type BoHV-1 virus challenge, both the BoHV-1 tmv and gE-deleted virus-immunized groups showed no clinical signs. As expected, the control uninfected calves had high fever, nasal discharge and lesions in the nasal mucosa after challenge which is typical for wild type BoHV-1 infection. As a result, their clinical scores were significantly higher following challenge (FIG. 6A).

Example 4: Nasal Virus Shedding, Pathogenicity and Protective Vaccine Efficacy of BoHV-1 Tmv Against Virulent BoHV-1 wt Challenge in Calves Compared with that of BoHV-1 gEdel This Example describes statistical analysis of the effects of BoHV-1 tmv treatment of calves followed by challenge with virulent BoHV-1 virus.

Calves were treated with BoHV-1 tmv and gE-deleted viruses as described in Example 3. Nasal virus shedding was recorded. To evaluate protective immune responses, blood was collected on 0, 7, 14 and 21 days post immunization/dpi and at day 0 (28 dpi), 7, 12 and 15 days post challenge (dpc) (see, Table 1).

Serum interferon γ levels were measured using high binding EIA plates (Costar, Corning, N.Y.) having wells coated with anti-bovine IFNγ-specific rabbit polyclonal antibodies (10 µg/ml, Endogen, Rockford, Ill.) to capture IFN-γ from serially diluted calf sera (100 µl) from different treatment groups. As a control, 100 µl of the serial diluted recombinant bovine IFNγ (Thermo, Pierce, Ill.) were added instead of sample sera. After incubation (for 1 hour), the test wells were washed and incubated (1 hr) with biotinylated rabbit anti-bovine IFNγ polyclonal Ab (Endogen, Rockford, Ill.). After washing, the test wells were incubated (for 1 hour) further with avidin-HRP (eBioscience, San Diego, Calif.) and developed with substrate 2,2'-azino-bis(3-ethyl-benzothiazoline-6-sulphonic acid) (ABTS, Sigma). The test results were measured at $OD_{405}$ by using an ELISA reader.

Data from the pathogenicity and vaccine efficacy studies, specifically the viral shedding titers, serum neutralization titers, and IFN-γ concentrations were analyzed using a repeated measures ANOVA to detect significant differences among treatments over the period of challenge. The SAS (Version 9.1.3) was used for statistical analysis. Post-hoc, pairwise comparisons were employed to estimate pairwise differences and conduct t tests. Significance was assessed at the $P<0.05$ level for all tests.

Results

Figure 6B:
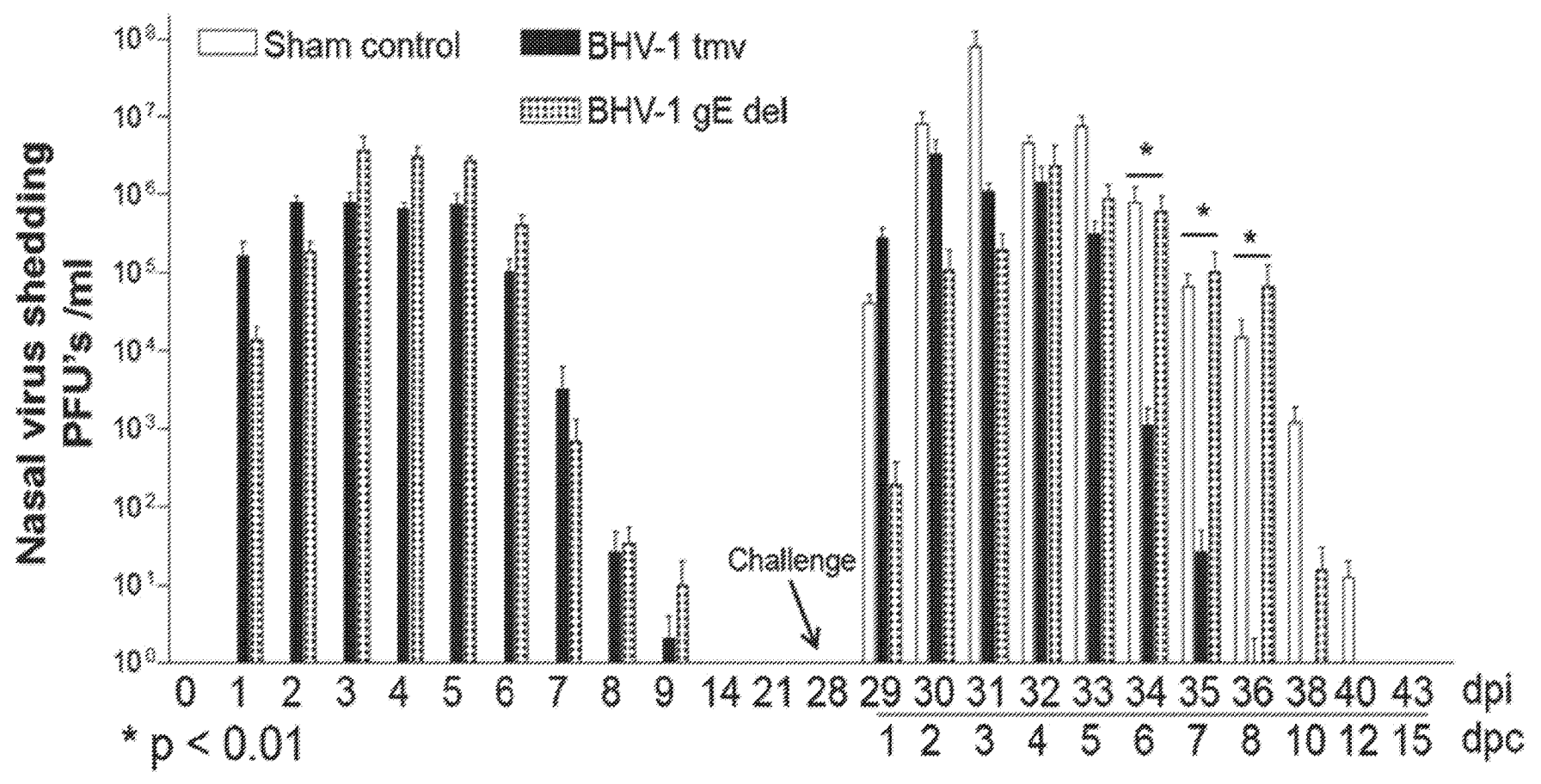

Nasal virus shedding data showed that while both triple mutant BoHV-1 tmv viruses and gE-deleted viruses replicated with similar yield during primary infection/immunization, following challenge with virulent BoHV-1, shedding of the triple mutant BoHV-1 tmv virus from immunized calves was for only the first 7 days after challenge (FIG. 6B). In contrast, the gE-deleted virus immunized calves shed virus for about 10 days (3 days longer than BoHV-1 tmv-immunized calves: FIG. 6B). The sham-infected/vaccinated control calves shed virus for 11 days (4 days longer than the BoHV-1 tmv-immunized calves, FIG. 6B). Additionally, on 6 and 7 days post-challenge, nasal virus shedding in the BoHV-1 tmv vaccinated group was reduced significantly compared with the gE-deleted virus group (FIG. 6B).

Figure 6C:
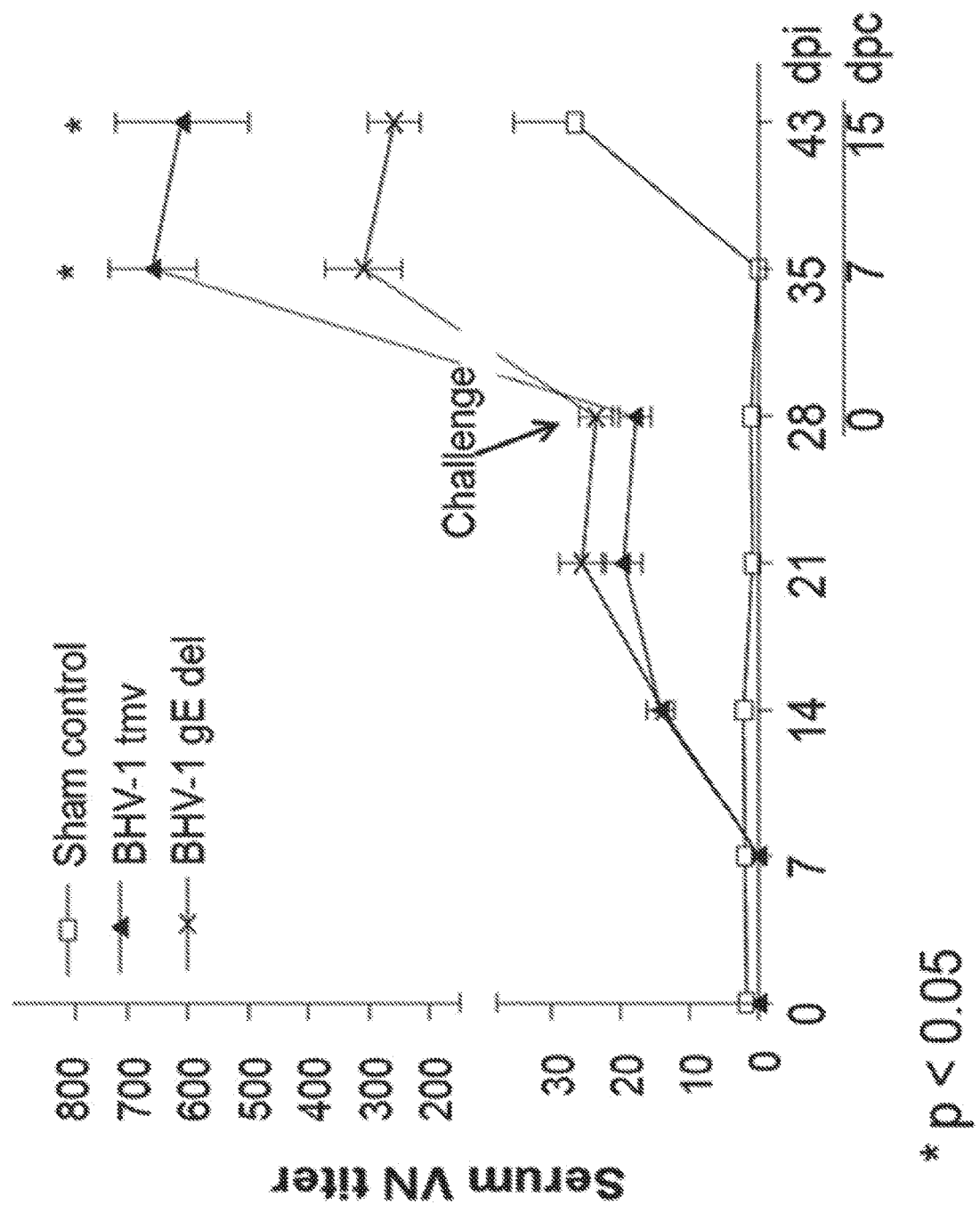

As shown in FIG. 6C, virus neutralizing antibody titers following primary infection/immunization with BoHV-1 tmv were similar to those observed for BoHV-1 tmv vaccinated group. However, following challenge by virulent wild type BoHV-1, the BoHV-1 tmv vaccinated group had significantly higher ($p<0.05$) virus neutralizing antibody titer (650) than the gE-deleted virus immunized group (300).

Notably, significantly increased levels of interferon-γ were produced in the triple mutant BoHV-1 tmv virus-immunized group both at 7 days ($p<0.01$) and 15 days ($p<0.05$) post challenge when compared with the gE-deleted virus immunized group (FIG. 6D).

Taken together these results show that the triple mutant BoHV-1 tmv virus can prime the humoral and cellular responses for a more rapid and exuberant neutralizing antibody and IFN-γ responses compared with the gE-deleted virus. The data indicated that the BoHV-1 tmv virus was better able to clear the challenge virus (FIG. 6B). These results show that the triple mutant BoHV-1 tmv virus lacking the MHC-I down regulation function is a more efficacious vaccine than the gE-deleted virus vaccine.

Example 5: Serological Properties of BoHV-1 Tmv

This Example illustrates some of the serological properties of the BoHV-1 tmv virus.

The sera of BoHV-1 tmv-infected calves and gE-deleted virally-infected calves were collected before virulent wild type BoHV-1 challenge, and tested for expression of gE antigens. In a first assay, the IDEXX gE antibody detection competitive ELISA test kit was used for detection of gE proteins. Based on the ELISA test results, BoHV-1 tmv-infected calves were slightly positive for gE protein expression (data not shown). However, the BoHV-1 tmv virus encodes and may express a portion of the gE protein (i.e., the cytoplasmic tail, CT). The part of glycoprotein E that is missing in the BoHV-1 tmv vaccine are amino acids 451-575, with the sequence shown below (SEQ ID NO:43).

```
  1  ASQKRTYDIL NPFGPVYTSL PTNEPLDVVV PVSDDEFSLD
 41  EDSFADDDSD DDGPASNPPA DAYDLAGAPE PTSGFARAPA
 81  NGTRSSRSGF KVWFRDPLED DAAPARTPAA PDYTVVAARL
121  KSILR
```

Therefore, the inventors have developed an ELISA test to detect the gE expressing wild type viruses, but not the gE-cytoplasmic tail expressed from the BoHV-1 tmv viral genome. ELISA plate test wells are coated with 120 amino acids of the gE SEQ ID NO:43 shown above that are missing from the BoHV-1 tmv viral genome. An HRP-conjugated indicator antibody was gE-CT specific was also used.

Figure 7:
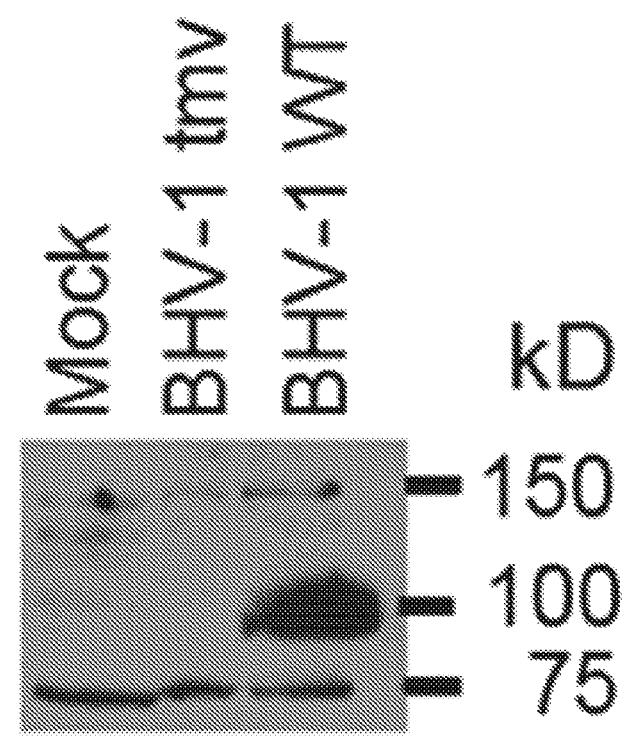

A protein containing BoHV-1 gE amino acid residues 451-564 (entire BoHV-1 gE CT coding region) was expressed as a GST fusion protein and purified GST fusion protein was purified and cleaved to release the gE CT protein. Monoclonal antibodies specific to the gE-CT antigen were generated. The gE CT-specific MAb specifically recognized the full length BoHV-1 gE but not the gEΔ CT in immunoblotting (FIG. 7). An optimized gE-CT-based serological marker assay employs an affinity purified-HRP conjugated gE-CT-specific monoclonal antibody and gE-CT antigen coated ELISA plates.

Example 6: Construction of BVDV Type 1 E2 (E2.1) Specific Chimeric Gene and a BoHV-1 Tmv Expressing E2.1

This Example illustrates construction of BVDV E2-specific chimeric gene and a BoHV-1 vector that expresses the E2 protein.

Construction of a BVDV E2-Specific Chimeric Gene

A nucleic acid segment encoding a BVDV1 E2 open reading frame (GenBank accession# GI:7960753) was codon-optimized with a bias for expression in bovine cells and for commercial synthesis. Codon-optimized 1.18 Kb long synthetic oligonucleotides for BVDV E2.1 also incorporated a consensus Kozak sequence (GCCATGG) plus BoHV-1 gD signal sequence (57 nucleotide) (BoHV-1 gD amino terminal 19 amino acids; Genbank accession #GI: 2653359) at the amino terminal end of the E2.1 sequence. The codon optimized synthetic BVDV1E2 gene (1.23 Kb), in a plasmid backbone, was amplified by PCR using Fail safe PCR kit and cloned into the TA cloning site of the eukaryotic expression vector plasmid pEF6/V5-His-TOPO (Invitrogen) (FIG. 8, panel A). The cloned fragment was verified by sequencing for the integrity of the E2.1 open reading frame, and for the in-frame fusion of the C-terminal end of the E2.1 open reading frame with the N-terminus (beginning) of the V5 epitope coding region. The PCR fragment containing the BVD E2.1 open reading frame was inserted in the correct orientation downstream of the strong EF-1α promoter and upstream of the V5 epitope. A Kozak sequence followed by gD signal sequence preceded the BVD E2.1 open reading frame, and a poly His tag with a bovine growth hormone (BGH) polyA signal followed the BVD E2.1 open reading frame (FIG. 8A). The in-frame fusion of the C-terminus of the E2.1 open reading frame with the vector sequence was designed to allow the expression of the V5 epitope and termination of the chimeric E2.1 transcript immediately downstream of the His tag within the pEF6/V5-His-TOPO vector. Therefore, the adjusted and predicted unprocessed molecular mass of the E2.1 fused to V5 epitope and His tag was approximately 48 kD, where the E2.1 portion was 43 kD, and the V5+ His tag portion was 5 kD. Transient expression of V5 epitope by the chimeric E2.1/V5 gene was verified after transfection of the plasmid DNA into T293 cells (data not shown).

Construction of a BoHV-1 Vector that Expresses the E2 Protein

The BVDV type 1 E2 (E2.1) chimeric expression cassette containing the PEF-1α promoter at the upstream 5' end, and the bGH poly A sequence at the 3' end was amplified by using a p1F and p2R primer pair, where the p1F primer has GCggtaccTC-GTGAGGCTCCGGTGCCCGTCAGTG (SEQ ID NO:44), which is specific for PEF-1α promoter sequences, and the p2R primer has GCggtaccCCAT-AGAGCCCACC-GCATCC-CCAGCATGCCTG (SEQ ID NO:45), which is specific for sequences immediately downstream of the bGH poly A (FIG. 8A). The p1F/p2R primer pair incorporated KpnI sites at each end of the amplified fragment. The PCR-amplified BVDV1 E2 expression cassette (approximately 2.9 kb) was digested with KpnI and cloned into the KpnI site of the insertion plasmid pBoHV-1gECTΔ/Us9Δ (FIG. 8B), resulting in a pBoHV-1 BVDV E2.1 insertion vector (pBoHV-1 INS/E2.1) (FIG. 8C).

To generate a modified BoHV-1 tmv vector that expresses the chimeric BVDV E2.1 protein, linearized pBoHV-1 INS/E2.1 plasmid DNA (FIG. 8C) was co-transfected with the full-length BoHV-1 tmv DNA (FIG. 3D) into MDBK cells. Putative recombinant viral plaques expressing BVDV E2.1 were initially screened by PCR and verified by sequencing. Several recombinant BoHV-1 tmv containing BVDV E2.1 chimeric gene sequences were further analyzed by immunoblotting using goat anti-BVDV-specific polyclonal antibody (VMRD Cat #210-70-BVD) or an anti-V5 monoclonal antibody (Invitrogen Cat # R96025).

Construction of a Stable Cell Line for Expressing BVDV Type 1 and 2 E2:

In another series of experiments, nucleic acid segments encoding BVDVE2-1 and/or BVDVE2-2 along with Kozak, gD signal and V5 were amplified using the forward primer-TAATCA<u>AAGCTT</u>CGCCGCCACCATGCAGGGACC (SEQ ID NO:46) and reverse primer CTCCG <u>GAATTC</u>CGTAGAATCGAGACCGAGGAGAGG (SEQ ID NO:47) using a BVDV1-E2 expression cassette (e.g., SEQ ID NO:9) and/or a BVDV2-E2 expression cassette (SEQ ID NO: 14) as template. Forward and reverse primers incorporated HindIII and EcoRI restriction sites (shown in italics), respectively. The PCRgenerated fragment was digested with HindIII and EcoRI and cloned into the corresponding sites in the multiple cloning site of pcDNA™3.1

(+) (Invitrogen, cat# V790-20). PCDNA3.1-BVDV1-E2 or BVDV2-E2 constructs were used to transfect MDBK cells. Transfected MDBK cells were selected for resistance against gentamycin (1 mg/ml) containing 5% DMEM media. Stably transfected isolated colonies were screened for determining the expression of BVDV1-E2 and BVDV2-E2 protein by immunoblotting and indirect immunofluorescence using anti-BVDV1-E2 and BVDV2-E2 specific monoclonal antibody (VMRD, cat#157 and cat#BA-2, respectively). These cell lines can be used for the cellular immune response against BVDV types 1 and 2 by cytotoxicity and cell proliferation assays.

Results

As depicted in FIG. 9B, the BVDV-specific polyclonal antibody detected two bands with molecular mass of 48 kD and 58/59 kD in the infected cell lysates of one representative BoHV-1 tmv/E2.1 recombinant virus. The 48 kD band is the unprocessed chimeric E2.1 expressed by BoHV-1 tmv/E2.1 recombinant virus which is predicted to be 5 kD larger (due to additional V5 epitope and His tag residues) than the 43 kD unprocessed BVDV E2.1 protein detected in the BVDV-infected cell lysates (FIG. 9B). The 58/59 kD protein is the processed chimeric E2.1 form, which in BVDV infected cells is the 53/54 kD band (FIG. 9B). These results indicate that BoHV-1 tmv vector encoding the E2.1 protein is processed appropriately in the infected MDBK cells.

Preliminary results also showed that in MDBK cells, the BoHV-1 tmv/E2.1 virus replicates with very similar kinetics and yield compared with the parent BoHV-1 tmv (data not shown).

Example 7: Immunoblotting and/or Immunoprecipitation Analysis

This Example describes radiolabeling infected cell proteins, immunoblotting, immunoprecipitation, and biochemical analysis of viral glycoproteins.

For immunoblotting and/or immunoprecipitation analysis, MDBK cells are mock-infected and infected with BoHV-1 tmv expression vector that encodes one or more antigenic proteins. The MDBK can be mock-infected or infected with BoHV-1 tmv expression vectors at a multiplicity of five.

Pulse labeling of cells with [$^{35}$S] methionine and [$^{35}$S] cysteine can be performed for 30 minutes starting at six hours post-infection as described (1, 2). Steady-state labeling is performed with [$^{35}$S] methionine and [$^{35}$S] cysteine for 10-12 hours starting at the same time as for pulse labeling. Processing of cell lysates, immunoprecipitation and SDS-PAGE are performed as described earlier (1).

For deglycosylation analysis of proteins, first [$^{35}$S] methionine and [$^{35}$S] cysteine labeled infected cell and purified virion proteins are immunoprecipitated. Then for N-glycosidase F and EndoH digestion, the immunoprecipitated viral proteins are incubated with 1,000 U of N-glycosidase F (New England Biolabs; NEB) or 100 U of EndoH (NEB) for 1 h at 37° C. as described earlier (1, 2). For neuraminidase and O-glycosidase digestion, immunoprecipitated proteins are digested overnight with 1 mU of neuraminidase (Boehringer) or 1 mU of neuraminidase and 1.5 mU of O-glycosidase (Boehringer). After the appropriate enzyme digestions above, the protein samples are subjected to SDS-PAGE and the results are visualized by autoradiography (1).

As described above a BoHV-1 vectored E2.1 protein has been generated and expression of antigenic protein therefrom has been characterized (FIG. 9). For BoHV-1 vectored E2.2, similar molecular weights of the ER processed precursor E2.2 (48 kD) and the Golgi processed mature E2.2 (58 kD/59 kD) are observed (FIG. 9). In addition for both E2.1 and E2.2, Golgi processed mature E2.1 and E 2.2 (58 kD/59 kD band) would be Endo H resistant. However, the ER processed precursor E2.2-specific 48 kD band would be Endo H sensitive and its molecular weight will be slightly reduced after Endo H treatment. In the case of glucosidase F treatment, both the 58 kD/59 kD and 48 kD bands would be deglycosylated and the digested bands will migrate faster than the respective untreated bands, as will the corresponding Endo H digested, ER processed 48 kD precursor-specific band above.

The BRSV F protein is synthesized as precursor 70 kD ($F_0$), which is proteolytically processed to F1 (48 kD) and F2 (18 kD) bands. However, in the chimeric BRSV F ORF coding sequence, the two Furin cleavage sites FCS 1 and FCS 2 are mutated. Therefore, 70 kD F protein ($F_0$) will not be cleaved to their F1 (48 kD) and F2 (18 kD) processed forms. To determine processing of the 70 kD chimeric $F_0$ protein, we will chase the $^{35}$S labeled 70 kD band for at least 120 minutes after pulse labeling. Pulse chase data analysis combined with Endo H and glycopeptidase F digestion data of pulse labeled chimeric F protein (expressed in BoHV-1 tmv/F- or BoHV-1 tmv/G-infected MDBK cells) will be critically evaluated and compared with the similarly treated pulse labeled BRSV F protein from BRSV-infected bovine turbinate (BT) cells. In BRSV-infected cells, F protein is glycosylated by N-linked oligosaccharides (41, 57). Therefore, the mature Golgi processed BoHV-1 tmv expressed 70 kD F-specific band is expected to be resistant to EndoH after 60-120 min. chase in the pulse-chase assay. Whereas a slightly smaller ER processed band containing high mannose glycans, immediately after pulse (0 min. chase) is expected to be Endo H sensitive and would be reduced to a slightly smaller size following Endo H treatment.

The BRSV G precursor is synthesized as a 43 kD protein which is further processed in the Golgi to 68-90 kD broad band form (51). The 43 kD band is the N-linked high mannose form and the 68-90 Kd band is both O-linked and N-linked complex carbohydrate modified forms. Since the chimeric G protein expressed by BoHV-1 tmv/G may lack residues 173-186 (14 amino acids), the corresponding band for the chimeric G precursor protein is expected to be approximately 38 kD. The mobility of the approximate 38 Kd band may migrate to a larger size if further processing of the protein in the Golgi has taken place. However, the nature of processing can only be determined based on the results from deglycosylation assays. The 38 kD chimeric G precursor band may also be sensitive to both glycopeptidase F and Endo H, in deglycosylation assays indicating that the 38 kD form is the N-linked precursor F protein synthesized in the ER, whereas the larger Golgi processed form (Approx. 70-76 kD) may be resistant to EndoH but partially sensitive to neuraminidase and O-glycosidase.

Example 8: Growth Properties of BoHV-1 Tmv Expressing BVDV E2.1, BVDV E2.2, BRSV F or BRSV G Characterization of the recombinant viruses with respect to their replication kinetics and plaque morphology can be performed to determine whether non-BoHV-1 proteins have effects on virus replication and/or plaque phenotype. One step growth curve studies can be performed as described earlier (90). In addition, incorporation of BVDV E2.1, BVDV E2.2, BRSV F and BRSV G chimeric proteins in the respective purified recombinant BoHV-1 vector viruses can be investigated by analyzing immunoblots containing purified virion lysates. Based on previous reports, both BVDV type 1 E2 and BRSV G proteins expressed by recombinant BoHV-1 were incorporated in the virus envelope (45, 77). Therefore, recombinant BoHV-1 expression of the BVDV E2.1 and BRSV G proteins may be incorporated in the virus envelope. The BRSV F chimeric protein may or may not be incorporated into the envelope.

Example 9: Vaccine Efficacy of Recombinant BoHV-1 Tmv Vectors

This Example describes procedures for evaluating the efficacy of individual BoHV-1 vector vaccine virus expressing BVDV E2.1 protein, BVDV E.2 protein, BRSV F protein. BRSV G protein, or a combination.

Determination of Sample Size for Animal Study

Sample size can be calculated following a power analysis of the primary variable of interest to maximize confidence in that metric. Data presented herein concerning viral titers and serum virus neutralizing antibody titers were used to estimate the expected differences (i.e. difference of 0.90 for viral titers) among treatment(s) at time points 6, 7 and 8 days post challenge. As these data indicate, days 6, 7 and 8 are most relevant for detecting differences in our variables of interest. Means and associated variances from our preliminary studies were then utilized in our sample size calculation, requesting a power of 90%. This resulted in a sufficient sample size of 6 calves per group.

Vaccination and Challenge of Calves:

For each of the three BoHV-1 vectored subunit vaccination challenge experiments, 18 calves (total 54 calves for the three vaccine efficacy study) free of BoHV-1, BVDV and BRSV antibodies or very low (<4 virus neutralization titers) will be purchased. For each vaccine efficacy study, they will be randomly divided into three groups of 6 calves each (BoHV-1 tmv vectored subunit vaccine group. Bovishield® vaccinated and control unvaccinated) and housed in separate biocontainment rooms. Six calves in the control group will be sham-infected, six calves in the experimental vaccinated group will be infected with BoHV-1 vectored subunit vaccine virus and the remaining six calves will be vaccinated I/M with Bovishield® following the manufacturers' recommendation. For vaccinating the calves with BoHV-1 vectored E2.1 or BoHV-1 vectored E2.2 vaccine, $1\times10^7$ PFU/ml/nostril (total $2\times10^7$ PFU/animal) of virus will be inoculated. For infecting the calves with BoHV-1 vectored BRSV F and G subunit vaccines, mixtures of each protein expressing BoHV-1 vector virus at IX $10^7$ PFU/ml/nostril for each virus (total $2\times10^7$ PFU/nostril for F and G combined) will be inoculated. At 28 days post infection, all sixteen calves for each experiment will be challenged with virulent BVDV type 1 or BVDV type 2 or BRSV virus depending on their specific subunit vaccination protocol (see tables 2 and 3 for detail).

For BVDV challenge, 1 ml of virus suspension/nostril containing $6\times10^{6.2}$ TCID$_{50}$ type strain Singer or type 2 strain 125-C will be inoculated using a syringe. For BRSV challenge, the calves will be inoculated with 1 ml of viral suspension containing $6\times10^{6.2}$ TCID$_{50}$ strain 236-652 (41) in each nostril via aerosolization (61).

Aerosolization will be accomplished with a siphon-fed spray gun (Sears Model 491, Hoffman Estates, Ill.) fitted to a 10 cm long by 10 mm i.d. plastic tube, which is inserted into the nasal passages. The gun is powered by compressed nitrogen gas at 40 p.s.i.

TABLE 2

Vaccine efficacy study scheme for BoHV-1 tmv expressing BVDV type 1 or 2 specific E2.1 and E2.2

| BHV-1 tmv/ BVDV-E2.1 or BVDV-E2.2 6 calves × 2 | Bovi-shield Gold 5 6 calves × 2 | Control 6 calves × 2 |
|---|---|---|
| Day 0 $1 \times 10^7$ PFUs/ml/nostril | Day 0 2 ml/IM | Day 0 Sham-infected with 1 ml media/nostril |
| Day 1, 2, 3, 4, 5, 6, 7, 8, 9, 12, 15, 21, 28 post infection nasal swabs, temps and clinical scores Day 0, 7, 14, 21, 28 serum, whole blood 28 dpi (vaccination) intranasal challenge with BVDV Type 1 strain Singer- $-6 \times 10^{6.2}$ TCID$_{50}$ (18 calves) or with BVDV Type 2 strain 125 -C $-6 \times 10^{5.2}$ TCID$_{50}$ (18 calves) corresponding to their vaccination group above. Day 0, 1, 2, 3, 4, 5, 6, 7, 8, 9, 10, 12, 14 post challenge nasal swabs, temps and clinical scores Day 0, 7, 14 day post challenge - whole blood and serum Day 15 post challenge euthanize, necropsy and score lung lesions | | |

TABLE 3

Vaccine efficacy study scheme for BoHV-1 tmv expressing chimeric BRSV F- and G-specific protective antigens.

| BHV-1 tmv/ BRSV -F/ BRSV-G 6 calves | Bovi-shield Gold 5 6 calves | Control 6 calves |
|---|---|---|
| Day 0 $1 \times 10^7$ PFUs/0.5 ml each of BHV-1 triple/BRSV-F and BRSV-G/nostril | Day 0 2 ml/IM | Day 0 Sham-infected with 1 ml media/nostril |
| Day 1, 2, 3, 4, 5, 6, 7, 8, 9, 12, 15, 21, 28 post infection nasal swabs, temps and clinical scores Day 0, 7, 14, 21, 28 serum, whole blood 28 dpi (vaccination) intranasal challenge with BRSV strain 236-652 $-6 \times 10^{6.2}$ TCID$_{50}$ Day 0, 1, 2, 3, 4, 5, 6, 7, 8, 9, 10, 12, 14 post challenge deep nasopharyngeal swabs, lung lavage, temps and clinical scores Day 0, 7, 14 day post challenge - whole blood and serum Day 15 post challenge euthanize, necropsy and score lung lesions | | |

For BoHV-1 tmv vectored BVDV type 1- or type 2-specific subunit vaccine efficacy studies, the schemes listed in Table 2 will be followed for the collection and evaluation of nasal swabs. Nasal swabs will be processed as described before (90) and MDBK cells will be used for plaque assay. For BoHV-1 triple mutant vectored BRSV subunit vaccine efficacy study, the scheme listed in Table 3 is similar up to 28 dpi as above in Table 2. However, after challenge with virulent BRSV strain 236-652 (41), deep nasopharyngeal swabs will be collected and twice during the first week of post challenge (3 pc and 6 dpc) lung lavage will be collected for virus isolation and/or for preparing formalin fixed slides containing cells pelleted from lung lavage (Table 3). Bovine turbinate cells will be used for BRSV isolation from lung lavage or nasopharyngeal swabs. In addition, formalin fixed slides containing smears prepared with cells pelleted from lung lavage will be tested for virus-specific antigens by FA. Alternatively, RNA isolated from the lung lavage/nasopharyngeal swab samples will be subjected to BRSV-specific semi quantitative RT-PCR as described earlier (55). In the case of calves challenged with BVDV, virus isolation from buffy coat cells and virus-specific RT-PCR will also be performed.

Determining Effects of BoHV-1 Tmv Vectored Subunit Vaccination Relative to Bovishield® Vaccination on Challenge and Virus Shedding in the Nose.

For this study, challenge virus replication in the nasal epithelium and/or in the lung tissues and clinical scores in infected verses uninfected control animals will be determined. Based on viral plaque assays on nasal swab samples (BVDV) or on deep nasopharyngeal swabs and lung lavage samples (BRSV), the level of protection conferred by recombinant viruses against challenge by wild type virus can be evaluated. Following challenge, a significant reduction in the duration and amount of virus in the nasal swabs (BVDV) or nasopharyngeal swabs (BRSV) or lung lavage (BRSV) of vaccinated animals compared with the similarly challenged sham-infected control animals will indicate efficacy.

We expect that like their parental virus (BoHV-1 tmv), the BoHV-1 tmv vector virus expressing BVDV E2.1 or E2.2 or BRSV-F/BRSV-G will replicate efficiently in the nasal epithelium of calves. As illustrated in FIG. 6A, the recombinant viruses may cause very mild or no respiratory disease. Although highly unlikely, increased clinical scores following primary infection with a recombinant virus would indicate that expression of the chimeric protein has affected the pathogenicity of the virus.

Determine Respective Protein-Specific Antibody Responses in Infected Calves.

Antigen-specific antibody (generated against subunit proteins BVDV E2.1, BVDV E2.2, BRSV F, BRSV G, or a combination thereof) can be detected by Cell ELISA test using respective virus-infected cells. Alternatively, ELISA plates can be coated with solubilized subunit protein-specific purified virion lysates (BVDV types 1 or 2 or BRSV) and tested by standard ELISA test (14). In addition, for the BRSV subunit vaccine group, sera from animals after primary infection/vaccination can be tested using a commercially available BRSV ELISA kit specific for F protein-specific antibodies (Cat # BIO K 061; Bio-X diagnostics, Belgium). Further, Western blots containing each wild-type BVDV types 1 and 2 and BRSV purified virion lysates, purified virion lysates of BoHV-1 triple mutant vector expressing BVDV E2.1/E2.2, BRSV-F/G will be tested to detect the subunit protein-specific as well as their corresponding band in their respective wt virion lysates.

Determine Virus Neutralizing Antibody and Cellular Immune Responses in BoHV-1 Triple Mutant Virus Vectored Subunit Vaccinated Relative to Bovishield™ Vaccinated and Uninfected Control Calves Before and after Challenge.

Virus neutralizing serum antibody titers against BoHV-1 can be determined by a plaque reduction assay described earlier (90, 91). For BVDV and BRSV, an immunofluorescence (IFA) based plaque reduction assay can be used in which after fixing the plates with formaldehyde, FA staining with virus-specific antibodies can be performed and fluorescent plaques will be counted. Compared with the uninfected control animals, the vaccinated animals can have higher serum neutralization (SN) titers against the BoHV-1 as well as against the respective subunit vaccine-specific wild-type virus at 21 dpi-28 dpi.

For assessing BoHV-1 specific cellular immune response, serum IFN-γ levels can be determined as described for FIG. 6D. In addition, cell proliferation assays and ELISPOT assays for interferon-γ, using PBMCs collected during primary infections from different vaccinated and control groups will be performed as described earlier (91). For assessing BVDV E2.1-, BVDV E2.2- and BRSV F/G-specific cell proliferation assay, PBMCs collected from vaccinated (subunit and Bovishield®) and control group before and after specific challenge can be sensitized with the corresponding UV-inactivated purified virions or for BVDV additionally with commercially available BVDV E2-specific codon optimized proteins (Bioclone Inc. Cat#PN0146, Cat # PN0143).

Following challenge, a rapid spike in virus-specific SN antibody and cell mediated immunity (CMI) responses in the vaccinated animals is expected. This spike will indicate that protective subunit vaccine antigen primed the vaccinated animal for a rapid memory response and a rapid rise in neutralizing antibody titers. For specific subunit antigen-specific cellular immune response in BoHV-1 triple mutant-infected calves expressing BVDV E2.1 or E2.2 or BRSV F/G, there can be increased proliferation of CD8 positive T cells and increased secretion of IFN-γ when PBMCs collected after primary vaccination as well as after challenge, are specifically stimulated with respective UV-inactivated virus or with specific BVDV codon optimized antigen. Following challenge, a rapid spike in virus-specific SN antibody and CMI responses in the vaccinated animals should also correlate with virus shedding/clearance data.

Determine Respiratory Tissue Lesions in BoHV-1 Triple Mutant Subunit Vaccinated Calves Relative to Bovishield® Vaccinated and Uninfected Control Calves Comparison of lung lesions of vaccinated animals with similarly challenged control animals using the subunit vaccine-specific wild type virus will show the protective effects in lungs following challenge. Relative to the similarly challenged control calves, a significant reduction in the lung lesions (>70%) or no lesions in the vaccinated animals challenged with either subunit-specific wild type virus will indicate protective efficacy of the vaccine. Lung lesions will be scored as follows: 0=normal, 1-=mild; 2=moderate; and 3=severe. The changes evaluated with the above scores will include bronchial epithelial necrosis; bronchial inflammation: peribronchial/perivascular inflammation: alveolar inflammation/necrosis; and syncytial cell formation (BRSV only).

Analysis of Statistical Significance

Nasal virus shedding, clinical scores and specific virus neutralizing titers will be analyzed as described herein, for example, utilizing repeated measures ANOVA and post-hoc pairwise comparisons. However, as explained in response to previous reviews, lung lesion scores will be analyzed using a nonparametric Kruskal-Wallis t-test.

Based on data provided herein, BoHV-1 triple mutant virus-infected calves will have BoHV-1-specific SN antibody titers and cellular immune responses. After vaccination with the novel BoHV-1 vectored subunit vaccines, similar BoHV-1-specific SN titers and cellular immune responses can be as illustrated in the foregoing Examples. Although unlikely, reduced levels of SN titers and/or weaker cellular immune responses against BoHV-1 vector would indicate that the specific subunit proteins have inhibitory effects on the host response to the vector virus. Based on the results from vaccine efficacy of vaccinia virus and adenovirus vectored subunit vaccines against BRSV (2) and the DNA subunit vaccine against BVDV (52, 53), SN antibody titers and cellular immune responses against the subunit vaccine-specific wild type viruses will be induced in the vaccinated calves, and the calves will be protected against the respective wild type viral challenges (reduced and shorter virus shedding, spike in SN antibody titers, increased level of IFN-γ production by PBMCs at 7 days post vaccination and increased CD8+ T cell proliferation following challenge with respective wt viruses). In the case of BVDV, an ideal protection would be when there is no viremia following challenge as judged by RT-PCR.

Potential Problems

One potential problem could be that in the case of BVDV and BRSV challenges, calves may come down with secondary bacterial infections. To avoid such problems following challenge infections, injection of Micotil 300 (8 mg/lbs.) on the day of challenge can be used.

BRSV is a highly sensitive to freezing and thawing. Therefore, another potential problem could be that virus in the nasopharyngeal swabs or in lung lavage samples may be inactivated due to freezing and thawing. To avoid such problems, the viral plaque assay can be performed on the day of sample collection without freezing the samples. Alternatively, FA staining can be performed on slides containing smears of nasopharyngeal swabs and/or lung lavage cells.

Example 10: Construction of Novel Bovine Herpesvirus Type 1 (BoHV-1) Vectored Vaccine Against Viral Infections Associated with Bovine Respiratory Disease Complex (BRDC)

The Example describes experiments relating to the following.

1. Construction of BoHV-1 tmv expressing BVDV types 1 and 2 envelope proteins E2.1 and E2.2, respectively.
2. Construction of BoHV-1 tmv expressing BRSV envelope proteins F and G.
3. Test the vaccine efficacy of the above constructs against the BVDV and BRSV infections compared with a commercial multivalent viral BRD vaccine Bovishield®).

The construction and testing of these recombinant viruses can provide a better and safer strategy to vaccinate beef and dairy cattle against BoHV-1, BVDV and BRSV, the three most significant bovine respiratory viruses that predispose to fatal secondary bacterial pneumonia. Ultimately, this vaccine will reduce the mortality and morbidity associated with BRDC.

FIG. 3A shows the structure of the BoHV-1 tmv recombinant virus previously developed by the inventors.

To construct BoHV-1 recombinants expressing BVDV E2-1 or 2, first the BVDV E2-1 or 2 insertion vectors were generated (FIG. 11). Second, linearized pBoHV-1 gEΔCTUs9Δ/BVDV E2-1 or 2 insertion vector DNA was used for transfection with full-length BoHV-1 tmv DNA (FIG. 3A). Putative recombinant plaques were verified initially by PCR for the incorporation of BVDV type 1- or type 2-specific E2 (E2-1 or E2-2) sequence. Subsequently, selected plaques were further characterized for the expression of E2-1 or E2-2 (FIG. 12)

Figures 12A, 12B:
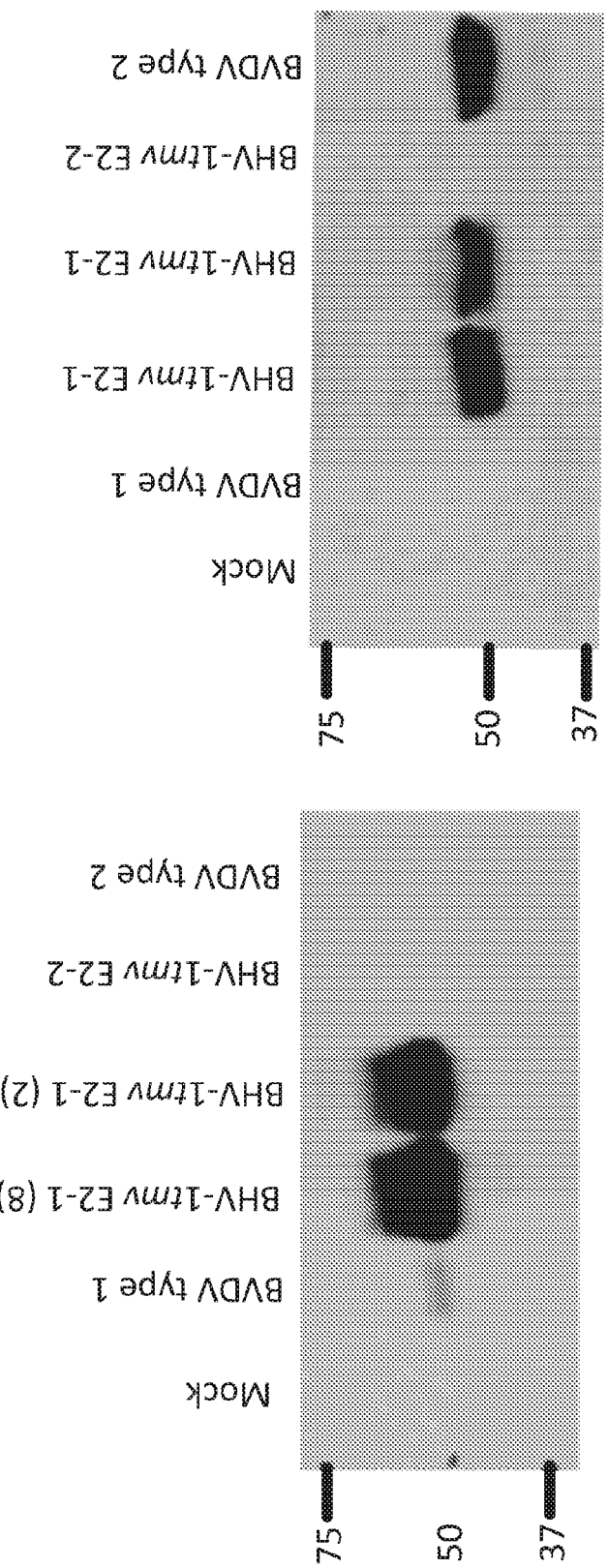
FIG. 12A-12B illustrate expression of BVDV E2 antigens from a recombinant BoHV-1 tmv vector.

FIG. 12A-12B illustrate expression of BVDV E2 antigens from a recombinant BoHV-1 tmv vector. FIG. 12A shows an immunoblot of MDBK cell lysates that were either mock-transfected or transfected with BoHV-1tmv recombinant vectors expressing either BVDV type 1 (BoHV-1 tmv E2-1 clone 8 and clone 2) or type 2 E2 proteins (BoHV-1 tmv E2-2) as detected by a BVDV type 1 E2-specific monoclonal antibody (VMRD #157). FIG. 12B shows an immunoblot of MDBK cell lysates that were either mock-transfected or transfected with BoHV-1tmv recombinant vectors expressing either BVDV type 1 (BoHV-1 tmv E2-1 clone 8 and clone 2) or type 2 E2 proteins (BoHV-1 tmv E2-2) as detected by a BVDV type 2 E2-specific monoclonal antibody (VMRD # BA-2). As control, the reactivity of the monoclonal antibody Ab 157 and the monoclonal antibody mAb BA-2 is illustrated for mock and BVDV-1 type 1 (strain sanger) and BVDV type 2 (strain 125) infected MDBK cell lysates.

Figure 13:
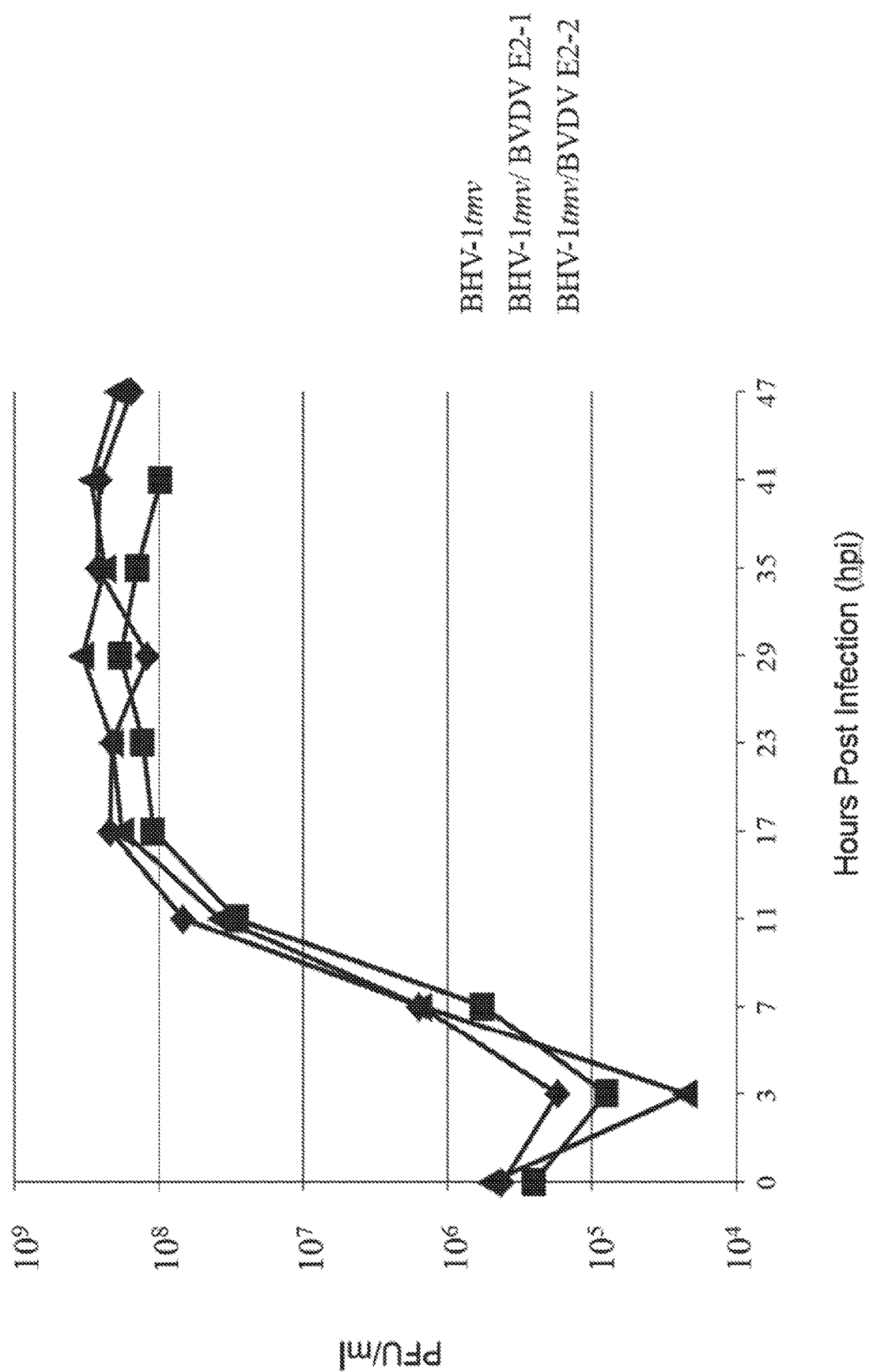
FIG. 13 graphically illustrates single step growth kinetics of BoHV-1tmv, BoHV-1tmv/E2-1 and BoHV-1tmv/E2-2. Samples were collected at 0 h, 3 h, 7 h, 11 h, 17 h, 23 h, 29 h, 35 h, 41 h and 47 hours post infection and titrated by plaque assay. The titration values of each time point were used to make the growth curve for comparison.

FIG. 13 graphically illustrates single step growth kinetics of BoHV-1tmv, BoHV-1tmv/E2-1 and BoHV-1tmv/E2-2. Samples were collected at 0 h, 3 h, 7 h, 11 h, 17 h, 23 h, 29 h, 35 h, 41 h and 47 hours post infection and titrated by plaque assay.

Figure 14:
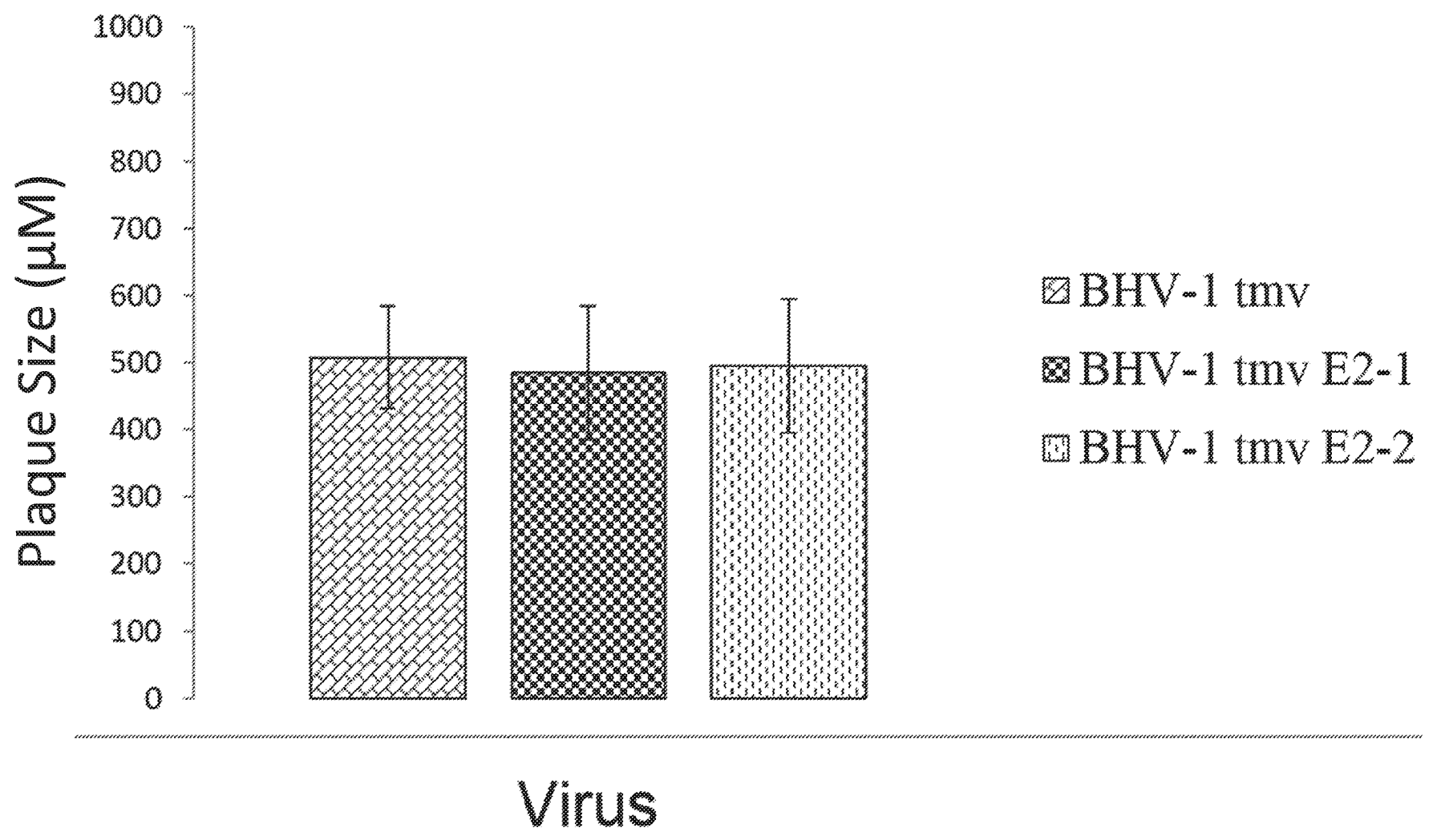

FIG. 14 graphically illustrates the plaque morphology of BoHV-1 tmv/E2-1 and BoHV-1tmv/E2. Plaque sizes produced by parental BoHV-1tmv, BoHV-1 tmv/E2-1 and BoHV-1tmv/E2 viruses were measured at 48 hours post-infection. Average plaque diameters of 50 randomly selected plaques are shown as mean±standard deviation.

Thus, two BoHV-1tmv recombinants expressing BVDV type 1 or 2 E2 proteins separately have successfully been constructed.

Example 11: Recombinant BHV-1 Tmv that Express BRSV F and G Proteins

Recombinant BHV-1 tmv that express BRSV F and G were generated as illustrated in FIGS. 3E-3J. First BRSV F and G insertion vectors were generated (FIG. 3F, 3I, 3J). Second, linearized pBHV-1 gEΔCTUs9Δ/BRSV F or G insertion vector DNA was transfected into host cells (Botur cells) with full-length BHV-1 tmv DNA (FIG. 3E).

Expression of BRSV F protein from recombinant BHV-1 tmv was determined by preparing an immunoblot of infected Botur cell lysates and staining the blot with a rabbit anti-BRSV F specific antibody (GenScript). Lysate from Botur cells infected with an unmodified BRSV Nebraska 236-652 strain served as positive control.

Expression of BRSV G protein from recombinant BHV-1 tmv was determined by preparing an immunoblot of infected MDBK cell lysates and staining the blot with anti-V5 specific monoclonal antibodies (Invitrogen, #R960-25). In a separate experiment, expression of BRSV G protein from recombinant BHV-1 tmv was determined by an immunoblot of infected Botur cell lysates using a rabbit anti-BRSV G specific antibody (GenScript).

Figures 24A, 24B, 24C:
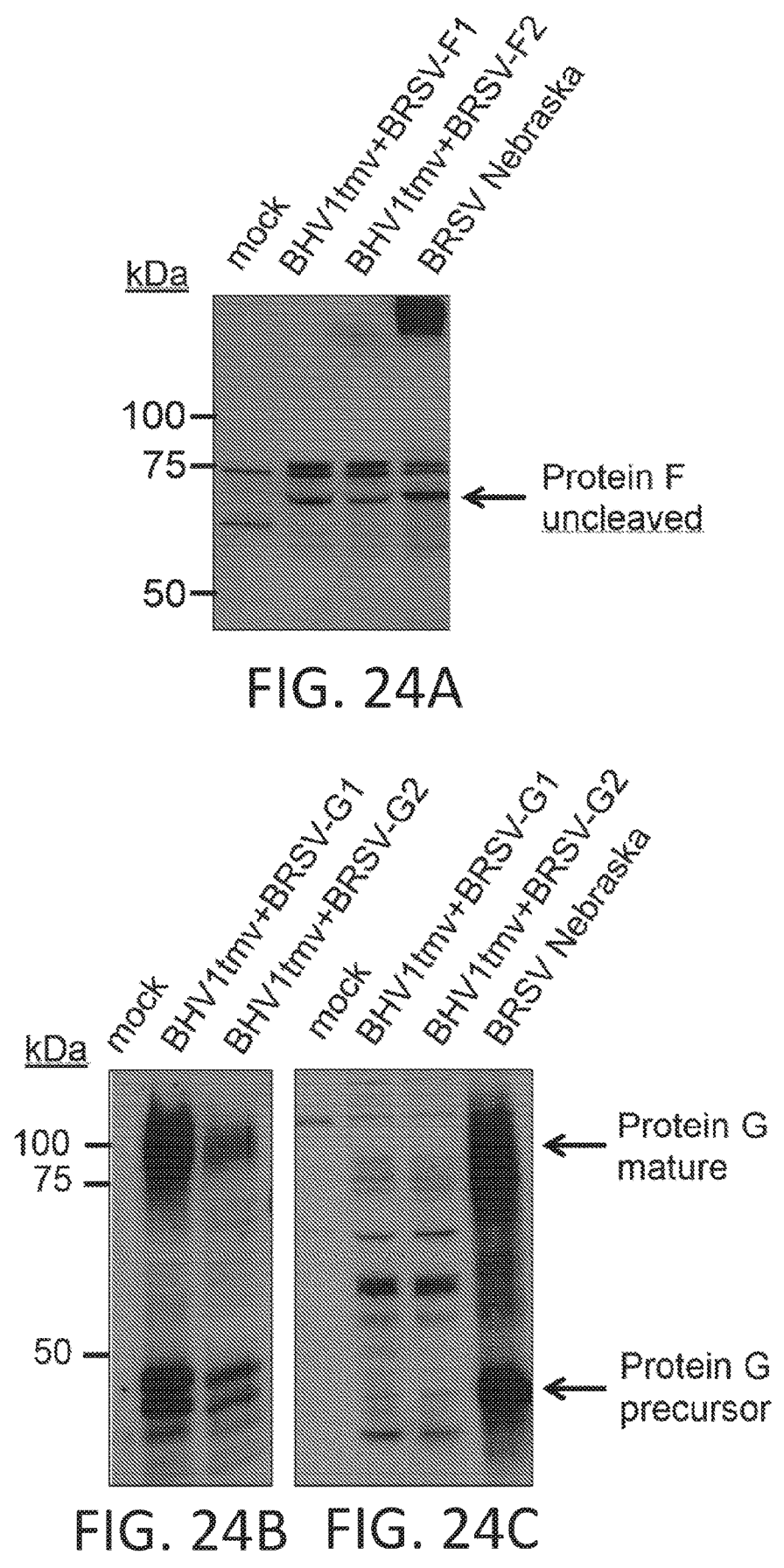

Expression of expression of BRSV F or G proteins from the recombinant BHV-1 tmv vectors is illustrated in FIG. 24A-24C.

BRSV F protein is typically synthesized as 67 kDa precursor protein that is proteolytically cleaved at two separate furin cleavage sites, to yield a peptide of 48 kDa and peptide of 18 kDa. However, the coding region of the F protein inserted into the recombinant BHV-1 tmv vector had mutated Furin cleavage sites to prevent such proteolytic cleavage. In particular, modified BRSV F1 was generated by mutating some arginines in furin cleavage sites to alanines, while a modified BRSV F2 is generated by mutating all arginines and lysines in furin cleavage sites to alanines. Hence, the uncleaved F protein is visible in FIG. 24A.

BRSV-G is synthesized as 43 kDa precursor protein which is further processed in the Golgi to a 68-90 kDa mature protein G. The recombinant BRSV-G1 expressed from the recombinant BHV-1 tmv vector has modifications that are not present in the wild type G protein. In particular, the recombinant BRSV-G1 expressed from the recombinant BHV-1 tmv vector has all four cysteines in the "cysteine noose" replaced by serines (amino acids C173S, C176S, C182S and C186S; $_{173}$SST$_{176}$SEGNLA$_{182}$SLSL$_{186}$S; GenBank accession #AL49398.1). The recombinant BRSV-G2 expressed from the recombinant BHV-1 tmv vector has a complete deletion of the "cysteine noose" (i.e., a deletion of CSTCEGNLACLSLC (SEQ ID NO:48), GenBank accession #AL49398.1, amino acids 173 . . . 186).

REFERENCES

1. Al-Mubarak, A., J. Simon, C. Coats, J. D. Okemba, M. D. Burton, and S. I. Chowdhury. 2007. Glycoprotein E (gE) specified by bovine herpesvirus type 5 (BHV-5) enables trans-neuronal virus spread and neurovirulence without being a structural component of enveloped virions. Virology 365:398-409.
2. Al-Mubarak, A., Y. Zhou, and S. I. Chowdhury. 2004. A glycine-rich bovine herpesvirus 5 (BHV-5) gE-specific epitope within the ectodomain is important for BHV-5 neurovirulence. J Virol 78:4806-16.
3. Antonis, A. F., R. S. Schrijver, F. Daus, P. J. Steverink, N. Stockhofe, E. J. Hensen, J. P. Langedijk, and R. G. van der Most. 2003. Vaccine-induced immunopathology during bovine respiratory syncytial virus infection: exploring the parameters of pathogenesis. J Virol 77:12067-73.
4. Antonis, A. F., R. G. van der Most, Y. Suezer, N. Stockhofe-Zurwieden, F. Daus, G. Sutter, and R. S. Schrijver. 2007. Vaccination with recombinant modified vaccinia virus Ankara expressing bovine respiratory syncytial virus (bRSV) proteins protects calves against RSV challenge. Vaccine 25:4818-27.
5. Baker, J. C., J. A. Ellis, and E. G. Clark. 1997. Bovine respiratory syncytial virus. Vet Clin North Am Food Anim Pract 13:425-54.
6. Baxi, M. K., D. Deregt, J. Robertson, L. A. Babiuk, T. Schlapp, and S. K. Tikoo. 2000. Recombinant bovine adenovirus type 3 expressing bovine viral diarrhea virus glycoprotein E2 induces an immune response in cotton rats. Virology 278:234-43.
7. Berghaus, L. J., L. B. Corbeil, R. D. Berghaus, W. V. Kalina, R. A. Kimball, and L. J. Gershwin. 2006. Effects of dual vaccination for bovine respiratory syncytial virus and *Haemophilus* somnus on immune responses. Vaccine 24:6018-27.
8. Brackenbury, L. S., B. V. Carr, and B. Charleston. 2003. Aspects of the innate and adaptive immune responses to acute infections with BVDV. Vet Microbiol 96:337-44.
9. Brock, K. V. 2003. The persistence of bovine viral diarrhea virus. Biologicals 31:133-5.
10. Brum, M. C., C. Coats, R. B. Sangena, A. Doster, C. Jones, and S. I. Chowdhury. 2009. Bovine herpesvirus type 1 (BoHV-1) anterograde neuronal transport from trigeminal ganglia to nose and eye requires glycoprotein E. J Neurovirol 15:196-201.
11. Butchi, N. B., C. Jones, S. Perez, A. Doster, and S. I. Chowdhury. 2007. Envelope protein Us9 is required for the anterograde transport of bovine herpesvirus type 1 from trigeminal ganglia to nose and eye upon reactivation. J Neurovirol 13:384-8.
12. Chase, C. C., G. Elmowalid, and A. A. Yousif. 2004. The immune response to bovine viral diarrhea virus: a constantly changing picture. Vet Clin North Am Food Anim Pract 20:95-114.
13. Chouljenko, V. N., X. Q. Lin, J. Storz, K. G. Kousoulas, and A. E. Gorbalenya. 2001. Comparison of genomic and predicted amino acid sequences of respiratory and enteric bovine coronaviruses isolated from the same animal with fatal shipping pneumonia. J Gen Virol 82:2927-33.
14. Chowdhury, S. I. 1997. Fine mapping of bovine herpesvirus 1 (BoHV-1) glycoprotein C neutralizing epitopes by type-specific monoclonal antibodies and synthetic peptides. Vet Microbiol 58:309-14.
15. Chowdhury, S. I., M. C. Brum, C. Coats, A. Doster, H. Wei, and C. Jones. The bovine herpesvirus type 1 envelope protein Us9 acidic domain is crucial for anterograde axonal transport. Vet Microbiol 152:270-9.
16. Chowdhury, S. I., J. Coats, R. A. Neis, S. M. Navarro, D. B. Paulsen, and J. M. Feng. A bovine herpesvirus type 1 mutant virus with truncated glycoprotein E cytoplasmic tail has defective anterograde neuronal transport in rabbit dorsal root ganglia primary neuronal cultures in a microfluidic chamber system. J Neurovirol 16:457-65.
17. Deplanche, M., M. Lemaire, C. Mirandette, M. Bonnet, F. Schelcher, and G. Meyer. 2007. In vivo evidence for quasispecies distributions in the bovine respiratory syncytial virus genome. J Gen Virol 88:1260-5.
18. Donofrio, G., C. Sartori, L. Ravanetti, S. Cavirani, L. Gillet, A. Vanderplasschen, S. Taddei, and C. F. Flammini. 2007. Establishment of a bovine herpesvirus 4 based vector expressing a secreted form of the bovine viral diarrhoea virus structural glycoprotein E2 for immunization purposes. BMC Biotechnol 7:68.
19. Durham, P. J., L. E. Hassard, and J. Van Donkersgoed. 1991. Serological studies of infectious bovine rhinotracheitis, parainfluenza 3, bovine viral diarrhea, and bovine respiratory syncytial viruses in calves following entry to a bull test station. Can Vet J 32:427-9.
20. Elliott, M. B., K. S. Pryharski, Q. Yu, L. A. Boutilier, N. Campeol, K. Melville, T. S. Laughlin, C. K. Gupta, R. A. Lerch, V. B. Randolph, N. A. LaPierre, K. M. Dack, and G. E. Hancock. 2004. Characterization of recombinant respiratory syncytial viruses with the region responsible for type 2 T-cell responses and pulmonary eosinophilia deleted from the attachment (G) protein. J Virol 78:8446-54.
21. Ellis, J., C. Waldner, C. Rhodes, and V. Ricketts. 2005. Longevity of protective immunity to experimental bovine herpesvirus-1 infection following inoculation with a combination modified-live virus vaccine in beef calves. J Am Vet Med Assoc 227:123-8.
22. Ellis, J. A. 2009. Update on viral pathogenesis in BRD. Anim Health Res Rev 10:149-53.
23. Fulton, R. W. 2009. Bovine respiratory disease research (1983-2009). Anim Health Res Rev 10:131-9.
24. Fulton, R. W., J. T. Saliki, L. J. Burge, and M. E. Payton. 2003. Humoral immune response and assessment of vaccine virus shedding in calves receiving modified live virus vaccines containing bovine herpesvirus-1 and bovine viral diarrhoea virus 1a. J Vet Med B Infect Dis Vet Public Health 50:31-7.
25. Furze, J., G. Wertz, R. Lerch, and G. Taylor. 1994. Antigenic heterogeneity of the attachment protein of bovine respiratory syncytial virus. J Gen Virol 75 (Pt 2):363-70.
26. Gershwin, L. J. 2007. Bovine respiratory syncytial virus infection: immunopathogenic mechanisms. Anim Health Res Rev 8:207-13.
27. Gershwin, L. J. Immunology of bovine respiratory syncytial virus infection of cattle. Comp Immunol Microbiol Infect Dis 35:253-7.
28. Goens, S. D. 2002. The evolution of bovine viral diarrhea: a review. Can Vet J 43:946-54.
29. Hagglund, S., M. Hjort, D. A. Graham, P. Ohagen, M. Tornquist, and S. Alenius. 2007. A six-year study on respiratory viral infections in a bull testing facility. Vet J 173:585-93.

30. Jericho, K. W., and E. V. Langford. 1978. Pneumonia in calves produced with aerosols of bovine herpesvirus 1 and *Pasteurella haemolytica*. Can J Comp Med 42:269-77.
31. Jones, C., and S. Chowdhury. Bovine herpesvirus type 1 (BoHV-1) is an important cofactor in the bovine respiratory disease complex. Vet Clin North Am Food Anim Pract 26:303-21.
32. Jones, C., and S. Chowdhury. 2007. A review of the biology of bovine herpesvirus type 1 (BoHV-1), its role as a cofactor in the bovine respiratory disease complex and development of improved vaccines. Anim Health Res Rev 8:187-205.
33. Jordan, R., O. V. Nikolaeva, L. Wang, B. Conyers, A. Mehta, R. A. Dwek, and T. M. Block. 2002. Inhibition of host ER glucosidase activity prevents Golgi processing of virion-associated bovine viral diarrhea virus E2 glycoproteins and reduces infectivity of secreted virions. Virology 295:10-9.
34. Kaashoek, M. J., F. A. Rijsewijk, R. C. Ruuls, G. M. Keil, E. Thiry, P. P. Pastoret, and J. T. Van Oirschot. 1998. Virulence, immunogenicity and reactivation of bovine herpesvirus 1 mutants with a deletion in the gC, gG, gI, gE, or in both the gI and gE gene. Vaccine 16:802-9.
35. Kaashoek, M. J., F. A. van Engelenburg, A. Moerman, A. L. Gielkens, F. A. Rijsewijk, and J. T. van Oirschot. 1996. Virulence and immunogenicity in calves of thymidine kinase- and glycoprotein E-negative bovine herpesvirus 1 mutants. Vet Microbiol 48:143-53.
36. Kalina, W. V., A. R. Woolums, and L. J. Gershwin. 2005. Formalin-inactivated bovine RSV vaccine influences antibody levels in bronchoalveolar lavage fluid and disease outcome in experimentally infected calves. Vaccine 23:4625-30.
37. Karger, A., U. Schmidt, and U. J. Buchholz. 2001. Recombinant bovine respiratory syncytial virus with deletions of the G or SH genes: G and F proteins bind heparin. J Gen Virol 82:631-40.
38. Keles, I., Z. Woldehiwet, and R. D. Murray. 1998. In-vitro studies on mechanisms of immunosuppression associated with bovine respiratory syncytial virus. J Comp Pathol 118:337-45.
39. Kelling, C. L. 2004. Evolution of bovine viral diarrhea virus vaccines. Vet Clin North Am Food Anim Pract 20:115-29.
40. Kimman, T. G., G. M. Zimmer, P. J. Straver, and P. W. de Leeuw. 1986. Diagnosis of bovine respiratory syncytial virus infections improved by virus detection in lung lavage samples. Am J Vet Res 47:143-7.
41. Klink, H. A., R. P. Brady, C. L. Topliff, K. M. Eskridge, S. Srikumaran, and C. L. Kelling. 2006. Influence of bovine respiratory syncytial virus F glycoprotein N-linked glycans on in vitro expression and on antibody responses in BALB/c mice. Vaccine 24:3388-95.
42. Konig, P., K. Giesow, and G. M. Keil. 2002. Glycoprotein M of bovine herpesvirus 1 (BoHV-1) is nonessential for replication in cell culture and is involved in inhibition of bovine respiratory syncytial virus F protein induced syncytium formation in recombinant BoHV-1 infected cells. Vet Microbiol 86:37-49.
43. Koppers-Lalic, D., E. A. Reits, M. E. Ressing, A. D. Lipinska, R. Abele, J. Koch, M. Marcondes Rezende, P. Admiraal, D. van Leeuwen, K. Bienkowska-Szewczyk, T. C. Mettenleiter, F. A. Rijsewijk, R. Tampe, J. Neefjes, and E. J. Wiertz. 2005. Varicelloviruses avoid T cell recognition by UL49.5-mediated inactivation of the transporter associated with antigen processing. Proc Natl Acad Sci USA 102:5144-9.
44. Koppers-Lalic, D., M. C. Verweij, A. D. Lipinska, Y. Wang, E. Quinten, E. A. Reits, J. Koch, S. Loch, M. Marcondes Rezende, F. Daus, K. Bienkowska-Szewczyk, N. Osterrieder, T. C. Mettenleiter, M. H. Heemskerk, R. Tampe, J. J. Neefjes, S. I. Chowdhury, M. E. Ressing, F. A. Rijsewijk, and E. J. Wiertz. 2008. Varicellovirus UL 49.5 proteins differentially affect the function of the transporter associated with antigen processing, TAP. PLoS Pathog 4:e1000080.
45. Kuhnle, G., A. Heinze, J. Schmitt, K. Giesow, G. Taylor, I. Morrison, F. A. Rijsewijk, J. T. van Oirschot, and G. M. Keil. 1998. The class II membrane glycoprotein G of bovine respiratory syncytial virus, expressed from a synthetic open reading frame, is incorporated into virions of recombinant bovine herpesvirus 1. J Virol 72:3804-11.
46. Langedijk, J. P., R. H. Meloen, G. Taylor, J. M. Furze, and J. T. van Oirschot. 1997. Antigenic structure of the central conserved region of protein G of bovine respiratory syncytial virus. J Virol 71:4055-61.
47. Larsen, L. E. 2000. Bovine respiratory syncytial virus (BRSV): a review. Acta Vet Scand 41:1-24.
48. Larsen, L. E., C. Tegtmeier, and E. Pedersen. 2001. Bovine respiratory syncytial virus (BRSV) pneumonia in beef calf herds despite vaccination. Acta Vet Scand 42:113-21.
49. Lathrop, S. L., T. E. Wittum, S. C. Loerch, L. J. Perino, and L. J. Saif. 2000. Antibody titers against bovine coronavirus and shedding of the virus via the respiratory tract in feedlot cattle. Am J Vet Res 61:1057-61.
50. Leite, F., C. Kuckleburg, D. Atapattu, R. Schultz, and C. J. Czuprynski. 2004. BoHV-1 infection and inflammatory cytokines amplify the interaction of Mannheimia *haemolytica* leukotoxin with bovine peripheral blood mononuclear cells in vitro. Vet Immunol Immunopathol 99:193-202.
51. Lerch, R. A., K. Anderson, and G. W. Wertz. 1990. Nucleotide sequence analysis and expression from recombinant vectors demonstrate that the attachment protein G of bovine respiratory syncytial virus is distinct from that of human respiratory syncytial virus. J Virol 64:5559-69.
52. Liang, R., J. V. van den Hurk, A. Landi, Z. Lawman, D. Deregt, H. Townsend, L. A. Babiuk, and S. van Drunen Littel-van den Hurk. 2008. DNA prime protein boost strategies protect cattle from bovine viral diarrhea virus type 2 challenge. J Gen Virol 89:453-66.
53. Liang, R., J. V. van den Hurk, C. Zheng, H. Yu, R. A. Pontarollo, L. A. Babiuk, and S. van Drunen Littel-van den Hurk. 2005. Immunization with plasmid DNA encoding a truncated, secreted form of the bovine viral diarrhea virus E2 protein elicits strong humoral and cellular immune responses. Vaccine 23:5252-62.
54. Lin, G. J., T. Y. Liu, Y. Y. Tseng, Z. W. Chen, C. C. You, S. L. Hsuan, M. S. Chien, and C. Huang. 2009. Yeast-expressed classical swine fever virus glycoprotein E2 induces a protective immune response. Vet Microbiol 139:369-74.
55. Liu, Z. F., M. C. Brum, A. Doster, C. Jones, and S. I. Chowdhury. 2008. A bovine herpesvirus type 1 mutant virus specifying a carboxyl-terminal truncation of glycoprotein E is defective in anterograde neuronal transport in rabbits and calves. J Virol 82:7432-42.
56. Lorenz, I., B. Earley, J. Gilmore, I. Hogan, E. Kennedy, and S. J. More. Calf health from birth to weaning. III. housing and management of calf pneumonia. Ir Vet J 64:14.

57. Mallipeddi, S. K., S. K. Samal, and S. B. Mohanty. 1990. Analysis of polypeptides synthesized in bovine respiratory syncytial virus-infected cells. Arch Virol 115:23-36.
58. Manoj, S., P. J. Griebel, L. A. Babiuk, and S. van Drunen Littel-van den Hurk. 2004. Modulation of immune responses to bovine herpesvirus-1 in cattle by immunization with a DNA vaccine encoding glycoprotein D as a fusion protein with bovine CD154. Immunology 112:328-38.
59. Martin, S. W., E. Nagy, P. E. Shewen, and R. J. Harland. 1998. The association of titers to bovine coronavirus with treatment for bovine respiratory disease and weight gain in feedlot calves. Can J Vet Res 62:257-61.
60. Martinod, S. 1995. Risk assessment related to veterinary biologicals: side-effects in target animals. Rev Sci Tech 14:979-89.
61. McBride, J. W., R. E. Corstvet, B. C. Taylor, and B. 1. Osburn. 1999. Primary and anamnestic responses of bovine bronchoalveolar and peripheral blood lymphocyte subsets to aerosolized *Pasteurella haemolytica* Al. Vet Immunol Immunopathol 67:161-70.
62. Meeusen, E. N., J. Walker, A. Peters, P. P. Pastoret, and G. Jungersen. 2007. Current status of veterinary vaccines. Clin Microbiol Rev 20:489-510, table of contents.
63. Murray, C. L., J. Marcotrigiano, and C. M. Rice. 2008. Bovine viral diarrhea virus core is an intrinsically disordered protein that binds RNA. J Virol 82:1294-304.
64. Nataraj, C., S. Eidmann, M. J. Hariharan, J. H. Sur, G. A. Perry, and S. Srikumaran. 1997. Bovine herpesvirus 1 downregulates the expression of bovine MHC class I molecules. Viral Immunol 10:21-34.
65. O'Toole, D., M. M. Miller, J. L. Cavender, and T. E. Cornish. Pathology in practice: abortion in the heifers of this report was a result of BoHV-1 infection. J Am Vet Med Assoc 241:189-91.
66. O'Toole, D., and H. Van Campen. Abortifacient vaccines and bovine herpesvirus-1. J Am Vet Med Assoc 237:259-60.
67. Plummer, P. J., B. W. Rohrbach, R. A. Daugherty, R. A. Daugherty, K. V. Thomas, R. P. Wilkes, F. E. Duggan, and M. A. Kennedy. 2004. Effect of intranasal vaccination against bovine enteric coronavirus on the occurrence of respiratory tract disease in a commercial backgrounding feedlot. J Am Vet Med Assoc 225:726-31.
68. Potgieter, L. N., M. D. McCracken, F. M. Hopkins, R. D. Walker, and J. S. Guy. 1984. Experimental production of bovine respiratory tract disease with bovine viral diarrhea virus. Am J Vet Res 45:1582-5.
69. Ridpath, J. F. Bovine viral diarrhea virus: global status. Vet Clin North Am Food Anim Pract 26:105-21, table of contents.
70. Ridpath, J. F. Immunology of BVDV vaccines. Biologicals.
71. Rivera-Rivas, J. J., D. Kisiela, and C. J. Czuprynski. 2009. Bovine herpesvirus type 1 infection of bovine bronchial epithelial cells increases neutrophil adhesion and activation. Vet Immunol Immunopathol 131:167-76.
72. Roth, J. A., and M. L. Kaeberle. 1983. Suppression of neutrophil and lymphocyte function induced by a vaccinal strain of bovine viral diarrhea virus with and without the administration of ACTH. Am J Vet Res 44:2366-72.
73. Saif, L. J. Bovine respiratory coronavirus. Vet Clin North Am Food Anim Pract 26:349-64.
74. Sandvik, T. 2004. Progress of control and prevention programs for bovine viral diarrhea virus in Europe. Vet Clin North Am Food Anim Pract 20:151-69.
75. Schlender, J., G. Zimmer, G. Herrier, and K. K. Conzelmann. 2003. Respiratory syncytial virus (RSV) fusion protein subunit F2, not attachment protein G, determines the specificity of RSV infection. J Virol 77:4609-16.
76. Schmidt, U., J. Beyer, U. Polster, L. J. Gershwin, and U. J. Buchholz. 2002. Mucosal immunization with live recombinant bovine respiratory syncytial virus (BRSV) and recombinant BRSV lacking the envelope glycoprotein G protects against challenge with wild-type BRSV. J Virol 76:12355-9.
77. Schmitt, J., P. Becher, H. J. Thiel, and G. M. Keil. 1999. Expression of bovine viral diarrhoea virus glycoprotein E2 by bovine herpesvirus-1 from a synthetic ORF and incorporation of E2 into recombinant virions. J Gen Virol 80 (Pt 11):2839-48.
78. Schrijver, R. S., J. P. Langedijk, G. M. Keil, W. G. Middel, M. Maris-Veldhuis, J. T. Van Oirschot, and F. A. Rijsewijk. 1998. Comparison of DNA application methods to reduce BRSV shedding in cattle. Vaccine 16:130-4.
79. Schrijver, R. S., J. P. Langedijk, G. M. Keil, W. G. Middel, M. Maris-Veldhuis, J. T. Van Oirschot, and F. A. Rijsewijk. 1997. Immunization of cattle with a BHV1 vector vaccine or a DNA vaccine both coding for the G protein of BRSV. Vaccine 15:1908-16.
80. Storz, J., X. Lin, C. W. Purdy, V. N. Chouljenko, K. G. Kousoulas, F. M. Enright, W. C. Gilmore, R. E. Briggs, and R. W. Loan. 2000. Coronavirus and *Pasteurella* infections in bovine shipping fever pneumonia and Evans' criteria for causation. J Clin Microbiol 38:3291-8.
81. Taylor, G., C. Bruce, A. F. Barbet, S. G. Wyld, and L. H. Thomas. 2005. DNA vaccination against respiratory syncytial virus in young calves. Vaccine 23:1242-50.
82. Taylor, G., F. A. Rijsewijk, L. H. Thomas, S. G. Wyld, R. M. Gaddum, R. S. Cook, W. I. Morrison, E. Hensen, J. T. van Oirschot, and G. Keil. 1998. Resistance to bovine respiratory syncytial virus (BRSV) induced in calves by a recombinant bovine herpesvirus-1 expressing the attachment glycoprotein of BRSV. J Gen Virol 79 (Pt 7):1759-67.
83. Taylor, G., E. J. Stott, J. Furze, J. Ford, and P. Sopp. 1992. Protective epitopes on the fusion protein of respiratory syncytial virus recognized by murine and bovine monoclonal antibodies. J Gen Virol 73 (Pt 9):2217-23.
84. Taylor, G., L. H. Thomas, J. M. Furze, R. S. Cook, S. G. Wyld, R. Lerch, R. Hardy, and G. W. Wertz. 1997. Recombinant vaccinia viruses expressing the F, G or N, but not the M2, protein of bovine respiratory syncytial virus (BRSV) induce resistance to BRSV challenge in the calf and protect against the development of pneumonic lesions. J Gen Virol 78 (Pt 12):3195-206.
85. Taylor, J. D., R. W. Fulton, T. W. Lehenbauer, D. L. Step, and A. W. Confer. The epidemiology of bovine respiratory disease: What is the evidence for preventive measures? Can Vet J 51:1351-9.
86. Tikoo, S. K., M. Campos, and L. A. Babiuk. 1995. Bovine herpesvirus 1 (BoHV-1): biology, pathogenesis, and control. Adv Virus Res 45:191-223.
87. Valarcher, J. F., J. Furze, S. G. Wyld, R. Cook, G. Zimmer, C. Herrler, and G. Taylor. 2006. Bovine respiratory syncytial virus lacking the virokinin or with a mutation in furin cleavage site RA(R/K)R109 induces less pulmonary inflammation without impeding the induction of protective immunity in calves. J Gen Virol 87:1659-67.
88. van Drunen Littel-van den Hurk, S., D. Myers, P. A. Doig, B. Karvonen, M. Habermehl, L. A. Babiuk, M. Jelinski, J. Van Donkersgoed, K. Schlesinger, and C. Rinehart. 2001. Identification of a mutant bovine herpes- 89. Wei, H., J. He, D. B. Paulsen, and S. I. Chowdhury. Bovine herpesvirus type 1 (BoHV-1) mutant lacking U(L)49.5 luminal domain residues 30-32 and cytoplasmic tail residues 80-96 induces more rapid onset of virus neutralizing antibody and cellular immune responses in calves than the wild-type strain Cooper. Vet Immunol Immunopathol 147:223-9.

90. Wei, H., Y. Wang, and S. I. Chowdhury. Bovine herpesvirus type 1 (BoHV-1) UL49.5 luminal domain residues 30 to 32 are critical for MHC-I down-regulation in virus-infected cells. PLoS One 6:e25742.

91. West, W. H., G. R. Lounsbach, C. Bourgeois, J. W. Robinson, M. J. Carter, S. Crompton, N. Duhindan, Z. A. Yazici, and G. L. Toms. 1994. Biological activity, binding site and affinity of monoclonal antibodies to the fusion protein of respiratory syncytial virus. J Gen Virol 75 (Pt 10):2813-9.

92. Xue, W., J. Ellis, D. Mattick, L. Smith, R. Brady, and E. Trigo. Immunogenicity of a modified-live virus vaccine against bovine viral diarrhea virus types 1 and 2, infectious bovine rhinotracheitis virus, bovine parainfluenza-3 virus, and bovine respiratory syncytial virus when administered intranasally in young calves. Vaccine 28:3784-92.

93. Yoo, D., and D. Deregt. 2001. A single amino acid change within antigenic domain II of the spike protein of bovine coronavirus confers resistance to virus neutralization. Clin Diagn Lab Immunol 8:297-302.

94. Zemke, J., P. Konig, K. Mischkale, I. Reimann, and M. Beer. Novel BVDV-2 mutants as new candidates for modified-live vaccines. Vet Microbiol 142:69-80.

95. Zimmer, G., L. Budz, and G. Herrler. 2001. Proteolytic activation of respiratory syncytial virus fusion protein. Cleavage at two furin consensus sequences. J Biol Chem 276:31642-50.

96. Chowdhury S I, et al., (2014). A triple gene mutant of BoHV-1 administered intranasally is significantly more efficacious than a BoHV-1 glycoprotein E-deleted virus against a virulent BoHV-1 Challenge. Vaccine 32 (39), 4909-4915.

97. Baggiolini, M. Chemokines and leukocyte traffic. Nature 1998, 392, 565-568.

98. Bryant, N. A.; Davis-Poynter. N.; Vanderplasschen, A.; Alcami, A. Glycoprotein G isoforms fromsome alphaherpesvirus function as broad-spectrum chemokine binding proteins. EMBO J. 2003, 22, 833-846.

99. Kaashoek M J, Fijsewijk F A M, Ruuls R C, Keil G M, Thiry E, Pastoret P P and Van Oirschot J T (1998). Virulence, immunogenicity and reactivation of bovine herpesvirus 1 mutants with a deletion in the gC, gG, gI, gE, or in both the gI and gE gene. Vaccine 16: 802-809.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:
1. A BoHV-1 recombinant vector comprising BoHV-1 tmv with at least one heterologous antigen from a respiratory RNA virus.
2. The BoHV-1 recombinant vector of statement 1, wherein the at least one antigen is from BoHV, BVDV, BRSV, or a combination thereof.
3. The BoHV-1 recombinant vector of statement 1 or 2, wherein the at least one antigen is BoHV-1, BVDV type 1, BVDV type 2, BRSV, or a combination thereof.
4. The BoHV-1 recombinant vector of statement 1, 2, or 3, wherein the at least one antigen is an E2 protein, BVDV Erns protein, BRSV F protein, BRSV G protein, or a combination thereof.
5. The BoHV-1 recombinant vector of statement 1-3 or 4, wherein at least heterologous antigen is inserted into a BoHV-1 tmv vector.
6. The BoHV-1 recombinant vector of statement 1-4 or 5, wherein at least heterologous antigen is inserted into a BoHV-1 tmv vector, where the BoHV-1 tmv vector has a deletion of a cytoplasmic tail of envelope glycoprotein gE (gE-CT), a BoHV-1 tmv deletion of an entire envelope protein, a BoHV-1 tmv deletion of envelope protein UL49.5 residues 30-32, a BoHV-1 tmv deletion of UL49.5 cytoplasmic tail residues 80-96, or a combination thereof.
7. The BoHV-1 recombinant vector of statement 1-5 or 6, wherein at least one heterologous antigen is a BVDV E2 antigen having at least 95%, at least 96%, at least 97%, at least 98%, at least 99%, or at least 99.5% amino acid sequence identity to SEQ ID NO:2, 3, 4, 5, 7, 10, 12, 55, or 57.
8. The BoHV-1 recombinant vector of statement 1-6 or 7, wherein at least one heterologous antigen is a BVDV E2 antigen encoded by a nucleic acid segment with at least 95%, at least 96%, at least 97%, at least 98%, at least 99%, or at least 99.5% nucleotide sequence identity to SEQ ID NO:6, 8, 9, 11, 13, 14, 56, or 58.
9. The BoHV-1 recombinant vector of statement 1-7 or 8, wherein at least one heterologous antigen is a BVDV Erns antigen having at least 95%, at least 96%, at least 97%, at least 98%, at least 99%, or at least 99.5% amino acid sequence identity to SEQ ID NO:39 or 42.
10. The BoHV-1 recombinant vector of statement 1-8 or 9, wherein at least one heterologous antigen is a BVDV Erns antigen encoded by a nucleic acid segment with at least 95%, at least 96%, at least 97%, at least 98%, at least 99%, or at least 99.5% nucleotide sequence identity to SEQ ID NO:40 or 42.
11. The BoHV-1 recombinant vector of statement 1-9 or 10, wherein at least one heterologous antigen is a BRSV F protein antigen having at least 95%, at least 96%, at least 97%, at least 98%, at least 99%, or at least 99.5% amino acid sequence identity to SEQ ID NO:15, 16, 17, 20, 22, or 24.
12. The BoHV-1 recombinant vector of statement 1-10 or 11, wherein at least one heterologous antigen is a BRSV F protein antigen encoded by a nucleic acid segment with at least 95%, at least 96%, at least 97%, at least 98%, at least 99%, or at least 99.5% nucleotide sequence identity to SEQ ID NO: 18, 19, 21, 23, or 25.
13. The BoHV-1 recombinant vector of statement 1-11 or 12, wherein at least one heterologous antigen is a BRSV G protein antigen having at least 95%, at least 96%, at least 97%, at least 98%, at least 99%, or at least 99.5% amino acid sequence identity to SEQ ID NO:26, 28, 29, 31, 34, or 36.

14. The BoHV-1 recombinant vector of statement 1-12 or 13, wherein at least one heterologous antigen is a BRSV G protein antigen encoded by a nucleic acid segment with at least 95%, at least 96%, at least 97%, at least 98%, at least 99%, or at least 99.5% nucleotide sequence identity to SEQ ID NO:30, 32, 33, 35, 37, or 38.

15. The BoHV-1 recombinant vector of statement 1-13 or 14, wherein at least one heterologous antigen is expressed from a heterologous promoter.

16. The BoHV-1 recombinant vector of statement 1-14 or 15, wherein at least one heterologous antigen is expressed from a heterologous promoter selected from a viral promoter, a bacterial promoter or a mammalian promoter.

17. The BoHV-1 recombinant vector of statement 1-15 or 16, wherein at least one heterologous antigen is expressed from a heterologous promoter selected from a strong, weak, or inducible promoter.

18. The BoHV-1 recombinant vector of statement 1-16 or 17, wherein at least one heterologous antigen is expressed from a heterologous promoter selected from a human elongation factor 1α promoter, a T7 promoter (e.g., optionally with the lac operator), a CaMV 35S promoter, a CaMV 19S promoter, a nos promoter, Adh1 promoter, sucrose synthase promoter, α-tubulin promoter, ubiquitin promoter, actin promoter, cab, PEP-Case promoter, the CCR promoter (cinnamoyl CoA: NADP oxidoreductase, EC 1.2.1.44, e.g., isolated from Lollium *perenne*, a baculovirus derived promoter, a p10 promoter, or a combination thereof.

19. The BoHV-1 recombinant vector of statement 1-17 or 18, wherein at least one heterologous antigen is expressed from a heterologous promoter that include one or more enhancer elements.

20. The BoHV-1 recombinant vector of statement 1-18 or 19, wherein at least one heterologous antigen is expressed from an elongation factor 1α promoter 21. The BoHV-1 recombinant vector of statement 1-19 or 20, wherein at least one heterologous antigen is expressed as a fusion protein.

22. The BoHV-1 recombinant vector of statement 1-20 or 21, wherein at least one heterologous antigen is expressed as a fusion protein with a fusion partner selected from a signal sequence, an epitope, a histidine tail, GM-CSF, or any combination thereof.

23. The BoHV-1 recombinant vector of statement 1-20 or 21, wherein at least one heterologous antigen is expressed as a fusion protein with a fusion partner selected from a gD signal sequence, a V5 epitope, a histidine tail comprising 2-10 histidine residues, GM-CSF, or any combination thereof.

24. The BoHV-1 recombinant vector of statement 1-22 or 23, wherein at least one heterologous antigen is encoded by a nucleic acid segment that includes a 3' polyA tail.

25. A composition comprising at least one BoHV-1 recombinant vector of statement 1-23 or 24.

26. A composition comprising at least two, or at least three, or at least four, or at least five of the BoHV-1 recombinant vectors of statement 1-23 or 24.

27. The composition of statement 25 or 26, further comprising a carrier.

28. The composition of statement 25, 26, or 27, further comprising a polypeptide or peptide.

29. The composition of statement 25-27 or 28, further comprising at least one antigenic polypeptide or peptide.

30. The composition of statement 25-28 or 29, further comprising at least one antigenic polypeptide or peptide selected from a *M. hemolytica, Pasteurella maltocida, Histophilus somni* or *Mycoplasma bovis* antigenic polypeptide or peptide.

31. The composition of statement 25-29 or 30, further comprising a GM-CSF polypeptide.

32. The composition of statement 25-30 or 31, further comprising an adjuvant.

33. The composition of statement 25-31 or 32, formulated for administration by an intranasal, subcutaneous, intravenous, intradermal, intramuscular, intraperitoneal, oral, nasal, or transdermal route.

34. The composition of statement 25-32 or 33, formulated for administration by an intranasal route.

35. A method comprising administering at least one BoHV-1 recombinant vector of statement 1-23 or 24 to a mammal.

36. The method of statement 35, which reduces the incidence or severity of respiratory symptoms in the mammal.

37. The method of statement 35 or 36, which reduces the incidence or severity of respiratory symptoms in the mammal.

38. The method of statement 35, 36, or 37, wherein the mammal is a bovine animal or an experimental animal.

39. The method of statement 35-37 or 38, which reduces the incidence or severity of respiratory symptoms of bovine respiratory disease complex (BRDC) in a bovine mammal to which the composition is administered.

40. The method of statement 35-38 or 39, which protects the mammal against respiratory disease.

41. The method of statement 35-39 or 40, which protects the mammal against bovine respiratory disease complex (BRDC).

42. A BoHV-1 recombinant vector comprising BoHV-1 gEΔCTUs9Δ/BVDV E2-1.

43. A BoHV-1 recombinant vector comprising BoHV-1 gEΔCTUs9Δ/BVDV E2-2.

The specific constructs, compositions, and methods described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A BoHV-1 recombinant vector comprising at least one heterologous antigen inserted therein, where the BoHV-1 vector has a deletion of a cytoplasmic tail of envelope glycoprotein gE (gE-CT), a deletion of an entire envelope protein, a deletion of envelope protein UL49.5 residues 30-32, a deletion of UL49.5 cytoplasmic tail residues 80-96, or a combination thereof,
   wherein at least one heterologous antigen is selected from the group consisting of a BVDV Erns antigen having at least 95% amino acid sequence identity to SEQ ID NO: 42, a BVDV E2 antigen having at least 95% amino acid sequence identity to SEQ ID NO:2, 3, 4, 5, 7, 10, 12, 55, or 57, BVDV E2 antigen encoded by a nucleic acid segment with at least 95% nucleotide sequence identity to SEQ ID NO:6, 8, 9, 11, 13, 14, 56, or 58, and a BVDV Erns antigen encoded by a nucleic acid segment with at least 95% nucleotide sequence identity to SEQ ID NO:40 or 59, and
   wherein the at least one heterologous antigen is inserted in the recombinant vector at least at a site of the deletion of the cytoplasmic tail of envelope glycoprotein gE (gE-CT) or at a site of a deletion of glycoprotein G (gG).

2. The BoHV-1 recombinant vector of claim 1, wherein at least one heterologous antigen is a BVDV E2 antigen having at least 95% amino acid sequence identity to SEQ ID NO:2, 3, 4, 5, 7, 10, 12, 55, or 57.

3. The BoHV-1 recombinant vector claim 1, wherein at least one heterologous antigen is a BVDV E2 antigen encoded by a nucleic acid segment with at least 95% nucleotide sequence identity to SEQ ID NO:6, 8, 9, 11, 13, 14, 56, or 58.

4. The BoHV-1 recombinant vector of claim 1, wherein at least one heterologous antigen is a BVDV Erns antigen encoded by a nucleic acid segment with at least 95% nucleotide sequence identity to SEQ ID NO:40 or 59.

5. The BoHV-1 recombinant vector of claim 1, wherein at least one heterologous antigen is a BRSV F protein antigen having at least 95% amino acid sequence identity to SEQ ID NO:15, 16, 17, 20, 22, or 24.

6. The BoHV-1 recombinant vector of claim 1, wherein at least one heterologous antigen is a BRSV F protein antigen encoded by a nucleic acid segment with at least 95% nucleotide sequence identity to SEQ ID NO: 18, 19, 21, 23, or 25.

7. The BoHV-1 recombinant vector of claim 1, wherein at least one heterologous antigen is a BRSV G protein antigen having at least 95% amino acid sequence identity to SEQ ID NO:26, 28, 29, 31, 34, or 36.

8. The BoHV-1 recombinant vector of claim 1, wherein at least one heterologous antigen is a BRSV G protein antigen encoded by a nucleic acid segment with at least 95% nucleotide sequence identity to SEQ ID NO:30, 32, 33, 35, 37, or 38.

9. The BoHV-1 recombinant vector of claim 1, wherein at least one heterologous antigen is expressed from a heterologous promoter.

10. The BoHV-1 recombinant vector of claim 1, wherein at least one heterologous antigen is expressed from a heterologous promoter selected from a viral promoter, a bacterial promoter or a mammalian promoter.

11. The BoHV-1 recombinant vector of claim 1, wherein at least one heterologous antigen is expressed from an elongation factor 1a promoter.

12. The BoHV-1 recombinant vector of claim 1, wherein at least one heterologous antigen is expressed as a fusion protein.

13. The BoHV-1 recombinant vector of claim 1, wherein at least one heterologous antigen is expressed as a fusion protein with a fusion partner selected from a gD signal sequence, a V5 epitope, a histidine tail comprising 2-10 histidine residues, GM-CSF, or any combination thereof.

14. A composition comprising a carrier and at least one BoHV-1 recombinant vector of claim 1.

15. The composition of claim 14, further comprising at least one antigenic polypeptide or peptide.

16. The composition of claim 14, further comprising a GM-CSF polypeptide.

17. The composition of claim 14, formulated for administration by an intranasal route.

18. A method comprising administering at least one BoHV-1 recombinant vector of claim 1 to a mammal.

19. The method of claim 18, which reduces the incidence or severity of respiratory symptoms in the mammal.

20. The method of claim 18, wherein the mammal is a bovine animal or an experimental animal.

21. The method of claim 18, which reduces the incidence or severity of respiratory symptoms of bovine respiratory disease complex (BRDC) in a bovine mammal to which the composition is administered.

* * * * *

UNITED STATES PATENT AND TRADEMARK OFFICE
CERTIFICATE OF CORRECTION

PATENT NO. : 11,083,787 B2
APPLICATION NO. : 15/780900
DATED : August 10, 2021
INVENTOR(S) : Shafiqul I. Chowdhury Page 1 of 1

It is certified that error appears in the above-identified patent and that said Letters Patent is hereby corrected as shown below:

In the Specification

1) Column 1, after Line 10, and before the SEQUENCE LISTING section heading, insert the following:
--This invention was made with government support under 2015-67015-23277 awarded by the U.S. Department of Agriculture National Institute of Food and Agriculture. The government has certain rights in the invention.--

2) Column 1, Delete Lines 17-20

3) Column 8, please amend Lines 22-50 to read as follows:
--FIG. 21A-21B illustrate examples of BVDV ERNS expression cassettes. FIG. 21A illustrates a nucleotide sequence (SEQ ID NO:40) an expression module encoding a BVDV1 ERNS fusion protein. Expression cassettes for BVDV1 ERNS can include, for example, the following components in a 5'-3' direction: i) Restriction site for PacI (lower case, bold, underlined) ii) Kozak sequence (upper case, italicized) iii) 57 bps BHV1gD signal (lower case, underlined; GenBank accession #AFV53430.1) iv) 681 bps BVDV1E.sup.rns coding sequence (upper case, bold; GenBank accession #NP_776261.1) v) 429 bps Bos taurus GM-CSF coding sequence (uppercase, underlined; GenBank accession # NP_776452.1) vi) 42 bps V5 epitope coding sequence (upper case, italicized) vii) a stop codon (TAA) (uppercase, bold, italicized) viii) Restriction site for NotI (lower case, bold, underlined). FIG. 21B illustrates a nucleotide sequence (SEQ ID NO:59) of an expression cassette for BVDV2 ERNS that includes the following in a 5'-3' direction: i) Restriction site for PacI (lower case, bold, underlined) ii) Kozak sequence (upper case, italicized) iii) 57 bps BHV1gD signal (lower case, underlined; GenBank accession #AFV53430.1) iv) 681 bps BVDV2E.sup.rns coding sequence (upper case, bold; GenBank accession #NP_777483.1) v) 429 bps Bos taurus GM-CSF coding sequence (uppercase, underlined: GenBank accession # NP_776452.1) vi) 42 bps V5 epitope coding sequence (upper case, italicized) vii) a stop codon (TAA) (uppercase, bold) viii) Restriction site for NotI (lower case, bold, underlined).--

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 59

<210> SEQ ID NO 1
<211> LENGTH: 1635
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ggtaccctcg tgaggctccg gtgcccgtca gtgggcagag cgcacatcgc ccacagtccc      60
cgagaagttg gggggagggg tcggcaattg aaccggtgcc tagagaaggt ggcgcggggt     120
aaactgggaa agtgatgtcg tgtactggct ccgcctttttt cccagggtg ggggagaacc     180 gtatataagt gcagtagtcg ccgtgaacgt tcttttttcgc aacgggtttg ccgccagaac    240
acaggtaagt gccgtgtgtg gttcccgcgg gcctggcctc tttacgggtt atggcccttg    300
cgtgccttga attacttcca cctggctgca gtacgtgatt cttgatcccg agcttcgggt    360
tggaagtggg tgggagagtt cgaggccttg cgcttaagga gccccttcgc ctcgtgcttg    420
agttgaggcc tggcctgggc gctggggccg ccgcgtgcga atctggtggc accttcgcgc    480
ctgtctcgct gctttcgata agtctctagc catttaaaat ttttgatgac ctgctgcgac    540
gctttttttc tggcaagata gtcttgtaaa tgcgggccaa gatctgcaca ctggtatttc    600 ggttttttggg gccgcgggcg gcgacggggc ccgtgcgtcc cagcgcacat gttcggcgag    660
gcggggcctg cgagcgcggc caccgagaat cggacggggg tagtctcaag ctggccggcc    720
tgctctggtg cctggcctcg cgccgccgtg tatcgccccg ccctgggcgg caaggctggc    780
ccggtcggca ccagttgcgt gagcggaaag atggccgctt cccggccctg ctgcaggag    840 ctcaaaatgg aggacgcggc gctcgggaga gcgggcgggt gagtcaccca cacaaaggaa    900
aagggccttt ccgtcctcag ccgtcgcttc atgtgactcc acgagtacc gggcgccgtc      960 caggcacctc gattagttct cgagcttttg gagtacgtcg tctttaggtt ggggggaggg   1020 gtttatgcg atggagtttc cccacactga gtgggtggag actgaagtta ggccagcttg    1080
gcacttgatg taattctcct tggaatttgc cctttttgag tttggatctt ggttcattct    1140
caagcctcag acagtggttc aaagttttttt tcttccatttt caggtgtcgt gaggaattag   1200
cttggtacta atacgactca ctataggag acccaagctg gctaggtaag tgtacgagct    1260
cgatcactag tccagtgtgg atcgatgata tctctagaat gcatggtaag cctatcccta    1320
accctctcct cggtctcgat tctacgcgta ccggtcatca tcaccatcac cattgagttt    1380
aaacccgctg atcagcctcg actgtgcctt ctagttgcca gccatctgtt gtttgcccct    1440
cccccgtgcc ttccttgacc ctggaaggtg ccactcccac tgtcctttcc taataaaatg    1500
aggaaattgc atcgcattgt ctgagtaggt gtcattctat tctggggggt ggggtggggc    1560
aggacagcaa gggggaggat tgggaagaca atagcaggca tgctggggat gcggtgggct    1620
ctatggcttg gtacc                                                    1635
```

<210> SEQ ID NO 2
<211> LENGTH: 3988
<212> TYPE: PRT
<213> ORGANISM: Bovine viral diarrhea virus

<400> SEQUENCE: 2

```
Met Glu Leu Ile Thr Asn Glu Leu Leu Tyr Lys Thr Tyr Lys Gln Lys
1               5                   10                  15

Pro Val Gly Val Glu Pro Val Tyr Asp Gln Ala Gly Asp Pro Leu
            20                  25                  30

Phe Gly Glu Arg Gly Ala Val His Pro Gln Ser Thr Leu Lys Leu Pro
        35                  40                  45

His Lys Arg Gly Glu Arg Asp Val Pro Thr Asn Leu Ala Ser Leu Pro
    50                  55                  60

Lys Arg Gly Asp Cys Arg Ser Gly Asn Ser Arg Gly Pro Val Ser Gly
65                  70                  75                  80

Ile Tyr Leu Lys Pro Gly Pro Leu Phe Tyr Gln Asp Tyr Lys Gly Pro
                85                  90                  95

Val Tyr His Arg Ala Pro Leu Glu Leu Phe Glu Glu Gly Ser Met Cys
            100                 105                 110

Glu Thr Thr Lys Arg Ile Gly Arg Val Thr Gly Ser Asp Gly Lys Leu
        115                 120                 125

Tyr His Ile Tyr Val Cys Ile Asp Gly Cys Ile Ile Lys Ser Ala
    130                 135                 140

Thr Arg Ser Tyr Gln Arg Val Phe Arg Trp Val His Asn Arg Leu Asp
145                 150                 155                 160

Cys Pro Leu Trp Val Thr Ser Cys Ser Asp Thr Lys Glu Glu Gly Ala
                165                 170                 175

Thr Lys Lys Lys Thr Gln Lys Pro Asp Arg Leu Glu Arg Gly Lys Met
            180                 185                 190

Lys Ile Val Pro Lys Glu Ser Glu Lys Asp Ser Lys Thr Lys Pro Pro
        195                 200                 205

Asp Ala Thr Ile Val Val Glu Gly Val Lys Tyr Gln Val Arg Lys Lys
    210                 215                 220

Gly Lys Thr Lys Ser Lys Asn Thr Gln Asp Gly Leu Tyr His Asn Lys
225                 230                 235                 240

Asn Lys Pro Gln Glu Ser Arg Lys Lys Leu Glu Lys Ala Leu Leu Ala
                245                 250                 255

Trp Ala Ile Ile Ala Ile Val Leu Phe Gln Val Thr Met Gly Glu Asn
            260                 265                 270

Ile Thr Gln Trp Asn Leu Gln Asp Asn Gly Thr Glu Gly Ile Gln Arg
        275                 280                 285

Ala Met Phe Gln Arg Gly Val Asn Arg Ser Leu His Gly Ile Trp Pro
    290                 295                 300

Glu Lys Ile Cys Thr Gly Val Pro Ser His Leu Ala Thr Asp Ile Glu
305                 310                 315                 320

Leu Lys Thr Ile His Gly Met Met Asp Ala Ser Glu Lys Thr Asn Tyr
                325                 330                 335

Thr Cys Cys Arg Leu Gln Arg His Glu Trp Asn Lys His Gly Trp Cys
            340                 345                 350

Asn Trp Tyr Asn Ile Glu Pro Trp Ile Leu Val Met Asn Arg Thr Gln
        355                 360                 365

Ala Asn Leu Thr Glu Gly Gln Pro Pro Arg Glu Cys Ala Val Thr Cys
```

-continued

```
            370                 375                 380
Arg Tyr Asp Arg Ala Ser Asp Leu Asn Val Val Thr Gln Ala Arg Asp
385                 390                 395                 400

Ser Pro Thr Pro Leu Thr Gly Cys Lys Lys Gly Lys Asn Phe Ser Phe
                405                 410                 415

Ala Gly Ile Leu Met Arg Gly Pro Cys Asn Phe Glu Ile Ala Ala Ser
                420                 425                 430

Asp Val Leu Phe Lys Glu His Glu Arg Ile Ser Met Phe Gln Asp Thr
                435                 440                 445

Thr Leu Tyr Leu Val Asp Gly Leu Thr Asn Ser Leu Glu Gly Ala Arg
            450                 455                 460

Gln Gly Thr Ala Lys Leu Thr Thr Trp Leu Gly Lys Gln Leu Gly Ile
465                 470                 475                 480

Leu Gly Lys Lys Leu Glu Asn Lys Ser Lys Thr Trp Phe Gly Ala Tyr
                485                 490                 495

Ala Ala Ser Pro Tyr Cys Asp Val Asp Arg Lys Ile Gly Tyr Ile Trp
                500                 505                 510

Tyr Thr Lys Asn Cys Thr Pro Ala Cys Leu Pro Lys Asn Thr Lys Ile
                515                 520                 525

Val Gly Pro Gly Lys Phe Asp Thr Asn Ala Glu Asp Gly Lys Ile Leu
            530                 535                 540

His Glu Met Gly Gly His Leu Ser Glu Val Leu Leu Ser Leu Val
545                 550                 555                 560

Val Leu Ser Asp Phe Ala Pro Glu Thr Ala Ser Val Met Tyr Leu Ile
                565                 570                 575

Leu His Phe Ser Ile Pro Gln Ser His Val Asp Val Met Asp Cys Asp
                580                 585                 590

Lys Thr Gln Leu Asn Leu Thr Val Glu Leu Thr Thr Ala Asp Val Ile
                595                 600                 605

Pro Gly Ser Val Trp Asn Leu Gly Lys Trp Val Cys Ile Arg Pro Asn
            610                 615                 620

Trp Trp Pro Tyr Glu Thr Thr Val Val Leu Ala Phe Glu Glu Val Ser
625                 630                 635                 640

Gln Val Val Lys Leu Val Leu Arg Ala Leu Arg Asp Leu Thr Arg Ile
                645                 650                 655

Trp Asn Ala Ala Thr Thr Thr Ala Phe Leu Ile Cys Leu Val Lys Ile
                660                 665                 670

Val Arg Gly Gln Met Val Gln Gly Ile Leu Trp Leu Leu Leu Ile Thr
                675                 680                 685

Gly Val Gln Gly His Leu Asp Cys Lys Pro Glu Phe Ser Tyr Ala Ile
            690                 695                 700

Ala Lys Asp Glu Arg Ile Gly Gln Leu Gly Ala Glu Gly Leu Thr Thr
705                 710                 715                 720

Thr Trp Lys Glu Tyr Ser Pro Gly Met Lys Leu Glu Asp Thr Met Val
                725                 730                 735

Ile Ala Trp Cys Glu Asp Gly Lys Leu Met Tyr Leu Gln Arg Cys Thr
                740                 745                 750

Arg Glu Thr Arg Tyr Leu Ala Ile Leu His Thr Arg Ala Leu Pro Thr
                755                 760                 765

Ser Val Val Phe Lys Lys Leu Phe Asp Gly Arg Lys Gln Glu Asp Val
            770                 775                 780

Val Glu Met Asn Asp Asn Phe Glu Phe Gly Leu Cys Pro Cys Asp Ala
785                 790                 795                 800
```

```
Lys Pro Ile Val Arg Gly Lys Phe Asn Thr Thr Leu Leu Asn Gly Pro
                805                 810                 815

Ala Phe Gln Met Val Cys Pro Ile Gly Trp Thr Gly Thr Val Ser Cys
                820                 825                 830

Thr Ser Phe Asn Met Asp Thr Leu Ala Thr Thr Val Val Arg Thr Tyr
                835                 840                 845

Arg Arg Ser Lys Pro Phe Pro His Arg Gln Gly Cys Ile Thr Gln Lys
                850                 855                 860

Asn Leu Gly Glu Asp Leu His Asn Cys Ile Leu Gly Gly Asn Trp Thr
865                 870                 875                 880

Cys Val Pro Gly Asp Gln Leu Leu Tyr Lys Gly Gly Ser Ile Glu Ser
                885                 890                 895

Cys Lys Trp Cys Gly Tyr Gln Phe Lys Glu Ser Glu Gly Leu Pro His
                900                 905                 910

Tyr Pro Ile Gly Lys Cys Lys Leu Glu Asn Glu Thr Gly Tyr Arg Leu
                915                 920                 925

Val Asp Ser Thr Ser Cys Asn Arg Glu Gly Val Ala Ile Val Pro Gln
                930                 935                 940

Gly Thr Leu Lys Cys Lys Ile Gly Lys Thr Thr Val Gln Val Ile Ala
945                 950                 955                 960

Met Asp Thr Lys Leu Gly Pro Met Pro Cys Arg Pro Tyr Glu Ile Ile
                965                 970                 975

Ser Ser Glu Gly Pro Val Glu Lys Thr Ala Cys Thr Phe Asn Tyr Thr
                980                 985                 990

Lys Thr Leu Lys Asn Lys Tyr Phe Glu Pro Arg Asp Ser Tyr Phe Gln
                995                 1000                1005

Gln Tyr Met Leu Lys Gly Glu Tyr Gln Tyr Trp Phe Asp Leu Glu
                1010                1015                1020

Val Thr Asp His His Arg Asp Tyr Phe Ala Glu Ser Ile Leu Val
                1025                1030                1035

Val Val Val Ala Leu Leu Gly Gly Arg Tyr Val Leu Trp Leu Leu
                1040                1045                1050

Val Thr Tyr Met Val Leu Ser Glu Gln Lys Ala Leu Gly Ile Gln
                1055                1060                1065

Tyr Gly Ser Gly Glu Val Val Met Met Gly Asn Leu Leu Thr His
                1070                1075                1080

Asn Asn Ile Glu Val Val Thr Tyr Phe Leu Leu Leu Tyr Leu Leu
                1085                1090                1095

Leu Arg Glu Glu Ser Val Lys Lys Trp Val Leu Leu Leu Tyr His
                1100                1105                1110

Ile Leu Val Val His Pro Ile Lys Ser Val Ile Val Ile Leu Leu
                1115                1120                1125

Met Ile Gly Asp Val Val Lys Ala Asp Ser Gly Gly Gln Glu Tyr
                1130                1135                1140

Leu Gly Lys Ile Asp Leu Cys Phe Thr Thr Val Val Leu Ile Val
                1145                1150                1155

Ile Gly Leu Ile Ile Ala Arg Arg Asp Pro Thr Ile Val Pro Leu
                1160                1165                1170

Val Thr Ile Met Ala Ala Leu Arg Val Thr Glu Leu Thr His Gln
                1175                1180                1185

Pro Gly Val Asp Ile Ala Val Ala Val Met Thr Ile Thr Leu Leu
                1190                1195                1200
```

```
Met Val Ser Tyr Val Thr Asp Tyr Phe Arg Tyr Lys Lys Trp Leu
1205                1210                1215

Gln Cys Ile Leu Ser Leu Val Ser Gly Val Phe Leu Ile Arg Ser
1220                1225                1230

Leu Ile Tyr Leu Gly Arg Ile Glu Met Pro Glu Val Thr Ile Pro
1235                1240                1245

Asn Trp Arg Pro Leu Thr Leu Ile Leu Leu Tyr Leu Ile Ser Thr
1250                1255                1260

Thr Ile Val Thr Arg Trp Lys Val Asp Val Ala Gly Leu Leu Leu
1265                1270                1275

Gln Cys Val Pro Ile Leu Leu Leu Val Thr Thr Leu Trp Ala Asp
1280                1285                1290

Phe Leu Thr Leu Ile Leu Ile Leu Pro Thr Tyr Glu Leu Val Lys
1295                1300                1305

Leu Tyr Tyr Leu Lys Thr Val Arg Thr Asp Ile Glu Arg Ser Trp
1310                1315                1320

Leu Gly Gly Ile Asp Tyr Thr Arg Val Asp Ser Ile Tyr Asp Val
1325                1330                1335

Asp Glu Ser Gly Glu Gly Val Tyr Leu Phe Pro Ser Arg Gln Lys
1340                1345                1350

Ala Gln Gly Asn Phe Ser Ile Leu Leu Pro Leu Ile Lys Ala Thr
1355                1360                1365

Leu Ile Ser Cys Val Ser Ser Lys Trp Gln Leu Ile Tyr Met Ser
1370                1375                1380

Tyr Leu Thr Leu Asp Phe Met Tyr Tyr Met His Arg Lys Val Ile
1385                1390                1395

Glu Glu Ile Ser Gly Gly Thr Asn Ile Ile Ser Arg Leu Val Ala
1400                1405                1410

Ala Leu Ile Glu Leu Asn Trp Ser Met Glu Glu Glu Ser Lys
1415                1420                1425

Gly Leu Lys Lys Phe Tyr Leu Leu Ser Gly Arg Leu Arg Asn Leu
1430                1435                1440

Ile Ile Lys His Lys Val Arg Asn Glu Thr Val Ala Ser Trp Tyr
1445                1450                1455

Gly Glu Glu Glu Val Tyr Gly Met Pro Lys Ile Met Thr Ile Ile
1460                1465                1470

Lys Ala Ser Thr Leu Ser Lys Ser Arg His Cys Ile Ile Cys Thr
1475                1480                1485

Val Cys Glu Gly Arg Glu Trp Lys Gly Gly Thr Cys Pro Lys Cys
1490                1495                1500

Gly Arg His Gly Lys Pro Ile Thr Cys Gly Met Ser Leu Ala Asp
1505                1510                1515

Phe Glu Glu Arg His Tyr Lys Arg Ile Phe Ile Arg Glu Gly Asn
1520                1525                1530

Phe Glu Gly Met Cys Ser Arg Cys Gln Gly Lys His Arg Arg Phe
1535                1540                1545

Glu Met Asp Arg Glu Pro Lys Ser Ala Arg Tyr Cys Ala Glu Cys
1550                1555                1560

Asn Arg Leu His Pro Ala Glu Glu Gly Asp Phe Trp Ala Glu Ser
1565                1570                1575

Ser Met Leu Gly Leu Lys Ile Thr Tyr Phe Ala Leu Met Asp Gly
1580                1585                1590

Lys Val Tyr Asp Ile Thr Glu Trp Ala Gly Cys Gln Arg Val Gly
```

-continued

```
            1595                1600                1605
Ile Ser Pro Asp Thr His Arg Val Pro Cys His Ile Ser Phe Gly
    1610                1615                1620

Ser Arg Met Pro Phe Arg Gln Glu Tyr Asn Gly Phe Val Gln Tyr
    1625                1630                1635

Thr Ala Arg Gly Gln Leu Phe Leu Arg Asn Leu Pro Val Leu Ala
    1640                1645                1650

Thr Lys Val Lys Met Leu Met Val Gly Asn Leu Gly Glu Glu Ile
    1655                1660                1665

Gly Asn Leu Glu His Leu Gly Trp Ile Leu Arg Gly Pro Ala Val
    1670                1675                1680

Cys Lys Lys Ile Thr Glu His Glu Lys Cys His Ile Asn Ile Leu
    1685                1690                1695

Asp Lys Leu Thr Ala Phe Phe Gly Ile Met Pro Arg Gly Thr Thr
    1700                1705                1710

Pro Arg Ala Pro Val Arg Phe Pro Thr Ser Leu Leu Lys Val Arg
    1715                1720                1725

Arg Gly Leu Glu Thr Gly Trp Ala Tyr Thr His Gln Gly Gly Ile
    1730                1735                1740

Ser Ser Val Asp His Val Thr Ala Gly Lys Asp Leu Leu Val Cys
    1745                1750                1755

Asp Ser Met Gly Arg Thr Arg Val Val Cys Gln Ser Asn Asn Arg
    1760                1765                1770

Leu Thr Asp Glu Thr Glu Tyr Gly Val Lys Thr Asp Ser Gly Cys
    1775                1780                1785

Pro Asp Gly Ala Arg Cys Tyr Val Leu Asn Pro Glu Ala Val Asn
    1790                1795                1800

Ile Ser Gly Ser Lys Gly Ala Val Val His Leu Gln Lys Thr Gly
    1805                1810                1815

Gly Glu Phe Thr Cys Val Thr Ala Ser Gly Thr Pro Ala Phe Phe
    1820                1825                1830

Asp Leu Lys Asn Leu Lys Gly Trp Ser Gly Leu Pro Ile Phe Glu
    1835                1840                1845

Ala Ser Ser Gly Arg Val Val Gly Arg Val Lys Val Gly Lys Asn
    1850                1855                1860

Glu Glu Ser Lys Pro Thr Lys Ile Met Ser Gly Ile Gln Thr Val
    1865                1870                1875

Ser Lys Asn Thr Ala Asp Leu Thr Glu Met Val Lys Lys Ile Thr
    1880                1885                1890

Ser Met Asn Arg Gly Asp Phe Lys Gln Ile Thr Leu Ala Thr Gly
    1895                1900                1905

Ala Gly Lys Thr Thr Glu Leu Pro Lys Ala Val Ile Glu Glu Ile
    1910                1915                1920

Gly Arg His Lys Arg Val Leu Val Leu Ile Pro Leu Arg Ala Ala
    1925                1930                1935

Ala Glu Ser Val Tyr Gln Tyr Met Arg Leu Lys His Pro Ser Ile
    1940                1945                1950

Ser Phe Asn Leu Arg Ile Gly Asp Met Lys Glu Gly Asp Met Ala
    1955                1960                1965

Thr Gly Ile Thr Tyr Ala Ser Tyr Gly Tyr Phe Cys Gln Met Pro
    1970                1975                1980

Gln Pro Lys Leu Arg Ala Ala Met Val Glu Tyr Ser Tyr Ile Phe
    1985                1990                1995
```

```
Leu Asp Glu Tyr His Cys Ala Thr Pro Glu Gln Leu Ala Ile Ile
2000                2005                2010

Gly Lys Ile His Arg Phe Ser Glu Ser Ile Arg Val Val Ala Met
2015                2020                2025

Thr Ala Thr Pro Ala Gly Ser Val Thr Thr Thr Gly Gln Lys His
2030                2035                2040

Pro Ile Glu Glu Phe Ile Ala Pro Glu Val Met Lys Gly Glu Asp
2045                2050                2055

Leu Gly Ser Gln Phe Leu Asp Ile Ala Gly Leu Lys Ile Pro Val
2060                2065                2070

Asp Glu Met Lys Gly Asn Met Leu Val Phe Val Pro Thr Arg Asn
2075                2080                2085

Met Ala Val Glu Val Ala Lys Lys Leu Lys Ala Lys Gly Tyr Asn
2090                2095                2100

Ser Gly Tyr Tyr Tyr Ser Gly Glu Asp Pro Ala Asn Leu Arg Val
2105                2110                2115

Val Thr Ser Gln Ser Pro Tyr Val Ile Val Ala Thr Asn Ala Ile
2120                2125                2130

Glu Ser Gly Val Thr Leu Pro Asp Leu Asp Thr Val Ile Asp Thr
2135                2140                2145

Gly Leu Lys Cys Glu Lys Arg Val Arg Val Ser Ser Lys Ile Pro
2150                2155                2160

Phe Ile Val Thr Gly Leu Lys Arg Met Ala Val Thr Val Gly Glu
2165                2170                2175

Gln Ala Gln Arg Arg Gly Arg Val Gly Arg Val Lys Pro Gly Arg
2180                2185                2190

Tyr Tyr Arg Ser Gln Glu Thr Ala Thr Gly Ser Lys Asp Phe His
2195                2200                2205

Tyr Asp Leu Leu Gln Ala Gln Arg Tyr Gly Ile Glu Asp Gly Ile
2210                2215                2220

Asn Val Thr Lys Ser Phe Arg Glu Met Asn Tyr Asp Trp Ser Leu
2225                2230                2235

Tyr Glu Glu Asp Ser Leu Leu Ile Thr Gln Leu Glu Ile Leu Asn
2240                2245                2250

Asn Leu Leu Ile Ser Glu Asp Leu Pro Ala Ala Val Lys Asn Ile
2255                2260                2265

Met Ala Arg Thr Asp His Pro Glu Pro Ile Gln Leu Ala Tyr Asn
2270                2275                2280

Ser Tyr Glu Val Gln Val Pro Val Leu Phe Pro Lys Ile Arg Asn
2285                2290                2295

Gly Glu Val Thr Asp Thr Tyr Glu Asn Tyr Ser Phe Leu Asn Ala
2300                2305                2310

Arg Lys Leu Gly Glu Asp Val Pro Val Tyr Ile Tyr Ala Thr Glu
2315                2320                2325

Asp Glu Asp Leu Ala Val Asp Leu Leu Gly Leu Asp Trp Pro Asp
2330                2335                2340

Pro Gly Asn Gln Gln Val Val Glu Thr Gly Lys Ala Leu Lys Gln
2345                2350                2355

Val Thr Gly Leu Ser Ser Ala Glu Asn Ala Leu Leu Val Ala Leu
2360                2365                2370

Phe Gly Tyr Val Gly Tyr Gln Ala Leu Ser Lys Arg His Val Pro
2375                2380                2385
```

```
Met Ile Thr Asp Ile Tyr Thr Ile Glu Asp Gln Arg Leu Glu Asp
    2390                2395                2400

Thr Thr His Leu Gln Tyr Ala Pro Asn Ala Ile Lys Thr Asp Gly
    2405                2410                2415

Thr Glu Thr Glu Leu Lys Glu Leu Ala Ser Gly Asp Val Glu Lys
    2420                2425                2430

Ile Met Gly Ala Ile Ser Asp Tyr Ala Ala Gly Leu Glu Phe
    2435                2440                2445

Val Lys Ser Gln Ala Glu Lys Ile Lys Thr Ala Pro Leu Phe Lys
    2450                2455                2460

Glu Asn Ala Glu Ala Lys Gly Tyr Val Gln Lys Phe Ile Asp
    2465                2470                2475

Ser Leu Ile Glu Asn Lys Glu Glu Ile Ile Arg Tyr Gly Leu Trp
    2480                2485                2490

Gly Thr His Thr Ala Leu Tyr Lys Ser Ile Ala Ala Arg Leu Gly
    2495                2500                2505

His Glu Thr Ala Phe Ala Thr Leu Val Leu Lys Trp Leu Ala Phe
    2510                2515                2520

Gly Gly Glu Ser Val Ser Asp His Val Lys Gln Ala Ala Val Asp
    2525                2530                2535

Leu Val Val Tyr Tyr Val Met Asn Lys Pro Ser Phe Pro Gly Asp
    2540                2545                2550

Ser Glu Thr Gln Gln Glu Gly Arg Arg Phe Val Ala Ser Leu Phe
    2555                2560                2565

Ile Ser Ala Leu Ala Thr Tyr Thr Tyr Lys Thr Trp Asn Tyr His
    2570                2575                2580

Asn Leu Ser Lys Val Val Glu Pro Ala Leu Ala Tyr Leu Pro Tyr
    2585                2590                2595

Ala Thr Ser Ala Leu Lys Met Phe Thr Pro Thr Arg Leu Glu Ser
    2600                2605                2610

Val Val Ile Leu Ser Thr Thr Ile Tyr Lys Thr Tyr Leu Ser Ile
    2615                2620                2625

Arg Lys Gly Lys Ser Asp Gly Leu Leu Gly Thr Gly Ile Ser Ala
    2630                2635                2640

Ala Met Glu Ile Leu Ser Gln Asn Pro Val Ser Val Gly Ile Ser
    2645                2650                2655

Val Met Leu Gly Val Gly Ala Ile Ala Ala His Asn Ala Ile Glu
    2660                2665                2670

Ser Ser Glu Gln Lys Arg Thr Leu Leu Met Lys Val Phe Val Lys
    2675                2680                2685

Asn Phe Leu Asp Gln Ala Ala Thr Asp Glu Leu Val Lys Glu Asn
    2690                2695                2700

Pro Glu Lys Ile Ile Met Ala Leu Phe Glu Ala Val Gln Thr Ile
    2705                2710                2715

Gly Asn Pro Leu Arg Leu Ile Tyr His Leu Tyr Gly Val Tyr Tyr
    2720                2725                2730

Lys Gly Trp Glu Ala Lys Glu Leu Ser Glu Arg Thr Ala Gly Arg
    2735                2740                2745

Asn Leu Phe Thr Leu Ile Met Phe Glu Ala Phe Glu Leu Leu Gly
    2750                2755                2760

Met Asp Ser Gln Gly Lys Ile Arg Asn Leu Ser Gly Asn Tyr Ile
    2765                2770                2775

Leu Asp Leu Ile Tyr Gly Leu His Lys Gln Ile Asn Arg Gly Leu
```

```
              2780                2785                2790
Lys Lys Met Val Leu Gly Trp Ala Pro Ala Pro Phe Ser Cys Asp
    2795                2800                2805

Trp Thr Pro Ser Asp Glu Arg Ile Arg Leu Pro Thr Asp Asn Tyr
    2810                2815                2820

Leu Arg Val Glu Thr Arg Cys Pro Cys Gly Tyr Glu Met Lys Ala
    2825                2830                2835

Phe Lys Asn Val Gly Gly Lys Leu Thr Lys Val Glu Glu Ser Gly
    2840                2845                2850

Pro Phe Leu Cys Arg Asn Arg Pro Gly Arg Gly Pro Val Asn Tyr
    2855                2860                2865

Arg Val Thr Lys Tyr Tyr Asp Asp Asn Leu Arg Glu Ile Lys Pro
    2870                2875                2880

Val Ala Lys Leu Glu Gly Gln Val Glu His Tyr Tyr Lys Gly Val
    2885                2890                2895

Thr Ala Lys Ile Asp Tyr Ser Lys Gly Lys Met Leu Leu Ala Thr
    2900                2905                2910

Asp Lys Trp Glu Val Glu His Gly Val Ile Thr Arg Leu Ala Lys
    2915                2920                2925

Arg Tyr Thr Gly Val Gly Phe Asn Gly Ala Tyr Leu Gly Asp Glu
    2930                2935                2940

Pro Asn His Arg Ala Leu Val Glu Arg Asp Cys Ala Thr Ile Thr
    2945                2950                2955

Lys Asn Thr Val Gln Phe Leu Lys Met Lys Lys Gly Cys Ala Phe
    2960                2965                2970

Thr Tyr Asp Leu Thr Ile Ser Asn Leu Thr Arg Leu Ile Glu Leu
    2975                2980                2985

Val His Arg Asn Asn Leu Glu Lys Glu Ile Pro Thr Ala Thr
    2990                2995                3000

Val Thr Thr Trp Leu Ala Tyr Thr Phe Val Asn Glu Asp Val Gly
    3005                3010                3015

Thr Ile Lys Pro Val Leu Gly Glu Arg Val Ile Pro Asp Pro Val
    3020                3025                3030

Val Asp Ile Asn Leu Gln Pro Glu Val Gln Val Asp Thr Ser Glu
    3035                3040                3045

Val Gly Ile Thr Ile Ile Gly Arg Glu Thr Leu Met Thr Thr Gly
    3050                3055                3060

Val Thr Pro Val Leu Glu Lys Val Glu Pro Asp Ala Ser Asp Asn
    3065                3070                3075

Gln Asn Ser Val Lys Ile Gly Leu Asp Glu Gly Asn Tyr Pro Gly
    3080                3085                3090

Pro Gly Ile Gln Thr His Thr Leu Thr Glu Glu Ile His Asn Arg
    3095                3100                3105

Asp Ala Arg Pro Phe Ile Met Ile Leu Gly Ser Arg Asn Ser Ile
    3110                3115                3120

Ser Asn Arg Ala Lys Thr Ala Arg Asn Ile Asn Leu Tyr Thr Gly
    3125                3130                3135

Asn Asp Pro Arg Glu Ile Arg Asp Leu Met Ala Ala Gly Arg Met
    3140                3145                3150

Leu Val Val Ala Leu Arg Asp Val Asp Pro Glu Leu Ser Glu Met
    3155                3160                3165

Val Asp Phe Lys Gly Thr Phe Leu Asp Arg Glu Ala Leu Glu Ala
    3170                3175                3180
```

-continued

Leu Ser Leu Gly Gln Pro Lys Pro Lys Gln Val Thr Lys Glu Ala
3185                3190                3195

Val Arg Asn Leu Ile Glu Gln Lys Lys Asp Val Glu Ile Pro Asn
3200                3205                3210

Trp Phe Ala Ser Asp Asp Pro Val Phe Leu Glu Val Ala Leu Lys
3215                3220                3225

Asn Asp Lys Tyr Tyr Leu Val Gly Asp Val Gly Glu Val Lys Asp
3230                3235                3240

Gln Ala Lys Ala Leu Gly Ala Thr Asp Gln Thr Arg Ile Ile Lys
3245                3250                3255

Glu Val Gly Ser Arg Thr Tyr Ala Met Lys Leu Ser Ser Trp Phe
3260                3265                3270

Leu Gln Ala Ser Asn Lys Gln Met Ser Leu Thr Pro Leu Phe Glu
3275                3280                3285

Glu Leu Leu Leu Arg Cys Pro Pro Ala Thr Lys Ser Asn Lys Gly
3290                3295                3300

His Met Ala Ser Ala Tyr Gln Leu Ala Gln Gly Asn Trp Glu Pro
3305                3310                3315

Leu Gly Cys Gly Val His Leu Gly Thr Ile Pro Ala Arg Arg Val
3320                3325                3330

Lys Ile His Pro Tyr Glu Ala Tyr Leu Lys Leu Lys Asp Phe Ile
3335                3340                3345

Glu Glu Glu Glu Lys Lys Pro Arg Val Lys Asp Thr Val Ile Arg
3350                3355                3360

Glu His Asn Lys Trp Ile Leu Lys Lys Ile Arg Phe Gln Gly Asn
3365                3370                3375

Leu Asn Thr Lys Lys Met Leu Asn Pro Gly Lys Leu Ser Glu Gln
3380                3385                3390

Leu Asp Arg Glu Gly Arg Lys Arg Asn Ile Tyr Asn His Gln Ile
3395                3400                3405

Gly Thr Ile Met Ser Ser Ala Gly Ile Arg Leu Glu Lys Leu Pro
3410                3415                3420

Ile Val Arg Ala Gln Thr Asp Thr Lys Thr Phe His Glu Ala Ile
3425                3430                3435

Arg Asp Lys Ile Asp Lys Ser Glu Asn Arg Gln Asn Pro Glu Leu
3440                3445                3450

His Asn Lys Leu Leu Glu Ile Phe His Thr Ile Ala Gln Pro Thr
3455                3460                3465

Leu Lys His Thr Tyr Gly Glu Val Thr Trp Glu Gln Leu Glu Ala
3470                3475                3480

Gly Ile Asn Arg Lys Gly Ala Ala Gly Phe Leu Glu Lys Lys Asn
3485                3490                3495

Ile Gly Glu Val Leu Asp Ser Glu Lys His Leu Val Glu Gln Leu
3500                3505                3510

Val Arg Asp Leu Lys Ala Gly Arg Lys Ile Lys Tyr Tyr Glu Thr
3515                3520                3525

Ala Ile Pro Lys Asn Glu Lys Arg Asp Val Ser Asp Asp Trp Gln
3530                3535                3540

Ala Gly Asp Leu Val Val Glu Lys Arg Pro Arg Val Ile Gln Tyr
3545                3550                3555

Pro Glu Ala Lys Thr Arg Leu Ala Ile Thr Lys Val Met Tyr Asn
3560                3565                3570

```
Trp Val Lys Gln Gln Pro Val Ile Pro Gly Tyr Glu Gly Lys
3575             3580             3585

Thr Pro Leu Phe Asn Ile Phe Asp Lys Val Arg Lys Glu Trp Asp
3590             3595             3600

Ser Phe Asn Glu Pro Val Ala Val Ser Phe Asp Thr Lys Ala Trp
3605             3610             3615

Asp Thr Gln Val Thr Ser Lys Asp Leu Gln Leu Ile Gly Glu Ile
3620             3625             3630

Gln Lys Tyr Tyr Tyr Lys Lys Glu Trp His Lys Phe Ile Asp Thr
3635             3640             3645

Ile Thr Asp His Met Thr Glu Val Pro Val Ile Thr Ala Asp Gly
3650             3655             3660

Glu Val Tyr Ile Arg Asn Gly Gln Arg Gly Ser Gly Gln Pro Asp
3665             3670             3675

Thr Ser Ala Gly Asn Ser Met Leu Asn Val Leu Thr Met Met Tyr
3680             3685             3690

Ala Phe Cys Glu Ser Thr Gly Val Pro Tyr Lys Ser Phe Asn Arg
3695             3700             3705

Val Ala Arg Ile His Val Cys Gly Asp Asp Gly Phe Leu Ile Thr
3710             3715             3720

Glu Lys Gly Leu Gly Leu Lys Phe Ala Asn Lys Gly Met Gln Ile
3725             3730             3735

Leu His Glu Ala Gly Lys Pro Gln Lys Ile Thr Glu Gly Glu Lys
3740             3745             3750

Met Lys Val Ala Tyr Arg Phe Glu Asp Ile Glu Phe Cys Ser His
3755             3760             3765

Thr Pro Val Pro Val Arg Trp Ser Asp Asn Thr Ser Ser His Met
3770             3775             3780

Ala Gly Arg Asp Thr Ala Val Ile Leu Ser Lys Met Ala Thr Arg
3785             3790             3795

Leu Asp Ser Ser Gly Glu Arg Gly Thr Thr Ala Tyr Glu Lys Ala
3800             3805             3810

Val Ala Phe Ser Phe Leu Leu Met Tyr Ser Trp Asn Pro Leu Val
3815             3820             3825

Arg Arg Ile Cys Leu Leu Val Leu Ser Gln Gln Pro Glu Thr Asp
3830             3835             3840

Pro Ser Lys His Ala Thr Tyr Tyr Tyr Lys Gly Asp Pro Ile Gly
3845             3850             3855

Ala Tyr Lys Asp Val Ile Gly Arg Asn Leu Ser Glu Leu Lys Arg
3860             3865             3870

Thr Gly Phe Glu Lys Leu Ala Asn Leu Asn Leu Ser Leu Ser Thr
3875             3880             3885

Leu Gly Ile Trp Thr Lys His Thr Ser Lys Arg Ile Ile Gln Asp
3890             3895             3900

Cys Val Ala Ile Gly Lys Glu Glu Gly Asn Trp Leu Val Asn Ala
3905             3910             3915

Asp Arg Leu Ile Ser Ser Lys Thr Gly His Leu Tyr Ile Pro Asp
3920             3925             3930

Lys Gly Phe Thr Leu Gln Gly Lys His Tyr Glu Gln Leu Gln Leu
3935             3940             3945

Arg Thr Glu Thr Asn Pro Val Met Gly Val Gly Thr Glu Arg Tyr
3950             3955             3960

Lys Leu Gly Pro Ile Val Asn Leu Leu Leu Arg Arg Leu Lys Ile
```

```
    3965                3970                3975

Leu Leu  Met Thr Ala Val Gly  Val Ser Ser
    3980                3985

<210> SEQ ID NO 3
<211> LENGTH: 407
<212> TYPE: PRT
<213> ORGANISM: Bovine viral diarrhea virus

<400> SEQUENCE: 3

Ala Thr Thr Thr Ala Phe Leu Val Cys Leu Val Lys Ile Val Arg Gly
1               5                   10                  15

Gln Met Val Gln Gly Ile Leu Trp Leu Leu Leu Ile Thr Gly Val Gln
            20                  25                  30

Gly His Leu Asp Cys Lys Pro Glu Phe Ser Tyr Ala Ile Ala Lys Asp
        35                  40                  45

Glu Arg Ile Gly Gln Leu Gly Ala Glu Gly Leu Thr Thr Thr Trp Lys
    50                  55                  60

Glu Tyr Ser Pro Gly Met Lys Leu Glu Asp Thr Met Val Ile Ala Trp
65                  70                  75                  80

Cys Glu Asp Gly Lys Leu Met Tyr Leu Gln Arg Cys Thr Arg Glu Thr
                85                  90                  95

Arg Tyr Leu Ala Ile Leu His Thr Arg Ala Leu Pro Thr Ser Val Val
            100                 105                 110

Phe Lys Lys Leu Phe Asp Gly Arg Lys Gln Glu Asp Val Val Glu Met
        115                 120                 125

Asn Asp Asn Phe Glu Phe Gly Leu Cys Pro Cys Asp Ala Lys Pro Ile
    130                 135                 140

Val Arg Gly Lys Phe Asn Thr Thr Leu Leu Asn Gly Pro Ala Phe Gln
145                 150                 155                 160

Met Val Cys Pro Ile Gly Trp Thr Gly Thr Val Ser Cys Thr Ser Phe
                165                 170                 175

Asn Met Asp Thr Leu Ala Thr Thr Val Val Arg Thr Tyr Arg Arg Ser
            180                 185                 190

Lys Pro Phe Pro His Arg Gln Gly Cys Ile Thr Gln Lys Asn Leu Gly
        195                 200                 205

Glu Asp Leu His Asn Cys Ile Leu Gly Gly Asn Trp Thr Cys Val Pro
    210                 215                 220

Gly Asp Gln Leu Leu Tyr Lys Gly Gly Ser Ile Glu Ser Cys Lys Trp
225                 230                 235                 240

Cys Gly Tyr Gln Phe Lys Glu Ser Glu Gly Leu Pro His Tyr Pro Ile
                245                 250                 255

Gly Lys Cys Lys Leu Glu Asn Glu Thr Gly Tyr Arg Leu Val Asp Ser
            260                 265                 270

Thr Ser Cys Asn Arg Glu Gly Val Ala Ile Val Pro Gln Gly Thr Leu
        275                 280                 285

Lys Cys Lys Ile Gly Lys Thr Thr Val Gln Val Ile Ala Met Asp Thr
    290                 295                 300

Lys Leu Gly Pro Met Pro Cys Arg Pro Tyr Glu Ile Ile Ser Ser Glu
305                 310                 315                 320

Gly Pro Val Glu Lys Thr Ala Cys Thr Phe Asn Tyr Thr Lys Thr Leu
                325                 330                 335

Lys Asn Lys Tyr Phe Glu Pro Arg Asp Ser Tyr Phe Gln Gln Tyr Met
            340                 345                 350
```

```
Leu Lys Gly Glu Tyr Gln Tyr Trp Phe Asp Leu Glu Val Thr Asp His
            355                 360                 365

His Arg Asp Tyr Phe Ala Glu Ser Ile Leu Val Val Val Ala Leu
        370                 375                 380

Leu Gly Gly Arg Tyr Val Leu Trp Leu Leu Val Thr Tyr Met Val Leu
385                 390                 395                 400

Ser Glu Gln Lys Ala Leu Gly
            405

<210> SEQ ID NO 4
<211> LENGTH: 372
<212> TYPE: PRT
<213> ORGANISM: Bovine viral diarrhea virus

<400> SEQUENCE: 4

Phe Pro Glu Cys Lys Glu Gly Phe Gln Tyr Ala Ile Ser Lys Asp Arg
1               5                   10                  15

Lys Ile Gly Pro Leu Gly Pro Glu Ser Leu Thr Thr Thr Trp His Leu
            20                  25                  30

Pro Thr Lys Lys Ile Val Asp Ser Met Val Gln Val Trp Cys Asp Gly
        35                  40                  45

Lys Asn Leu Lys Ile Leu Glu Thr Cys Thr Lys Glu Glu Arg Tyr Leu
    50                  55                  60

Val Ala Val His Glu Arg Ala Leu Ser Thr Ser Ala Glu Phe Met Gln
65                  70                  75                  80

Ile Ser Ser Gly Thr Lys Gly Pro Glu Val Ile Asp Met His Asp Asp
                85                  90                  95

Phe Glu Phe Gly Leu Cys Pro Cys Asp Ser Lys Pro Val Met Arg Gly
            100                 105                 110

Lys Phe Asn Ala Ser Leu Leu Asn Gly Pro Ala Phe Gln Met Val Cys
        115                 120                 125

Pro Gln Gly Trp Thr Gly Thr Ile Glu Cys Ile Leu Ala Asn Gln Asp
    130                 135                 140

Thr Leu Asp Thr Thr Val Val Arg Thr Tyr Arg Arg Thr Thr Pro Phe
145                 150                 155                 160

Gln Arg Arg Lys Trp Cys Thr Tyr Glu Lys Ile Ile Gly Glu Asp Ile
                165                 170                 175

His Glu Cys Ile Leu Gly Gly Asn Trp Thr Cys Ile Thr Gly Asp His
            180                 185                 190

Ser Lys Leu Lys Asp Gly Pro Ile Lys Lys Cys Lys Trp Cys Gly Tyr
        195                 200                 205

Asp Phe Phe Asp Ser Glu Gly Leu Pro His Tyr Pro Ile Gly Lys Cys
    210                 215                 220

Met Leu Ser Asn Glu Ser Gly Tyr Arg Tyr Val Asp Asp Thr Ser Cys
225                 230                 235                 240

Asp Arg Gly Gly Val Ala Ile Val Pro Thr Gly Thr Leu Lys Cys Arg
                245                 250                 255

Ile Gly Lys Ala Thr Val Gln Val Ile Ala Thr Asn Thr Asp Leu Gly
            260                 265                 270

Pro Met Pro Cys Ser Pro Asp Glu Val Ile Ala Ser Glu Gly Pro Val
        275                 280                 285

Glu Lys Thr Ala Cys Thr Phe Asn Tyr Ser Lys Thr Leu Pro Asn Lys
    290                 295                 300

Tyr Tyr Glu Pro Arg Asp Arg Tyr Phe Gln Gln Tyr Met Leu Lys Gly
305                 310                 315                 320
```

```
Glu Trp Gln Tyr Trp Phe Asp Leu Asp Thr Val Asp His His Lys Asp
                325                 330                 335

Tyr Phe Ser Glu Phe Ile Val Ile Ala Val Val Ala Leu Leu Gly Gly
            340                 345                 350

Lys Tyr Val Leu Trp Leu Leu Val Thr Tyr Met Ile Leu Ser Glu Gln
        355                 360                 365

Met Ala Met Gly
    370

<210> SEQ ID NO 5
<211> LENGTH: 374
<212> TYPE: PRT
<213> ORGANISM: Bovine viral diarrhea virus

<400> SEQUENCE: 5

His Leu Asp Cys Lys Pro Glu Phe Ser Tyr Ala Ile Ala Lys Asp Glu
1               5                   10                  15

Arg Ile Gly Gln Leu Gly Ala Glu Gly Leu Thr Thr Thr Trp Lys Glu
            20                  25                  30

Tyr Ser Pro Gly Met Lys Leu Glu Asp Thr Met Val Ile Ala Trp Cys
        35                  40                  45

Glu Asp Gly Lys Leu Met Tyr Leu Gln Arg Cys Thr Arg Glu Thr Arg
    50                  55                  60

Tyr Leu Ala Ile Leu His Thr Arg Ala Leu Pro Thr Ser Val Val Phe
65                  70                  75                  80

Lys Lys Leu Phe Asp Gly Arg Lys Gln Glu Asp Val Val Glu Met Asn
                85                  90                  95

Asp Asn Phe Glu Phe Gly Leu Cys Pro Cys Asp Ala Lys Pro Ile Val
            100                 105                 110

Arg Gly Lys Phe Asn Thr Thr Leu Leu Asn Gly Pro Ala Phe Gln Met
        115                 120                 125

Val Cys Pro Ile Gly Trp Thr Gly Thr Val Ser Cys Thr Ser Phe Asn
    130                 135                 140

Met Asp Thr Leu Ala Thr Thr Val Val Arg Thr Tyr Arg Arg Ser Lys
145                 150                 155                 160

Pro Phe Pro His Arg Gln Gly Cys Ile Thr Gln Lys Asn Leu Gly Glu
                165                 170                 175

Asp Leu His Asn Cys Ile Leu Gly Gly Asn Trp Thr Cys Val Pro Gly
            180                 185                 190

Asp Gln Leu Leu Tyr Lys Gly Gly Ser Ile Glu Ser Cys Lys Trp Cys
        195                 200                 205

Gly Tyr Gln Phe Lys Glu Ser Glu Gly Leu Pro His Tyr Pro Ile Gly
    210                 215                 220

Lys Cys Lys Leu Glu Asn Glu Thr Gly Tyr Arg Leu Val Asp Ser Thr
225                 230                 235                 240

Ser Cys Asn Arg Glu Gly Val Ala Ile Val Pro Gln Gly Thr Leu Lys
                245                 250                 255

Cys Lys Ile Gly Lys Thr Thr Val Gln Val Ile Ala Met Asp Thr Lys
            260                 265                 270

Leu Gly Pro Met Pro Cys Arg Pro Tyr Glu Ile Ile Ser Ser Glu Gly
        275                 280                 285

Pro Val Glu Lys Thr Ala Cys Thr Phe Asn Tyr Thr Lys Thr Leu Lys
    290                 295                 300

Asn Lys Tyr Phe Glu Pro Arg Asp Ser Tyr Phe Gln Gln Tyr Met Leu
```

```
                305                 310                 315                 320
Lys Gly Glu Tyr Gln Tyr Trp Phe Asp Leu Glu Val Thr Asp His His
                    325                 330                 335

Arg Asp Tyr Phe Ala Glu Ser Ile Leu Val Val Val Ala Leu Leu
                340                 345                 350

Gly Gly Arg Tyr Val Leu Trp Leu Val Thr Tyr Met Val Leu Ser
            355                 360                 365

Glu Gln Lys Ala Leu Gly
        370

<210> SEQ ID NO 6
<211> LENGTH: 1122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
cacctggatt gcaagcctga gttctcatac gccatcgcta agacgagag aattggccag      60
ctggggccg aaggactgac cacaacttgg aaggagtatt ctccaggcat gaaactggaa    120
gataccatgg tcatcgcttg gtgcgaggac gggaagctga tgtacctgca gcggtgcaca    180
agagaaactc gatatctggc cattctgcat actcgagctc tgcccaccag tgtggtcttc    240
aagaaactgt ttgacggacg gaagcaggag gatgtggtcg aaatgaacga caatttcgag    300
tttggcctgt gcccctgtga tgccaagcct atcgtgaggg gaaaattcaa caccacactg    360
ctgaatggcc cagcttttca gatggtgtgc cccattggct ggaccgggac agtctcatgt    420
accagcttca acatggacac tctggccact accgtggtcc gcacttaccg gaggtctaag    480
ccctttcctc acagacaggg ctgcatcacc cagaaaaacc tggggagga tctgcataac    540
tgcattctgg gaggaaattg gacctgcgtg ccaggggacc agctgctgta caagggaggc    600
tccatcgaat cttgcaagtg gtgtggctac cagttcaaag agagcgaagg gctgcctcac    660
tatccaattg gaaagtgtaa actggagaac gaaaccggct atcggctggt ggattctaca    720
agttgcaata gggagggagt ggctatcgtc cctcagggga cactgaagtg taaaatcgga    780
aagacaactg tgcaggtcat tgctatggac actaaactgg ggccaatgcc ctgcagacct    840
tacgagatca ttagctccga gggaccagtg aaaagaccg cctgtacctt caactacact    900
aaaacctga gaacaagta tttcgaaccc cgagattcct actttcagca gtatatgctg    960
aagggcgagt accagtattg gttcgacctg gaagtgacag accaccatag ggattacttt   1020
gccgagagca tcctggtggt cgtggtcgct ctgctgggag gacgctacgt gctgtggctg   1080
ctggtgacct atatggtcct gtccgagcag aaggccctgg gc                      1122

<210> SEQ ID NO 7
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gln Gly Pro Thr Leu Ala Val Leu Gly Ala Leu Leu Ala Val Ala
1               5                   10                  15

Val Ser Leu His Leu Asp Cys Lys Pro Glu Phe Ser Tyr Ala Ile Ala
            20                  25                  30
```

```
Lys Asp Glu Arg Ile Gly Gln Leu Gly Ala Glu Gly Leu Thr Thr Thr
             35                  40                  45

Trp Lys Glu Tyr Ser Pro Gly Met Lys Leu Glu Asp Thr Met Val Ile
 50                  55                  60

Ala Trp Cys Glu Asp Gly Lys Leu Met Tyr Leu Gln Arg Cys Thr Arg
 65                  70                  75                  80

Glu Thr Arg Tyr Leu Ala Ile Leu His Thr Arg Ala Leu Pro Thr Ser
                 85                  90                  95

Val Val Phe Lys Lys Leu Phe Asp Gly Arg Lys Gln Glu Asp Val Val
            100                 105                 110

Glu Met Asn Asp Asn Phe Glu Phe Gly Leu Cys Pro Cys Asp Ala Lys
            115                 120                 125

Pro Ile Val Arg Gly Lys Phe Asn Thr Thr Leu Leu Asn Gly Pro Ala
            130                 135                 140

Phe Gln Met Val Cys Pro Ile Gly Trp Thr Gly Thr Val Ser Cys Thr
145                 150                 155                 160

Ser Phe Asn Met Asp Thr Leu Ala Thr Thr Val Val Arg Thr Tyr Arg
                165                 170                 175

Arg Ser Lys Pro Phe Pro His Arg Gln Gly Cys Ile Thr Gln Lys Asn
            180                 185                 190

Leu Gly Glu Asp Leu His Asn Cys Ile Leu Gly Gly Asn Trp Thr Cys
            195                 200                 205

Val Pro Gly Asp Gln Leu Leu Tyr Lys Gly Gly Ser Ile Glu Ser Cys
            210                 215                 220

Lys Trp Cys Gly Tyr Gln Phe Lys Glu Ser Glu Gly Leu Pro His Tyr
225                 230                 235                 240

Pro Ile Gly Lys Cys Lys Leu Glu Asn Glu Thr Gly Tyr Arg Leu Val
                245                 250                 255

Asp Ser Thr Ser Cys Asn Arg Glu Gly Val Ala Ile Val Pro Gln Gly
            260                 265                 270

Thr Leu Lys Cys Lys Ile Gly Lys Thr Thr Val Gln Val Ile Ala Met
            275                 280                 285

Asp Thr Lys Leu Gly Pro Met Pro Cys Arg Pro Tyr Glu Ile Ile Ser
            290                 295                 300

Ser Glu Gly Pro Val Glu Lys Thr Ala Cys Thr Phe Asn Tyr Thr Lys
305                 310                 315                 320

Thr Leu Lys Asn Lys Tyr Phe Glu Pro Arg Asp Ser Tyr Phe Gln Gln
                325                 330                 335

Tyr Met Leu Lys Gly Glu Tyr Gln Tyr Trp Phe Asp Leu Glu Val Thr
            340                 345                 350

Asp His His Arg Asp Tyr Phe Ala Glu Ser Ile Leu Val Val Val Val
            355                 360                 365

Ala Leu Leu Gly Gly Arg Tyr Val Leu Trp Leu Leu Val Thr Tyr Met
370                 375                 380

Val Leu Ser Glu Gln Lys Ala Leu Gly
385                 390

<210> SEQ ID NO 8
<211> LENGTH: 1194
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 8

```
atcgatgccg ccaccatgca gggaccaaca ctggccgtgc tggggctct gctggctgtg      60
gctgtctccc tgttccccga gtgcaaggaa ggatttcagt acgccatcag caaggaccgg    120
aaaattggac cactgggacc agagtccctg accacaactt ggcacctgcc caccaagaaa    180
atcgtggact ctatggtgca ggtctggtgc gatggcaaga acctgaaaat tctggagaca    240
tgtactaagg aggagagata cctggtggct gtccacgagc gcgctctgtc taccagtgcc    300
gagttcatgc agatcagctc cggaacaaag ggccctgaag tgatcgacat gcacgacgat    360
ttcgaatttg gcctgtgccc ctgtgatagt aagcctgtga tgcgcggaaa attcaacgct    420
tcactgctga atggccctgc ctttcagatg gtgtgcccac aggggtggac cggaacaatc    480
gagtgtattc tggctaacca ggacacactg gataccacag tggtccggac ttaccggagg    540
actacccctt ttcagcgcag aaagtggtgc acctatgaga aaatcattgg cgaggacatc    600
cacgagtgca tcctgggcgg gaattggacc tgtatcacag gcgaccattc taagctgaaa    660
gatgggccaa ttaagaaatg caagtggtgt ggctacgact tctttgatag tgagggactg    720
cctcattatc caatcggcaa atgtatgctg tcaaacgaaa gcgggtacag atatgtggac    780
gatactagct gcgatcgagg aggagtggct atcgtcccaa ctgggaccct gaagtgtagg    840
atcggaaaag ctaccgtgca ggtcattgcc acaaatactg acctgggacc aatgccttgc    900
tccccagatg aagtgatcgc ttctgaggga cctgtcgaaa agactgcctg taccttcaac    960
tactccaaga cactgccaaa caagtactat gagccccgag accggtactt ccagcagtat   1020
atgctgaagg gggaatggca gtactggttt gacctggata ccgtggacca ccataaggat   1080
tacttctcag agtttatcgt gattgccgtg gtcgctctgc tggggggaaa gtacgtgctg   1140
tggctgctgg tcacctatat gatcctgagt gaacagatgg ccatgggcat gcat         1194
```

<210> SEQ ID NO 9
<211> LENGTH: 2812
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
ggtaccctcg tgaggctccg gtgcccgtca gtgggcagag cgcacatcgc ccacagtccc      60
cgagaagttg gggggagggg tcggcaattg aaccggtgcc tagagaaggt ggcgcggggt    120
aaactgggaa agtgatgtcg tgtactggct ccgcctttt cccgagggtg ggggagaacc     180
gtatataagt gcagtagtcg ccgtgaacgt tcttttttcgc aacgggtttg ccgccagaac   240
acaggtaagt gccgtgtgtg gttcccgcgg gcctggcctc tttacgggtt atggcccttg    300
cgtgccttga attacttcca cctggctgca gtacgtgatt cttgatcccg agcttcgggt    360
tggaagtggg tgggagagtt cgaggccttg cgcttaagga gccccttcgc ctcgtgcttg    420
agttgaggcc tggcctgggc gctggggccg ccgcgtgcga atcggtggc accttcgcgc     480
ctgtctcgct gctttcgata agtctctagc catttaaaat ttttgatgac ctgctgcgac    540
gcttttttc tggcaagata gtcttgtaaa tgcgggccaa gatctgcaca ctggtatttc     600
ggttttgggg gccgcgggcg gcgacggggc ccgtgcgtcc cagcgcacat gttcggcgag    660
gcggggcctg cgagcgcggc caccgagaat cggacggggg tagtctcaag ctggccggcc    720
tgctctggtg cctggcctcg cgccgccgtg tatcgccccg ccctgggcgg caaggctggc    780
```

| | | |
|---|---|---|
| ccggtcggca ccagttgcgt gagcggaaag atggccgctt cccggccctg ctgcagggag | 840 |
| ctcaaaatgg aggacgcggc gctcgggaga gcgggcgggt gagtcaccca cacaaaggaa | 900 |
| aagggccttt ccgtcctcag ccgtcgcttc atgtgactcc acggagtacc gggcgccgtc | 960 |
| caggcacctc gattagttct cgagcttttg gagtacgtcg tctttaggtt gggggggaggg | 1020 |
| gttttatgcg atggagtttc cccacactga gtgggtggag actgaagtta ggccagcttg | 1080 |
| gcacttgatg taattctcct tggaatttgc ccttttgag tttggatctt ggttcattct | 1140 |
| caagcctcag acagtggttc aaagttttt tcttccattt caggtgtcgt gaggaattag | 1200 |
| cttggtacta atacgactca ctatagggag acccaagctg gctaggtaag tgtacgagct | 1260 |
| cgatcactag tccagtgtgg atcgatcgcc gccaccatgc agggaccacc cctggccgtg | 1320 |
| ctgggcgctc tgctggctgt ggctgtcagt ctgcacctgg attgcaagcc tgagttctca | 1380 |
| tacgccatcg ctaaagacga gagaattggc cagctggggg ccgaaggact gaccacaact | 1440 |
| tggaaggagt attctccagg catgaaactg gaagatacca tggtcatcgc ttggtgcgag | 1500 |
| gacgggaagc tgatgtacct gcagcggtgc acaagagaaa ctcgatatct ggccattctg | 1560 |
| catactcgag ctctgcccac cagtgtggtc ttcaagaaac tgtttgacgg acggaagcag | 1620 |
| gaggatgtgg tcgaaatgaa cgacaatttc gagtttggcc tgtgccctg tgatgccaag | 1680 |
| cctatcgtga ggggaaaatt caacaccaca ctgctgaatg cccagctttt cagatggtg | 1740 |
| tgccccattg gctggaccgg acagtctca tgtaccagct tcaacatgga cactctggcc | 1800 |
| actaccgtgg tccgcactta ccggaggtct aagcccttc ctcacagaca gggctgcatc | 1860 |
| acccagaaaa acctggggga ggatctgcat aactgcattc tggaggaaaa ttggacctgc | 1920 |
| gtgccagggg accagctgct gtacaaggga ggctccatcg aatcttgcaa gtggtgtggc | 1980 |
| taccagttca agagagcga agggctgcct cactatccaa ttggaaagtg taaactggag | 2040 |
| aacgaaaccg gctatcggct ggtggattct acaagttgca ataggagggg agtggctatc | 2100 |
| gtccctcagg ggacactgaa gtgtaaaatc ggaaagacaa ctgtgcaggt cattgctatg | 2160 |
| gacactaaac tggggccaat gccctgcaga ccttacgaga tcattagctc cgagggacca | 2220 |
| gtggaaaaga ccgcctgtac cttcaactac actaaaaccc tgaagaacaa gtatttcgaa | 2280 |
| ccccgagatt cctactttca gcagtatatg ctgaagggcg agtaccagta ttggttcgac | 2340 |
| ctggaagtga cagaccacca tagggattac tttgccgaga gcatcctggt ggtcgtggtc | 2400 |
| gctctgctgg aggacgcta cgtgctgtgg ctgctggtga cctatatggt cctgtccgag | 2460 |
| cagaaggccc tggcatgca tggtaagcct atccctaacc ctctcctcgg tctcgattct | 2520 |
| acgcgtaccg gtcatcatca ccatcaccat tgagtttaaa cccgctgatc agcctcgact | 2580 |
| gtgccttcta gttgccagcc atctgttgtt tgccctcc ccgtgccttc cttgaccctg | 2640 |
| gaaggtgcca ctcccactgt cctttcctaa taaaatgagg aaattgcatc gcattgtctg | 2700 |
| agtaggtgtc attctattct gggggtggg gtgggcagg acagcaaggg ggaggattgg | 2760 |
| gaagacaata gcaggcatgc tggggatgcg gtgggctcta ggcttggta cc | 2812 |

<210> SEQ ID NO 10
<211> LENGTH: 372
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Phe Pro Glu Cys Lys Glu Gly Phe Gln Tyr Ala Ile Ser Lys Asp Arg
1               5                   10                  15

Lys Ile Gly Pro Leu Gly Pro Glu Ser Leu Thr Thr Thr Trp His Leu
            20                  25                  30

Pro Thr Lys Lys Ile Val Asp Ser Met Val Gln Val Trp Cys Asp Gly
            35                  40                  45

Lys Asn Leu Lys Ile Leu Glu Thr Cys Thr Lys Glu Glu Arg Tyr Leu
50                  55                  60

Val Ala Val His Glu Arg Ala Leu Ser Thr Ser Ala Glu Phe Met Gln
65                  70                  75                  80

Ile Ser Ser Gly Thr Lys Gly Pro Glu Val Ile Asp Met His Asp Asp
                85                  90                  95

Phe Glu Phe Gly Leu Cys Pro Cys Asp Ser Lys Pro Val Met Arg Gly
            100                 105                 110

Lys Phe Asn Ala Ser Leu Leu Asn Gly Pro Ala Phe Gln Met Val Cys
            115                 120                 125

Pro Gln Gly Trp Thr Gly Thr Ile Glu Cys Ile Leu Ala Asn Gln Asp
            130                 135                 140

Thr Leu Asp Thr Thr Val Val Arg Thr Tyr Arg Arg Thr Thr Pro Phe
145                 150                 155                 160

Gln Arg Arg Lys Trp Cys Thr Tyr Glu Lys Ile Ile Gly Glu Asp Ile
                165                 170                 175

His Glu Cys Ile Leu Gly Gly Asn Trp Thr Cys Ile Thr Gly Asp His
                180                 185                 190

Ser Lys Leu Lys Asp Gly Pro Ile Lys Lys Cys Lys Trp Cys Gly Tyr
            195                 200                 205

Asp Phe Phe Asp Ser Glu Gly Leu Pro His Tyr Pro Ile Gly Lys Cys
            210                 215                 220

Met Leu Ser Asn Glu Ser Gly Tyr Arg Tyr Val Asp Asp Thr Ser Cys
225                 230                 235                 240

Asp Arg Gly Gly Val Ala Ile Val Pro Thr Gly Thr Leu Lys Cys Arg
                245                 250                 255

Ile Gly Lys Ala Thr Val Gln Val Ile Ala Thr Asn Thr Asp Leu Gly
                260                 265                 270

Pro Met Pro Cys Ser Pro Asp Glu Val Ile Ala Ser Glu Gly Pro Val
            275                 280                 285

Glu Lys Thr Ala Cys Thr Phe Asn Tyr Ser Lys Thr Leu Pro Asn Lys
290                 295                 300

Tyr Tyr Glu Pro Arg Asp Arg Tyr Phe Gln Gln Tyr Met Leu Lys Gly
305                 310                 315                 320

Glu Trp Gln Tyr Trp Phe Asp Leu Asp Thr Val Asp His His Lys Asp
                325                 330                 335

Tyr Phe Ser Glu Phe Ile Val Ile Ala Val Ala Leu Leu Gly Gly
            340                 345                 350

Lys Tyr Val Leu Trp Leu Leu Val Thr Tyr Met Ile Leu Ser Glu Gln
            355                 360                 365

Met Ala Met Gly
        370

<210> SEQ ID NO 11
<211> LENGTH: 1116
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 11

```
ttccccgagt gcaaggaagg atttcagtac gccatcagca aggaccggaa aattggacca        60
ctgggaccag agtccctgac cacaacttgg cacctgccca ccaagaaaat cgtggactct       120
atggtgcagg tctggtgcga tggcaagaac ctgaaaattc tggagacatg tactaaggag       180
gagagatacc tggtggctgt ccacgagcgc gctctgtcta ccagtgccga gttcatgcag       240
atcagctccg gaacaaaggg ccctgaagtg atcgacatgc acgacgattt cgaatttggc       300
ctgtgcccct gtgatagtaa gcctgtgatg cgcggaaaat caacgcttc actgctgaat        360
ggccctgcct ttcagatggt gtgcccacag gggtggaccg aacaatcga gtgtattctg        420
gctaaccagg acacactgga taccacagtg gtccggactt accggaggac taccccttt        480
cagcgcagaa agtggtgcac ctatgagaaa atcattggcg aggacatcca cgagtgcatc       540
ctgggcggga attggacctg tatcacaggc gaccattcta agctgaaaga tgggccaatt       600
aagaaatgca agtggtgtgg ctacgacttc tttgatagtg agggactgcc tcattatcca       660
atcggcaaat gtatgctgtc aaacgaaagc gggtacagat atgtggacga tactagctgc       720
gatcgaggag gagtggctat cgtcccaact gggaccctga agtgtaggat cggaaaagct       780
accgtgcagg tcattgccac aaatactgac ctgggaccaa tgccttgctc cccagatgaa       840
gtgatcgctt ctgagggacc tgtcgaaaag actgcctgta ccttcaacta ctccaagaca       900
ctgccaaaca agtactatga gccccgagac cggtacttcc agcagtatat gctgaagggg       960
gaatggcagt actggtttga cctggatacc gtggaccacc ataaggatta cttctcagag      1020
tttatcgtga ttgccgtggt cgctctgctg gggggaaagt acgtgctgtg gctgctggtc      1080
acctatatga tcctgagtga acagatggcc atgggc                                1116
```

<210> SEQ ID NO 12
<211> LENGTH: 393
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Met Gln Gly Pro Thr Leu Ala Val Leu Gly Ala Leu Leu Ala Val Ala
1               5                   10                  15

Val Ser Leu Phe Pro Glu Cys Lys Glu Gly Phe Gln Tyr Ala Ile Ser
            20                  25                  30

Lys Asp Arg Lys Ile Gly Pro Leu Gly Pro Glu Ser Leu Thr Thr Thr
        35                  40                  45

Trp His Leu Pro Thr Lys Lys Ile Val Asp Ser Met Val Gln Val Trp
    50                  55                  60

Cys Asp Gly Lys Asn Leu Lys Ile Leu Glu Thr Cys Thr Lys Glu Glu
65                  70                  75                  80

Arg Tyr Leu Val Ala Val His Glu Arg Ala Leu Ser Thr Ser Ala Glu
                85                  90                  95

Phe Met Gln Ile Ser Ser Gly Thr Lys Gly Pro Glu Val Ile Asp Met
            100                 105                 110

His Asp Asp Phe Glu Phe Gly Leu Cys Pro Cys Asp Ser Lys Pro Val
        115                 120                 125

Met Arg Gly Lys Phe Asn Ala Ser Leu Leu Asn Gly Pro Ala Phe Gln
    130                 135                 140
```

Met Val Cys Pro Gln Gly Trp Thr Gly Thr Ile Glu Cys Ile Leu Ala
145                 150                 155                 160

Asn Gln Asp Thr Leu Asp Thr Thr Val Val Arg Thr Tyr Arg Arg Thr
                165                 170                 175

Thr Pro Phe Gln Arg Arg Lys Trp Cys Thr Tyr Glu Lys Ile Ile Gly
            180                 185                 190

Glu Asp Ile His Glu Cys Ile Leu Gly Gly Asn Trp Thr Cys Ile Thr
        195                 200                 205

Gly Asp His Ser Lys Leu Lys Asp Gly Pro Ile Lys Lys Cys Lys Trp
    210                 215                 220

Cys Gly Tyr Asp Phe Phe Asp Ser Glu Gly Leu Pro His Tyr Pro Ile
225                 230                 235                 240

Gly Lys Cys Met Leu Ser Asn Glu Ser Gly Tyr Arg Tyr Val Asp Asp
                245                 250                 255

Thr Ser Cys Asp Arg Gly Gly Val Ala Ile Val Pro Thr Gly Thr Leu
                260                 265                 270

Lys Cys Arg Ile Gly Lys Ala Thr Val Gln Val Ile Ala Thr Asn Thr
            275                 280                 285

Asp Leu Gly Pro Met Pro Cys Ser Pro Asp Glu Val Ile Ala Ser Glu
290                 295                 300

Gly Pro Val Glu Lys Thr Ala Cys Thr Phe Asn Tyr Ser Lys Thr Leu
305                 310                 315                 320

Pro Asn Lys Tyr Tyr Glu Pro Arg Asp Arg Tyr Phe Gln Gln Tyr Met
                325                 330                 335

Leu Lys Gly Glu Trp Gln Tyr Trp Phe Asp Leu Asp Thr Val Asp His
            340                 345                 350

His Lys Asp Tyr Phe Ser Glu Phe Ile Val Ile Ala Val Val Ala Leu
        355                 360                 365

Leu Gly Gly Lys Tyr Val Leu Trp Leu Leu Val Thr Tyr Met Ile Leu
    370                 375                 380

Ser Glu Gln Met Ala Met Gly Met His
385                 390

<210> SEQ ID NO 13
<211> LENGTH: 1179
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgcagggac caacactggc cgtgctgggg gctctgctgg ctgtggctgt ctccctgttc      60
cccgagtgca aggaaggatt tcagtacgcc atcagcaagg accggaaaat tggaccactg     120
ggaccagagt ccctgaccac aacttggcac ctgcccacca agaaaatcgt ggactctatg     180
gtgcaggtct ggtgcgatgg caagaacctg aaaattctgg acacatgtac taaggaggag     240
agatacctgg tggctgtcca cgagcgcgct ctgtctacca gtgccgagtt catgcagatc     300
agctccggaa caagggccc tgaagtgatc gacatgcacg acgatttcga atttggcctg     360
tgcccctgtg atagtaagcc tgtgatgcgc ggaaaattca acgcttcact gctgaatggc     420
cctgcctttc agatggtgtg cccacagggg tggaccggaa caatcgagtg tattctggct     480
aaccaggaca cactggatac cacagtggtc cggacttacc ggaggactac ccctttcag      540 cgcagaaagt ggtgcaccta tgagaaaatc attggcgagg acatccacga gtgcatcctg     600

```
ggcgggaatt ggacctgtat cacaggcgac cattctaagc tgaaagatgg gccaattaag      660
aaatgcaagt ggtgtggcta cgacttcttt gatagtgagg gactgcctca ttatccaatc      720
ggcaaatgta tgctgtcaaa cgaaagcggg tacagatatg tggacgatac tagctgcgat      780
cgaggaggag tggctatcgt cccaactggg accctgaagt gtaggatcgg aaaagctacc      840
gtgcaggtca ttgccacaaa tactgacctg gaccaatgc cttgctcccc agatgaagtg       900
atcgcttctg agggacctgt cgaaaagact gcctgtacct tcaactactc caagacactg      960
ccaaacaagt actatgagcc ccgagaccgg tacttccagc agtatatgct gaagggggaa     1020
tggcagtact ggtttgacct ggataccgtg gaccaccata aggattactt ctcagagttt     1080
atcgtgattg ccgtggtcgc tctgctgggg ggaaagtacg tgctgtggct gctggtcacc     1140
tatatgatcc tgagtgaaca gatggccatg ggcatgcat                            1179

<210> SEQ ID NO 14
<211> LENGTH: 2806
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
ggtaccctcg tgaggctccg gtgcccgtca gtgggcagag cgcacatcgc ccacagtccc       60
cgagaagttg gggggagggg tcggcaattg aaccggtgcc tagagaaggt ggcgcggggt      120
aaactgggaa agtgatgtcg tgtactggct ccgccttttt cccgagggtg ggggagaacc      180
gtatataagt gcagtagtcg ccgtgaacgt tcttttttcgc aacgggtttg ccgccagaac    240
acaggtaagt gccgtgtgtg gttcccgcgg gcctggcctc tttacgggtt atggcccttg      300
cgtgccttga attacttcca cctggctgca gtacgtgatt cttgatcccg agcttcgggt      360
tggaagtggg tgggagagtt cgaggccttg cgcttaagga gccccttcgc ctcgtgcttg      420
agttgaggcc tggcctgggc gctggggccg ccgcgtgcga atctggtggc accttcgcgc      480
ctgtctcgct gctttcgata gtctctagc catttaaaat ttttgatgac ctgctgcgac       540 gcttttttc tggcaagata gtcttgtaaa tgcgggccaa gatctgcaca ctggtatttc       600
ggtttttggg gccgcgggcg cgacgggcc cgtgcgtcc cagcgcacat gttcggcgag        660
gcggggcctg cgagcgcggc caccgagaat cggacggggg tagtctcaag ctggccggcc      720
tgctctggtg cctggcctcg cgccgccgtg tatcgccccg ccctgggcgg caaggctggc      780
ccggtcggca ccagttgcgt gagcggaaag atggccgctt cccggccctg ctgcagggag      840
ctcaaaatgg aggacgcggc gctcgggaga gcgggcgggt gagtcaccca cacaaaggaa      900
aagggccttt ccgtcctcag ccgtcgcttc atgtgactcc acggagtacc gggcgccgtc      960
caggcacctc gattagttct cgagcttttg gagtacgtcg tctttaggtt ggggggaggg     1020
gttttatgcg atggagtttc cccacactga gtgggtggag actgaagtta ggccagcttg     1080
gcacttgatg taattctcct tggaatttgc cctttttgag tttggatctt ggttcattct     1140
caagcctcag acagtggttc aaagtttttt tcttccattt caggtgtcgt gaggaattag     1200
cttggtacta atacgactca ctatagggag acccaagctg gctaggtaag tgtacgagct     1260
cgatcactag tccagtgtgg atcgatcgcc gccaccatgc agggaccaac actggccgtg     1320
ctgggggctc tgctggctgt ggctgtctcc ctgttccccg agtgcaagga aggatttcag     1380
tacgccatca gcaaggaccg gaaaattgga ccactgggac cagagtccct gaccacaact     1440
```

```
tggcacctgc ccaccaagaa aatcgtggac tctatggtgc aggtctggtg cgatggcaag    1500
aacctgaaaa ttctggagac atgtactaag gaggagagat acctggtggc tgtccacgag    1560
cgcgctctgt ctaccagtgc cgagttcatg cagatcagct ccggaacaaa gggccctgaa    1620
gtgatcgaca tgcacgacga tttcgaattt ggcctgtgcc cctgtgatag taagcctgtg    1680
atgcgcggaa aattcaacgc ttcactgctg aatggccctg cctttcagat ggtgtgccca    1740
caggggtgga ccggaacaat cgagtgtatt ctggctaacc aggacacact ggataccaca    1800
gtggtccgga cttaccggag gactacccct tttcagcgca gaaagtggtg cacctatgag    1860
aaaatcattg gcgaggacat ccacgagtgc atcctgggcg ggaattggac ctgtatcaca    1920
ggcgaccatt ctaagctgaa agatgggcca attaagaaat gcaagtggtg tggctacgac    1980
ttctttgata gtgagggact gcctcattat ccaatcggca aatgtatgct gtcaaacgaa    2040
agcgggtaca gatatgtgga cgatactagc tgcgatcgag gaggagtggc tatcgtccca    2100
actgggaccc tgaagtgtag gatcggaaaa gctaccgtgc aggtcattgc cacaaatact    2160
gacctgggac caatgccttg ctccccagat gaagtgatcg cttctgaggg acctgtcgaa    2220
aagactgcct gtaccttcaa ctactccaag acactgccaa acaagtacta tgagccccga    2280
gaccggtact tccagcagta tatgctgaag ggggaatggc agtactggtt tgacctggat    2340 accgtgacc accataagga ttacttctca gagtttatcg tgattgccgt ggtcgctctg    2400 ctgggggaa agtacgtgct gtggctgctg gtcacctata tgatcctgag tgaacagatg    2460
gccatgggca tgcatggtaa gcctatccct aaccctctcc tcggtctcga ttctacgcgt    2520
accggtcatc atcaccatca ccattgagtt taaacccgct gatcagcctc gactgtgcct    2580
tctagttgcc agccatctgt tgtttgcccc tccccgtgc cttccttgac cctggaaggt    2640
gccactccca ctgtcctttc ctaataaaat gaggaaattg catcgcattg tctgagtagg    2700
tgtcattcta ttctggggg tggggtgggg caggacagca aggggagga ttgggaagac    2760 aatagcaggc atgctgggga tgcggtgggc tctatggctt ggtacc              2806
```

<210> SEQ ID NO 15
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Gln Asn Glu Pro Ala Ser Phe Ser Arg Ala Lys Arg Gly Ile Pro
            100                 105                 110
```

```
Glu Leu Ile His Tyr Thr Arg Asn Ser Thr Lys Arg Phe Tyr Gly Leu
            115                 120                 125

Met Gly Lys Lys Arg Lys Arg Arg Phe Leu Gly Phe Leu Leu Gly Ile
130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Lys Val Asn
        195                 200                 205

Asn His Asp Cys Arg Ile Ser Asn Ile Glu Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Val Val Lys Glu Glu Val Ile Ala Tyr Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Thr Asp Val Asn Leu Cys Asn Thr
    370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
        515                 520                 525

Thr Ile Ile Ile Val Ile Val Val Val Ile Leu Met Leu Ile Ala Val
```

```
                530             535             540
Gly Leu Leu Phe Tyr Cys Lys Thr Arg Ser Thr Pro Ile Met Leu Gly
545                 550             555                 560

Lys Asp Gln Leu Ser Gly Ile Asn Asn Leu Ser Phe Ser Lys
                565             570
```

<210> SEQ ID NO 16
<211> LENGTH: 574
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
                20                  25                  30

Tyr Gln Ser Thr Cys Ser Ala Val Ser Arg Gly Tyr Leu Ser Ala Leu
                35                  40                  45

Arg Thr Gly Trp Tyr Thr Ser Val Val Thr Ile Glu Leu Ser Lys Ile
50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Gln Asn Glu Pro Ala Ser Phe Ser Ala Ala Lys Ala Gly Ile Pro
                100                 105                 110

Glu Leu Ile His Tyr Thr Arg Asn Ser Thr Lys Arg Phe Tyr Gly Leu
                115                 120                 125

Met Gly Lys Lys Ala Lys Ala Ala Phe Leu Gly Phe Leu Leu Gly Ile
                130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Glu Leu Leu Pro Lys Val Asn
                195                 200                 205

Asn His Asp Cys Arg Ile Ser Asn Ile Glu Thr Val Ile Glu Phe Gln
                210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Ser Asn Val Gln Ile Val Arg Gln Gln Ser Tyr Ser Ile
                275                 280                 285

Met Ser Val Val Lys Glu Glu Val Ile Ala Tyr Val Val Gln Leu Pro
                290                 295                 300

Ile Tyr Gly Val Ile Asp Thr Pro Cys Trp Lys Leu His Thr Ser Pro
305                 310                 315                 320
```

Leu Cys Thr Thr Asp Asn Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
            355                 360                 365

Thr Met Asn Ser Leu Thr Leu Pro Thr Asp Val Asn Leu Cys Asn Thr
    370                 375                 380

Asp Ile Phe Asn Thr Lys Tyr Asp Cys Lys Ile Met Thr Ser Lys Thr
385                 390                 395                 400

Asp Ile Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Leu Glu Gly
    450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
        515                 520                 525

Thr Ile Ile Ile Val Ile Val Val Ile Leu Met Leu Ile Ala Val
    530                 535                 540

Gly Leu Leu Phe Tyr Cys Lys Thr Arg Ser Thr Pro Ile Met Leu Gly
545                 550                 555                 560

Lys Asp Gln Leu Ser Gly Ile Asn Asn Leu Ser Phe Ser Lys
                565                 570

<210> SEQ ID NO 17
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Thr Thr Ala Met Thr Met Ile Ile Ser Ile Ile Phe Ile Ser
1               5                   10                  15

Thr Tyr Val Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Val Glu Leu Gln Ser Leu
                85                  90                  95

Met Gln Asn Glu Pro Ala Ser Phe Ser Ala Ala Lys Ala Ser Ile Pro
            100                 105                 110

```
Glu Leu Ile His Tyr Thr Arg Asn Ser Thr Lys Lys Phe Tyr Gly Leu
            115                 120                 125

Met Gly Lys Lys Ala Lys Ala Ala Phe Leu Gly Phe Leu Leu Gly Ile
130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Lys Val Asn
            195                 200                 205

Asn His Asp Cys Arg Ile Ser Asn Ile Ala Thr Val Ile Glu Phe Gln
            210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Ser Val Val Lys Glu Val Ile Ala Tyr Val Val Gln Leu Pro
            290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Thr Asp Val Asn Leu Cys Asn Thr
            370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
            485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
            515                 520                 525
```

```
Thr Ile Ile Ile Val Ile Val Val Ile Leu Met Leu Ile Ala Val
            530                 535                 540
Gly Leu Leu Phe Tyr Cys Lys Thr Arg Ser Thr Pro Ile Met Leu Gly
545                 550                 555                 560
Lys Asp Gln Leu Ser Gly Ile Asn Asn Leu Ser Phe Ser Lys
                565                 570
```

<210> SEQ ID NO 18
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atggctacaa ccgctatgac tatgattatc agcatcatct tcatctccac ctacgtgacc      60
cacatcaccc tgtgccagaa catcaccgag gagttctacc agtccacctg cagcgctgtg     120
tccaggggct acctgtccgc tctgagaacc ggctggtaca cctccgtggt gaccatcgag     180
ctgagcaaga tccagaagaa cgtgtgcaag agcaccgact ccaaggtgaa gctgatcaag     240
caggagctgg agcggtacaa caacgccgtg gtggagctgc agagcctgat gcagaacgag     300
cctgcttcct tcagcgctgc taaggcctcc atccctgagc tgatccacta caccaggaac     360
agcaccaaga agttctacgg cctgatgggc aagaaggcca aggccgcctt cctgggcttc     420
ctgctgggaa tcggcagcgc tatcgcttcc ggagtggctg tgtccaaggt gctgcacctg     480
gagggcgagt gaacaagat caagaacgcc ctgctgagca ccaacaaggc cgtggtgtcc     540
ctgagcaacg gcgtgagcgt gctgacctcc aaggtgctgg acctgaagaa ctacatcgac     600
aaggagctgc tgcctaaggt caacaaccac gactgccgga tctccaacat cgccaccgtg     660
atcgagttcc agcagaagaa caaccggctg ctggagatcg ccagggagtt ctccgtgaac     720
gccggcatca ccacccctct gagcacctac atgctgacca cagcgagct gctgtccctg     780
atcaacgaca tgcccatcac caacgaccag aagaagctga tgagctccaa cgtgcagatc     840
gtgaggcagc agtcctacag catcatgagc gtggtgaagg aggaggtgat cgcctacgtg     900
gtgcagctgc ccatctacgg cgtgatcgac accccttgct ggaagctgca cacctccccc    960
ctgtgcacca ccgacaacaa ggagggcagc aacatctgcc tgacccgcac cgacagaggc    1020
tggtactgcg acaacgccgg ctccgtgagc ttcttccctc aggccgagac ctgcaaggtg    1080
cagtccaacc gcgtgttctg cgacaccatg aacagcctga ccctgcccac cgacgtgaac    1140
ctgtgcaaca ccgacatctt caacaccaag tacgactgca gatcatgac cagcaagacc    1200
gacatcagct ccagcgtgat caccagcatc ggcgccatcg tgtcctgcta cggcaagacc    1260
aagtgcaccg cctccaacaa gaacagaggc atcatcaaga ccttctccaa cggctgcgac    1320
tacgtgagca acaagggcgt ggacaccgtg agcgtgggca caccctgta ctacgtgaac    1380
aagctggagg gcaaggccct gtacatcaag ggcgagccca tcatcaacta ctacgacccc    1440
ctggtgttcc ctagcgacga gttcgacgcc tccatcgccc aggtgaacgc caagatcaac    1500
cagtccctgg ccttcatccg gaggagcgac gagctgctgc actccgtgga cgtgggcaag    1560
agcaccacca acgtggtgat caccaccatc atcatcgtga tcgtggtggt gatcctgatg    1620
ctgatcgccg tgggcctgct gttctactgc aagacccgca gcacctatat gctgggc       1680
aaggaccagc tgagcggaat caacaatctg tcatttctca ag                      1722
```

```
<210> SEQ ID NO 19
<211> LENGTH: 3413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
ggtaccctcg tgaggctccg gtgcccgtca gtgggcagag cgcacatcgc ccacagtccc      60
cgagaagttg gggggagggg tcggcaattg aaccggtgcc tagagaaggt ggcgcggggt     120
aaactgggaa agtgatgtcg tgtactggct ccgccttttt cccgagggtg ggggagaacc     180
gtatataagt gcagtagtcg ccgtgaacgt tcttttttcgc aacgggtttg ccgccagaac    240
acaggtaagt gccgtgtgtg gttcccgcgg gcctggcctc tttacgggtt atggcccttg     300
cgtgccttga attacttcca cctggctgca gtacgtgatt cttgatcccg agcttcgggt     360
tggaagtggg tgggagagtt cgaggccttg cgcttaagga gcccttcgc ctcgtgcttg      420 agttgaggcc tggcctgggc gctggggccg ccgcgtgcga atctggtggc accttcgcgc    480
ctgtctcgct gctttcgata agtctctagc catttaaaat ttttgatgac ctgctgcgac     540
gctttttttc tggcaagata gtcttgtaaa tgcgggccaa gatctgcaca ctggtatttc     600
ggtttttggg gccgcgggcg gcgacggggc ccgtgcgtcc cagcgcacat gttcggcgag     660
gcggggcctg cgagcgcggc caccgagaat cggacgggg tagtctcaag ctggccggcc     720
tgctctggtg cctggcctcg cgccgccgtg tatcgccccg ccctgggcgg caaggctggc     780
ccggtcggca ccagttgcgt gagcggaaag atggccgctt cccggccctg ctgcagggag     840
ctcaaaatgg aggacgcggc gctcgggaga gcggcgggt gagtcaccca cacaaggaa      900 aagggccttt ccgtcctcag ccgtcgcttc atgtgactcc acggagtacc gggcgccgtc     960
caggcacctc gattagttct cgagcttttg gagtacgtcg tctttaggtt ggggggaggg    1020
gttttatgcg atggagtttc cccacactga gtgggtggag actgaagtta ggccagcttg    1080
gcacttgatg taattctcct tggaatttgc cctttttgag tttggatctt ggttcattct    1140
caagcctcag acagtggttc aaagtttttt tcttccattt caggtgtcgt gaggaattag    1200
cttggtacta atacgactca ctatagggag acccaagctg gctaggtaag tgtacgagct    1260
cgatcactag tccagtgtgg atcgatgccg ccaccatgca gggaccaact ctggctgtgc    1320
tgggggctct gctggctgtc gccgtctctc tgcctatggc tacaaccgct atgactatga    1380
ttatcagcat catcttcatc tccacctacg tgacccacat caccctgtgc cagaacatca    1440
ccgaggagtt ctaccagtcc acctgcagcg ctgtgtccag gggctacctg tccgctctga    1500
gaaccggctg gtacacctcc gtggtgacca tcgagctgag caagatccag aagaacgtgt    1560
gcaagagcac cgactccaag gtgaagctga tcaagcagga gctggagcgg tacaacaacg    1620
ccgtggtgga gctgcagagc ctgatgcaga acgagcctgc ttccttcagc gctgctaagg    1680
cctccatccc tgagctgatc cactacacca ggaacagcac caagaagttc tacggcctga    1740
tgggcaagaa ggccaaggcc gccttcctgg gcttcctgct gggaatcggc agcgctatcg    1800
cttccggagt ggctgtgtcc aaggtgctgc acctggaggg cgaggtgaac aagatcaaga    1860
acgccctgct gagcaccaac aaggccgtgg tgtccctgag caacggcgtg agcgtgctga    1920
cctccaaggt gctggacctg aagaactaca tcgacaagga gctgctgcct aaggtcaaca    1980
accacgactg ccgatctcc aacatcgcca ccgtgatcga gttccagcag aagaacaacc    2040
ggctgctgga gatcgccagg gagttctccg tgaacgccgg catcaccacc cctctgagca    2100
```

```
cctacatgct gaccaacagc gagctgctgt ccctgatcaa cgacatgccc atcaccaacg    2160
accagaagaa gctgatgagc tccaacgtgc agatcgtgag gcagcagtcc tacagcatca    2220
tgagcgtggt gaaggaggag gtgatcgcct acgtggtgca gctgcccatc tacggcgtga    2280
tcgacacccc ttgctggaag ctgcacacct ccccctgtg caccaccgac aacaaggagg     2340
gcagcaacat ctgcctgacc cgcaccgaca gaggctggta ctgcgacaac gccggctccg    2400
tgagcttctt ccctcaggcc gagacctgca aggtgcagtc caaccgcgtg ttctgcgaca    2460
ccatgaacag cctgaccctg cccaccgacg tgaacctgtg caacaccgac atcttcaaca    2520
ccaagtacga ctgcaagatc atgaccagca agaccgacat cagctccagc gtgatcacca    2580
gcatcggcgc catcgtgtcc tgctacggca agaccaagtg caccgcctcc aacaagaaca    2640
gaggcatcat caagaccttc tccaacggct gcgactacgt gagcaacaag ggcgtggaca    2700
ccgtgagcgt gggcaacacc ctgtactacg tgaacaagct ggagggcaag gccctgtaca    2760
tcaagggcga gcccatcatc aactactacg acccctggt gttccctagc gacgagttcg     2820
acgcctccat cgcccaggtg aacgccaaga tcaaccagtc cctggccttc atccggagga    2880
gcgagagctg ctgcactccg tggacgtggg caagagcacc accaacgtgg tgatcaccac    2940
catcatcatc gtgatcgtgg tggtgatcct gatgctgatc gccgtgggcc tgctgttcta    3000
ctgcaagacc cgcagcacac ctattatgct gggcaaggac cagctgagcg gaatcaacaa    3060
tctgtcattt tctaagatgc atggtaagcc tatccctaac cctctcctcg gtctcgattc    3120
tacgcgtacc ggtcatcatc accatcacca ttgagtttaa accgctgat cagcctcgac     3180 tgtgccttct agttgccagc catctgttgt ttgcccctcc cccgtgcctt ccttgaccct    3240
ggaaggtgcc actcccactg tcctttccta ataaaatgag gaaattgcat cgcattgtct    3300
gagtaggtgt cattctattc tggggggtgg ggtggggcag gacagcaagg gggaggattg    3360
ggaagacaat agcaggcatg ctggggatgc ggtgggctct atggcttggt acc           3413
```

<210> SEQ ID NO 20
<211> LENGTH: 619
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Met Gln Gly Pro Thr Leu Ala Val Leu Gly Ala Leu Leu Ala Val Ala
1               5                   10                  15

Val Ser Leu Pro Met Ala Thr Thr Ala Met Thr Met Ile Ile Ser Ile
                20                  25                  30

Ile Phe Ile Ser Thr Tyr Val Thr His Ile Thr Leu Cys Gln Asn Ile
            35                  40                  45

Thr Glu Glu Phe Tyr Gln Ser Thr Cys Ser Ala Val Ser Arg Gly Tyr
        50                  55                  60

Leu Ser Ala Leu Arg Thr Gly Trp Tyr Thr Ser Val Val Thr Ile Glu
65                  70                  75                  80

Leu Ser Lys Ile Gln Lys Asn Val Cys Lys Ser Thr Asp Ser Lys Val
                85                  90                  95

Lys Leu Ile Lys Gln Glu Leu Glu Arg Tyr Asn Asn Ala Val Val Glu
            100                 105                 110

Leu Gln Ser Leu Met Gln Asn Glu Pro Ala Ser Phe Ser Ala Ala Lys
        115                 120                 125
```

```
Ala Ser Ile Pro Glu Leu Ile His Tyr Thr Arg Asn Ser Thr Lys Lys
            130                 135                 140

Phe Tyr Gly Leu Met Gly Lys Lys Ala Lys Ala Ala Phe Leu Gly Phe
145                 150                 155                 160

Leu Leu Gly Ile Gly Ser Ala Ile Ala Ser Gly Val Ala Val Ser Lys
                165                 170                 175

Val Leu His Leu Glu Gly Glu Val Asn Lys Ile Lys Asn Ala Leu Leu
            180                 185                 190

Ser Thr Asn Lys Ala Val Val Ser Leu Ser Asn Gly Val Ser Val Leu
        195                 200                 205

Thr Ser Lys Val Leu Asp Leu Lys Asn Tyr Ile Asp Lys Glu Leu Leu
        210                 215                 220

Pro Lys Val Asn Asn His Asp Cys Arg Ile Ser Asn Ile Ala Thr Val
225                 230                 235                 240

Ile Glu Phe Gln Gln Lys Asn Asn Arg Leu Leu Glu Ile Ala Arg Glu
            245                 250                 255

Phe Ser Val Asn Ala Gly Ile Thr Thr Pro Leu Ser Thr Tyr Met Leu
            260                 265                 270

Thr Asn Ser Glu Leu Leu Ser Leu Ile Asn Asp Met Pro Ile Thr Asn
        275                 280                 285

Asp Gln Lys Lys Leu Met Ser Ser Asn Val Gln Ile Val Arg Gln Gln
        290                 295                 300

Ser Tyr Ser Ile Met Ser Val Val Lys Glu Glu Val Ile Ala Tyr Val
305                 310                 315                 320

Val Gln Leu Pro Ile Tyr Gly Val Ile Asp Thr Pro Cys Trp Lys Leu
                325                 330                 335

His Thr Ser Pro Leu Cys Thr Thr Asp Asn Lys Glu Gly Ser Asn Ile
                340                 345                 350

Cys Leu Thr Arg Thr Asp Arg Gly Trp Tyr Cys Asp Asn Ala Gly Ser
            355                 360                 365

Val Ser Phe Phe Pro Gln Ala Glu Thr Cys Lys Val Gln Ser Asn Arg
370                 375                 380

Val Phe Cys Asp Thr Met Asn Ser Leu Thr Leu Pro Thr Asp Val Asn
385                 390                 395                 400

Leu Cys Asn Thr Asp Ile Phe Asn Thr Lys Tyr Asp Cys Lys Ile Met
                405                 410                 415

Thr Ser Lys Thr Asp Ile Ser Ser Ser Val Ile Thr Ser Ile Gly Ala
                420                 425                 430

Ile Val Ser Cys Tyr Gly Lys Thr Lys Cys Thr Ala Ser Asn Lys Asn
            435                 440                 445

Arg Gly Ile Ile Lys Thr Phe Ser Asn Gly Cys Asp Tyr Val Ser Asn
450                 455                 460

Lys Gly Val Asp Thr Val Ser Val Gly Asn Thr Leu Tyr Tyr Val Asn
465                 470                 475                 480

Lys Leu Glu Gly Lys Ala Leu Tyr Ile Lys Gly Glu Pro Ile Ile Asn
                485                 490                 495

Tyr Tyr Asp Pro Leu Val Phe Pro Ser Asp Glu Phe Asp Ala Ser Ile
                500                 505                 510

Ala Gln Val Asn Ala Lys Ile Asn Gln Ser Leu Ala Phe Ile Arg Arg
            515                 520                 525

Ser Asp Glu Leu Leu His Ser Val Asp Val Gly Lys Ser Thr Thr Asn
530                 535                 540
```

```
Val Val Ile Thr Thr Ile Ile Val Ile Val Val Ile Leu Met
545                 550                 555                 560

Leu Ile Ala Val Gly Leu Leu Phe Tyr Cys Lys Thr Arg Ser Thr Pro
            565                 570                 575

Ile Met Leu Gly Lys Asp Gln Leu Ser Gly Ile Asn Asn Leu Ser Phe
        580                 585                 590

Ser Lys Met His Gly Lys Pro Ile Pro Asn Pro Leu Leu Gly Leu Asp
    595                 600                 605

Ser Thr Arg Thr Gly His His His His His
    610                 615
```

<210> SEQ ID NO 21
<211> LENGTH: 1875
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atcgatgccg ccaccatgca gggaccaact ctggctgtgc tgggggctct gctggctgtc    60
gccgtctctc tgcctatggc tacaaccgct atgactatga ttatcagcat catcttcatc   120
tccacctacg tgacccacat cccctgtgc cagaacatca ccgaggagtt ctaccagtcc   180
acctgcagcg ctgtgtccag gggctacctg tccgctctga accggctg gtacacctcc    240
gtggtgacca tcgagctgag caagatccag aagaacgtgt gcaagagcac cgactccaag   300
gtgaagctga tcaagcagga gctggagcgg tacaacaacg ccgtggtgga gctgcagagc   360
ctgatgcaga acgagcctgc ttccttcagc gctgctaagg cctccatccc tgagctgatc   420
cactacacca ggaacagcac caagaagttc acggcctga tgggcaagaa ggccaaggcc    480
gccttcctgg gcttcctgct gggaatcggc agcgctatcg cttccggagt ggctgtgtcc   540
aaggtgctgc acctggaggg cgaggtgaac aagatcaaga acgccctgct gagcaccaac   600
aaggccgtgg tgtccctgag caacggcgtg agcgtgctga cctccaaggt gctggacctg   660
aagaactaca tcgacaagga gctgctgcct aaggtcaaca accacgactg ccggatctcc   720
aacatcgcca ccgtgatcga gttccagcag aagaacaacc ggctgctgga gatcgccagg   780
gagttctccg tgaacgccgg catcaccacc cctctgagca cctacatgct gaccaacagc   840
gagctgctgt ccctgatcaa cgacatgccc atcaccaacg accagaagaa gctgatgagc   900
tccaacgtgc agatcgtgag gcagcagtcc tacagcatca tgagcgtggt gaaggaggag   960
gtgatcgcct acgtggtgca gctgcccatc tacggcgtga tcgacacccc ttgctggaag  1020
ctgcacacct cccccctgtg caccaccgac aacaaggagg gcagcaacat ctgcctgacc  1080
cgcaccgaca gaggctggta ctgcgacaac gccggctccg tgagcttctt ccctcaggcc  1140
gagacctgca aggtgcagtc caaccgcgtg ttctgcgaca ccatgaacag cctgaccctg  1200
cccaccgacg tgaacctgtg caacaccgac atcttcaaca ccaagtacga ctgcaagatc  1260
atgaccagca agaccgacat cagctccagc gtgatcacca gcatcggcgc catcgtgtcc  1320
tgctacggca agaccaagtg caccgcctcc aacaagaaca aggcatcat caagaccttc  1380
tccaacggct gcgactacgt gagcaacaag ggcgtggaca ccgtgagcgt gggcaacacc  1440
ctgtactacg tgaacaagct ggagggcaag gccctgtaca tcaagggcga gcccatcatc  1500
aactactacg accccctggt gttccctagc gacgagttcg acgcctccat cgcccaggtg  1560
aacgccaaga tcaaccagtc cctggccttc atccggagga gcgacgagct gctgcactcc  1620
```

-continued

```
gtggacgtgg gcaagagcac caccaacgtg gtgatcacca ccatcatcat cgtgatcgtg    1680
gtggtgatcc tgatgctgat cgccgtgggc ctgctgttct actgcaagac ccgcagcaca    1740
cctattatgc tgggcaagga ccagctgagc ggaatcaaca atctgtcatt ttctaagatg    1800
catggtaagc ctatccctaa ccctctcctc ggtctcgatt ctacgcgtac cggtcatcat    1860
caccatcacc attga                                                     1875
```

<210> SEQ ID NO 22
<211> LENGTH: 574
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Ala Thr Thr Ala Met Thr Met Ile Ile Ser Ile Ile Phe Ile Ser
1               5                   10                  15

Thr Tyr Val Thr His Ile Thr Leu Cys Gln Asn Ile Thr Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Val Glu Leu Gln Ser Leu
                85                  90                  95

Met Gln Asn Glu Pro Ala Ser Phe Ser Ala Ala Ala Ser Ile Pro
            100                 105                 110

Glu Leu Ile His Tyr Thr Arg Asn Ser Thr Lys Lys Phe Tyr Gly Leu
        115                 120                 125

Met Gly Lys Lys Ala Ala Ala Phe Leu Gly Phe Leu Leu Gly Ile
    130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Lys Val Asn
        195                 200                 205

Asn His Asp Cys Arg Ile Ser Asn Ile Ala Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Val Val Lys Glu Glu Val Ile Ala Tyr Val Val Gln Leu Pro
    290                 295                 300
```

```
Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Thr Asp Val Leu Cys Asn Thr
370                 375                 380

Asp Ile Phe Asn Thr Lys Tyr Asp Cys Lys Ile Met Thr Ser Lys Thr
385                 390                 395                 400

Asp Ile Ser Ser Val Ile Thr Ser Ile Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
            485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
            515                 520                 525

Thr Ile Ile Ile Val Ile Val Val Ile Leu Met Leu Ile Ala Val
530                 535                 540

Gly Leu Leu Phe Tyr Cys Lys Thr Arg Ser Thr Pro Ile Met Leu Gly
545                 550                 555                 560

Lys Asp Gln Leu Ser Gly Ile Asn Asn Leu Ser Phe Ser Lys
            565                 570
```

<210> SEQ ID NO 23
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atggctacaa ccgctatgac tatgattatc agcatcatct tcatctccac ctacgtgacc      60
cacatcaccc tgtgccagaa catcaccgag gagttctacc agtccacctg cagcgctgtg     120
tccaggggct acctgtccgc tctgagaacc ggctggtaca cctccgtggt gaccatcgag     180
ctgagcaaga tccagaagaa cgtgtgcaag agcaccgact ccaaggtgaa gctgatcaag     240
caggagctgg agcggtacaa caacgccgtg gtggagctgc agagcctgat gcagaacgag     300
cctgcttcct tcagcgctgc tgccgcctcc atccctgagc tgatccacta ccaccaggaaa    360 agcaccaaga agttctacgg cctgatgggc aagaaggccg ccgccgcctt cctgggcttc     420
ctgctgggaa tcggcagcgc tatcgcttcc ggagtggctg tgtccaaggt gctgcacctg     480
gagggcgagg tgaacaagat caagaacgcc ctgctgagca ccaacaaggc cgtggtgtcc     540
```

```
ctgagcaacg gcgtgagcgt gctgacctcc aaggtgctgg acctgaagaa ctacatcgac    600
aaggagctgc tgcctaaggt caacaaccac gactgccgga tctccaacat cgccaccgtg    660
atcgagttcc agcagaagaa caaccggctg ctggagatcg ccagggagtt ctccgtgaac    720
gccggcatca ccacccctct gagcacctac atgctgacca cagcgagct gctgtccctg    780 atcaacgaca tgcccatcac caacgaccag aagaagctga tgagctccaa cgtgcagatc    840
gtgaggcagc agtcctacag catcatgagc gtggtgaagg aggaggtgat cgcctacgtg    900
gtgcagctgc ccatctacgg cgtgatcgac accccttgct ggaagctgca cacctccccc    960
ctgtgcacca ccgacaacaa ggagggcagc aacatctgcc tgacccgcac cgacagaggc   1020
tggtactgcg acaacgccgg ctccgtgagc ttcttccctc aggccgagac ctgcaaggtg   1080
cagtccaacc gcgtgttctg cgacaccatg aacagcctga ccctgcccac cgacgtgaac   1140
ctgtgcaaca ccgacatctt caacaccaag tacgactgca agatcatgac cagcaagacc   1200
gacatcagct ccagcgtgat caccagcatc ggcgccatcg tgtcctgcta cggcaagacc   1260
aagtgcaccg cctccaacaa gaacagaggc atcatcaaga ccttctccaa cggctgcgac   1320
tacgtgagca caagggcgt ggacaccgtg agcgtgggca caccctgta ctacgtgaac   1380 aagctggagg caaggcct gtacatcaag ggcgagccca tcatcaacta ctacgacccc   1440
ctggtgttcc ctagcgacga gttcgacgcc tccatcgccc aggtgaacgc caagatcaac   1500
cagtccctgg ccttcatccg gaggagcgac gagctgctgc actccgtgga cgtgggcaag   1560
agcaccacca acgtggtgat caccaccatc atcatcgtga tcgtggtggt gatcctgatg   1620
ctgatcgccg tgggcctgct gttctactgc aagacccgca gcacacctat tatgctgggc   1680
aaggaccagc tgagcggaat caacaatctg tcattttcta ag                      1722
```

<210> SEQ ID NO 24
<211> LENGTH: 594
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Gln Gly Pro Thr Leu Ala Val Leu Gly Ala Leu Leu Ala Val Ala
1               5                   10                  15

Val Ser Leu Pro Met Ala Thr Thr Ala Met Thr Met Ile Ile Ser Ile
                20                  25                  30

Ile Phe Ile Ser Thr Tyr Val Thr His Ile Thr Leu Cys Gln Asn Ile
            35                  40                  45

Thr Glu Glu Phe Tyr Gln Ser Thr Cys Ser Ala Val Ser Arg Gly Tyr
        50                  55                  60

Leu Ser Ala Leu Arg Thr Gly Trp Tyr Thr Ser Val Val Thr Ile Glu
65                  70                  75                  80

Leu Ser Lys Ile Gln Lys Asn Val Cys Lys Ser Thr Asp Ser Lys Val
                85                  90                  95

Lys Leu Ile Lys Gln Glu Leu Glu Arg Tyr Asn Asn Ala Val Val Glu
            100                 105                 110

Leu Gln Ser Leu Met Gln Asn Glu Pro Ala Ser Phe Ser Ala Ala Ala
        115                 120                 125

Ala Ser Ile Pro Glu Leu Ile His Tyr Thr Arg Asn Ser Thr Lys Lys
    130                 135                 140
```

```
Phe Tyr Gly Leu Met Gly Lys Lys Ala Ala Ala Phe Leu Gly Phe
145                 150                 155                 160

Leu Leu Gly Ile Gly Ser Ala Ile Ala Ser Gly Val Ala Val Ser Lys
            165                 170                 175

Val Leu His Leu Glu Gly Glu Val Asn Lys Ile Lys Asn Ala Leu Leu
            180                 185                 190

Ser Thr Asn Lys Ala Val Val Ser Leu Ser Asn Gly Val Ser Val Leu
            195                 200                 205

Thr Ser Lys Val Leu Asp Leu Lys Asn Tyr Ile Asp Lys Glu Leu Leu
            210                 215                 220

Pro Lys Val Asn His Asp Cys Arg Ile Ser Asn Ile Ala Thr Val
225                 230                 235                 240

Ile Glu Phe Gln Gln Lys Asn Asn Arg Leu Leu Glu Ile Ala Arg Glu
                245                 250                 255

Phe Ser Val Asn Ala Gly Ile Thr Thr Pro Leu Ser Thr Tyr Met Leu
            260                 265                 270

Thr Asn Ser Glu Leu Leu Ser Leu Ile Asn Asp Met Pro Ile Thr Asn
            275                 280                 285

Asp Gln Lys Lys Leu Met Ser Ser Asn Val Gln Ile Val Arg Gln Gln
290                 295                 300

Ser Tyr Ser Ile Met Ser Val Val Lys Glu Glu Val Ile Ala Tyr Val
305                 310                 315                 320

Val Gln Leu Pro Ile Tyr Gly Val Ile Asp Thr Pro Cys Trp Lys Leu
                325                 330                 335

His Thr Ser Pro Leu Cys Thr Thr Asp Asn Lys Glu Gly Ser Asn Ile
            340                 345                 350

Cys Leu Thr Arg Thr Asp Arg Gly Trp Tyr Cys Asp Asn Ala Gly Ser
            355                 360                 365

Val Ser Phe Phe Pro Gln Ala Glu Thr Cys Lys Val Gln Ser Asn Arg
            370                 375                 380

Val Phe Cys Asp Thr Met Asn Ser Leu Thr Leu Pro Thr Asp Val Asn
385                 390                 395                 400

Leu Cys Asn Thr Asp Ile Phe Asn Thr Lys Tyr Asp Cys Lys Ile Met
                405                 410                 415

Thr Ser Lys Thr Asp Ile Ser Ser Val Ile Thr Ser Ile Gly Ala
                420                 425                 430

Ile Val Ser Cys Tyr Gly Lys Thr Lys Cys Thr Ala Ser Asn Lys Asn
            435                 440                 445

Arg Gly Ile Ile Lys Thr Phe Ser Asn Gly Cys Asp Tyr Val Ser Asn
450                 455                 460

Lys Gly Val Asp Thr Val Ser Val Gly Asn Thr Leu Tyr Tyr Val Asn
465                 470                 475                 480

Lys Leu Glu Gly Lys Ala Leu Tyr Ile Lys Gly Glu Pro Ile Ile Asn
                485                 490                 495

Tyr Tyr Asp Pro Leu Val Phe Pro Ser Asp Glu Phe Ala Ser Ile
            500                 505                 510

Ala Gln Val Asn Ala Lys Ile Asn Gln Ser Leu Ala Phe Ile Arg Arg
            515                 520                 525

Ser Asp Glu Leu Leu His Ser Val Asp Val Gly Lys Ser Thr Thr Asn
            530                 535                 540

Val Val Ile Thr Thr Ile Ile Ile Val Ile Val Val Ile Leu Met
545                 550                 555                 560

Leu Ile Ala Val Gly Leu Leu Phe Tyr Cys Lys Thr Arg Ser Thr Pro
```

```
                      565                 570                 575
Ile Met Leu Gly Lys Asp Gln Leu Ser Gly Ile Asn Asn Leu Ser Phe
            580                 585                 590
Ser Lys

<210> SEQ ID NO 25
<211> LENGTH: 1803
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atcgatgccg ccaccatgca gggaccaact ctggctgtgc tgggggctct gctggctgtc      60
gccgtctctc tgcctatggc tacaaccgct atgactatga ttatcagcat catcttcatc     120
tccacctacg tgacccacat cacccctgtg cagaacatca ccgaggagtt ctaccagtcc     180
acctgcagcg ctgtgtccag gggctacctg tccgctctga aaccggctg gtacacctcc     240 gtggtgacca tcgagctgag caagatccag aagaacgtgt gcaagagcac cgactccaag     300
gtgaagctga tcaagcagga gctggagcgg tacaacaacg ccgtggtgga gctgcagagc     360
ctgatgcaga acgagcctgc ttccttcagc gctgctgccg cctccatccc tgagctgatc     420
cactacacca ggaacagcac caagaagttc tacggcctgt gggcaagaa ggccgccgcc     480 gccttcctgg gcttcctgct gggaatcggc agcgctatcg cttccggagt ggctgtgtcc     540
aaggtgctgc acctggaggg cgaggtgaac aagatcaaga cgccctgct gagcaccaac     600 aaggccgtgg tgtccctgag caacggcgtg agcgtgctga cctccaaggt gctggacctg     660
aagaactaca tcgacaagga gctgctgcct aaggtcaaca ccacgactg ccggatctcc     720 aacatcgcca ccgtgatcga gttccagcag aagaacaacc ggctgctgga gatcgccagg     780
gagttctccg tgaacgccgg catcaccacc cctctgagca cctacatgct gaccaacagc     840
gagctgctgt ccctgatcaa cgacatgccc atcaccaacg accagaagaa gctgatgagc     900
tccaacgtgc agatcgtgag gcagcagtcc tacagcatca tgagcgtggt gaaggaggag     960
gtgatcgcct acgtggtgca gctgcccatc tacggcgtga tcgacacccc ttgctggaag    1020
ctgcacacct cccccctgtg caccaccgac aacaaggagg cagcaacat ctgcctgacc    1080 cgcaccgaca gaggctggta ctgcgacaac gccggctccg tgagcttctt ccctcaggcc    1140
gagacctgca aggtgcagtc caaccgcgtg ttctgcgaca ccatgaacag cctgaccctg    1200
cccaccgacg tgaacctgtg caacaccgac atcttcaaca ccaagtacga ctgcaagatc    1260
atgaccagca gaccgacat cagctccagc gtgatcacca gcatcggcgc catcgtgtcc    1320
tgctacggca gaccaagtg caccgcctcc aacaagaaca gaggcatcat caagaccttc    1380
tccaacggct gcgactacgt gagcaacaag ggcgtggaca ccgtgagcgt gggcaacacc    1440
ctgtactacg tgaacaagct ggagggcaag gccctgtaca tcaagggcga gcccatcatc    1500
aactactacg acccctggt gttccctagc gacgagttcg acgcctccat cgcccaggtg    1560
aacgccaaga tcaaccagtc cctggccttc atccggagga gcgacgagct gctgcactcc    1620
gtggacgtgg gcaagagcac caccaacgtg gtgatcacca ccatcatcat cgtgatcgtg    1680
gtggtgatcc tgatgctgat cgccgtgggc ctgctgttct actgcaagac ccgcagcaca    1740
cctattatgc tgggcaagga ccagctgagc ggaatcaaca atctgtcatt ttctaagatg    1800
cat                                                                   1803
```

<210> SEQ ID NO 26
<211> LENGTH: 257
<212> TYPE: PRT
<213> ORGANISM: Bovine respiratory syncytial virus

<400> SEQUENCE: 26

```
Met Ser Asn His Thr His His Leu Lys Phe Lys Thr Leu Lys Arg Ala
1               5                   10                  15

Trp Lys Ala Ser Lys Tyr Phe Ile Val Gly Leu Ser Cys Leu Tyr Lys
            20                  25                  30

Phe Asn Leu Lys Ser Leu Val Gln Thr Ala Leu Thr Thr Leu Ala Met
        35                  40                  45

Ile Thr Leu Thr Ser Leu Val Ile Thr Ala Ile Ile Tyr Ile Ser Val
    50                  55                  60

Gly Asn Ala Lys Ala Lys Pro Thr Ser Lys Pro Thr Ile Gln Gln Thr
65                  70                  75                  80

Gln Gln Pro Gln Asn His Thr Ser Pro Phe Phe Thr Glu His Asn Tyr
                85                  90                  95

Lys Ser Thr His Thr Ser Ile Gln Ser Thr Thr Leu Ser Gln Leu Pro
            100                 105                 110

Asn Thr Asp Thr Thr Arg Glu Thr Thr Tyr Ser His Ser Ile Asn Glu
        115                 120                 125

Thr Gln Asn Arg Lys Ile Lys Ser Gln Ser Thr Leu Pro Ala Thr Arg
    130                 135                 140

Lys Pro Pro Ile Asn Pro Ser Gly Ser Asn Pro Pro Glu Asn His Gln
145                 150                 155                 160

Asp His Asn Asn Ser Gln Thr Leu Pro Tyr Val Pro Cys Ser Thr Cys
                165                 170                 175

Glu Gly Asn Leu Ala Cys Leu Ser Leu Cys Gln Ile Gly Pro Glu Arg
            180                 185                 190

Ala Pro Ser Arg Ala Pro Thr Ile Thr Leu Lys Lys Thr Pro Lys Pro
        195                 200                 205

Lys Thr Thr Lys Lys Pro Thr Lys Thr Ile His His Arg Thr Ser
    210                 215                 220

Pro Glu Ala Lys Leu Gln Pro Lys Asn Asn Thr Ala Ala Pro Gln Gln
225                 230                 235                 240

Gly Ile Leu Ser Ser Pro Glu His His Thr Asn Gln Ser Thr Thr Gln
                245                 250                 255

Ile
```

<210> SEQ ID NO 27
<211> LENGTH: 14
<212> TYPE: PRT
<213> ORGANISM: Bovine respiratory syncytial virus

<400> SEQUENCE: 27

```
Cys Ser Thr Cys Glu Gly Asn Leu Ala Cys Leu Ser Leu Cys
1               5                   10
```

<210> SEQ ID NO 28
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Ser Asn His Thr His His Leu Lys Phe Lys Thr Leu Lys Arg Ala
1               5                   10                  15

Trp Lys Ala Ser Lys Tyr Phe Ile Val Gly Leu Ser Cys Leu Tyr Lys
            20                  25                  30

Phe Asn Leu Lys Ser Leu Val Gln Thr Ala Leu Thr Thr Leu Ala Met
        35                  40                  45

Ile Thr Leu Thr Ser Leu Val Ile Thr Ala Ile Ile Tyr Ile Ser Val
    50                  55                  60

Gly Asn Ala Lys Ala Lys Pro Thr Ser Lys Pro Thr Ile Gln Gln Thr
65                  70                  75                  80

Gln Gln Pro Gln Asn His Thr Ser Pro Phe Phe Thr Glu His Asn Tyr
                85                  90                  95

Lys Ser Thr His Thr Ser Ile Gln Ser Thr Thr Leu Ser Gln Leu Pro
            100                 105                 110

Asn Thr Asp Thr Thr Arg Glu Thr Thr Tyr Ser His Ser Ile Asn Glu
        115                 120                 125

Thr Gln Asn Arg Lys Ile Lys Ser Gln Ser Thr Leu Pro Ala Thr Arg
    130                 135                 140

Lys Pro Pro Ile Asn Pro Ser Gly Ser Asn Pro Glu Asn His Gln
145                 150                 155                 160

Asp His Asn Asn Ser Gln Thr Leu Pro Tyr Val Pro Gln Ile Gly Pro
                165                 170                 175

Glu Arg Ala Pro Ser Arg Ala Pro Thr Ile Thr Leu Lys Lys Thr Pro
            180                 185                 190

Lys Pro Lys Thr Thr Lys Lys Pro Thr Lys Thr Thr Ile His His Arg
        195                 200                 205

Thr Ser Pro Glu Ala Lys Leu Gln Pro Lys Asn Asn Thr Ala Ala Pro
    210                 215                 220

Gln Gln Gly Ile Leu Ser Ser Pro Glu His His Thr Asn Gln Ser Thr
225                 230                 235                 240

Thr Gln Ile
```

<210> SEQ ID NO 29
<211> LENGTH: 257
<212> TYPE: PRT
<213> ORGANISM: Bovine respiratory syncytial virus

<400> SEQUENCE: 29

```
Met Ser Asn His Thr His His Leu Lys Phe Lys Thr Leu Lys Arg Ala
1               5                   10                  15

Trp Lys Ala Ser Lys Tyr Phe Ile Val Gly Leu Ser Cys Leu Tyr Lys
            20                  25                  30

Phe Asn Leu Lys Ser Leu Val Gln Thr Ala Leu Thr Thr Leu Ala Met
        35                  40                  45

Ile Thr Leu Thr Ser Leu Val Ile Thr Ala Ile Ile Tyr Ile Ser Val
    50                  55                  60

Gly Asn Ala Lys Ala Lys Pro Thr Ser Lys Pro Thr Ile Gln Gln Thr
65                  70                  75                  80

Gln Gln Pro Gln Asn His Thr Ser Pro Phe Phe Thr Glu His Asn Tyr
                85                  90                  95

Lys Ser Thr His Thr Ser Ile Gln Ser Thr Thr Leu Ser Gln Leu Pro
            100                 105                 110

Asn Thr Asp Thr Thr Arg Glu Thr Thr Tyr Ser His Ser Ile Asn Glu
```

```
                    115                 120                 125
Thr Gln Asn Arg Lys Ile Lys Ser Gln Ser Thr Leu Pro Ala Thr Arg
            130                 135                 140

Lys Pro Pro Ile Asn Pro Ser Gly Ser Asn Pro Glu Asn His Gln
145                 150                 155                 160

Asp His Asn Asn Ser Gln Thr Leu Pro Tyr Val Pro Ser Ser Thr Ser
                165                 170                 175

Glu Gly Asn Leu Ala Ser Leu Ser Leu Ser Gln Ile Gly Pro Glu Arg
            180                 185                 190

Ala Pro Ser Arg Ala Pro Thr Ile Thr Leu Lys Lys Thr Pro Lys Pro
        195                 200                 205

Lys Thr Thr Lys Lys Pro Thr Lys Thr Ile His His Arg Thr Ser
    210                 215                 220

Pro Glu Ala Lys Leu Gln Pro Lys Asn Asn Thr Ala Ala Pro Gln Gln
225                 230                 235                 240

Gly Ile Leu Ser Ser Pro Glu His His Thr Asn Gln Ser Thr Thr Gln
                245                 250                 255

Ile

<210> SEQ ID NO 30
<211> LENGTH: 771
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
atgtctaacc atactcacca tctgaagttc aagaccctga agcgggcctg gaaggcctcc     60
aagtacttca tcgtgggcct gagctgcctg tacaagttca acctgaagag cctggtgcag    120
accgctctga ccaccctggc catgatcacc ctgacctccc tggtgatcac cgccatcatc    180
tacatcagcg tgggcaacgc caaggccaag cccacctcca gcctaccat ccagcagacc     240 cagcagcctc agaaccacac cagccccttc ttcaccgagc acaactacaa gtccaccac    300 acctccatcc agagcaccac cctgtcccag ctgcctaaca ccgacaccac ccgcgagacc    360
acctacagcc actccatcaa cgagacccag aaccgcaaga tcaagagcca gtccaccctg    420
cctgccacca gaaagccccc tatcaacccc agcggctcca ccccctga gaaccaccag     480 gaccacaaca acagccagac cctgccctac gtgcctagct ccacctccga gggaaacctg    540
gctagcctgt ccctgagcca gatcggacct gagagggctc ctagcagggc tcccaccatc    600
accctgaaga gaccccccaa gcctaagacc accaagaagc ccaccaagac caccatccac    660
cacaggaccc cccctgaggc taagctgcag cccaagaaca acaccgccgc ccccagcag    720 ggaatcctga gcagccccga acaccacaca aaccagagca ctacccagat c             771

<210> SEQ ID NO 31
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Gln Gly Pro Thr Leu Ala Val Leu Gly Ala Leu Leu Ala Val Ala
1               5                  10                  15
```

```
Val Ser Leu Pro Met Ser Asn His Thr His His Leu Lys Phe Lys Thr
            20                  25                  30

Leu Lys Arg Ala Trp Lys Ala Ser Lys Tyr Phe Ile Val Gly Leu Ser
        35                  40                  45

Cys Leu Tyr Lys Phe Asn Leu Lys Ser Leu Val Gln Thr Ala Leu Thr
 50                  55                  60

Thr Leu Ala Met Ile Thr Leu Thr Ser Leu Val Ile Thr Ala Ile Ile
 65                  70                  75                  80

Tyr Ile Ser Val Gly Asn Ala Lys Ala Lys Pro Thr Ser Lys Pro Thr
                 85                  90                  95

Ile Gln Gln Thr Gln Gln Pro Gln Asn His Thr Ser Pro Phe Phe Thr
                100                 105                 110

Glu His Asn Tyr Lys Ser Thr His Thr Ser Ile Gln Ser Thr Thr Leu
            115                 120                 125

Ser Gln Leu Pro Asn Thr Asp Thr Thr Arg Glu Thr Thr Tyr Ser His
        130                 135                 140

Ser Ile Asn Glu Thr Gln Asn Arg Lys Ile Lys Ser Gln Ser Thr Leu
145                 150                 155                 160

Pro Ala Thr Arg Lys Pro Pro Ile Asn Pro Ser Gly Ser Asn Pro Pro
                165                 170                 175

Glu Asn His Gln Asp His Asn Asn Ser Gln Thr Leu Pro Tyr Val Pro
            180                 185                 190

Ser Ser Thr Ser Glu Gly Asn Leu Ala Ser Leu Ser Leu Ser Gln Ile
        195                 200                 205

Gly Pro Glu Arg Ala Pro Ser Arg Ala Pro Thr Ile Thr Leu Lys Lys
210                 215                 220

Thr Pro Lys Pro Lys Thr Thr Lys Lys Pro Thr Lys Thr Thr Ile His
225                 230                 235                 240

His Arg Thr Ser Pro Glu Ala Lys Leu Gln Pro Lys Asn Asn Thr Ala
                245                 250                 255

Ala Pro Gln Gln Gly Ile Leu Ser Ser Pro Glu His His Thr Asn Gln
            260                 265                 270

Ser Thr Thr Gln Ile
            275

<210> SEQ ID NO 32
<211> LENGTH: 831
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atgcagggac caactctggc tgtgctgggg gctctgctgg ctgtcgctgt gtcactgcct      60
atgtctaacc atactcacca tctgaagttc aagaccctga gcgggcctg aaggcctcc      120 aagtacttca tcgtgggcct gagctgcctg tacaagttca cctgaagag cctggtgcag     180 accgctctga ccaccctggc catgatcacc ctgacctccc tggtgatcac cgccatcatc     240
tacatcagcg tgggcaacgc caaggccaag cccacctcca agcctaccat ccagcagacc     300
cagcagcctc agaaccacac cagcccctt ttcaccgagc acaactacaa gtccacccac      360
acctccatcc agagcaccac cctgtcccag ctgcctaaca ccgacaccac ccgcgagacc     420
acctacagcc actccatcaa cgagacccag aaccgcaaga tcaagagcca gtccaccctg     480
cctgccacca gaaagccccc tatcaacccc agcggctcca accccctga gaaccaccag      540
```

```
gaccacaaca acagccagac cctgccctac gtgcctagct ccacctccga gggaaacctg    600
gctagcctgt ccctgagcca gatcggacct gagagggctc ctagcagggc tcccaccatc    660
accctgaaga agaccccaa gcctaagacc accagaagc ccaccaagac caccatccac      720
cacaggacct cccctgaggc taagctgcag cccaagaaca caccgccgc cccccagcag     780 ggaatcctga gcagccccga acaccacaca aaccagagca ctacccagat c             831
```

<210> SEQ ID NO 33
<211> LENGTH: 2463
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
ggtaccctcg tgaggctccg gtgcccgtca gtgggcagag cgcacatcgc ccacagtccc    60
cgagaagttg gggggagggg tcggcaattg aaccggtgcc tagagaaggt ggcgcggggt    120
aaactgggaa agtgatgtcg tgtactggct ccgccttttt cccgagggtg ggggagaacc    180
gtatataagt gcagtagtcg ccgtgaacgt tcttttttcgc aacgggtttg ccgccagaac    240
acaggtaagt gccgtgtgtg gttcccgcgg gcctggcctc tttacgggtt atggcccttg    300
cgtgccttga attacttcca cctggctgca gtacgtgatt cttgatcccg agcttcgggt    360
tggaagtggg tgggagagtt cgaggccttg cgcttaagga gccccttcgc ctcgtgcttg    420
agttgaggcc tggcctgggc gctggggccg ccgcgtgcga atctggtggc accttcgcgc    480
ctgtctcgct gctttcgata agtctctagc catttaaaat ttttgatgac ctgctgcgac    540
gctttttttc tggcaagata gtcttgtaaa tgcgggccaa gatctgcaca ctggtatttc    600 ggttttggg gccgcgggcg gcgacggggc ccgtgcgtcc cagcgcacat gttcggcgag    660
gcggggcctg cgagcgcggc caccgagaat cggacggggg tagtctcaag ctggccggcc    720
tgctctggtg cctggcctcg cgccgccgtg tatcgccccg ccctgggcgg caaggctggc    780
ccggtcggca ccagttgcgt gagcggaaag atggccgctt cccggccctg ctgcaggag     840 ctcaaaatgg aggacgcggc gctcgggaga gcgggcgggt gagtcaccca cacaaaggaa    900
aagggccttt ccgtcctcag ccgtcgcttc atgtgactcc acggagtacc gggcgccgtc    960
caggcacctc gattagttct cgagcttttg gagtacgtcg tctttaggtt ggggggaggg    1020
gttttatgcg atggagtttc cccacactga gtgggtggag actgaagtta ggccagcttg    1080
gcacttgatg taattctcct tggaatttgc cctttttgag tttggatctt ggttcattct    1140
caagcctcag acagtggttc aaagttttt tcttccattt caggtgtcgt gaggaattag    1200
cttggtacta atacgactca ctataggag acccaagctg gctaggtaag tgtacgagct    1260
cgatcactag tccagtgtgg atcgatgccg ccaccatgca ggaccaact ctggctgtgc     1320 tggggctct gctggctgtc gctgtgtcac tgcctatgtc taaccatact caccatctga    1380
agttcaagac cctgaagcgg gcctggaagg cctccaagta cttcatcgtg ggcctgagct    1440
gcctgtacaa gttcaacctg aagagcctgg tgcagaccgc tctgaccacc ctggccatga    1500
tcaccctgac ctccctggtg atcaccgcca tcatctacat cagcgtgggc aacgccaagg    1560
ccaagcccac ctccaagcct accatccagc agacccagca gcctcagaac acaccagcc     1620 ccttcttcac cgagcacaac tacaagtcca cccacacctc catccagagc accccctgt     1680 cccagctgcc taacaccgac accaccgcg agaccaccta cagccactcc atcaacgaga    1740
```

```
cccagaaccg caagatcaag agccagtcca ccctgcctgc caccagaaag cccctatca    1800 acccagcgg ctccaacccc cctgagaacc accaggacca caacaacagc cagaccctgc    1860
cctacgtgcc tagctccacc tccgagggaa acctggctag cctgtccctg agccagatcg    1920
gacctgagag ggctcctagc agggctccca ccatcaccct gaagaagacc cccaagccta    1980
agaccaccaa gaagcccacc aagaccacca tccaccacag gacctcccct gaggctaagc    2040
tgcagcccaa gaacaacacc gccgccccca gcagggaat cctgagcagc ccgaacacc    2100 acacaaacca gagcactacc cagatcatgc atggtaagcc tatccctaac cctctcctcg    2160
gtctcgattc tacgcgtacc ggtcatcatc accatcacca ttgagtttaa acccgctgat    2220
cagcctcgac tgtgccttct agttgccagc catctgttgt ttgcccctcc ccgtgcctt     2280 ccttgaccct ggaaggtgcc actcccactg tcctttccta ataaaatgag gaaattgcat    2340
cgcattgtct gagtaggtgt cattctattc tggggggtgg ggtggggcag gacagcaagg    2400
gggaggattg ggaagacaat agcaggcatg ctggggatgc ggtgggctct atggcttggt    2460
acc                                                                  2463
```

<210> SEQ ID NO 34
<211> LENGTH: 243
<212> TYPE: PRT
<213> ORGANISM: Bovine respiratory syncytial virus

<400> SEQUENCE: 34

```
Met Ser Asn His Thr His His Leu Lys Phe Lys Thr Leu Lys Arg Ala
1               5                   10                  15

Trp Lys Ala Ser Lys Tyr Phe Ile Val Gly Leu Ser Cys Leu Tyr Lys
            20                  25                  30

Phe Asn Leu Lys Ser Leu Val Gln Thr Ala Leu Thr Thr Leu Ala Met
        35                  40                  45

Ile Thr Leu Thr Ser Leu Val Ile Thr Ala Ile Ile Tyr Ile Ser Val
    50                  55                  60

Gly Asn Ala Lys Ala Lys Pro Thr Ser Lys Pro Thr Ile Gln Gln Thr
65                  70                  75                  80

Gln Gln Pro Gln Asn His Thr Ser Pro Phe Phe Thr Glu His Asn Tyr
                85                  90                  95

Lys Ser Thr His Thr Ser Ile Gln Ser Thr Thr Leu Ser Gln Leu Pro
            100                 105                 110

Asn Thr Asp Thr Thr Arg Glu Thr Thr Tyr Ser His Ser Ile Asn Glu
        115                 120                 125

Thr Gln Asn Arg Lys Ile Lys Ser Gln Ser Thr Leu Pro Ala Thr Arg
    130                 135                 140

Lys Pro Pro Ile Asn Pro Ser Gly Ser Asn Pro Glu Asn His Gln
145                 150                 155                 160

Asp His Asn Asn Ser Gln Thr Leu Pro Tyr Val Pro Gln Ile Gly Pro
                165                 170                 175

Glu Arg Ala Pro Ser Arg Ala Pro Thr Ile Thr Leu Lys Lys Thr Pro
            180                 185                 190

Lys Pro Lys Thr Thr Lys Lys Pro Thr Lys Thr Thr Ile His His Arg
        195                 200                 205

Thr Ser Pro Glu Ala Lys Leu Gln Pro Lys Asn Asn Thr Ala Ala Pro
    210                 215                 220

Gln Gln Gly Ile Leu Ser Ser Pro Glu His His Thr Asn Gln Ser Thr
225                 230                 235                 240
```

<210> SEQ ID NO 35
<211> LENGTH: 729
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
atgtctaacc atactcacca tctgaagttc aagaccctga agcgggcctg gaaggcctcc      60
aagtacttca tcgtgggcct gagctgcctg tacaagttca acctgaagag cctggtgcag     120
accgctctga ccaccctggc catgatcacc ctgacctccc tggtgatcac cgccatcatc     180
tacatcagcg tgggcaacgc caaggccaag cccacctcca agcctaccat ccagcagacc     240
cagcagcctc agaaccacac cagcccttc ttcaccgagc acaactacaa gtccacccac     300
acctccatcc agagcaccac cctgtcccag ctgcctaaca ccgacaccac ccgcgagacc     360
acctacagcc actccatcaa cgagacccag aaccgcaaga tcaagagcca gtccaccctg     420
cctgccacca gaaagccccc tatcaacccc agcggctcca cccccctga gaccaccag       480
gaccacaaca cagccagac cctgccctac gtgcctcaga tcggacctga gagggctcct      540
agcagggctc ccaccatcac cctgaagaag accccaagc taagaccac caagaagccc      600
accaagacca ccatccacca caggacctcc cctgaggcta agctgcagcc aagaacaac      660
accgccgccc cccagcaggg aatcctgagc agccccgaac caccacaaa ccagagcact      720
acccagatc                                                             729
```

<210> SEQ ID NO 36
<211> LENGTH: 263
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Met Gln Gly Pro Thr Leu Ala Val Leu Gly Ala Leu Leu Ala Val Ala
1               5                   10                  15

Val Ser Leu Pro Met Ser Asn His Thr His His Leu Lys Phe Lys Thr
                20                  25                  30

Leu Lys Arg Ala Trp Lys Ala Ser Lys Tyr Phe Ile Val Gly Leu Ser
            35                  40                  45

Cys Leu Tyr Lys Phe Asn Leu Lys Ser Leu Val Gln Thr Ala Leu Thr
        50                  55                  60

Thr Leu Ala Met Ile Thr Leu Thr Ser Leu Val Ile Thr Ala Ile Ile
65                  70                  75                  80

Tyr Ile Ser Val Gly Asn Ala Lys Ala Lys Pro Thr Ser Lys Pro Thr
                85                  90                  95

Ile Gln Gln Thr Gln Gln Pro Gln Asn His Thr Ser Pro Phe Phe Thr
            100                 105                 110

Glu His Asn Tyr Lys Ser Thr His Thr Ser Ile Gln Ser Thr Thr Leu
        115                 120                 125

Ser Gln Leu Pro Asn Thr Asp Thr Thr Arg Glu Thr Thr Tyr Ser His
    130                 135                 140

Ser Ile Asn Glu Thr Gln Asn Arg Lys Ile Lys Ser Gln Ser Thr Leu
```

```
145                 150                 155                 160
Pro Ala Thr Arg Lys Pro Pro Ile Asn Pro Ser Gly Ser Asn Pro Pro
                165                 170                 175
Glu Asn His Gln Asp His Asn Asn Ser Gln Thr Leu Pro Tyr Val Pro
            180                 185                 190
Gln Ile Gly Pro Glu Arg Ala Pro Ser Arg Ala Pro Thr Ile Thr Leu
        195                 200                 205
Lys Lys Thr Pro Lys Pro Lys Thr Thr Lys Pro Thr Lys Thr Thr
210                 215                 220
Ile His His Arg Thr Ser Pro Glu Ala Lys Leu Gln Pro Lys Asn Asn
225                 230                 235                 240
Thr Ala Ala Pro Gln Gln Gly Ile Leu Ser Ser Pro Glu His His Thr
                245                 250                 255
Asn Gln Ser Thr Thr Gln Ile
            260

<210> SEQ ID NO 37
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37 atgcaggggac caactctggc tgtgctgggg gctctgctgg ctgtcgctgt gtcactgcct      60
atgtctaacc atactcacca tctgaagttc aagaccctga gcgggcctg gaaggcctcc     120 aagtacttca tcgtgggcct gagctgcctg tacaagttca acctgaagag cctggtgcag     180
accgctctga ccaccctggc catgatcacc ctgacctccc tggtgatcac cgccatcatc     240
tacatcagcg tgggcaacgc caaggccaag cccacctcca agcctaccat ccagcagacc     300
cagcagcctc agaaccacac cagccccttc ttcaccgagc acaactacaa gtccacccac     360
acctccatcc agagcaccac cctgtcccag ctgcctaaca ccgacaccac ccgcgagacc     420
acctacagcc actccatcaa cgagacccag aaccgcaaga tcaagagcca gtccaccctg     480
cctgccacca gaaagccccc tatcaacccc agcggctcca cccccctga gaaccaccag     540 gaccacaaca cagccagac cctgccctac gtgcctcaga tcggacctga gagggctcct     600
agcagggctc ccaccatcac cctgaagaag acccccaagc ctaagaccac caagaagccc     660
accaagacca ccatccacca caggacctcc cctgaggcta agctgcagcc caagaacaac     720
accgccgccc cccagcaggg aatcctgagc agccccgaac caccacaaa ccagagcact     780 acccagatc                                                             789

<210> SEQ ID NO 38
<211> LENGTH: 2421
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
ggtaccctcg tgaggctccg gtgcccgtca gtgggcagag cgcacatcgc ccacagtccc      60
cgagaagttg gggggagggg tcggcaattg aaccggtgcc tagagaaggt ggcgcggggt     120
aaactgggaa agtgatgtcg tgtactggct ccgccttttt cccgaggggtg ggggagaacc     180
```

```
gtatataagt gcagtagtcg ccgtgaacgt tcttttcgc aacgggtttg ccgccagaac    240
acaggtaagt gccgtgtgtg gttcccgcgg gcctggcctc tttacgggtt atggcccttg    300
cgtgccttga attacttcca cctggctgca gtacgtgatt cttgatcccg agcttcgggt    360
tggaagtggg tgggagagtt cgaggccttg cgcttaagga gccccttcgc ctcgtgcttg    420
agttgaggcc tggcctgggc gctggggccg ccgcgtgcga atctggtggc accttcgcgc    480
ctgtctcgct gctttcgata agtctctagc catttaaaat ttttgatgac ctgctgcgac    540
gcttttttc tggcaagata gtcttgtaaa tgcgggccaa gatctgcaca ctggtatttc    600
ggttttggg gccgcgggcg gcgacggggc ccgtgcgtcc cagcgcacat gttcggcgag    660
gcggggcctg cgagcgcggc caccgagaat cggacggggg tagtctcaag ctggccggcc    720
tgctctggtg cctggcctcg cgccgccgtg tatcgcccg ccctgggcgg caaggctggc    780
ccggtcggca ccagttgcgt gagcggaaag atggccgctt cccggccctg ctgcagggag    840
ctcaaaatgg aggacgcggc gctcgggaga gcgggcgggt gagtcaccca cacaaaggaa    900
aagggccttt ccgtcctcag ccgtcgcttc atgtgactcc acgagtacc gggcgccgtc    960
caggcacctc gattagttct cgagcttttg gagtacgtcg tctttaggtt ggggggaggg    1020
gttttatgcg atggagtttc cccacactga gtgggtggag actgaagtta ggccagcttg    1080
gcacttgatg taattctcct tggaatttgc cctttttgag tttggatctt ggttcattct    1140
caagcctcag acagtggttc aaagtttttt tcttccattt caggtgtcgt gaggaattag    1200
cttggtacta atacgactca ctataggag acccaagctg gctaggtaag tgtacgagct    1260
cgatcactag tccagtgtgg atcgatgccg ccaccatgca gggaccaact ctggctgtgc    1320
tgggggctct gctggctgtc gctgtgtcac tgcctatgtc taaccatact caccatctga    1380
agttcaagac cctgaagcgg gcctggaagg cctccaagta cttcatcgtg ggcctgagct    1440
gcctgtacaa gttcaacctg aagagcctgg tgcagaccgc tctgaccacc ctggccatga    1500
tcaccctgac ctccctggtg atcaccgcca tcatctacat cagcgtgggc aacgccaagg    1560
ccaagcccac ctccaagcct accatccagc agaccccagca gcctcagaac acaccagcc    1620
ccttcttcac cgagcacaac tacaagtcca cccacacctc catccagagc accaccctgt    1680
cccagctgcc taacaccgac accccccgcg agaccaccta cagccactcc atcaacgaga    1740
cccagaaccg caagatcaag agccagtcca ccctgcctgc caccagaaag ccccctatca    1800
accccagcgg ctccaacccc ctgagaacc accaggacca caacaacagc cagaccctgc    1860
cctacgtgcc tcagatcgga cctgagaggg ctcctagcag ggctccacc atcaccctga    1920
agaagacccc caagcctaag accaccaaga gcccaccaa gaccaccatc caccacagga    1980
cctcccctga ggctaagctg cagcccaaga caacaccgc cgcccccag cagggaatcc    2040
tgagcagccc cgaacaccac acaaaccaga gcactaccca gatcatgcat ggtaagccta    2100
tccctaaccc tctcctcggt ctcgattcta cgcgtaccgg tcatcatcac catcaccatt    2160
gagtttaaac ccgctgatca gcctcgactg tgccttctag ttgccagcca tctgttgttt    2220
gcccctcccc cgtgccttcc ttgaccctgg aaggtgccac tcccactgtc ctttcctaat    2280
aaaatgagga aattgcatcg cattgtctga gtaggtgtca ttctattctg ggggtgggg    2340
tggggcagga cagcaagggg gaggattggg aagacaatag caggcatgct ggggatgcgg    2400
tgggctctat ggcttggtac c                                              2421
```

<210> SEQ ID NO 39
<211> LENGTH: 227

<212> TYPE: PRT
<213> ORGANISM: Bovine viral diarrhea virus

<400> SEQUENCE: 39

```
Glu Asn Ile Thr Gln Trp Asn Leu Gln Asp Asn Gly Thr Glu Gly Ile
1               5                   10                  15

Gln Arg Ala Met Phe Gln Arg Gly Val Asn Arg Ser Leu His Gly Ile
            20                  25                  30

Trp Pro Glu Lys Ile Cys Thr Gly Val Pro Ser His Leu Ala Thr Asp
        35                  40                  45

Ile Glu Leu Lys Thr Ile His Gly Met Met Asp Ala Ser Glu Lys Thr
    50                  55                  60

Asn Tyr Thr Cys Cys Arg Leu Gln Arg His Glu Trp Asn Lys His Gly
65                  70                  75                  80

Trp Cys Asn Trp Tyr Asn Ile Glu Pro Trp Ile Leu Val Met Asn Arg
                85                  90                  95

Thr Gln Ala Asn Leu Thr Glu Gly Gln Pro Pro Arg Glu Cys Ala Val
            100                 105                 110

Thr Cys Arg Tyr Asp Arg Ala Ser Asp Leu Asn Val Val Thr Gln Ala
        115                 120                 125

Arg Asp Ser Pro Thr Pro Leu Thr Gly Cys Lys Lys Gly Lys Asn Phe
    130                 135                 140

Ser Phe Ala Gly Ile Leu Met Arg Gly Pro Cys Asn Phe Glu Ile Ala
145                 150                 155                 160

Ala Ser Asp Val Leu Phe Lys Glu His Glu Arg Ile Ser Met Phe Gln
                165                 170                 175

Asp Thr Thr Leu Tyr Leu Val Asp Gly Leu Thr Asn Ser Leu Glu Gly
            180                 185                 190

Ala Arg Gln Gly Thr Ala Lys Leu Thr Thr Trp Leu Gly Lys Gln Leu
        195                 200                 205

Gly Ile Leu Gly Lys Lys Leu Glu Asn Lys Ser Lys Thr Trp Phe Gly
    210                 215                 220

Ala Tyr Ala
225
```

<210> SEQ ID NO 40
<211> LENGTH: 1235
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
ttaattaacg ccaccatgca ggaacctact ctggctgtgc tgggggctct gctggctgtc      60
gccgtcagtc tggaaaacat cactcagtgg aatctgcagg ataacggcac cgaggggatc     120
cagcgcgcca tgttccagcg aggcgtgaac cggtcactgc acgggatctg gccagaaaag     180
atttgcaccg gagtcccaag ccacctggct accgacatcg agctgaagac aattcatgga     240
atgatggatg ctagcgaaaa aaccaactac acatgctgtc ggctgcagag gcacgagtgg     300
aataagcatg gctggtgtaa ctggtataat atcgaaccct ggatcctggt catgaacaga     360
acacaggcca atctgactga gggacagcca cctcgagaat gcgctgtcac ttgtcgctac     420
gacagagcta gcgatctgaa cgtggtcaca caggctcgag actccccaac tcctctgacc     480
ggctgcaaga aagggaagaa cttctccttt gctgggatcc tgatgcgcgg accctgtaat     540
```

```
tttgagattg ccgcttctga tgtgctgttc aaagagcacg aaagaatcag tatgtttcag    600
gacaccacac tgtacctggt ggatggcctg accaactccc tggagggagc taggcaggga    660
acagctaagc tgactacctg gctggggaaa cagctgggaa ttctgggcaa gaaactggaa    720
aacaagtcta aaacctggtt cggagcctat gctatgtggc tgcagaatct gctgctgctg    780
ggcacagtgg tctgctcttt tagtgcccct actaggccac ccaatacagc tactcgccca    840
tggcagcacg tggacgccat caaggaggct ctgagtctgc tgaaccatag ctccgacact    900
gatgccgtga tgaatgacac cgaggtggtc tccgaaaaat tgattctca ggagcccacc     960 tgtctgcaga cacggctgaa gctgtacaaa acgggctgc agggatcact gaccagcctg    1020
atgggaagcc tgactatgat ggccacccac tatgagaagc attgccctcc aacacctgaa   1080
actagttgtg ggacccagtt catcagcttc aagaatttca agaagacct gaaagagttc    1140 ctgtttatca ttccatttga ctgttgggag ccagcccaga aggtaagcc tatccctaac    1200 cctctcctcg gtctcgattc tacgtaagcg ccgc                               1235
```

<210> SEQ ID NO 41
<211> LENGTH: 143
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Met Trp Leu Gln Asn Leu Leu Leu Gly Thr Val Val Cys Ser Phe
1               5                   10                  15

Ser Ala Pro Thr Arg Pro Pro Asn Thr Ala Thr Arg Pro Trp Gln His
                20                  25                  30

Val Asp Ala Ile Lys Glu Ala Leu Ser Leu Leu Asn His Ser Ser Asp
            35                  40                  45

Thr Asp Ala Val Met Asn Asp Thr Glu Val Val Ser Glu Lys Phe Asp
        50                  55                  60

Ser Gln Glu Pro Thr Cys Leu Gln Thr Arg Leu Lys Leu Tyr Lys Asn
65                  70                  75                  80

Gly Leu Gln Gly Ser Leu Thr Ser Leu Met Gly Ser Leu Thr Met Met
                85                  90                  95

Ala Thr His Tyr Glu Lys His Cys Pro Pro Thr Pro Glu Thr Ser Cys
            100                 105                 110

Gly Thr Gln Phe Ile Ser Phe Lys Asn Phe Lys Glu Asp Leu Lys Glu
        115                 120                 125

Phe Leu Phe Ile Ile Pro Phe Asp Cys Trp Glu Pro Ala Gln Lys
    130                 135                 140

<210> SEQ ID NO 42
<211> LENGTH: 227
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Glu Asn Ile Thr Gln Trp Asn Leu Met Asp Asn Gly Thr Glu Gly Ile
1               5                   10                  15

Gln Gln Ala Met Phe Leu Arg Gly Val Asn Arg Ser Leu His Gly Ile
                20                  25                  30

```
Trp Pro Glu Lys Ile Cys Thr Gly Val Pro Thr His Leu Ala Thr Asp
        35                  40                  45

Tyr Glu Leu Lys Glu Ile Val Gly Met Met Asp Ala Ser Glu Lys Thr
    50                  55                  60

Asn Tyr Thr Cys Cys Arg Leu Gln Arg His Glu Trp Asn Lys His Gly
65                  70                  75                  80

Trp Cys Asn Trp Phe His Ile Glu Pro Trp Ile Trp Leu Met Asn Lys
                85                  90                  95

Thr Gln Asn Asn Leu Thr Glu Gly Gln Pro Leu Arg Glu Cys Ala Val
            100                 105                 110

Thr Cys Arg Tyr Asp Lys Glu Thr Glu Leu Asn Ile Val Thr Gln Ala
        115                 120                 125

Arg Asp Arg Pro Thr Thr Leu Thr Gly Cys Lys Lys Gly Lys Asn Phe
    130                 135                 140

Ser Phe Ala Gly Val Ile Leu Asp Gly Pro Cys Asn Phe Lys Val Ser
145                 150                 155                 160

Val Glu Asp Val Leu Phe Lys Glu His Asp Cys Gly Asn Met Leu Gln
                165                 170                 175

Glu Thr Ala Ile Gln Leu Leu Asp Gly Ala Thr Asn Thr Ile Glu Gly
            180                 185                 190

Ala Arg Val Gly Thr Ala Lys Leu Thr Thr Trp Leu Gly Lys Gln Leu
        195                 200                 205

Gly Ile Leu Gly Lys Lys Leu Glu Asn Lys Ser Lys Ala Trp Phe Gly
    210                 215                 220

Ala His Ala
225

<210> SEQ ID NO 43
<211> LENGTH: 125
<212> TYPE: PRT
<213> ORGANISM: Bovine herpesvirus 1

<400> SEQUENCE: 43

Ala Ser Gln Lys Arg Thr Tyr Asp Ile Leu Asn Pro Phe Gly Pro Val
1               5                   10                  15

Tyr Thr Ser Leu Pro Thr Asn Glu Pro Leu Asp Val Val Val Pro Val
            20                  25                  30

Ser Asp Asp Glu Phe Ser Leu Asp Glu Asp Ser Phe Ala Asp Asp Asp
        35                  40                  45

Ser Asp Asp Asp Gly Pro Ala Ser Asn Pro Pro Ala Asp Ala Tyr Asp
    50                  55                  60

Leu Ala Gly Ala Pro Glu Pro Thr Ser Gly Phe Ala Arg Ala Pro Ala
65                  70                  75                  80

Asn Gly Thr Arg Ser Ser Arg Ser Gly Phe Lys Val Trp Phe Arg Asp
                85                  90                  95

Pro Leu Glu Asp Asp Ala Ala Pro Ala Arg Thr Pro Ala Ala Pro Asp
            100                 105                 110

Tyr Thr Val Val Ala Ala Arg Leu Lys Ser Ile Leu Arg
        115                 120                 125

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 44
gcggtacctc gtgaggctcc ggtgcccgtc agtg                                34

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gcggtacccc atagagccca ccgcatcccc agcatgcctg                          40

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
taatcaaagc ttcgccgcca ccatgcaggg acc                                33

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ctccggaatt ccgtagaatc gagaccgagg agagg                              35

<210> SEQ ID NO 48
<211> LENGTH: 14
<212> TYPE: PRT
<213> ORGANISM: Bovine respiratory syncytial virus

<400> SEQUENCE: 48

Cys Ser Thr Cys Glu Gly Asn Leu Ala Cys Leu Ser Leu Cys
1               5                   10

<210> SEQ ID NO 49
<211> LENGTH: 2852
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gatatcaggc aacggggcct gctccgcgc aggagcacgt ggtgctcaag atcggggcct    60
cggcctctac gctggccgag gctatgctac tgcgaacctt ggaccacgcc aacgtggtca   120
agctgaaggc cgtgctcttc acggggagc tggtgtgcgt ggtgctggcg cgctaccgcg   180
aggacctgca cacgcacctc tggagaatca accgcccgct ggcgctcccc gcggcgctgg   240
cggtgacgcg ggccgtgctg cggggcctcg cgtacctgca ctcccgcgg atcgctcacc   300 gggacgtcaa aacggaaaac gtcttcctca acggcccagg cgacgtgtgc ctgggcgact   360 tggcgcggc acacgggccg gtcaccgagc ccgctacta cggcctggcc ggcacccctgg   420

```
agacgaactc gccagagctg ctggcgcgcg cgcgctacga ctgccgcacg gacgtgtgga      480
gcgcgggcgt cgtcgcgtac gagatgctgg cataccccgcg cgcgctgttc gacagccccg     540
cgggcccgca gggcgaggac gccgaggcat cgggcccgcc gacgatcttg ggcgaccgcg      600
actgcgcccg gcagctgctc cgcgtgattc gccggctggc cgtgcacgcc gaagagtttc      660
cacccagccc cactgaccgg ctgacccgca acttcaagcg ccacgcgagc acgcgccgag      720
agccgcacag cccgtaccgc tgcctggcgg tgctccggct gccctgcgac gccgaccgcc      780
tcctacacca gatgctgacc tttgactttc gcgcgcgccc caccgccgcg gagctgctgg      840
agcaccccgt cttcggtgcg gcctcggggt agccccgggg gtttcccgca aaactgaggc      900
atataaggcg cgggcaccgg caagtttggc atccacactt cgcgctgtgg acacgagagc      960
gaacgcgagc gaacgcgagc gcaagcgcga gcacacgact gcgatcgttg acattgatta     1020
ttgactagtt attaatagta atcaattacg gggtcattag ttcatagccc atatatggag     1080
ttccgcgtta cataacttac ggtaaatggc ccgcctggct gaccgcccaa cgaccccgc      1140
ccattgacgt caataatgac gtatgttccc atagtaacgc caatagggac tttccattga     1200
cgtcaatggg tggagtattt acggtaaact gcccacttgg cagtacatca agtgtatcat     1260
atgccaagta cgcccctat tgacgtcaat gacggtaaat ggcccgcctg gcattatgcc      1320
cagtacatga cctattggga cttcctact tggcagtaca tctacgtatt agtcatcgct      1380
attaccatgg tgatgcggtt ttggcagtac atcaatgggc gtggatagcg gttgactca      1440
cggggatttc caagtctcca ccccattgac gtcaatggga gtttgttttg gcaccaaaat     1500
caacgggact ttccaaaatg tcgtaacaac tccgccccat tgacgcaaat gggcggtagg     1560
cgtgtacggt gggaggtcta tataagcaga gctcttaatt aagtgtgtgt gtgcggccgc     1620
ctgtgccttc tagttgccag ccatctgttg tttgcccctc ccccgtgcct tccttgaccc     1680
tggaaggtgc cactcccact gtcctttcct aataaaatga ggaaattgca tcgcattgtc     1740
tgagtaggtg tcattctatt ctggggggtg gggtggggca ggacagcaag ggggaggatt     1800
gggaagacaa tagcaggcat gctggggatg cggtgggctc tatggtcgcc ggcaccccac     1860
gccgcccga ccccgctgtc ccgcgtttac aataaacagt tattcttacc aacgttggtg      1920
cgcctgtcgc gtgtctattg cgagttaaac cgagtgcccc acccaggcag ggcgggggtt     1980
gggccgggcc gcagccccgg ctgggtatat atccccgacg ggcgactaga gatacactcg     2040
ccccgcgcgg ctgctgcgag cgggcgaaca tgcaagggcc gacattggcc gtgctgggcg     2100
cgctgctcgc cgttgcggtg agcttgccta cacccgcgcc gcgggtgacg gtatacgtcg     2160
acccgccggc gtacccgatg ccgcgataca ctacactga acgctggcac actaccgggc     2220
ccataccgtc gccttcgca gacggccgcg agcagcccgt cgaggtgcgc tacgcgacga      2280
gcgcggcggc gtgcgacatg ctggcgctga tcgcagaccc gcaggtgggg cgcacgctgt     2340
gggaagcggt acgccggcac gcgcgcgcgt acaacgccac ggtcatatgg tacaagatcg     2400
agagcgggtg cgcccggccg ctgtactaca tggagtacac cgagtgcgag cccaggaagc     2460
actttgggta ctgccgctac cgcacacccc cgttttggga cagcttcctg gcgggcttcg     2520
cctaccccac ggacgacgag ctgggactga ttatggcggc gcccgcgcgg ctcgtcgagg     2580
gccagtaccg acgcgcgctg tacatcgacg gcacggtcgc ctatacagat ttcatggttt     2640
cgctgccggc cggggactgc tggttctcga aactcggcgc ggctcgcggg tacacctttg     2700
gcgcgtgctt cccggcccgg gattacgagc aaaagaaggt tctgcgcctg acgtatctca     2760
```

```
cgcagtacta cccgcaggag gcacacaagg ccatagtcga ctactggttc atgcgccacg    2820
ggggcgtcgt tccgccgtat tttgagaagc tt                                  2852
```

<210> SEQ ID NO 50
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

```
gtgtgtgtgt                                                             10
```

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ala Lys Arg
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Ala Lys Ala
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Lys Arg Arg
1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Lys Ala Ala
1

<210> SEQ ID NO 55
<211> LENGTH: 393
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 55

```
Met Gln Gly Pro Thr Leu Ala Val Leu Gly Ala Leu Leu Ala Val Ala
1               5                   10                  15

Val Ser Leu His Leu Asp Cys Lys Pro Glu Phe Ser Tyr Ala Ile Ala
            20                  25                  30

Lys Asp Glu Arg Ile Gly Gln Leu Gly Ala Glu Gly Leu Thr Thr Thr
        35                  40                  45

Trp Lys Glu Tyr Ser Pro Gly Met Lys Leu Glu Asp Thr Met Val Ile
    50                  55                  60

Ala Trp Cys Glu Asp Gly Lys Leu Met Tyr Leu Gln Arg Cys Thr Arg
65                  70                  75                  80

Glu Thr Arg Tyr Leu Ala Ile Leu His Thr Arg Ala Leu Pro Thr Ser
                85                  90                  95

Val Val Phe Lys Lys Leu Phe Asp Gly Arg Lys Gln Glu Asp Val Val
            100                 105                 110

Glu Met Asn Asp Asn Phe Glu Phe Gly Leu Cys Pro Cys Asp Ala Lys
        115                 120                 125

Pro Ile Val Arg Gly Lys Phe Asn Thr Thr Leu Leu Asn Gly Pro Ala
    130                 135                 140

Phe Gln Met Val Cys Pro Ile Gly Trp Thr Gly Thr Val Ser Cys Thr
145                 150                 155                 160

Ser Phe Asn Met Asp Thr Leu Ala Thr Val Val Arg Thr Tyr Arg
                165                 170                 175

Arg Ser Lys Pro Phe Pro His Arg Gln Gly Cys Ile Thr Gln Lys Asn
            180                 185                 190

Leu Gly Glu Asp Leu His Asn Cys Ile Leu Gly Gly Asn Trp Thr Cys
        195                 200                 205

Val Pro Gly Asp Gln Leu Leu Tyr Lys Gly Gly Ser Ile Glu Ser Cys
    210                 215                 220

Lys Trp Cys Gly Tyr Gln Phe Lys Glu Ser Glu Gly Leu Pro His Tyr
225                 230                 235                 240

Pro Ile Gly Lys Cys Lys Leu Glu Asn Glu Thr Gly Tyr Arg Leu Val
                245                 250                 255

Asp Ser Thr Ser Cys Asn Arg Glu Gly Val Ala Ile Val Pro Gln Gly
            260                 265                 270

Thr Leu Lys Cys Lys Ile Gly Lys Thr Thr Val Gln Val Ile Ala Met
        275                 280                 285

Asp Thr Lys Leu Gly Pro Met Pro Cys Arg Pro Tyr Glu Ile Ile Ser
    290                 295                 300

Ser Glu Gly Pro Val Glu Lys Thr Ala Cys Thr Phe Asn Tyr Thr Lys
305                 310                 315                 320

Thr Leu Lys Asn Lys Tyr Phe Glu Pro Arg Asp Ser Tyr Phe Gln Gln
                325                 330                 335

Tyr Met Leu Lys Gly Glu Tyr Gln Tyr Trp Phe Asp Leu Glu Val Thr
            340                 345                 350

Asp His His Arg Asp Tyr Phe Ala Glu Ser Ile Leu Val Val Val Val
        355                 360                 365

Ala Leu Leu Gly Gly Arg Tyr Val Leu Trp Leu Leu Val Thr Tyr Met
    370                 375                 380

Val Leu Ser Glu Gln Lys Ala Leu Gly
385                 390
```

<210> SEQ ID NO 56
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
atgcaggac ccaccctggc cgtgctgggc gctctgctgg ctgtggctgt cagtctgcac     60
ctggattgca agcctgagtt ctcatacgcc atcgctaaag acgagagaat tggccagctg    120
ggggccgaag gactgaccac aacttggaag gagtattctc aggcatgaa actggaagat    180
accatggtca tcgcttggtg cgaggacggg aagctgatgt acctgcagcg gtgcacaaga    240
gaaactcgat atctggccat tctgcatact cgagctctgc ccaccagtgt ggtcttcaag    300
aaactgtttg acggacgaa gcaggaggat gtggtcgaaa tgaacgacaa tttcgagttt    360
ggcctgtgcc cctgtgatgc caagcctatc gtgaggggaa aattcaacac cacactgctg    420
aatggcccag cttttcagat ggtgtgcccc attggctgga ccgggacagt ctcatgtacc    480
agcttcaaca tggacactct ggccactacc gtggtccgca cttaccggag gtctaagccc    540
tttcctcaca gacagggctg catcacccag aaaaacctgg gggaggatct gcataactgc    600
attctgggag aaaattggac ctgcgtgcca ggggaccagc tgctgtacaa gggaggctcc    660
atcgaatctt gcaagtggtg tggctaccag ttcaaagaga gcgaagggct gcctcactat    720
ccaattggaa agtgtaaact ggagaacgaa accggctatc ggctggtgga ttctacaagt    780
tgcaataggg agggagtggc tatcgtccct caggggacac tgaagtgtaa aatcggaaag    840
acaactgtgc aggtcattgc tatggacact aaactggggc caatgccctg cagaccttac    900
gagatcatta gctccgaggg accagtggaa aagaccgcct gtaccttcaa ctacactaaa    960
accctgaaga caagtatttt cgaaccccga gattcctact ttcagcagta tatgctgaag   1020
ggcgagtacc agtattggtt cgacctggaa gtgacagacc accatagga ttactttgcc   1080
gagagcatcc tggtggtcgt ggtcgctctg ctgggaggac gctacgtgct gtggctgctg   1140
gtgacctata tggtcctgtc cgagcagaag gccctgggca tgcat               1185
```

<210> SEQ ID NO 57
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Met Gln Gly Pro Thr Leu Ala Val Leu Gly Ala Leu Leu Ala Val Ala
1               5                   10                  15

Val Ser Leu Phe Pro Glu Cys Lys Glu Gly Phe Gln Tyr Ala Ile Ser
            20                  25                  30

Lys Asp Arg Lys Ile Gly Pro Leu Gly Pro Glu Ser Leu Thr Thr Thr
        35                  40                  45

Trp His Leu Pro Thr Lys Lys Ile Val Asp Ser Met Val Gln Val Trp
    50                  55                  60

Cys Asp Gly Lys Asn Leu Lys Ile Leu Glu Thr Cys Thr Lys Glu Glu
65                  70                  75                  80

Arg Tyr Leu Val Ala Val His Glu Arg Ala Leu Ser Thr Ser Ala Glu
```

|     |     |     |     |     | 85  |     |     |     |     | 90  |     |     |     |     | 95  |     |     |
| --- | --- | --- | --- | --- | --- | --- | --- | --- | --- | --- | --- | --- | --- | --- | --- | --- | --- |
| Phe | Met | Gln | Ile | Ser | Ser | Gly | Thr | Lys | Gly | Pro | Glu | Val | Ile | Asp | Met |
|     |     |     | 100 |     |     |     |     | 105 |     |     |     |     | 110 |     |     |
| His | Asp | Asp | Phe | Glu | Phe | Gly | Leu | Cys | Pro | Cys | Asp | Ser | Lys | Pro | Val |
|     |     | 115 |     |     |     |     | 120 |     |     |     |     | 125 |     |     |     |
| Met | Arg | Gly | Lys | Phe | Asn | Ala | Ser | Leu | Leu | Asn | Gly | Pro | Ala | Phe | Gln |
|     | 130 |     |     |     |     | 135 |     |     |     |     | 140 |     |     |     |     |
| Met | Val | Cys | Pro | Gln | Gly | Trp | Thr | Gly | Thr | Ile | Glu | Cys | Ile | Leu | Ala |
| 145 |     |     |     |     | 150 |     |     |     |     | 155 |     |     |     |     | 160 |
| Asn | Gln | Asp | Thr | Leu | Asp | Thr | Thr | Val | Val | Arg | Thr | Tyr | Arg | Arg | Thr |
|     |     |     |     | 165 |     |     |     |     | 170 |     |     |     |     | 175 |     |
| Thr | Pro | Phe | Gln | Arg | Arg | Lys | Trp | Cys | Thr | Tyr | Glu | Lys | Ile | Ile | Gly |
|     |     |     | 180 |     |     |     |     | 185 |     |     |     |     | 190 |     |     |
| Glu | Asp | Ile | His | Glu | Cys | Ile | Leu | Gly | Gly | Asn | Trp | Thr | Cys | Ile | Thr |
|     |     |     | 195 |     |     |     |     | 200 |     |     |     |     | 205 |     |     |
| Gly | Asp | His | Ser | Lys | Leu | Lys | Asp | Gly | Pro | Ile | Lys | Lys | Cys | Lys | Trp |
|     | 210 |     |     |     |     | 215 |     |     |     |     | 220 |     |     |     |     |
| Cys | Gly | Tyr | Asp | Phe | Phe | Asp | Ser | Glu | Gly | Leu | Pro | His | Tyr | Pro | Ile |
| 225 |     |     |     |     | 230 |     |     |     |     | 235 |     |     |     |     | 240 |
| Gly | Lys | Cys | Met | Leu | Ser | Asn | Glu | Ser | Gly | Tyr | Arg | Tyr | Val | Asp | Asp |
|     |     |     |     | 245 |     |     |     |     | 250 |     |     |     |     | 255 |     |
| Thr | Ser | Cys | Asp | Arg | Gly | Gly | Val | Ala | Ile | Val | Pro | Thr | Gly | Thr | Leu |
|     |     |     | 260 |     |     |     |     | 265 |     |     |     |     | 270 |     |     |
| Lys | Cys | Arg | Ile | Gly | Lys | Ala | Thr | Val | Gln | Val | Ile | Ala | Thr | Asn | Thr |
|     |     | 275 |     |     |     |     | 280 |     |     |     |     | 285 |     |     |     |
| Asp | Leu | Gly | Pro | Met | Pro | Cys | Ser | Pro | Asp | Glu | Val | Ile | Ala | Ser | Glu |
|     | 290 |     |     |     |     | 295 |     |     |     |     | 300 |     |     |     |     |
| Gly | Pro | Val | Glu | Lys | Thr | Ala | Cys | Thr | Phe | Asn | Tyr | Ser | Lys | Thr | Leu |
| 305 |     |     |     |     | 310 |     |     |     |     | 315 |     |     |     |     | 320 |
| Pro | Asn | Lys | Tyr | Tyr | Glu | Pro | Arg | Asp | Arg | Tyr | Phe | Gln | Gln | Tyr | Met |
|     |     |     |     | 325 |     |     |     |     | 330 |     |     |     |     | 335 |     |
| Leu | Lys | Gly | Glu | Trp | Gln | Tyr | Trp | Phe | Asp | Leu | Asp | Thr | Val | Asp | His |
|     |     |     | 340 |     |     |     |     | 345 |     |     |     |     | 350 |     |     |
| His | Lys | Asp | Tyr | Phe | Ser | Glu | Phe | Ile | Val | Ile | Ala | Val | Val | Ala | Leu |
|     |     | 355 |     |     |     |     | 360 |     |     |     |     | 365 |     |     |     |
| Leu | Gly | Gly | Lys | Tyr | Val | Leu | Trp | Leu | Leu | Val | Thr | Tyr | Met | Ile | Leu |
|     | 370 |     |     |     |     | 375 |     |     |     |     | 380 |     |     |     |     |
| Ser | Glu | Gln | Met | Ala | Met | Gly |
| 385 |     |     |     |     | 390 |     |

<210> SEQ ID NO 58
<211> LENGTH: 1179
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

| atgcaggac | caacactggc | cgtgctgggg | gctctgctgg | ctgtggctgt | ctccctgttc | 60  |
| cccgagtgca | aggaaggatt | tcagtacgcc | atcagcaagg | accggaaaat | tggaccactg | 120 |
| ggaccagagt | ccctgaccac | aacttggcac | ctgcccacca | agaaaatcgt | ggactctatg | 180 |
| gtgcaggtct | ggtgcgatgg | caagaacctg | aaaattctgg | agacatgtac | taaggaggag | 240 |
| agatacctgg | tggctgtcca | cgagcgcgct | ctgtctacca | gtgccgagtt | catgcagatc | 300 |

```
agctccggaa caaagggccc tgaagtgatc gacatgcacg acgatttcga atttggcctg    360
tgcccctgtg atagtaagcc tgtgatgcgc ggaaaattca acgcttcact gctgaatggc    420
cctgcctttc agatggtgtg cccacagggg tggaccggaa caatcgagtg tattctggct    480
aaccaggaca cactggatac cacagtggtc cggacttacc ggaggactac ccctttcag     540 cgcagaaagt ggtgcaccta tgagaaaatc attggcgagg acatccacga gtgcatcctg    600
ggcgggaatt ggacctgtat cacaggcgac cattctaagc tgaaagatgg ccaattaag     660 aaatgcaagt ggtgtggcta cgacttcttt gatagtgagg gactgcctca ttatccaatc    720
ggcaaatgta tgctgtcaaa cgaaagcggg tacagatatg tggacgatac tagctgcgat    780
cgaggaggag tggctatcgt cccaactggg accctgaagt gtaggatcgg aaaagctacc    840
gtgcaggtca ttgccacaaa tactgacctg gaccaatgc cttgctcccc agatgaagtg     900
atcgcttctg agggacctgt cgaaaagact gcctgtacct tcaactactc aagacactg     960 ccaaacaagt actatgagcc ccgagaccgg tacttccagc agtatatgct gaaggggaa     1020 tggcagtact ggtttgacct ggataccgtg gaccaccata aggattactt ctcagagttt    1080
atcgtgattg ccgtggtcgc tctgctgggg gaaagtacg tgctgtggct gctggtcacc     1140
tatatgatcc tgagtgaaca gatggccatg ggcatgcat                           1179
```

<210> SEQ ID NO 59
<211> LENGTH: 1235
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

```
ttaattaacg ccaccatgca gggacctact ctggctgtgc tgggggctct gctggctgtg     60
gctgtctctc tggaaaacat tactcagtgg aatctgatgg acaatggcac cgaagggatc    120
cagcaggcca tgtttctgcg aggcgtgaac cggtctctgc acgggatctg gcctgagaag    180
atttgcaccg gcgtgccaac acatctggcc actgactacg agctgaagga aattgtcggg    240
atgatggatg ctagtgagaa aactaattat acctgctgtc gcctgcagag acacgaatgg    300
aacaagcatg ggtggtgtaa ttggttccac atcgagccat ggatttggct gatgaacaaa    360
acacagaaca atctgactga gggacagcca ctgagggaat gcgctgtgac ctgtcgctac    420
gacaaggaga ccgaactgaa tatcgtcaca caggctcggg ataggcctac cacactgacc    480
ggctgcaaga agggaaaaa cttcagcttt gccggcgtga tcctggacgg accatgcaac    540
ttcaaggtga gcgtcgagga cgtgctgttc aaggaacacg attgtggaaa catgctgcag    600
gaaacagcca tccagctgct ggatggcgct acaaatacta ttgagggagc tcgagtggga    660
accgctaagc tgactacctg gctgggcaaa cagctgggaa tcctgggcaa gaaactggag    720
aacaagtcta agcctggtt tggggcccat gctatgtggc tgcagaatct gctgctgctg    780
ggaacagtgg tctgctcttt cagtgccccc actagaccccc taacaccgc tacacgacct    840 tgcagcacg tggacgccat taaggaggct ctgagcctgc tgaaccatag ctccgacact    900
gatgccgtga tgaatgacac cgaggtggtc tccgaaaagt ttgattctca ggagcccacc    960
tgtctgcaga cacggctgaa gctgtacaaa acgggctgc agggatcact gaccagcctg    1020
atgggatccc tgactatgat ggctacccac tatgagaagc attgcccacc cacacctgaa    1080
actagttgtg caccccagtt catcagcttc aagaacttca agaagacctg aaagagttc    1140
```

```
ctgtttatta ttccatttga ctgttgggag cctgcccaga agggtaagcc tatccctaac    1200
cctctcctcg gtctcgattc tacgtaagcg gccgc                              1235
```